(12) United States Patent
Van Eenennaam et al.

(10) Patent No.: US 7,605,244 B2
(45) Date of Patent: *Oct. 20, 2009

(54) **GAMMA TOCOPHEROL METHYLTRANSFERASE CODING SEQUENCE FROM *BRASSICA* AND USES THEREOF**

(75) Inventors: Alison Van Eenennaam, Davis, CA (US); Henry E. Valentin, Chesterfield, MO (US); Balasulojini Karunanandaa, Creve Coeur, MO (US); Ming Hao, St. Louis, MO (US); Eric Aasen, Woodland, CA (US); Charlene Levering, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/776,441

(22) Filed: Jul. 11, 2007

(65) Prior Publication Data

US 2008/0020444 A1    Jan. 24, 2008

Related U.S. Application Data

(62) Division of application No. 10/219,810, filed on Aug. 16, 2002, now Pat. No. 7,244,877.

(60) Provisional application No. 60/312,758, filed on Aug. 17, 2001.

(51) Int. Cl.
C07H 21/04 (2006.01)
C12N 15/82 (2006.01)
A01H 5/00 (2006.01)

(52) U.S. Cl. ............ 536/23.2; 536/23.6; 800/281; 800/287; 800/298; 800/306; 800/312; 435/419; 435/468; 530/377; 530/370

(58) Field of Classification Search .......... None
See application file for complete search history.

(56) References Cited

U.S. PATENT DOCUMENTS

| | | | |
|---|---|---|---|
| 4,727,219 A | 2/1988 | Brar et al. | 800/266 |
| 5,304,478 A | 4/1994 | Bird et al. | 800/282 |
| 5,429,939 A | 7/1995 | Misawa et al. | 435/67 |
| 5,432,069 A | 7/1995 | Grüninger et al. | 435/183 |
| 5,545,816 A | 8/1996 | Ausich et al. | 800/298 |
| 5,618,988 A | 4/1997 | Hauptmann et al. | 800/282 |
| 5,684,238 A | 11/1997 | Ausich et al. | 800/298 |
| 5,693,507 A | 12/1997 | Daniell et al. | 435/470 |
| 5,702,933 A | 12/1997 | Klee et al. | 800/283 |
| 5,750,865 A | 5/1998 | Bird et al. | 800/282 |
| 5,792,903 A | 8/1998 | Hirschberg et al. | 800/282 |
| 5,876,964 A | 3/1999 | Croteau et al. | 435/69.1 |
| 5,908,940 A | 6/1999 | Lane et al. | 549/413 |
| 6,281,017 B1 | 8/2001 | Croteau et al. | 435/468 |
| 6,303,365 B1 | 10/2001 | Martin et al. | 435/252.3 |
| 6,541,259 B1 | 4/2003 | Lassner et al. | 435/468 |
| 6,642,434 B1 | 11/2003 | DellaPenna et al. | 800/278 |
| 2002/0069426 A1 | 6/2002 | Boronat et al. | 800/278 |
| 2002/0108148 A1 | 8/2002 | Boronat et al. | 800/284 |
| 2003/0148300 A1 | 8/2003 | Valentin et al. | 435/6 |
| 2003/0150015 A1 | 8/2003 | Norris et al. | 800/278 |
| 2003/0154513 A1 | 8/2003 | van Eenennaam et al. | 800/281 |
| 2003/0166205 A1 | 9/2003 | van Eenennaam et al. | 435/193 |
| 2003/0170833 A1 | 9/2003 | Lassner et al. | 435/125 |
| 2003/0176675 A1 | 9/2003 | Valentin et al. | 536/23.1 |
| 2003/0213017 A1 | 11/2003 | Valentin et al. | 800/287 |
| 2004/0018602 A1 | 1/2004 | Lassner et al. | 435/193 |
| 2004/0045051 A1 | 3/2004 | Norris et al. | 800/278 |

FOREIGN PATENT DOCUMENTS

| | | |
|---|---|---|
| CA | 2239519 | 2/2000 |
| CA | 2343919 | 3/2000 |
| CA | 2372332 | 11/2000 |
| DE | 198 35 219 | 8/1998 |
| EP | 0 531 639 | 3/1993 |
| EP | 0 674 000 | 9/1995 |
| EP | 0 723 017 | 7/1996 |
| EP | 0 763 542 | 3/1997 |
| EP | 1 033 405 | 9/2000 |
| EP | 1 063 297 | 12/2000 |
| FR | 2 778 527 | 11/1999 |

(Continued)

OTHER PUBLICATIONS

Lazar et al. Transforming growth factor alpha: mutation of aspartic acit 47 and leucine 48 results in different biological activities. (1988) MCB; vol. 8, pp. 1247-1252.*

(Continued)

*Primary Examiner*—Cathy Kingdon Worley
(74) *Attorney, Agent, or Firm*—Chunping Li, Esq.; Sonnenschein Nath & Rosenthal LLP

(57) ABSTRACT

The present invention relates to genes associated with the tocopherol biosynthesis pathway. More particularly, the present invention provides and includes nucleic acid molecules, proteins, and antibodies associated with genes that encode polypeptides that have methyltransferase activity. The present invention also provides methods for utilizing such agents, for example in gene isolation, gene analysis and the production of transgenic plants. Moreover, the present invention includes transgenic plants modified to express the aforementioned polypeptides. In addition, the present invention includes methods for the production of products from the tocopherol biosynthesis pathway.

24 Claims, 36 Drawing Sheets

FOREIGN PATENT DOCUMENTS

| | | |
|---|---|---|
| GB | 560529 | 4/1944 |
| WO | WO 91/02059 | 2/1991 |
| WO | WO 91/09128 | 6/1991 |
| WO | WO 91/13078 | 9/1991 |
| WO | WO 93/18158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |
| WO | WO 95/18220 | 7/1995 |
| WO | WO 95/23863 | 9/1995 |
| WO | WO 95/34668 | 12/1995 |
| WO | WO 96/02650 | 2/1996 |
| WO | WO 96/06172 | 2/1996 |
| WO | WO 96/13149 | 5/1996 |
| WO | WO 96/13159 | 5/1996 |
| WO | WO 96/36717 | 11/1996 |
| WO | WO 96/38567 | 12/1996 |
| WO | WO 97/17447 | 5/1997 |
| WO | WO 97/27285 | 7/1997 |
| WO | WO 97/49816 | 12/1997 |
| WO | WO 98/04685 | 2/1998 |
| WO | WO 98/06862 | 2/1998 |
| WO | WO 98/18910 | 5/1998 |
| WO | WO 99/04021 | 1/1999 |
| WO | WO 99/04622 * | 2/1999 |
| WO | WO 99/06580 | 2/1999 |
| WO | WO 99/07867 | 2/1999 |
| WO | WO 99/11757 | 3/1999 |
| WO | WO 99/19460 | 4/1999 |
| WO | WO 99/55889 | 11/1999 |
| WO | WO 99/58649 | 11/1999 |
| WO | WO 00/01650 | 1/2000 |
| WO | WO 00/08169 | 2/2000 |
| WO | WO 00/08187 | 2/2000 |
| WO | WO 00/10380 | 3/2000 |
| WO | WO 00/11165 | 3/2000 |
| WO | WO 00/14207 | 3/2000 |
| WO | WO 00/17233 | 3/2000 |
| WO | WO 00/22150 | 4/2000 |
| WO | WO 00/28005 | 5/2000 |
| WO | WO 00/32757 * | 6/2000 |
| WO | WO 00/34448 | 6/2000 |
| WO | WO 00/42205 | 7/2000 |
| WO | WO 00/46346 | 8/2000 |
| WO | WO 00/61771 | 10/2000 |
| WO | WO 00/63389 | 10/2000 |
| WO | WO 00/63391 | 10/2000 |
| WO | WO 00/65036 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 | 11/2001 |
| WO | WO 02/00901 | 1/2002 |
| WO | WO 02/26933 | 4/2002 |
| WO | WO 02/29022 | 4/2002 |
| WO | WO 02/31173 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

Hill et al. Functional analysis of conserved histidines in ADP-glucose pyrophosphorylase from *Eschericia coli*. (1998) Biochem. Biophys. Res. Comm.; vol. 244 pp. 573-577.*

Guo et al. Protein tolerance to random amino acid change (2004) PNAS; vol. 101, pp. 9205-9210.*

Addlesee et al., "Cloning, sequencing and functional assignment of the chlorophyll biosyntheses gene, *chlP*, of *synechocystis* sp. PCC 6803," *FEBS Letters*, 389:126-130, 1996.

Arango et al., "Tocopherol synthesis from homogentisate in *Capsicum anuum* L. (yellow pepper) chromoplast membranes: evidence for *Tocopherol cyclase*," *Biochem J.*, 336:531-533, 1998.

Baker et al., "Sequence and characterization of the gcpE gene of *Escherichia coli*," *FEMS Microbiology Letters*, 94:175-180, 1992.

Bayley et al., "Engineering 2, 4-D resistance into cotton," *Theor. Appl. Genet.*, 83:645-649, 1992.

Bentley, "The shikimate pathway—A metabolic tree with many branches," *Critical Reviews Biochemistry and Molecular Biology*, 25(5):307-384, 1990.

Bevan, "Binary *Agrobacterium* vectors for plant transformation," *Nucleic Acids Research*, 12:8711-8721, 1984.

Beyer et al., "Phytoene-forming activities in wild-type and transformed rice endosperm," *IRRN* 21(2-3):44-45, Aug.-Dec. 1996.

Bork et al, "Go hunting in sequence databases but watch out for the traps," *TIG*, 12(10):425-427, 1996.

Bramley et al, "Biochemical characterization of transgenic tomato plants in which carotenoid synthesis has been inhibited through the expression of antisense RNA to pTOM5," *The Plant Journal*, 2(3):343-349, 1992.

Breitenbach et al., "Expression in *Eschenichia coli* and properties of the carotene ketolase from *Haematococcus pluvialis*," *FEMS microbiology Letters*, 140:241-246, 1996.

Broun et al., "Catalytic plasticity of fatty acid modification enzymes underlying chemical diversity of plant lipids," *Science*, 282:1315-1317, 1998.

Buckner at al., "The $y^1$ gene of maize codes for phytoene synthase," *Genetics*, 143(5):479-488, 1996.

Burkhardt et al., "Genetic engineering of provitamin A biosynthesis in rice endosperm," *Experientia*, 818-821.

Burkhardt et al, "Transgenic rice (*Oryza sativa*) endosperm expressing daffodil (*Narcissus pseudonarcissus*) phytoene synthase accumulates phytoene, a key intermediate of provitamin A biosynthesis," *The Plant Journal*, 11(5):1071-1078, 1997.

Cahoon et al., "Production of fatty acid components of meadowfoam oil in somatic soybean embryos," *Plant Physiology*, 124:243-251, 2000.

Chaudhuri et al., "The purification of shikimate dehydrogenase from *Escherichia coli*," *Biochem. J.*, 226:217-223, 1985.

Cheng et al. "Highly divergent methyltransferases catalyze a conserved reaction in tocopherol and plastoquinone synthesis in cyanobacteria and photosynthetic eukaryotes," *The Plant Cell*, 15:2343-2356, 2003.

Collakova et al., "Homogentisate phytyltransferase activity is limiting for tocopherol biosynthesis in *Arabiodopsis*," *Plant Physiology*, 131(2):632-642, 2003.

Collakova et al., "Isolation and characterization of tocopherol prenyl transferase from *synechocystis* and *Arabidopsis*," Poster Abstract, see REN-01-026.

Collakova at al., "Isolation and functional anlaysis of homogentisate phytyltransferase from *synechocystis* sp. PCC 6803 and *Arabidopsis*," *Plant Physiology*, 127:1113-1124, 2001.

Cook at al., "Nuclear mutations affecting plastoquinone accumulation in maize," *Photosynthesis Research*, 31:99-111, 1992.

Cunillera at al., "Characterization of dehydrodolichyl diphosphate synthase of *Arabidopsis thaliana*, a key enzyme in dolichol biosynthesis," *FEBS Letters*, 477:170-174, 2000.

d'Amato et al., "Subcellular localization of chorismate-mutase isoenzymes in protoplasts from mesophyll and suspension-cultured cells of *Nicotiana silvestris*," *Planta*, 162:104-108, 1984.

Doerks et al., "Protein annotation: detective work for function prediction," *TIG*, 14:248-250, 1998.

d'Harlingue et al., "Plastid enzymes of terpenoid biosynthesis, purification and characterization of γ-tocopherol methyltransferase from capsicum chromoplasts," the *Journal of Biological Chemistry*, 260(28):15200-15203, 1985.

DeLuca, "Molecular characterization of secondary metabolic pathways," *AgBiotech News and Information*, 5(6):225N-229N, 1993.

Duncan et al., "The overexpression and complete amino acid sequence of escherichia coli 3-dehydroquinase," *Biochem. J.*, 238:475-483, 1986.

Duvold at al., "Incorporation of 2-C-methyl-D-erythritol, a putative isoprenoid precursor in the mevalonate-independent pathway, into ubiquinone and menaquinone of *Escherichia coli*," *Tetrahedron Letters*, 38(35):6181-6184, 1997.

Elliott, "A method for constructing single-copy lac fusions in salmonella typhimurium and its application to the hemA-prfA operon," *Journal of Bacteriology*, 174:245-253, 1992.

Ericson et al., "Analysis of the promoter region of napin genes from *Brassica napus* demonstrates binding of nuclear protein in vitro to a conserved sequence motif," *Eur. J. Biochem.*, 197:741-746, 1991.

Estévez et al., "1-deoxy-D-xylulose-5-phosphate synthase, a limiting enzyme for plastidic isoprenoid biosynthesis in plants," *The Journal of Biological Chemistry*, 276(25):22901-22909, 2001.

Fellermeier et al., "Cell-free conversion of 1-deoxy-D-xylulose 5-phosphate and 2-C-methyl-D-erythritol 4-phosphate into β-carotene in higher plants and its inhibition by fosmidomycin," *Tetrahedron Letters*, 40:2743-2746, 1999.

Fourgoux-Nicol et al., "Isolation of rapeseed genes expressed early and specifically during development of the male gametophyte," *Plant Molecular Biology*, 40:857-872, 1999.

Fraser at al., "Enzymic confirmation of reactions involved in routes to astaxanthin formation, elucidated using a direct substrate in vitro assay," *Eur. J. Biochem.*, 252:229-236, 1998.

Fraser et al., "In vitro characterization of astaxanthin biosynthetic enzymes," *The Journal of Biological Chemistry*, 272(10):6128-6135, 1997.

Fray et al., "Constitutive expression of a fruit phytoene synthase gene in transgenic tomatoes causes dwarfism by redirecting metabolites from the gibberellin pathway," *The Plant Journal*, 8(5):693-701, 1995.

Fray et al., "Identification and genetic analysis of normal and mutant phytoene synthase genes of tomato by sequencing, complementation and co-suppression," *Plant Molecular Biology*, 22:589-602, 1993.

Fuqua et al., "Characterization of melA: a gene encoding melanin biosynthesis from the marine bacterium *Shewanella colwelliana*," *Gene*, 109:131-136, 1991.

Furuya et al., "Production of tocopherols by cell culture of safflower," *Phytochemistry*, 26(10):2741-2747,1987.

Garcia et al., "Subcellular localization and purification of a p-hydroxyphenylpyruvate dioxygenase from cultured carrot cells and characterization of the corresponding cDNA," *Biochem. J.*, 325:761-769, 1997.

Gaubier et al., "A chlorophyll synthetase gene from *Arabidopsis thaliana*," *Mol. Gen. Genet.*, 249:58-64, 1995.

Goers et al., "Separation and characterization of two chorismate-mutase isoenzymes from *Nicotiana silvestris*," *Planta*, 162:109-116, 1984.

Grabse et al., "Loss of α-tocopherol in tobacco plants with decreased geranygeranyl reductase activity does not modify photosynthesis in optimal growth conditions but increases sensitivity to high-light stress," *Planta*, 213:620-628, 2001.

Harker et al., "Biosynthesis of ketocarotenoids in transgenic cyanobacteria expressing the algal gene for β-C-4-oxygenase, crtO," *FEBS Letters*, 404:129-134, 1997.

Harker et al., "Expression of prokaryotic 1-deoxy-D-xylulose-5-phosphatases in *Escherichia coli* increases carotenoid and ubiquinone biosynthesis," *FEBS Letters*, 448:115-119, 1999.

Hecht et al., "Studies of the nonmevalonate pathway to terpenes: The role of the GcpE (1spG) protein," *PNAS*, 98(26):14837-14842, 2001.

Herrmann, "The shikimate pathway as an entry to aromatic secondary metabolism," *Plant Physiol.*, 107:7-12, 1995.

Kajiwara et al., "Isolation and functional identification of a novel cDNA for astaxanthin biosynthesis from *Haematococcus pluvialis*, and astaxanthin synthesis in *Escherichia coli*," *Plant Molecular Biology*, 29:343-352, 1995.

Kishore et al., "Amino acid biosynthesis ihibitors as herbicides," *Ann. Rev. Biochem.*, 57:627-663, 1988.

Koziel et al., "Optimizing expression of transgenes with an emphasis on post-transcriptional events," *Plant Molecular Biology*, 32:393-405, 1996.

Kumagai et al., "Cytoplasmic inhibition of carotenoid biosynthesis with virus-derived RNA," *Proc. Nat'l Acad. Sci. USA*, 92:1679-1683, 1995.

Kuntz et al., "Identification of a cDNA for the plastid-located geranylgeranyl pyrophosphate synthase from *Capsicum annuum*: correlative increase in enzyme activity and transcript level during fruit ripening," *The Plant Journal*, 2(1):25-34, 1992.

Lange et al., "Isoprenoid biosynthesis via a mevalonate-independent pathway in plants: cloning and heterologous expression of 1-deoxy-D-xylulose-5-phosphate reductoisomerase from peppermint," *Archives of Biochemistry and Biophysics*, 365(1):170-174, 1999.

Li et al., "Identification of a maize endosperm-specific cDNA encoding farnesyl pyrophosphate synthetase," *Gene*, 171:193-196, 1996.

Linthorst et al., "Constitutive expression of pathogenesis-related proteins PR-1, GRP, and PR-S in tobacco has no effect on virus infection," *The Plant Cell*, 1:285-291, 1989.

Lopez et al., "Sequence of the bchG Gene from *Chloroflexus aurantiacus*: relationship between chlorophyll synthase and other polyprenyltransferases," *Journal of Bacteriology*, 178(11):3369-3373, 1996.

Lotan et al., "Cloning and expression in *Escherichia coli* of the gene encoding β-C-4-oxygenase, that converts β-carotene to the ketocarotenoid canthaxanthin in *Haematococcus pluvialis*," *FEBS Letters*, 364:125-128, 1995.

Mahmoud et al., "Metabolic engineering of essential oil yield and composition in mint by altering expression of deoxyxylulose phosphate reductoisomerase and menthofuran synthase," *PNAS*, 98(15):8915-8920, 2001.

Mandel et al., "CLA1, a novel gene required for chloroplast development, is highly conserved in evolution," *The Plant Journal*, 9(5):649-658, 1996.

Misawa et al., "Expression of an erwinia phytoene desaturase gene not only confers multiple resistance to herbicides interfering with carotenoid biosynthesis but also alters xanthophyll metabolism in transgenic plants," *The Plant Journal*, 6(4):481-489, 1994.

Misawa et al., "Elucidation of the erwinia uredovora carotenoid biosynthetic pathway by functional analysis of gene products expressed in *Escherichia coli*," *Journal of Bacteriology*, 172(12):6704-6712, 1990.

Misawa et al., "Functional expression of the erwinia uredovora carotenoid biosynthesis gene crtI in transgenic plants showing an increase of β-carotene biosynthesis activity and resistance to the bleaching herbicide norflurazon," *The Plant Journal*, 4(5):833-840, 1993.

Misawa et al., "Structure and functional analysis of a marine bacterial carotenoid biosynthesis gene cluster and astaxanthin biosynthetic pathway proposed at the gene level," *Journal of Bacteriology*, 177(22):6575-6584, 1995.

Nakamura et al., "Structural analysis of *Arabidopsis thaliana* chromosome 5. III. sequence features of the regions of 1,191,918 bp covered by seventeen physically assigned P1 clones," *DNA Research*, 4(6):401-414, 1997.

Oh et al., "Molecular cloning expression, and functional analysis of a cis-prenyltransferase from *Arabidopsis thaliana*," *The Journal of Biological Chemistry*, 275(24):18482-18488, 2000.

Oommen et al., "The elicitor-inducible alfalfa isoflavone reductase promoter confers different patterns of developmental expression in homologous and heterologous transgenic plants," *The Plant Cell*, 6:1789-1803, 1994.

Oster et al., "The G4 gene of *Arabidopsis thaliana* encodes a chlorophyll synthase of etiolated plants," *Bot. Acta*, 110:420-423, 1997.

Peisker et al., "Phytol and the breakdown of chlorophyll in senescent leaves," *J. Plant Physiol.*, 135:428-432, 1989.

Pompliano et al., "Probing lethal metabolic perturbations in plants with chemical inhibition of dehydroquinate synthase," *J. Am. Chem. Soc.*, 111:1866-1871, 1989.

Porfirova et al., "Isolation of an *Arabidopsis* mutant lacking vitamin E and identification of a cyclase essential for all tocopherol biosynthesis," *PNAS*, 99(19):12495-12500, 2002.

Querol et al., "Functional analysis of the *Arabidopsis thaliana* GCPE protein involved in plastid isoprenoid biosynthesis," *FEBS Letters*, 514:343-346, 2002.

Rippert et al., "Molecular and biochemical characterization of an *Arabidopsis thaliana* arogenate dehydrogenase with two highly similar and active protein domains," *Plant Mol. Biol.*, 48:361-368, 2002.

Rippert et al., "Engineering plant shikimate pathway for production of tocotrienol and improving herbicide resistance," *Plant Physiology*, 134:92-100, 2004.

Rodriguez-Concepción et al., "Elucidation of the methylerythritol phosphate pathway for isoprenoid biosynthesis in bacteria and plastids. A metabolic milestone achieved through genomics," *Plant Physiology*, 130:1079-1089, 2002.

Rodriguez-Concepción et al., "1-deoxy-D-xylulose 5-phosphate reductoisomerase and plastid isoprenoid biosynthesis during tomato fruit ripening," *The Plant Journal*, 27(3):213-222, 2001.

Romer et al., "Expression of the genes encoding the early carotenoid biosynthetic enzymes in *Capsicum annuum*," *Biochemical and Biophysical Research Communications*, l96(3):1414-1421, 1993.

Ruzafa et al., "The protein encoded by the shewanella colwelliana melA gene is a phydroxyphenylpyruvate dioxygenase," *FEMS Microbiology Letters*, 124:179-184, 1994.

Sandmann et al., "New functional assignment of the carotenogenic genes crtB and crtE with constructs of these genes from *erwinia* species," *FEMS Microbiology Letters*, 90:253-258, 1992.

Sato et al., "Structural analysis of *Arabidopsis thaliana* chromosome 5. X. sequence features of the regions of 3,076,755 bp covered by sixty P1 and TAC clones," *DNA Research*, 7(1):31-63, 2000.

Savidge et al., "Isolation and characterization of homogentisate phytyltransferase genes from *synechocystis* sp. PCC 6803 and *Arabidopsis*," Plant Physiology, 129:321-332, 2002.

Schwender et al., "Cloning and heterologous expression of a cDNA encoding 1-deoxy-Dxylulose-5-phosphate reductoisomerase of *Arabidopsis thaliana*," *FEBS Letters*, 455:140-144, 1999.

Shewmaker et al., "Seed-specific overexpression of phytoene synthase: increase in carotenoids and other metabolic effects," *The Plant Journal*, 20(4):401-412, 1999.

Shigeoka et al., "Isolation and properties of γ-tocopherol methyltransferase in *Euglena gracilis*," *Biochimica et Biophysica Acta*, 1128:220-226, 1992.

Singh et al., "Chorismate mutase isoenzymes from *Sorghum bicolor*. Purification and properties," *Archives of Biochemistry and Biophysics*, 243(2):374-384, 1985.

Smith et al., "Antisense RNA inhibition of polygalacturonase gene expresson in transgenic tomatoes," *Nature*, 334:724-726, 1998.

Smith et al., The challenges of genome sequence annotation or "the devil is in the details," *Nature Biotechnology*, 15:1222-1223, 1997.

Soll et al., "Hydrogenation of geranylgeraniol," *Plant Physiol*, 71:849-854, 1983.

Soll et al., "2-methyl-6-phytylquinol and 2, 3-dimethyl-5-phytylquinol as precursors of tocopherol synthesis in spinach chloroplasts," *Phytochemistry*, 19:215-218, 1980.

Spurgeon et al., "Biosynthesis of isoprenoid compounds," 1:1-45, 1981.

Stam et al., "The silence of genes in transgenic plants," *Annals of Botany*, 79:3-12, 1997.

Stocker et al., "Identification of the tocopherol-cyclase in the blue-green algae *Anabaena variabilis* Kūtzing (cyanobacteria)," *Helvetica Chimica Acta*, 76:1729-1738, 1993.

Stocker et al., "The substrate specificity of tocopherol cyclase," *Bioorganic & Medicinal Chemistry*, 4(7):1129-1134, 1996.

Sun et al., "Cloning and functional analysis of the β-carotene hydroxylase of *Arabidopsis thaliana*," the *Journal of Biological Chemistry*, 271(40):24349-24352, 1996.

Suzich et al., "3-deoxy-D-arabino-heplulosonate 7-phosphate synthase from carrot root (*Daucus carota*) is a hysteretic enzyme," *Plant Physiol*, 79:765-770, 1985.

Svab et al., "High-frequency plastid transformation in tobacco by selection for a chimeric aadA gene," *Proc. Natl. Acad. Sci. USA*, 90:913-917, 1993.

Svab et al., "Stable transformation of plastids in higher plants," *Proc. Natl. Acad. Sci., USA*, 87:8526-8530, 1990.

Takatsuji, "Zinc-finger transcription factors in plants," *CMLS Cell. Mot Life Sci.*, Birkhauser Verlag Basel CH, 54(6):582-596, 1998.

Tjaden et al., "Altered plastidic ATP/ADP-transporter activity influences potato (*Solanum tubersomum* I) tuber morphology, yield and composition of tuber starch," *The Plant Journal*, 16(5):531-540, 1998.

Town et al., "Whole genome shotgun sequencing of *Brassica oleracea*, BOGKS71TR BOGK *Brassica oleracea* genomic clone BOGKS71, DNA sequence," Database EMBL Accession No. BH534089, Dec. 2001.

Town et al., "Whole genome shotgun sequencing of *Brassica oleracea*, BOGAU46TR BOGA *Brassica oleracea* genomic clone BOGAU46, DNA sequence," Database EMBL Accession No. BH248880, Nov. 2001.

Verwoert et al., "Developmental specific expression and organelle targeting of the *Escherichia coli* fabD gene, encoding malonyl coenzyme A-acyl carrier protein transacylase in transgenic rape and tobacco seeds," *Plant Molecular Biology*, 26:189-202, 1994.

Yamamoto, "Purification and metal requirements of 3-dehydroquinate synthase from *Phaseolus mungo* seedlings," *Phytochemistry*, 19:779-781, 1980.

Zaka et al., "Changes in carotenoids and tocopherols during maturation of cassia seeds," *Pakistan J. Sci. Ind. Res.*, 30(11):812-814, 1987.

Zeidler et al., "Inhibition of the non-mevalonate 1-deoxy-D-xylulose-5-phosphate pathway of plant isoprenoid biosynthesis by fosmidomycin," *A Journal of Biosciences*, Zeitschrift flier Naturforschung, Section C, 53(11/12):980-986, 1998.

Zhu et al., "Geranylgeranyl pyrophosphate synthase encoded by the newly isolated gene GGPS6 from *Arabidopsis thaliana* is localized in mitochondria," *Plant Molecular Biology*, 35:331-341, 1997.

Zhu et al., "Cloning and functional expression of a novel geranylgeranyl pyrophosphate synthase gene from *Arabidopsis thaliana* in *Escherichia coli*," *Plant Cell Physiol.*, 38(3):357-361, 1997.

Kaneko et al., NCBI General Identifier No. 1001725, Accession No. BAA10562, Feb. 2003.

Alcala et al., Genbank Accession No. A1897027, Jul. 1999.

Bevan et al., Database EMBL, Accession No. AL035394, Feb. 1999.

Bevan et al., TREMBL Database Accession No. 065524, Aug. 1998.

Campos et al., NCBI General Identifier BAA18485, Database EMBL, Accession No. AF148852, 2000.

Chen et al., EMBL Sequence Database Accession No. AI995392, Sep. 1999.

Desprez et al., Database EMBL, Accession No. Z34566, Jun. 1994.

Fedenko et al., Abstract: RU 2005353, Derwent Accession No. 1994-253787.

Gaubier et al., Database EMBL, Accession No. Q38833, Nov. 1996.

Kaneko et al., Database EMBL, Accession No. P73726, Feb. 1997.

Kaneko et al., Database EMBL, Accession No. P73962, Jul. 1998.

Kaneko et al., EMBL Sequence Database Accession No. D90909, Oct. 1996.

Kaneko et al., TREMBL Database Accession No. P73727, Feb. 1997.

Lange et al., "*Mentha x piperita* 1-deoxy-D-xylulose-5-phosphate reductoisomerase (DXR) mRNA," complete cds, Entrez Report, Accession No. AF116825, Apr. 1999.

Lin et al., Database EMBL, Accession No. AC003672, Dec. 1997.

Lin et al., Database EMBL, Accession No. AC003673, Dec. 1997.

Malakhov et al., Database TREMBL, Accession No. Q55207, Nov. 1996.

Murata et al., EMBL Sequence Database Accession No. D13960, Mar. 1996.

Nakamura et al., Database EMBL, Accession No. AB009053, Abstract, Dec. 1997, 1998, 2000.

Nakamura et al., Database EMBL, Accession No. AB005246, Jul. 1997.

Newman et al., Database EMBL, Accession No. AA586087, Abstract, Sep. 1997.

Newman et al., Database EMBL, Accession No. R30625, Aug. 1995.

Newman et al., Database EMBL, Accession No. T44803, Feb. 1995.
Newman et al., DEBEST ID:1262303, Entrez Report, Accession No. AA586087, Sep. 1997.
Oster et al., Database Biosis, Accession No. PREV199800047824, Oct. 1997.
Ouyang et al., Database EMBL, Accession No. AF381248, Jan. 2003.
Rounsley et al., Database EMBL, Accession No. B24116, Oct. 1997.
Rounsley et al., Database EMBL, Accession No. B29398, Oct., 1997.
Rounsley et al., Database TREMBL, Accession No. 064684, Aug. 1998.
Schwender et al., "*Arabidopsis thaliana* mRNA for partial 1-deoxy-D-xylulose-5-phosphate reductoisomerase (DXR gene)," Entrez Report, Accession No. AJ242588, Aug. 1999.
Scolnik et al., Database EMBL, Accession No. L40577, Apr. 1995.
Shintani et al., Database NCBI, Accession No. AF104220, Jan. 1999.
Shoemaker et al., Database EMBL, Accession No. AI748688, Jun. 1999.
Shoemaker et al., Database EMBL, Accession No. AI938569, Aug. 1999.
Shoemaker et al., Database EMBL, Accession No. AI988542, Sep. 1999.
Shoemaker et al., Database EMBL, Accession No. AW306617, Jan. 2000.
Tabata et al., Database EMBL, Accession No. D64001, Sep. 1995.
Tabata et al., Database EMBL, Accession No. D64006, Sep. 1995.
Tabata et al., Database EMBL, Accession No. D90909, Oct. 1996.
Tabata et al., Database EMBL, Accession No. D90911, Oct. 1996.
Tabata et al., Database EMBL, Accession No. Q55145, Nov. 1996.
Tabata et al., Database EMBL, Accession No. Q55500, Nov. 1996.
Walbot, Database EMBL, Accession No. AI795655, Jul. 1999.
Wing et al., Database EMBL, Accession No. AQ690643, Jul. 1999.
Xia et al., Database EMBL, Accession No. M74133, Jun. 1993.
Bevan et al., Accession T4 8445.
Lin et al., Database EMBL, Accession No. AC004077, Feb. 1998.
Hill et al., "Functional analysis of conserved histidines in ADP-Glucose pyrophosphorylase from *Escherichia coli,*" *Biochemical and Biophysical Research Communications*, 244:573-577, 1998.
Lazar et al., "Transforming growth factor alpha: mutation of aspartic acid 47 and leucine 48 results in different biological activities," *Molecular and Cellular Biology*, 8:1247-1252, 1988.
Guo et al., "Protein tolerance to random amino acid change," *PNAS*, 101:9205-9210, 2004.
Elomaa et al., "Transformation of antisense constructs of the chalcone synthase gene superfamily into *Gerbera hybrida*: differential effect on the expression of family members," *Molecular Breeding*, 2:41-50, 1996.
Karunanandaa et al., Metabolically enhanced oilseed crops with enhanced seed tocopherol, *Metabol. Eng.*, 7:384-400, 2005.
Valentin et al., "The *Arabidopsis* vitamin E pathway gene5-1 mutant reveals a critical role for phytol kinase in seed tocopherol biosynthesis," *Plant Cell*, 18:212-224, 2005.
Bowie et al., "Deciphering the message in protein sequences: tolerance to amino acid substitutions," *Science*, 247:1306-1310, 1990.
McConnell et al., "Role of phabulosa and phavoluta in determining radial patterning in shoots," *Nature*, 441(6838):709-713, 2001.
Baker et al., NCBI Accession No. X64451, Dec. 1993.
Colliver et al., "Differential modification of flavonoid and isoflavonoid biosynthesis with an antisense chalcone synthase construct in transgenic lotus corniculatus," *PMB*, 35:509-522, 1997.
Ye, "Supply and demand of soybeans as feedstock for soy diesel," Market Research Report for Agricultural Marketing and Development Division of Minnesota Dept. of Agriculture, pp. 1-68, 2000.
Shintani et al., "Elevating the vitamin E content of plants through metabolic engineering," *Science*, 282:2098-2100, 1998.
Norris et al., "Genetic dissection of carotenoid synthesis in *Arabidopsis* defines plastoquinone as an essential component of phytoene desaturation," *Th Plant Cell*, 7:2139-2149, 1995.
Xia et al., "The pheA / tyrA / aroF region from *Erwinia herbicola*: an emerging comparative basis for analysis of gene organization and regulation in enteric bacteria," Database GenBank on STN, GenBank Accession No. (GBN): M74133, *J. Mol. Evol.*, 36(2):P107-120, Abstract, 1993.

Arigoni et al., "Terpenoid biosynthesis from 1-deoxy-D-xylulose in higher plants by intramolecular skeletal rearrangement," *Poc. Natl. Acad. Sci. USA*, 94:10600-10605, 1997.
Bouvier et al., "Dedicated roles of plastid transketolases during the early onset of isoprenoid biogenesis in peper fruits," *Plant Physiol.*, 117:1423-1431, 1998.
Eisenreich et al., The deoxyxylulose phosphate pathway of terpenoid biosynthesis in plants and microorganisms, *Chemistry & Biology*, 5(9):R221-R233, 1998.
Fiedler et al., "The formation of homogentisate in the biosynthesis of tocopherol and plastoquinone in spinach chloroplasts," *Planta*, 155:511-515, 1982.
Herz et al., "Biosynthesis of terpenoids: YgbB protein converts 4-diphosphocytidyl-2C-methyl-D-erythritol 2-phosphate to 2C-methyl-D-erythritol 2,4-cyclodiphosphate," *Proc. Natl. Acad. Sci. USA*, 97(6):2486-2490, 2000.
Kaneko et al., "Complete genomic sequence of the filamentous nitrogen-fixing cyanobacterium *anabaena* sp. strain PCC 7120," *DNA Research*, 8(5):205-213, 2001.
Keegstra, "Transport and routing of proteins into chloroplasts," *Cell*, 56(2):247-253, 1989.
Keller et al., "Metabolic compartmentation of plastid prenyllip biosynthesis evidence for the involvement of a multifunctional geranylgeranyl reductase," *Eur. J. Biochem.*, 251:413-417, 1998.
Lange et al., "A family of transketolases that directs isoprenoid biosynthesis via a mevalonate-independent pathway," *Proc. Natl. Acad. Sci USA*, 95:2100-2104, 1998.
Lois et al., "Cloning and characterization of a gene from *Escherichia coli* encoding a transketolase-like enzyme that catalyzes the synthesis of D-1-deoxyxylulose 5-phosphate, a common precursor for isoprenoid, thiamin, and pyridoxol biosynthesis," *Proc. Natl. Acad. Sci. USA*, 95(5):2105-2110, 1998.
Marshall et al., "Biosynthesis of tocopherols: a re-examination of the biosynthesis and metabolism of 2-methyl-6-phytyl-1,4-benzoquinol,"*Phytochemistry*, 24(8):1705-1711, 1985.
Nawrath et al., "Targeting of the polyhydroxybutyrate biosynthetic pathway to the plastids of *Arabidopsis thaliana* results in high levels of polymer accumulation," *Proc. Natl. Acad. Sci. USA*, 91:12760-12764, 1994.
NCBI General Identifier No. 1001725, Accession No. BAA10562.
NCBI General Identifier No. 1001725, Accession No. BAA18485.
Norris et al., "complementation of th earabidopsis pds1 mutation with the gene encoding p-hydroxyphenylpyruvate dioxygenase," *Plant Physiology*, 117:1317-1323, 1998.
Okada et al., "Five geranylgeranyl diphosphate synthases expressed in different organs are localized into three subcellular compartments in *Arabidopsis,*" *Plant Physiology*, 122:1045-1056, 2000.
Rohdich et al., "Cytidine 5'-triphosphate-dependent biosynthesis of isoprenoids: YgbP protein of *Escherichia coli* catalyzes the formation of 4-diphosphocytidyl-2-C-methylerythritol," *Proc. Natl. Acad. Sci. USA*, 96(21):11758-11763, 1999.
Rohmer et al., "Glyceraldehyde 3-phosphate and pyruvate as precursors of isoprenic units in an alternative non-mavalonate pathway for terpenoid biosynthesis," *J. Am. Chem. Soc.*, 118:2564-2566, 1996.
Rohmer et al., "Isoprenoid biosynthesis in bacteria: a novel pathway for the early steps leading to isopentenyl diphosphate," *Biochem. J.*, 295:517-524, 1993.
Rohmer, "Isoprenoid biosynthesis via the mevalonate-independent route, a novel target for antibacterial drugs," *Progress in Drug Research*, 50:136-154, 1998.
Rohmer, "A mevalonate-independent route to isopentenyl diphosphate," *Comprehensive Natural Products Chemistry*, 2:45-67, 1999.
Saint-Guily et al., "Complementary DNA sequence of an adenylate translocator from *Arabidopsis thaliana,*" *Plant Physiology*, 100(2):1069-1071, 1992.
Sato et al., "Structural analysis of *Arabidopsis thaliana* chromosome 5. X. sequence features of the regions of 3,076,755 bp covered by sixty P1 and TAC clones," *DNA Research*, 7(1):31-63, 2000.
Scolink et al., "Nucleotide sequence of an *Arabidopsis* cDNA for geranylgeranyl pyrophosphate synthase," *Plant Physiology*, 104(4)a;1469-1470, 1994.

Smith et al., "The cloning of two *Arabidopsis* genes belonging to a phosphate transporter family," *Plant Journal*, 11(1):83-92, 1997.

Soll et al., "Tocopherol and plastoquinone synthesis in spinach chloroplasts subfractions," *Arch. Biochem. Biophys.*, 204(2):544-550, 1980.

Sprenger et al., "Identification of a thiamin-dependent synthase in *Escherichia coli* required for the formation of the 1-deoxy-D-xylulose 5-phosphate precursor to isoprenoids, thiamin, and pyridoxol," *Proc. Natl. Acad. Sci. USA*, 94:12857-12862, 1997.

Takahashi et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis," *Proc. Natl. Acad. Sci. USA*, 95(17):9879-9884, 1998.

Xia et al., "A monofunctional prephenate dehydrogenase created by cleavage of the 5' 109 bp of the tyrA gene from *Erwinia herbicola*," *J. Gn. Microbiol.*, 138(7):1309-1316, 1992.

* cited by examiner

GAMMA TOCOPHEROL METHYLTRANSFERASE CODING SEQUENCE FROM *BRASSICA* AND USES THEREOF

CROSS REFERENCE TO RELATED APPLICATIONS

This application is a divisional application of application Ser. No. 10/219,810, filed Aug. 16, 2002, which is issued as U.S. Pat. No. 7,244,877 and claims the benefit of and priority to U.S. provisional application No. 60/312,758, filed Aug. 17, 2001, the entire disclosures of which are each specifically herein incorporated by reference in its entirety.

FIELD OF THE INVENTION

The present invention is in the field of plant genetics and biochemistry. More specifically, the invention relates to genes associated with the tocopherol biosynthesis pathway, namely those encoding methyltransferase activity, and uses of such genes.

BACKGROUND

Tocopherols are an important component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.* 16:321-347 (1996)). Tocopherol functions, in part, by stabilizing the lipid bilayer of biological membranes (Skrypin and Kagan, *Biochim. Biophys. Acta* 815:209 (1995); Kagan, *N.Y. Acad. Sci. p* 121, (1989); Gomez-Fernandez et al., *Ann. N.Y. Acad. Sci.* p 109 (1989)), reducing polyunsaturated fatty acid (PUFA) free radicals generated by lipid oxidation (Fukuzawa et al., *Lipids* 17: 511-513 (1982)), and scavenging oxygen free radicals, lipid peroxy radicals and singlet oxygen species (Diplock et al. *Ann. N.Y. Acad. Sci.* 570: 72 (1989); Fryer, *Plant Cell Environ.* 15(4):381-392 (1992)).

α-Tocopherol, often referred to as vitamin E, belongs to a class of lipid-soluble antioxidants that includes α, β, γ, and δ-tocopherols and α, β, γ, and δ-tocotrienols. Although α, β, γ, and δ-tocopherols and α, β, γ, and δ-tocotrienols are sometimes referred to collectively as "vitamin E", vitamin E is more appropriately defined chemically as α-tocopherol. α-Tocopherol is significant for human health, in part because it is readily absorbed and retained by the body, and therefore has a higher degree of bioactivity than other tocopherol species (Traber and Sies, *Annu. Rev. Nutr.* 16:321-347 (1996)). However, other tocopherols such as β, γ, and δ-tocopherols, also have significant health and nutritional benefits.

Tocopherols are primarily synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with α-tocopherol the predominant tocopherol species found in green, photosynthetic plant tissues. Leaf tissue can contain from 10-50 μg of total tocopherols per gram fresh weight, but most of the world's major staple crops (e.g., rice, corn, wheat, potato) produce low to extremely low levels of total tocopherols, of which only a small percentage is α-tocopherol (Hess, Vitamin E, α-tocopherol, In *Antioxidants in Higher Plants*, R. Alscher and J. Hess, Eds., CRC Press, Boca Raton. pp. 111-134 (1993)). Oil seed crops generally contain much higher levels of total tocopherols, but α-tocopherol is present only as a minor component in most oilseeds (Taylor and Barnes, *Chem. Ind.*, October:722-726 (1981)).

The recommended daily dietary intake of 15-30 mg of vitamin E is quite difficult to achieve from the average American diet. For example, it would take over 750 grams of spinach leaves in which α-tocopherol comprises 60% of total tocopherols, or 200-400 grams of soybean oil to satisfy this recommended daily vitamin E intake. While it is possible to augment the diet with supplements, most of these supplements contain primarily synthetic vitamin E, having eight stereoisomers, whereas natural vitamin E is predominantly composed of only a single isomer. Furthermore, supplements tend to be relatively expensive, and the general population is disinclined to take vitamin supplements on a regular basis. Therefore, there is a need in the art for compositions and methods that either increase the total tocopherol production or increase the relative percentage of α-tocopherol produced by plants.

In addition to the health benefits of tocopherols, increased α-tocopherol levels in crops have been associated with enhanced stability and extended shelf life of plant products (Peterson, *Cereal-Chem.* 72(1):21-24 (1995); Ball, *Fat-soluble vitamin assays in food analysis. A comprehensive review*, London, Elsevier Science Publishers Ltd. (1988)). Further, tocopherol supplementation of swine, beef, and poultry feeds has been shown to significantly increase meat quality and extend the shelf life of post-processed meat products by retarding post-processing lipid oxidation, which contributes to the undesirable flavor components (Sante and Lacourt, *J. Sci. Food Agric.* 65(4):503-507 (1994); Buckley et al., *J. of Animal Science* 73:3122-3130 (1995)).

Tocopherol Biosynthesis

The plastids of higher plants exhibit interconnected biochemical pathways leading to secondary metabolites including tocopherols. The tocopherol biosynthetic pathway in higher plants involves condensation of homogentisic acid and phytylpyrophosphate to form 2-methyl-6 phytylplastoquinol (Fiedler et al., *Planta* 155: 511-515 (1982); Soll et al., *Arch. Biochem. Biophys.* 204: 544-550 (1980); Marshall et al., *Phytochem.* 24: 1705-1711 (1985)). This plant tocopherol pathway can be divided into four parts: 1) synthesis of homogentisic acid, which contributes to the aromatic ring of tocopherol; 2) synthesis of phytylpyrophosphate, which contributes to the side chain of tocopherol; 3) joining of HGA and phytylpyrophosphate via a prenyltransferase followed by a subsequent cyclization; 4) and S-adenosyl methionine dependent methylation of an aromatic ring, which affects the relative abundance of each of the tocopherol species.

Synthesis of Homogentisic Acid

Homogentisic acid is the common precursor to both tocopherols and plastoquinones. In at least some bacteria the synthesis of homogentisic acid is reported to occur via the conversion of chorismate to prephenate and then to p-hydroxyphenylpyruvate via a bifunctional prephenate dehydrogenase. Examples of bifunctional bacterial prephenate dehydrogenase enzymes include the proteins encoded by the tyrA genes of *Erwinia herbicola* and *Escherichia coli*. The tyrA gene product catalyzes the production of prephenate from chorismate, as well as the subsequent dehydrogenation of prephenate to form p-hydroxyphenylpyruvate (p-HPP), the immediate precursor to homogentisic acid. p-HPP is then converted to homogentisic acid by hydroxyphenylpyruvate dioxygenase (HPPD). In contrast, plants are believed to lack prephenate dehydrogenase activity, and it is generally believed that the synthesis of homogentisic acid from chorismate occurs via the synthesis and conversion of the intermediate arogenate. Since pathways involved in homogentisic acid synthesis are also responsible for tyrosine formation, any alterations in these pathways can also result in the alteration in tyrosine synthesis and the synthesis of other aromatic amino acids.

Synthesis of Phytylpyrophosphate

Tocopherols are a member of the class of compounds referred to as the isoprenoids. Other isoprenoids include carotenoids, gibberellins, terpenes, chlorophyll and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, HMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., *Chem. Bio.*, 5:R221-R233 (1998); Rohmer, *Prog. Drug. Res.*, 50:135-154 (1998); Rohmer, *Comprehensive Natural Products Chemistry*, Vol. 2, pp. 45-68, Barton and Nakanishi (eds.), Pergamon Press, Oxford, England (1999)), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate of the novel pathway, now referred to as the MEP pathway (Rohmer et al., *Biochem. J.*, 295:517-524 (1993); Schwarz, Ph.D. thesis, Eidgenössiche Technische Hochschule, Zurich, Switzerland (1994)). Recent studies showed the formation of 1-deoxyxylulose 5-phosphate (Broers, Ph.D. thesis (Eidgenössiche Technische Hochschule, Zurich, Switzerland) (1994)) from one molecule each of glyceraldehyde 3-phosphate (Rohmer, *Comprehensive Natural Products Chemistry*, Vol. 2, pp. 45-68, Barton and Nakanishi, eds., Pergamon Press, Oxford, England (1999)) and pyruvate (Eisenreich et al., *Chem. Biol.*, 5:R223-R233 (1998); Schwarz supra; Rohmer et al., *J. Am. Chem. Soc.*, 118:2564-2566 (1996); and Sprenger et al., *Proc. Natl. Acad. Sci. USA*, 94:12857-12862 (1997)) by an enzyme encoded by the dxs gene (Lois et al., *Proc. Natl. Acad. Sci. USA*, 95:2105-2110 (1997); and Lange et al., *Proc. Natl. Acad. Sci. USA*, 95:2100-2104 (1998)). 1-Deoxyxylulose 5-phosphate can be further converted into 2-C-methylerythritol 4-phosphate (Arigoni et al., *Proc. Natl. Acad. Sci. USA*, 94:10600-10605 (1997)) by a reductoisomerase encoded by the dxr gene (Bouvier et al., *Plant Physiol*, 117:1421-1431 (1998); and Rohdich et al., *Proc. Natl. Acad. Sci. USA*, 96:11758-11763 (1999)).

Reported genes in the MEP pathway also include ygbP, which catalyzes the conversion of 2-C-methylerythritol 4-phosphate into its respective cytidyl pyrophosphate derivative and ygbB, which catalyzes the conversion of 4-phospho-cytidyl-2C-methyl-D-erythritol into 2C-methyl-D-erythritol, 3,4-cyclophosphate. These genes are tightly linked on the *E. coli* genome (Herz et al., *Proc. Natl. Acad. Sci. U.S.A.*, 97(6): 2485-2490 (2000)).

Once IPP is formed by the MEP pathway, it is converted to GGDP by GGDP synthase, and then to phytylpyrophosphate, which is the central constituent of the tocopherol side chain.

Combination and Cyclization

Homogentisic acid is combined with either phytyl-pyrophosphate or solanylpyrophosphate by phytyl/prenyl transferase forming 2-methyl-6-phytyl plastoquinol or 2-methyl-6-solanyl plastoquinol, respectively. 2-methyl-6-solanyl plastoquinol is a pre-cursor to the biosynthesis of plastoquinones, while 2-methyl-6-phytyl plastoquinol is ultimately converted to tocopherol.

Methylation of the Aromatic Ring

The major structural difference between each of the tocopherol subtypes is the position of the methyl groups around the phenyl ring. Both 2-methyl-6-phytyl plastoquinol and 2-methyl-6-solanyl plastoquinol serve as substrates for 2-methyl-6-phytylplastoquinol/2-methyl-6-solanylplastoquinol-9 methyltransferase (Methyl Transferase 1; MT1), which catalyzes the formation of plastoquinol-9 and γ-tocopherol respectively, by methylation of the 7 position. Subsequent methylation at the 5 position of γ-tocopherol by γ-tocopherol methyl-transferase (GMT) generates the biologically active α-tocopherol. Additional potential MT1 substrates include 2-methyl-5-phytylplastoquinol and 2-methyl-3-phytylplastoquinol. Additional potential substrates for GMT include δ-tocopherol and γ- and δ-tocotrienol.

There is a need in the art for nucleic acid molecules encoding enzymes involved in tocopherol biosynthesis, as well as related enzymes and antibodies for the enhancement or alteration of tocopherol production in plants. There is a further need for transgenic organisms expressing those nucleic acid molecules involved in tocopherol biosynthesis, which are capable of nutritionally enhancing food and feed sources.

SUMMARY OF THE INVENTION

The present invention includes and provides a substantially purified nucleic acid molecule comprising a nucleic acid sequence selected from the group consisting of SEQ ID NOs: 2-17, 50, and 85.

The present invention includes and provides a substantially purified nucleic acid molecule comprising a nucleic acid sequence that encodes an amino acid sequence selected from the group consisting of SEQ ID NO: 19-31 and 33-38.

The present invention includes and provides a substantially purified nucleic acid molecule comprising as operably linked components: (A) a promoter region which functions in a plant cell to cause the production of an mRNA molecule; (B) a heterologous nucleic acid molecule encoding a polypeptide molecule comprising a sequence selected from the group consisting of SEQ ID NOs: 19-31, 33-41.

The present invention includes and provides a substantially purified protein comprising an amino acid sequence selected from the group consisting of SEQ ID NOs: 19-31, and 33-38.

The present invention includes and provides an antibody capable of specifically binding a substantially purified protein comprising an amino acid sequence selected from the group consisting of SEQ ID NOs: 19-31, and 33-38.

The present invention includes and provides a transformed plant having an exogenous nucleic acid molecule that encodes a polypeptide molecule comprising a sequence selected from the group consisting of SEQ ID NOs: 19-31, and 33-41.

The present invention includes and provides a transformed plant having an exogenous nucleic acid molecule that encodes a polypeptide molecule comprising a sequence selected from the group consisting of SEQ ID NOs: 46-49.

The present invention includes and provides a method for reducing expression of MT1 or GMT in a plant comprising:

(A) transforming a plant with a nucleic acid molecule, said nucleic acid molecule having an exogenous promoter region which functions in plant cells to cause the production of a mRNA molecule, wherein said exogenous promoter region is linked to a transcribed nucleic acid molecule having a transcribed strand and a non-transcribed strand, wherein said transcribed strand is complementary to a nucleic acid molecule comprising a nucleic acid sequence selected from the group consisting of SEQ ID NOs: 2-17, 50, and 85; and wherein said transcribed nucleic acid molecule is linked to a 3' non-translated sequence that functions in the plant cells to cause termination of transcription and addition of polyadenylated ribonucleotides to a 3' end of the mRNA sequence; and (B) growing said transformed plant.

The present invention includes and provides a transformed plant comprising a nucleic acid molecule comprising an exogenous promoter region which functions in plant cells to cause the production of a mRNA molecule, wherein the exogenous promoter region is linked to a transcribed nucleic acid molecule having a transcribed strand and a non-transcribed strand, wherein the transcribed strand is complementary to a nucleic acid molecule comprising a nucleic acid sequence selected from the group consisting of SEQ ID NOs: 2-17, 50, 85, and wherein the transcribed nucleic acid molecule is linked to a 3' non-translated sequence that functions in the plant cells to cause termination of transcription and addition of polyadenylated ribonucleotides to a 3' end of the mRNA sequence; wherein, the expression of MT1, GMT or both is reduced relative to a plant with a similar genetic background but lacking the exogenous nucleic acid molecule.

The present invention includes and provides method for increasing the γ-tocopherol content in a plant comprising: (A) transforming a plant with a nucleic acid molecule, the nucleic acid molecule comprising an exogenous promoter region which functions in plant cells to cause the production of a mRNA molecule, wherein the exogenous promoter region is linked to a transcribed nucleic acid molecule comprising a transcribed strand and a non-transcribed strand, wherein the transcribed strand is complementary to a nucleic acid molecule comprising a nucleic acid sequence selected from the group consisting of SEQ ID NOs: 2-17, 50, and 85; and wherein the transcribed nucleic acid molecule is linked to a 3' non-translated sequence that functions in the plant cells to cause termination of transcription and addition of polyadenylated ribonucleotides to a 3' end of the mRNA sequence; and (C) growing the transformed plant.

The current invention further includes and provides a transformed plant comprising: (A) a first nucleic acid molecule comprising an exogenous promoter region which functions in plant cells to cause the production of a mRNA molecule, wherein the exogenous promoter region is linked to a transcribed nucleic acid molecule having a transcribed strand and a non-transcribed strand, wherein the transcribed strand is complementary to a nucleic acid molecule comprising a nucleic acid sequence selected from the group consisting of SEQ ID NOs: 2-17, 50, and 85, and wherein the transcribed nucleic acid molecule is linked to a 3' non-translated sequence that functions in the plant cells to cause termination of transcription and addition of polyadenylated ribonucleotides to a 3' end of the mRNA sequence; and (B) a second nucleic acid molecule comprising an exogenous promoter region which functions in plant cells to cause the production of a mRNA molecule, wherein the exogenous promoter region is linked to a nucleic acid molecule comprising a sequence selected from the group consisting of SEQ ID NOs: 42-45, wherein the γ-tocopherol content of the transformed plant is increased relative to a plant with a similar genetic background but lacking the exogenous nucleic acid molecule.

The present invention includes and provides a method of producing a plant having a seed with an increased γ-tocopherol level comprising: (A) transforming the plant with a nucleic acid molecule, wherein the nucleic acid molecule comprises a sequence encoding a polypeptide molecule comprising a sequence selected from the group consisting of SEQ ID NOs: 19-31, 33-38, and 39-41; and (B) growing the transformed plant.

The present invention includes and provides a method of producing a plant having a seed with an increased γ-tocopherol level comprising: (A) transforming the plant with a nucleic acid molecule, wherein the nucleic acid molecule comprises a nucleic acid sequence that encodes a polypeptide molecule comprising a sequence selected from the group consisting of SEQ ID NOs: 46-49; and (B) growing the transformed plant.

The present invention includes and provides a method of accumulating α-tocopherol in a seed comprising: (A) growing a plant with a heterologous nucleic acid molecule, wherein the heterologous nucleic acid molecule comprises a sequence encoding a polypeptide molecule comprising an amino acid sequence selected from the group consisting of SEQ ID NOs: 19-31, 33-38, and 39-41; and (B) isolating said seed from said plant with a heterologous nucleic acid molecule.

The present invention includes and provides a method of accumulating γ-tocopherol in a seed comprising: (A) growing a plant with a heterologous nucleic acid molecule, wherein the heterologous nucleic acid molecule comprises a sequence encoding a polypeptide molecule comprising an amino acid sequence selected from the group consisting of SEQ ID NOs: 46-49; and (B) isolating said seed from said plant with a heterologous nucleic acid molecule.

The present invention includes and provides a seed derived from a transformed plant having an exogenous nucleic acid molecule comprising a nucleic acid sequence encoding an polypeptide molecule comprising a sequence selected from the group consisting of SEQ ID NOs: 19-31, 33-38, and 39-41, wherein the seed has an increased α-tocopherol level relative to seeds from a plant having a similar genetic background but lacking the exogenous nucleic acid molecule.

The present invention includes and provides an oil derived from a seed of a transformed plant, wherein the transformed plant contains an exogenous nucleic acid molecule comprising a nucleic acid sequence encoding a polypeptide molecule comprising a sequence selected from the group consisting of SEQ ID NOs: 19-31, 33-38, and 39-41.

The present invention includes and provides feedstock comprising a transformed plant or part thereof, wherein the transformed plant has an exogenous nucleic acid molecule that comprises a nucleic acid sequence encoding a polypeptide molecule comprising a sequence selected from the group consisting of SEQ ID NO s: 19-31, 33-38, and 39-41.

The present invention includes and provides a meal comprising plant material manufactured from a transformed plant, wherein the transformed plant has an exogenous nucleic acid molecule that comprises a nucleic acid sequence encoding a polypeptide molecule comprising a sequence selected from the group consisting of SEQ ID NOs: 19-31, 33-38, and 39-41.

The present invention includes and provides a seed derived from a transformed plant having an exogenous nucleic acid molecule comprising a sequence encoding a polypeptide molecule comprising a sequence selected from the group consisting of SEQ ID NOs: 46-49, wherein the seed has an increased tocopherol level relative to seeds from a plant having a similar genetic background but lacking the exogenous nucleic acid molecule.

The present invention includes and provides oil derived from a seed of a transformed plant, wherein the transformed plant contains an exogenous nucleic acid molecule comprising a nucleic acid sequence encoding a polypeptide molecule comprising a sequence selected from the group consisting of SEQ ID NOs: 46-49.

The present invention also includes and provides feedstock comprising a transformed plant or part thereof, wherein the transformed plant has an exogenous nucleic acid molecule that comprises a nucleic acid sequence encoding a polypeptide molecule comprising a sequence selected from the group consisting of SEQ ID NOs: 46-49.

The present invention also includes and provides meal comprising plant material manufactured from a transformed plant, wherein the transformed plant has an exogenous nucleic acid molecule that comprises a nucleic acid sequence encoding a polypeptide molecule comprising a sequence selected from the group consisting of SEQ ID NO: 46-49.

The present invention also includes and provides a host cell comprising a nucleic acid molecule comprising a nucleic acid sequence selected from the group consisting of SEQ ID NOs: 2-17, 42-45 and complements thereof.

The present invention also includes and provides an introduced first nucleic acid molecule that encodes a polypeptide molecule comprising an amino acid sequence selected from the group consisting of SEQ ID NOs: 19-31, 33-38, and 39-41, and an introduced second nucleic acid molecule encoding an enzyme selected from the group consisting of tyrA, slr1736, ATPT2, dxs, dxr, GGPPS, HPPD, GMT, MT1, tMT2, AANT1, slr1737, and an antisense construct for homogentisic acid dioxygenase.

The present invention also includes and provides a transformed plant comprising an introduced first nucleic acid molecule that encodes a polypeptide molecule comprising an amino acid sequence selected from the group consisting of SEQ ID NOs: 46-49, and an introduced second nucleic acid molecule encoding an enzyme selected from the group consisting of tyrA, slr1736, ATPT2, dxs, dxr, GGPPS, HPPD, GMT, MT1, tMT2, AANT1, slr1737, and an antisense construct for homogentisic acid dioxygenase.

The present invention also includes and provides a plant comprising an introduced nucleic acid molecule comprising a nucleic acid sequence selected from the group consisting of SEQ ID NOs: 42-45, wherein said transformed plant produces a seed having increased total tocopherol relative to seed of a plant with a similar genetic background but lacking said introduced nucleic acid molecule.

The present invention also includes and provides a plant comprising an introduced nucleic acid molecule comprising a nucleic acid sequence selected from the group consisting of SEQ ID NOs: 2-17, 50, 85, wherein said transformed plant produces a seed having increased total tocopherol relative to seed of a plant with a similar genetic background but lacking said introduced nucleic acid molecule.

The present invention also includes and provides a plant comprising a first introduced nucleic acid molecule comprising a nucleic acid sequence selected from the group consisting of SEQ ID NOs: 2-17, 50, and 85 and a second introduced nucleic acid molecule comprising a nucleic acid sequence selected from the group consisting of SEQ ID NOs: 42-45, wherein said transformed plant produces a seed having increased total tocopherol relative to seed of a plant with a similar genetic background but lacking both said introduced first nucleic acid molecule and said introduced second nucleic acid molecule.

DESCRIPTION OF THE NUCLEIC AND AMINO ACID SEQUENCES

SEQ ID NO: 1 sets forth a nucleic acid sequence of a DNA molecule that encodes an *Arabidopsis thaliana* gamma-tocopherol methyltransferase.

SEQ ID NO: 2 sets forth a nucleic acid sequence of a DNA molecule that encodes an *Arabidopsis thaliana*, Columbia ecotype, gamma-tocopherol methyltransferase.

SEQ ID NO: 3 sets forth a nucleic acid sequence of a DNA molecule that encodes an *Oryza sativa* gamma-tocopherol methyltransferase.

SEQ ID NO: 4 sets forth a nucleic acid sequence of a DNA molecule that encodes a *Gossypium hirsutum* gamma-tocopherol methyltransferase.

SEQ ID NO: 5 sets forth a nucleic acid sequence of a DNA molecule that encodes a *Cuphea pulcherrima* gamma-tocopherol methyltransferase.

SEQ ID NO: 6 sets forth a nucleic acid sequence of a DNA molecule that encodes a *Brassica napus* S8 gamma-tocopherol methyltransferase.

SEQ ID NO: 7 sets forth a nucleic acid sequence of a DNA molecule that encodes a *Brassica napus* P4 gamma-tocopherol methyltransferase.

SEQ ID NO: 8 sets forth a nucleic acid sequence of a DNA molecule that encodes a *Brassica napus* S8 gamma-tocopherol methyltransferase.

SEQ ID NO: 9 sets forth a nucleic acid sequence of a DNA molecule that encodes a *Brassica napus* P4 gamma-tocopherol methyltransferase.

SEQ ID NO: 10 sets forth a nucleic acid sequence of a DNA molecule that encodes a *Lycopersicon esculentum* gamma-tocopherol methyltransferase.

SEQ ID NO: 11 sets forth a nucleic acid sequence of a DNA molecule that encodes a *Glycine max* gamma-tocopherol methyltransferase 1.

SEQ ID NO: 12 sets forth a nucleic acid sequence of a DNA molecule that encodes a *Glycine max* gamma-tocopherol methyltransferase 2.

SEQ ID NO: 13 sets forth a nucleic acid sequence of a DNA molecule that encodes a *Glycine max* gamma-tocopherol methyltransferase 3.

SEQ ID NO: 14 sets forth a nucleic acid sequence of a DNA molecule that encodes a *Tagetes erecta* gamma-tocopherol methyltransferase.

SEQ ID NO: 15 sets forth a nucleic acid sequence of a DNA molecule that encodes a *Sorghum bicolor* gamma-tocopherol methyltransferase.

SEQ ID NO: 16 sets forth a nucleic acid sequence of a DNA molecule that encodes a *Nostoc punctiforme* gamma-tocopherol methyltransferase.

SEQ ID NO: 17 sets forth a nucleic acid sequence of a DNA molecule that encodes an *Anabaena* gamma-tocopherol methyltransferase.

SEQ ID NO: 18 set forth a derived amino acid sequence of an *Arabidopsis thaliana* gamma-tocopherol methyltransferase.

SEQ ID NO: 19 sets forth a derived amino acid sequence of an *Arabidopsis thaliana*, Columbia ecotype, gamma-tocopherol methyltransferase.

SEQ ID NO: 20 sets forth a derived amino acid sequence of an *Oryza sativa* gamma-tocopherol methyltransferase.

SEQ ID NO: 21 sets forth a derived amino acid sequence of a *Zea mays* gamma-tocopherol methyltransferase.

SEQ ID NO: 22 sets forth a derived amino acid sequence of a *Gossypium hirsutum* gamma-tocopherol methyltransferase.

SEQ ID NO: 23 sets forth a derived amino acid sequence of a *Cuphea pulcherrima* gamma-tocopherol methyltransferase.

SEQ ID NO: 24 sets forth a derived amino acid sequence of a *Brassica napus* S8 gamma-tocopherol methyltransferase.

SEQ ID NO: 25 sets forth a derived amino acid sequence of a *Brassica napus* P4 gamma-tocopherol methyltransferase.

SEQ ID NO: 26 sets forth a derived amino acid sequence of a *Lycopersicon esculentum* gamma-tocopherol methyltransferase.

SEQ ID NO: 27 sets forth a derived amino acid sequence of a *Glycine max* gamma-tocopherol methyltransferase.

SEQ ID NO: 28 sets forth a derived amino acid sequence of a *Glycine max* gamma-tocopherol methyltransferase.

SEQ ID NO: 29 sets forth a derived amino acid sequence of a *Glycine max* gamma-tocopherol methyltransferase.

SEQ ID NO: 30 sets forth a derived amino acid sequence of a *Tagetes erecta* gamma-tocopherol methyltransferase.

SEQ ID NO: 31 sets forth a derived amino acid sequence of a *Sorghum bicolor* gamma-tocopherol methyltransferase.

SEQ ID NO: 32 sets forth an amino acid sequence of a pea rubisco small subunit chloroplast targeting sequence (CTP1).

SEQ ID NO: 33 sets forth a derived mature amino acid sequence of a *Brassica napus* S8 gamma-tocopherol methyltransferase.

SEQ ID NO: 34 sets forth a derived mature amino acid sequence of a *Brassica napus* P4 gamma-tocopherol methyltransferase.

SEQ ID NO: 35 sets forth a derived mature amino acid sequence of a *Cuphea pulcherrima* gamma-tocopherol methyltransferase.

SEQ ID NO: 36 sets forth a derived mature amino acid sequence of a *Gossypium hirsutum* gamma-tocopherol methyltransferase.

SEQ ID NO: 37 sets forth a derived mature amino acid sequence of a *Tagetes erecta* gamma-tocopherol methyltransferase.

SEQ ID NO: 38 sets forth a derived mature amino acid sequence of a *Zea mays* gamma-tocopherol methyltransferase.

SEQ ID NO: 39 sets forth a derived amino acid sequence of a *Nostoc punctiforme* gamma-tocopherol methyltransferase.

SEQ ID NO: 40 sets forth a derived amino acid sequence of an *Anabaena* gamma-tocopherol methyltransferase.

SEQ ID NO: 41 sets forth an amino acid sequence of *Synechocystis* gamma-tocopherol methyltransferase.

SEQ ID NO: 42 sets forth a nucleic acid sequence of a nucleic acid molecule encoding a *Synechocystis* pcc 6803 2-methyl-6-phytylplastoquinol/2-methyl-6-solanylplastoquinol-9 methyltransferase.

SEQ ID NO: 43 sets forth a nucleic acid sequence of a nucleic acid molecule encoding an *Anabaena* 2-methyl-6-phytylplastoquinol/2-methyl-6-solanylplastoquinol-9 methyltransferase.

SEQ ID NO: 44 sets forth a nucleic acid sequence of a nucleic acid molecule encoding a *Synechococcus* 2-methyl-6-phytylplastoquinol/2-methyl-6-solanylplastoquinol-9 methyltransferase.

SEQ ID NO: 45 sets forth a nucleic acid sequence of a nucleic acid molecule encoding a *Prochlorococcus marinus* 2-methyl-6-phytylplastoquinol/2-methyl-6-solanylplastoquinol-9 methyltransferase.

SEQ ID NO: 46 sets forth a derived amino acid sequence of an *Synechocystis* pcc 6803 2-methyl-6-phytylplastoquinol/2-methyl-6-solanylplastoquinol-9 methyltransferase.

SEQ ID NO: 47 sets forth a derived amino acid sequence of an *Anabaena* 2-methyl-6-phytylplastoquinol/2-methyl-6-solanylplastoquinol-9 methyltransferase.

SEQ ID NO: 48 sets forth a derived amino acid sequence of a *Synechococcus* 2-methyl-6-phytylplastoquinol/2-methyl-6-solanylplastoquinol-9 methyltransferase SEQ ID NO: 49 sets forth a derived amino acid sequence of a *Prochlorococcus* 2-methyl-6-phytylplastoquinol/2-methyl-6-solanylplastoquinol-9 methyltransferase.

SEQ ID NO: 50 sets forth a nucleic acid sequence of an *Oryza saliva* gamma-tocopherol methyltransferase.

SEQ ID NOs: 51 and 52 set forth a nucleic acid sequence of primers for use in amplifying a *Brassica napus* S8 gamma methyl transferase.

SEQ ID NOs: 53 and 54 set forth a nucleic acid sequence of primers for use in amplifying a *Brassica napus* P4 gamma methyl transferase.

SEQ ID NOs: 55 and 56 set forth a nucleic acid sequence of primers for use in amplifying a *Cuphea pulcherrima* gamma methyl transferase.

SEQ ID NOs: 57 and 58 set forth a nucleic acid sequence of primers for use in amplifying a *Gossypium hirsutum* gamma methyl transferase.

SEQ ID NOs: 59 and 60 set forth a nucleic acid sequence of primers for use in amplifying a mature *Brassica napus* S8 gamma methyl transferase and a mature *Brassica napus* P4 gamma methyl transferase.

SEQ ID NOs: 61 and 62 set forth a nucleic acid sequence of primers for use in amplifying a mature *Cuphea pulcherrima* gamma methyl transferase.

SEQ ID NOs: 63 and 64 set forth a nucleic acid sequence of primers for use in amplifying a mature *Gossypium hirsutum* gamma methyl transferase.

SEQ ID NOs: 65 and 66 set forth a nucleic acid sequence of primers for use in amplifying a mature *Tagetes erecta* gamma methyl transferase.

SEQ ID NOs: 67 and 68 set forth a nucleic acid sequence of primers for use in amplifying a *Nostoc punctiforme* gamma methyl transferase.

SEQ ID NOs: 69 and 70 set forth a nucleic acid sequence of primers for use in amplifying an *Anabaena* gamma methyl transferase.

SEQ ID NOs: 71 and 72 set forth a nucleic acid sequence of primers for use in amplifying an *Anabaena* 2-methyl-6-phytylplastoquinol/2-methyl-6-solanylplastoquinol-9 methyltransferase.

SEQ ID NOs: 73 and 74 set forth a nucleic acid sequence of primers for use in amplifying a mature *Zea mays* gamma methyl transferase.

SEQ ID NOs: 75 and 76 set forth a nucleic acid sequence of primers for use in amplifying an *Arabidopsis* gamma methyl transferase.

SEQ ID NOs: 77 and 78 set forth a nucleic acid sequence of primers for use in amplifying an *Arabidopsis* gamma methyl transferase.

SEQ ID NOs: 79 and 80 set forth a nucleic acid sequence of primers for use in amplifying an Arcelin 5 promoter.

SEQ ID NO: 81 sets forth a 5' translational start region of a nucleic acid sequence corresponding to an Arcelin 5 promoter from pARC5-1

SEQ ID NO: 82 sets forth a 5' translational start region of a nucleic acid sequence corresponding to an Arcelin 5 promoter from pARC5-1M.

SEQ ID NOs: 83 and 84 set forth nucleic acid sequences of primers for use in amplifying an *Anabaena* putative-MT1 coding sequence.

SEQ ID NO: 85 sets forth a nucleic acid sequence of a *Zea mays* gamma-tocopherol methyltransferase.

DETAILED DESCRIPTION

Figure 1:
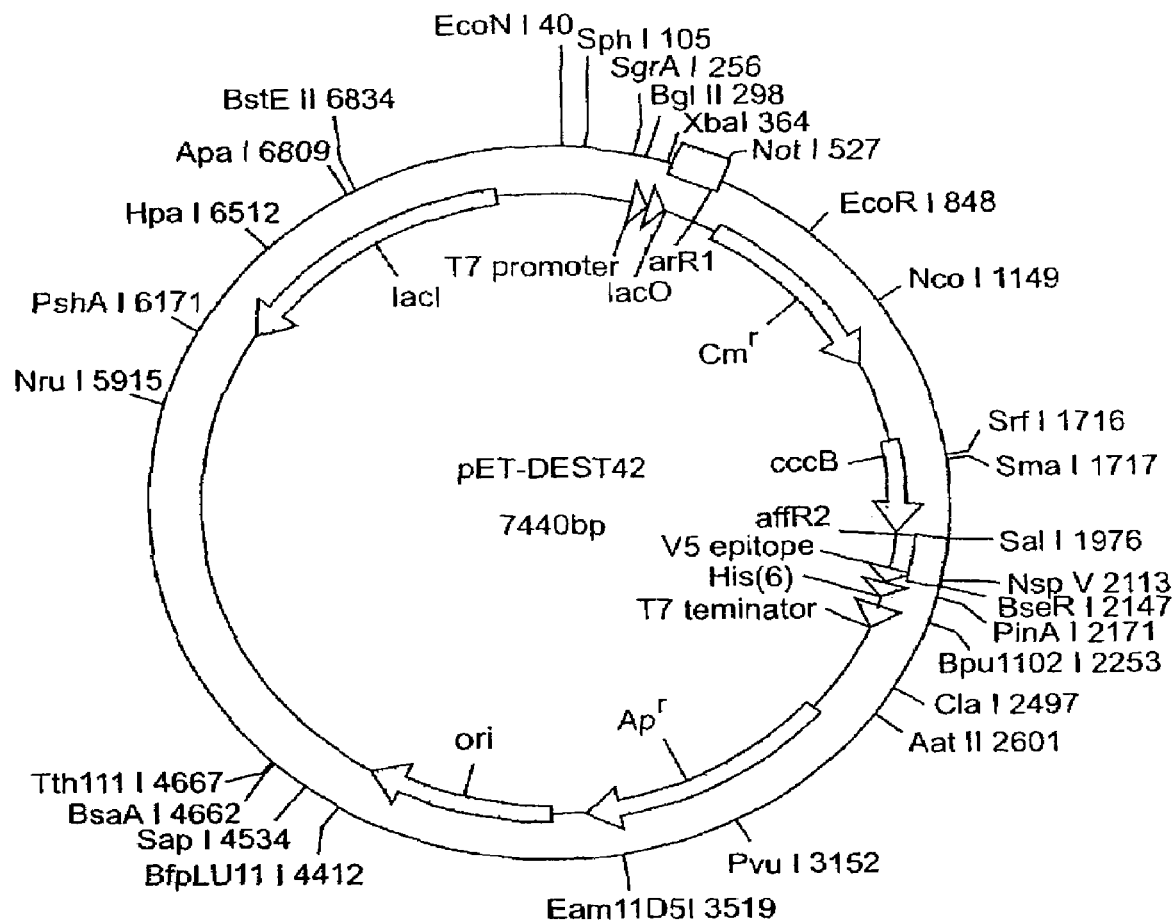
FIG. 1 is a schematic of construct pET-DEST42.

The present invention provides a number of agents, for example, nucleic acid molecules and polypeptides associated with the synthesis of tocopherol, and provides uses of such agents.

Agents

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the invention may also be recombinant. As used herein, the term recombinant means any agent (e.g., DNA, peptide etc.), that is, or results, however indirectly, from human manipulation of a nucleic acid molecule.

It is understood that the agents of the invention may be labeled with reagents that facilitate detection of the agent (e.g., fluorescent labels, Prober et al., Science 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

Nucleic Acid Molecules

Agents of the invention include nucleic acid molecules. In a preferred aspect of the present invention the nucleic acid molecule comprises a nucleic acid sequence, which encodes a gamma-tocopherol methyltransferase. As used herein a gamma-tocopherol methyltransferase (also referred to as GMT, γ-GMT, γ-MT, γ-TMT or gamma-methyltransferase) is any polypeptide that is capable of specifically catalyzing the conversion of γ-tocopherol into α-tocopherol. In certain plant species such as soybean, GMT can also catalyze the conversion of β-tocopherol to β-tocopherol. In other plants, mainly monocotyledons such as corn and wheat, GMT can also catalyze the conversion of γ-tocotrienol to α-tocotrienol and δ-tocotrienol to β-tocotrienol. A preferred gamma-tocopherol methyltransferase is a plant or cynobacterial gamma-tocopherol methyltransferase, more preferably a gamma-tocopherol methyltransferase that is also found in an organism selected from the group consisting of Arabidopsis, rice, corn, cotton, cuphea, oilseed rape, tomato, soybean, marigold, sorghum, and leek, most preferably a gamma-tocopherol methyltransferase that is also found in an organism selected from the group consisting of Arabidopsis thaliana, Oryza saliva, Zea mays, Gossypium hirsutum, Cuphea pulcherrima, Brassica napus, Lycopersicon esculentum, Glycine max, Tagetes erecta, and Lilium asiaticum. An example of a more preferred gamma-tocopherol methyltransferase is a polypeptide with one of the amino acid sequences set forth in SEQ ID NOs: 19-31 and 33-38.

In another embodiment of the invention, genomic DNA is used to transform any of the plants disclosed herein. Genomic DNA (e.g. SEQ ID NOs: 6 and 7) can be particularly useful for transforming monocotyledonous plants (e.g. SEQ ID NOs: 6 and 7).

In another preferred aspect of the present invention the nucleic acid molecule of the invention comprises a nucleic acid sequence selected from the group consisting of SEQ ID NOs: 2-17, 50, and 85, and complements thereof and fragments of either. In a further aspect of the present invention the nucleic acid molecule comprises a nucleic acid sequence encoding an amino acid sequence selected from the group consisting of SEQ ID NOs: 19-31, 33, and 38 and fragments thereof.

In another preferred aspect of the present invention the nucleic acid molecule comprises a nucleic acid sequence, which encodes a 2-methyl-6-phytylplastoquinol/2-methyl-6-solanylplastoquinol-9 methyltransferase. As used herein a 2-methyl-6-phytylplastoquinol/2-methyl-6-solanylplastoquinol-9 methyltransferase (MT1) is any protein that is capable of specifically catalyzing the conversion of 2-methyl-6-phytylplastoquinol, 2-methyl-5-phytylplastoquinol or 2-methyl-3-phytylplastoquinol to 2,3-dimethyl-6-phytylplastoquinol. A preferred MT 1 is a cyanobacterial MT 1, more preferably an MT 1 that is also found in an organism selected from the group consisting of Anabaena, Synechococcus and Prochlorococcus marinus. An example of a more preferred MT 1 is a polypeptide with the amino acid sequence selected from the group consisting of SEQ ID NOs: 46-49.

In another preferred aspect of the present invention the nucleic acid molecule of the invention comprises a nucleic acid sequence selected from the group consisting of SEQ ID NOs: 42-45 and complements thereof and fragments of either. In a further aspect of the present invention the nucleic acid molecule comprises a nucleic acid sequence encoding an amino acid sequence selected from the group consisting of SEQ ID NOs: 46-49 and fragments thereof.

In another preferred aspect of the present invention a nucleic acid molecule comprises nucleotide sequences encoding a plastid transit peptide operably fused to a nucleic acid molecule that encodes a protein or fragment of the present invention.

It is understood that in a further aspect of the present invention, the nucleic acids can encode a protein that differs from any of the proteins in that one or more amino acids have been deleted, substituted or added without altering the function. For example, it is understood that codons capable of coding for such conservative amino acid substitutions are known in the art.

One subset of the nucleic acid molecules of the invention is fragment nucleic acids molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www.genome.wi.mit.edu/cgi-bin/primer/primer3.cgi), STSPipeline (www.genome.wi.mit.edu/cgi-bin/www-STS_Pipeline), or GeneUp (Pesole et al., BioTechniques 25:112-123 (1998)), for example, can be used to identify potential PCR primers.

Another subset of the nucleic acid molecules of the invention include nucleic acid molecules that encode a polypeptide or fragment thereof.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs: 2-17, 50, and 85, and complements thereof. Nucleic acid molecules of the present invention also include those that specifically hybridize to nucleic acid molecules encoding an amino acid sequence selected from SEQ ID NOs: 19-31 and 33-38 and fragments thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989), and by Haymes et al., *Nucleic Acid Hybridization, A Practical Approach, IRL Press*, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 20-25° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NOs: 2-17, 50, and 85 and complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NOs: 2-17, 50, and 85 and complements thereof under high stringency conditions such as 0.2×SSC and about 65° C.

In one aspect of the present invention, the nucleic acid molecules of the present invention have one or more of the nucleic acid sequences set forth in SEQ ID NOs: 2-17, 50, and 85 and complements thereof. In another aspect of the present invention, one or more of the nucleic acid molecules of the present invention share between 100% and 90% sequence identity with one or more of the nucleic acid sequences set forth in SEQ ID NOs: 2-17, 50, and 85 and complements thereof and fragments of either. In a further aspect of the present invention, one or more of the nucleic acid molecules of the present invention share between 100% and 95% sequence identity with one or more of the nucleic acid sequences set forth in SEQ ID NOs: 2-17, 50, and 85, complements thereof, and fragments of either. In a more preferred aspect of the present invention, one or more of the nucleic acid molecules of the present invention share between 100% and 98% sequence identity with one or more of the nucleic acid sequences set forth in SEQ ID NOs: 2-17, 50, and 85, complements thereof and fragments of either. In an even more preferred aspect of the present invention, one or more of the nucleic acid molecules of the present invention share between 100% and 99% sequence identity with one or more of the sequences set forth in SEQ ID NOs: 2-17, 50, and 85, complements thereof, and fragments of either.

In a preferred embodiment the percent identity calculations are performed using BLASTN or BLASTP (default, parameters, version 2.0.8, Altschul et al., *Nucleic Acids Res.* 25: 3389-3402 (1997)).

A nucleic acid molecule of the invention can also encode a homolog polypeptide. As used herein, a homolog polypeptide molecule or fragment thereof is a counterpart protein molecule or fragment thereof in a second species (e.g., corn rubisco small subunit is a homolog of *Arabidopsis* rubisco small subunit). A homolog can also be generated by molecular evolution or DNA shuffling techniques, so that the molecule retains at least one functional or structure characteristic of the original polypeptide (see, for example, U.S. Pat. No. 5,811,238).

In another embodiment, the homolog is selected from the group consisting of alfalfa, *Arabidopsis*, barley, *Brassica campestris*, oilseed rape, broccoli, cabbage, canola, citrus, cotton, garlic, oat, onion, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, corn, *Phaseolus*, crambe, mustard, castor bean, sesame, cottonseed, linseed, safflower, and oil palm. More particularly, preferred homologs are selected from canola, corn, *Brassica campestris*, oilseed rape, soybean, crambe, mustard, castor bean, peanut, sesame, cottonseed, linseed, rapeseed, safflower, oil palm, flax, and sunflower. In an even more preferred embodiment, the homolog is selected from the group consisting of canola, rapeseed, corn, *Brassica campestris, Brassica napus*, soybean, sunflower, safflower, oil palms, and peanut. In a particularly preferred embodiment, the homolog is soybean. In a particularly preferred embodiment, the homolog is canola. In a particularly preferred embodiment, the homolog is *Brassica napus*.

In another further aspect of the present invention, nucleic acid molecules of the present invention can comprise sequences that differ from those encoding a polypeptide or fragment thereof in SEQ ID NOs: 19-31 and 33-38 due to the fact that a polypeptide can have one or more conservative amino acid changes, and nucleic acid sequences coding for the polypeptide can therefore have sequence differences. It is understood that codons capable of coding for such conservative amino acid substitutions are known in the art.

It is well known in the art that one or more amino acids in a native sequence can be substituted with other amino acid(s), the charge and polarity of which are similar to that of the native amino acid, i.e., a conservative amino acid substitution. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid substitution within the native polypeptide sequence can be made by replacing one amino acid from within one of these groups with another amino acid from within the same group. In a preferred aspect, biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the polypeptides of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105-132 (1982)). It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157:105-132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those that are within ±1 are particularly preferred, and those within ±0.5 are even more particularly preferred.

In a further aspect of the present invention, one or more of the nucleic acid molecules of the present invention differ in nucleic acid sequence from those for which a specific sequence is provided herein because one or more codons has been replaced with a codon that encodes a conservative substitution of the amino acid originally encoded.

Agents of the invention include nucleic acid molecules that encode at least about a contiguous 10 amino acid region of a polypeptide of the present invention, more preferably at least about a contiguous 25, 40, 50, 100, or 125 amino acid region of a polypeptide of the present invention.

In a preferred embodiment, any of the nucleic acid molecules of the present invention can be operably linked to a promoter region that functions in a plant cell to cause the production of an mRNA molecule, where the nucleic acid molecule that is linked to the promoter is heterologous with respect to that promoter. As used herein, "heterologous" means not naturally occurring together.

Protein and Peptide Molecules

A class of agents includes one or more of the polypeptide molecules encoded by a nucleic acid agent of the invention. A particular preferred class of proteins is that having an amino acid sequence selected from the group consisting of SEQ ID NOs: 19-31 and 33-38 and fragments thereof. Polypeptide agents may have C-terminal or N-terminal amino acid sequence extensions. One class of N-terminal extensions employed in a preferred embodiment are plastid transit peptides. When employed, plastid transit peptides can be operatively linked to the N-terminal sequence, thereby permitting the localization of the agent polypeptides to plastids. In a preferred embodiment the plastid targeting sequence is a CTP1 sequence (SEQ ID NO: 32). See WO 00/61771.

In a preferred aspect a protein of the present invention is targeted to a plastid using either a native transit peptide sequence or a heterologous transit peptide sequence. In the case of nucleic acid sequences corresponding to nucleic acid sequences of non-higher plant organisms such as cyanobacteria, such nucleic acid sequences can be modified to attach the coding sequence of the protein to a nucleic acid sequence of a plastid targeting peptide. Examples of cynobacterial nucleic acid sequences that can be so attached are those having amino acid sequence set forth in SEQ ID NOs: 42-45.

As used herein, the term "protein," "peptide molecule," or "polypeptide" includes any molecule that comprises five or more amino acids. It is well known in the art that protein, peptide or polypeptide molecules may undergo modification, including posttranslational modifications, such as, but not limited to, disulfide bond formation, glycosylation, phosphorylation, or oligomerization. Thus, as used herein, the term "protein," "peptide molecule," or "polypeptide" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragments thereof, peptide molecules, or polypeptide molecules may be produced via chemical synthesis, or more preferably, by expression in a suitable bacterial or eukaryotic host. Suitable methods for expression are described by Sambrook et al., In: *Molecular*

Cloning, A Laboratory Manual, 2nd Edition, Cold Spring Harbor Press, Cold Spring Harbor, N.Y. (1989) or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the invention are preferably produced via recombinant means.

Another class of agents comprise protein, peptide molecules, or polypeptide molecules or fragments or fusions thereof comprising SEQ ID NOs: 19-31 and 33-38 and fragments thereof in which conservative, non-essential or non-relevant amino acid residues have been added, replaced or deleted. Computerized means for designing modifications in protein structure are known in the art (Dahiyat and Mayo, Science 278:82-87 (1997)).

A protein, peptide or polypeptide of the invention can also be a homolog protein, peptide or polypeptide. As used herein, a homolog protein, peptide or polypeptide or fragment thereof is a counterpart protein, peptide or polypeptide or fragment thereof in a second species. A homolog can also be generated by molecular evolution or DNA shuffling techniques, so that the molecule retains at least one functional or structure characteristic of the original (see, for example, U.S. Pat. No. 5,811,238).

In another embodiment, the homolog is selected from the group consisting of alfalfa, Arabidopsis, barley, broccoli, cabbage, canola, citrus, cotton, garlic, oat, onion, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, corn, and Phaseolus. More particularly, preferred homologs are selected from canola, rapeseed, corn, Brassica campestris, oilseed rape, soybean, crambe, mustard, castor bean, peanut, sesame, cottonseed, linseed, safflower, oil palm, flax, and sunflower. In an even more preferred embodiment, the homolog is selected from the group consisting of canola, rapeseed, corn, Brassica campestris, oilseed rape, soybean, sunflower, safflower, oil palms, and peanut. In a preferred embodiment, the homolog is soybean. In a preferred embodiment, the homolog is canola. In a preferred embodiment, the homolog is Brassica napus.

In a preferred embodiment, the nucleic acid molecules of the present invention or complements and fragments of either can be utilized to obtain such homologs.

Agents of the invention include proteins and fragments thereof comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism.

In a preferred aspect of the present invention the exogenous genetic material comprises a nucleic acid sequence that encodes a gamma-tocopherol methyltransferase. In a particularly preferred embodiment of the present invention, the exogenous genetic material of the invention comprises a nucleic acid sequence of SEQ ID NO: 2. In a further aspect of the present invention the exogenous genetic material comprises a nucleic acid sequence encoding an amino acid sequence selected from the group consisting of SEQ ID NOs: 19-31, 33-38, 39-41, and 46-49 and fragments thereof.

In another preferred aspect of the present invention the exogenous genetic material comprises a nucleic acid sequence that encodes a 2-methyl-6-phytylplastoquinol/2-methyl-6-solanylplastoquinol-9 methyltransferase. In another preferred aspect of the present invention the exogenous genetic material of the invention comprises a nucleic acid sequence selected from the group consisting of SEQ ID NOs: 42-45 and complements thereof and fragments of either. In a further aspect of the present invention the exogenous genetic material comprises a nucleic acid sequence encoding an amino acid sequence selected from the group consisting of SEQ ID NOs: 46-49 and fragments thereof. In a further aspect of the present invention, the nucleic acid sequences of the invention also encode peptides involved in intracellular localization, export, or posttranslational modification.

In an embodiment of the present invention, exogenous genetic material comprising a GMT or fragment thereof is introduced into a plant with one or more additional genes. In another embodiment of the present invention, exogenous genetic material comprising a MT1 or fragment thereof is introduced into a plant with one or more additional genes. In one embodiment, preferred combinations of genes include two or more of the following genes: tyrA, slr1736, A TPT2, dxs, dxr, GGPPS, HPPD, GMT MT1, tMT2, AANT1, sir 1737, or a plant ortholog and an antisense construct for homogentisic acid dioxygenase (Kridl et al., Seed Sci. Res. 1:209:219 (1991); Keegstra, Cell 56(2):247-53 (1989); Nawrath, et al., Proc. Natl. Acad. Sci. U.S.A. 91:12760-12764 (1994); Xia et al., J. Gen. Microbiol. 138:1309-1316 (1992); Cyanobase, www.kazusa.or.jp/cyanobase; Lois et al., Proc. Natl. Acad. Sci. U.S. 95 (5):2105-2110 (1998); Takahashi et al. Proc. Natl. Acad. Sci. USA. 95 (17), 9879-9884 (1998); Norris et al, Plant Physiol. 117:1317-1323 (1998); Bartley and Scolnik, Plant Physiol. 104:1469-1470 (1994), Smith et al, Plant J. 11: 83-92 (1997); WO 00/32757; WO 00/10380; Saint Guily, et al., Plant Physiol, 100(2):1069-1071 (1992); Sato et al, J DNA Res. 7 (1):31-63 (2000)). In such combinations, one or more of the gene products can be directed to the plastid by the use of a plastid targeting sequence. Alternatively, one or more of the gene products can be localized in the cytoplasm. In a preferred aspect the gene products of tyrA and HPPD are targeted to the cytoplasm. Such genes can be introduced, for example, with the MT1 or GMT or both or fragment of either or both on a single construct, introduced on different constructs but the same transformation event or introduced into separate plants followed by one or more crosses to generate the desired combination of genes. In such combinations, a preferred promoter is a napin promoter and a preferred plastid targeting sequence is a CTP1 sequence. It is preferred that gene products are targeted to the plastid.

A particularly preferred combination that can be introduced is a nucleic acid molecule encoding a GMT polypeptide and a nucleic acid molecule encoding an MT1 polypeptide, where both polypeptides are targeted to the plastid and where one of such polypeptides is present and the other is introduced. Both nucleic acid sequences encoding such polypeptides are introduced using a single construct, or each polypeptide is introduced on separate constructs.

Another particularly preferred combination that can be introduced is a nucleic acid molecule encoding an MT1 protein and a nucleic acid molecule that results in the down regulation of a GMT protein. In such an aspect, it is preferred that the plant accumulates either γ-tocopherol or γ-tocotrienol or both.

Such genetic material may be transferred into either monocotyledons or dicotyledons including, but not limited to canola, corn, soybean, *Arabidopsis* phaseolus, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee and dioscorea (Christou, In: *Particle Bombardment for Genetic Engineering of Plants*, Biotechnology Intelligence Unit. Academic Press, San Diego, Calif. (1996)), with canola, corn, *Brassica campestris, Brassica napus*, rapeseed, soybean, crambe, mustard, castor bean, peanut, sesame, cottonseed, linseed, safflower, oil palm, flax, and sunflower preferred, and canola, rapeseed, corn, *Brassica campestris, Brassica napus*, soybean, sunflower, safflower, oil palms, and peanut preferred. In a more preferred embodiment, the genetic material is transferred into canola. In another more preferred embodiment, the genetic material is transferred into *Brassica napus*. In another particularly preferred embodiment, the genetic material is transferred into soybean. In another particularly preferred embodiment of the present invention, the genetic material is transferred into soybean line 3244.

Transfer of a nucleic acid molecule that encodes a protein can result in expression or overexpression of that polypeptide in a transformed cell or transgenic plant. One or more of the proteins or fragments thereof encoded by nucleic acid molecules of the invention may be overexpressed in a transformed cell or transformed plant. Such expression or overexpression may be the result of transient or stable transfer of the exogenous genetic material.

In a preferred embodiment, expression or overexpression of a polypeptide of the present invention in a plant provides in that plant, relative to an untransformed plant with a similar genetic background, an increased level of tocopherols.

In a preferred embodiment, expression, or overexpression of a polypeptide of the present invention in a plant provides in that plant, relative to an untransformed plant with a similar genetic background, an increased level of α-tocopherols.

In a preferred embodiment, expression, or overexpression of a polypeptide of the present invention in a plant provides in that plant, relative to an untransformed plant with a similar genetic background, an increased level of γ-tocopherols.

In a preferred embodiment, reduction of the expression, expression, or overexpression of a polypeptide of the present invention in a plant provides in that plant, relative to an untransformed plant with a similar genetic background, an increased level of δ-tocopherols.

In a preferred embodiment, reduction of the expression, expression or overexpression of a polypeptide of the present invention in a plant provides in that plant, relative to an untransformed plant with a similar genetic background, an increased level of tocotrienols.

In a preferred embodiment, reduction of the expression, expression, or overexpression of a polypeptide of the present invention in a plant provides in that plant, relative to an untransformed plant with a similar genetic background, an increased level of α-tocotrienols.

In a preferred embodiment, reduction of the expression, expression, or overexpression of a polypeptide of the present invention in a plant provides in that plant, relative to an untransformed plant with a similar genetic background, an increased level of δ-tocotrienols.

In a preferred embodiment, reduction of the expression, expression, or overexpression of a polypeptide of the present invention in a plant provides in that plant, relative to an untransformed plant with a similar genetic background, an increased level of δ-tocotrienols.

In another embodiment, reduction of the expression, expression, overexpression of a polypeptide of the present invention in a plant provides in that plant, or a tissue of that plant, relative to an untransformed plant or plant tissue, with a similar genetic background, an increased level of an MT 1 or GMT protein or both or fragment of either.

In some embodiments, the levels of one or more products of the tocopherol biosynthesis pathway, including any one or more of tocopherols, α-tocopherols, γ-tocopherols, δ-tocopherols, β-tocopherols, tocotrienols, α-tocotrienols, γ-tocotrienols, δ-tocotrienols, β-tocotrienols, are increased by greater than about 10%, or more preferably greater than about 25%, 50%, 200%, 1,000%, 2,000%, 2,500% or 25,000%. The levels of products may be increased throughout an organism such as a plant or localized in one or more specific organs or tissues of the organism. For example the levels of products may be increased in one or more of the tissues and organs of a plant including without limitation: roots, tubers, stems, leaves, stalks, fruit, berries, nuts, bark, pods, seeds and flowers. A preferred organ is a seed.

In some embodiments, the levels of tocopherols or a species such as α-tocopherol may be altered. In some embodiments, the levels of tocotrienols may be altered. Such alteration can be compared to a plant with a similar background.

In another embodiment, either the α-tocopherol level, α-tocotrienol level, or both of plants that natively produce high levels of either α-tocopherol, α-tocotrienol or both (e.g., sunflowers), can be increased by the introduction of a gene coding for an MT1 enzyme.

In a preferred aspect, a similar genetic background is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

In another preferred embodiment, reduction of the expression, expression, overexpression of a polypeptide of the present invention in a transformed plant may provide tolerance to a variety of stress, e.g. oxidative stress tolerance such as to oxygen or ozone, UV tolerance, cold tolerance, or fungal/microbial pathogen tolerance.

As used herein in a preferred aspect, a tolerance or resistance to stress is determined by the ability of a plant, when challenged by a stress such as cold to produce a plant having a higher yield than one without such tolerance or resistance to stress. In a particularly preferred aspect of the present invention, the tolerance or resistance to stress is measured relative to a plant with a similar genetic background to the tolerant or resistance plant except that the plant reduces the expression, expresses or over expresses a protein or fragment thereof of the present invention.

Exogenous genetic material may be transferred into a host cell by the use of a DNA vector or construct designed for such a purpose. Design of such a vector is generally within the skill of the art (See, *Plant Molecular Biology: A Laboratory Manual*, Clark (ed.), Springer, N.Y. (1997)).

A construct or vector may include a plant promoter to express the polypeptide of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include the nopaline synthase (NOS) promoter (Ebert et al., *Proc. Natl. Acad. Sci.* (U.S.A.) 84:5745-5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987)) and the CaMV 35S promoter (Odell et al., *Nature* 313:810-812 (1985)), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci.* (U.S.A.) 84:6624-6628 (1987)), the sucrose synthase promoter (Yang et al., *Proc. Natl. Acad. Sci.* (U.S.A.) 87:4144-4148 (1990)), the R gene complex promoter (Chandler et al., *The Plant Cell* 1:1175-1183 (1989)) and the chlorophyll a/b binding protein gene promoter, etc. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or enhanced expression. Examples of such promoters reported in the literature include the chloroplast glutamine synthetase GS2 promoter from pea (Edwards et al., *Proc. Natl. Acad. Sci.* (U.S.A.) 87:3459-3463 (1990)), the chloroplast fructose-1,6-biphosphatase (FB-Pase) promoter from wheat (Lloyd et al., *Mol. Gen. Genet.* 225:209-216 (1991)), the nuclear photosynthetic ST-LS1 promoter from potato (Stockhaus et al., *EMBO J.* 8:2445-2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994)), the promoter for the Cab-1 gene from wheat (Fejes et al., *Plant Mol. Biol.* 15:921-932 (1990)), the promoter for the CAB-1 gene from spinach (Lubberstedt et al., *Plant Physiol.* 104:997-1006 (1994)), the promoter for the cab1R gene from rice (Luan et al., *Plant Cell.* 4:971-981 (1992)), the pyruvate, orthophosphate dikinase (PPDK) promoter from corn (Matsuoka et al., *Proc. Natl. Acad. Sci.* (U.S.A.) 90: 9586-9590 (1993)), the promoter for the tobacco Lhcb1*2 gene (Cerdan et al., *Plant Mol. Biol.* 33:245-255 (1997)), the *Arabidopsis thaliana* SUC2 sucrose-H+ symporter promoter (Truemit et al., *Planta.* 196:564-570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (*Sinapis alba*; Kretsch et al., *Plant Mol. Biol.* 28:219-229 (1995)).

For the purpose of expression in sink tissues of the plant, such as the tuber of the potato plant, the fruit of tomato, or the seed of corn, wheat, rice and barley, it is preferred that the promoters utilized in the invention have relatively high expression in these specific tissues. A number of promoters for genes with tuber-specific or tuber-enhanced expression are known, including the class I patatin promoter (Bevan et al., *EMBO J.* 8:1899-1906 (1986); Jefferson et al., *Plant Mol. Biol.* 14:995-1006 (1990)), the promoter for the potato tuber ADPGPP genes, both the large and small subunits, the sucrose synthase promoter (Salanoubat and Belliard, *Gene* 60:47-56 (1987), Salanoubat and Belliard, *Gene* 84:181-185 (1989)), the promoter for the major tuber proteins including the 22 kd protein complexes and protease inhibitors (Hannapel, *Plant Physiol.* 101:703-704 (1993)), the promoter for the granule-bound starch synthase gene (GBSS) (Visser et al., *Plant Mol. Biol.* 17:691-699 (1991)) and other class I and II patatins promoters (Koster-Topfer et al., *Mol. Gen. Genet.* 219:390-396 (1989); Mignery et al., *Gene.* 62:27-44 (1988)).

Other promoters can also be used to express a polypeptide in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res.* 1:209:219 (1991)), phaseolin (Bustos, et al., *Plant Cell*, 1(9): 839-853 (1989)), soybean trypsin inhibitor (Riggs, et al., *Plant Cell* 1(6):609-621 (1989)), ACP (Baerson, et al., *Plant Mol. Biol.*, 22(2):255-267 (1993)), stearoyl-ACP desaturase (Slocombe, et al., *Plant Physiol.* 104(4):167-176 (1994)), soybean α' subunit of β-conglycinin (soy 7s, (Chen et al., *Proc. Natl. Acad. Sci.*, 83:8560-8564 (1986))), and oleosin (see, for example, Hong, et al., *Plant Mol. Biol.*, 34(3):549-555 (1997)). Further examples include the promoter for β-conglycinin (Chen et al., *Dev. Genet.* 10: 112-122 (1989)). Also included are the zeins, which are a group of storage proteins found in corn endosperm. Genomic clones for zein genes have been isolated (Pedersen et al., *Cell* 29:1015-1026 (1982), and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. A particularly preferred promoter for corn endosperm expression is the promoter for the glutelin gene from rice, more particularly the Osgt-1 promoter (Zheng et al., *Mol. Cell. Biol.* 13:5829-5842 (1993)). Examples of promoters suitable for expression in wheat include those promoters for the ADP glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins. A preferred promoter for expression in the seed is a napin promoter. Another preferred promoter for expression is an Arcelin 5 promoter.

Root specific promoters may also be used. An example of such a promoter is the promoter for the acid chitinase gene (Samac et al., *Plant Mol. Biol.* 25:587-596 (1994)). Expression in root tissue could also be accomplished by utilizing the root specific subdomains of the CaMV35S promoter that have been identified (Lam et al., *Proc. Natl. Acad. Sci.* (U.S.A.) 86:7890-7894 (1989)). Other root cell specific promoters include those reported by Conkling et al. (Conkling et al., *Plant Physiol.* 93:1203-1211 (1990)).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell* 1:977-984 (1989)).

In a preferred embodiment of the invention, a nucleic acid molecule having a sequence encoding either a GMT or an MT1 enzyme is linked to a P7 or Arcelin 5 promoter. In a particularly preferred embodiment of the present invention, the promoter comprises a nucleic acid molecule having a sequence selected from the group consisting of SEQ ID NOs 81 and 82. In a particularly preferred embodiment, the invention relates to a soybean line 3244 plant, comprising an exogenous nucleic acid molecule comprising a nucleic acid sequence selected of SEQ ID NO: 2, operably linked to a nucleic acid molecule comprising a nucleotide sequence selected from the group consisting of SEQ ID NO: 81 and 82.

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671-680 (1989); Bevan et al., *Nucleic Acids Res.* 11:369-385 (1983)). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements. Examples of such include the Adh intron 1 (Callis et al., *Genes and Develop.* 1:1183-1200 (1987)), the sucrose synthase intron (Vasil et al., *Plant Physiol.* 91:1575-1579 (1989)) and the TMV omega element (Gallie et al., *The Plant Cell* 1:301-311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183-188 (1985)), which codes for kanamycin resistance and can be selected for using kanamycin, RptII, G418, hpt etc.; a bar gene which codes for bialaphos resistance; a mutant EPSP synthase gene (Hinchee et al., *Bio/Technology* 6:915-922 (1988); Reynaerts et al., Selectable and Screenable Markers. In Gelvin and Schilperoort. Plant Molecular Biology Manual, Kluwer, Dordrecht (1988); Reynaerts et al., Selectable and screenable markers. In Gelvin and Schilperoort. Plant Molecular Biology Manual, Kluwer, Dordrecht (1988)), aadA (Jones et al., *Mol. Gen. Genet.* (1987)),) which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (European Patent Application 154,204 (Sep. 11, 1985)), ALS (D'Halluin et al., Bio/Technology 10: 309-314 (1992)), and a methotrexate resistant DHFR gene (Thillet et al., *J. Biol. Chem.* 263:12500-12508 (1988)).

A vector or construct may also include a transit peptide. Incorporation of a suitable chloroplast transit peptide may also be employed (European Patent Application Publication Number 0218571). Translational enhancers may also be incorporated as part of the vector DNA. DNA constructs could contain one or more 5' non-translated leader sequences, which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996). A preferred transit peptide is CTP1.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., Stadler Symposium 11:263-282 (1988)); a β-lactamase gene (Sutcliffe et al., *Proc. Natl. Acad. Sci.* (U.S.A.) 75:3737-3741 (1978)), a gene which encodes an enzyme for which various chromogenic substrates are known (e.g., PADAC, a chromogenic cephalosporin); a luciferase gene (Ow et al., *Science* 234:856-859 (1986)); a xy/E gene (Zukowsky et al., *Proc. Natl. Acad. Sci.* (U.S.A.) 80:1101-1105 (1983)) which encodes a catechol dioxygenase that can convert chromogenic catechols; an α-amylase gene (Ikatu et al., *Bio/Technol.* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, and the like. (Potrykus, *Ann. Rev. Plant Physiol. Plant Mol. Biol.* 42:205-225 (1991); Vasil, *Plant Mol. Biol.* 25:925-937 (1994)). For example, electroporation has been used to transform corn protoplasts (Fromm et al., *Nature* 312:791-793 (1986)).

Other vector systems suitable for introducing transforming DNA into a host plant cell include but are not limited to binary artificial chromosome (BIBAC) vectors (Hamilton et al., *Gene* 200:107-116 (1997)); and transfection with RNA viral vectors (Della-Cioppa et al., *Ann. N.Y. Acad. Sci.* (1996), 792 (Engineering Plants for Commercial Products and Applications), 57-61). Additional vector systems also include plant selectable YAC vectors such as those described in Mullen et al., *Molecular Breeding* 4:449-457 (1988).

Technology for introduction of DNA into cells is well known to those of skill in the art. Four general methods for delivering a gene into cells have been described: (1) chemical methods (Graham and van der Eb, *Virology* 54:536-539 (1973)); (2) physical methods such as microinjection (Capecchi, *Cell* 22:479-488 (1980)), electroporation (Wong and Neumann, *Biochem. Biophys. Res. Commun.* 107:584-587 (1982); Fromm et al., *Proc. Natl. Acad. Sci.* (U.S.A.) 82:5824-5828 (1985); U.S. Pat. No. 5,384,253); the gene gun (Johnston and Tang, *Methods Cell Biol.* 43:353-365 (1994)); and vacuum infiltration (Bechtold et al., *CR. Acad. Sci. Paris, Life Sci.* 316:1194-1199. (1993)); (3) viral vectors (Clapp, *Clin. Perinatol.* 20:155-168 (1993); Lu et al., *J. Exp. Med.* 178:2089-2096 (1993); Eglitis and Anderson, *Biotechniques* 6:608-614 (1988)); and (4) receptor-mediated mechanisms (Curiel et al., *Hum. Gen. Ther.* 3:147-154 (1992), Wagner et al., *Proc. Natl. Acad. Sci.* ( USA) 89:6099-6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994)). Non-biological particles (microprojectiles) may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671-674 (1988)) nor the susceptibility to *Agrobacterium* infection is required. An illustrative embodiment of a method for delivering DNA into corn cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603-618 (1990)). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, Calif.)(Sanford et al., *Technique* 3:3-16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus that express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci.* (U.S.A.) 87:8526-8530 (1990); Svab and Maliga, *Proc. Natl. Acad. Sci.* (U.S.A.) 90:913-917 (1993); Staub and Maliga, *EMBO J.* 12:601-606 (1993); U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby by passing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629-635 (1985) and Rogers et al., *Methods Enzymol.* 153:253-277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986)).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179-203 (1985)). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988)).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor. Appl. Genet.* 205:34 (1986); Yamada et al., *Plant Cell Rep.* 4:85 (1986); Abdullah et al., *Biotechnology* 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988)). In addition, "particle gun" or high-velocity microprojectile technology can be utilized (Vasil et al., *Bio/Technology* 10:667 (1992)).

Using the latter technology, DNA is carried through the cell wall and into the cytoplasm on the surface of small metal particles as described (Klein et al., *Nature* 328:70 (1987); Klein et al., *Proc. Natl. Acad. Sci.* (U.S.A.) 85:8502-8505 (1988); McCabe et al., *Bio/Technology* 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.* 107:367 (1987); Luo et al., *Plant Mol. Biol. Reporter* 6:165 (1988)), by direct injection of DNA into reproductive organs of a plant (Pena et al., *Nature* 325:274 (1987)), or by direct injection of DNA into the cells of immature embryos followed by the rehydration of desiccated embryos (Neuhaus et al., *Theor. Appl. Genet.* 75:30 (1987)).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908); soybean (U.S. Pat. No. 5,569,834; U.S. Pat. No. 5,416,011; McCabe et al., *Biotechnology* 6:923 (1988); Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; pea (Grant et al., *Plant Cell Rep.* 15:254-258 (1995)); and *Arabidopsis thaliana* (Bechtold et al., *C.R. Acad. Sci. Paris, Life Sci.* 316:1194-1199 (1993)). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al, *Proc. Natl. Acad. Sci.* (USA) 84:5354 (1987)); barley (Wan and Lemaux, *Plant Physiol* 104:37 (1994)); corn (Rhodes et al., *Science* 240:204 (1988); Gordon-Kamm et al., *Plant Cell* 2:603-618 (1990); Fromm et al, *Bio/Technology* 8:833 (1990); Koziel et al, *Bio/Technology* 11:194 (1993); Armstrong et al, *Crop Science* 35:550-557 (1995)); oat (Somers et al., *Bio/Technology* 10:1589 (1992)); orchard grass (Horn et al., *Plant Cell Rep.*

7:469 (1988)); rice (Toriyama et al., *Theor. Appl. Genet.* 205:34 (1986); Part et al, *Plant Mol. Biol.* 32:1135-1148 (1996); Abedinia et al, *Aust. J. Plant Physiol.* 24:133-141 (1997); Zhang and Wu, *Theor. Appl. Genet.* 76:835 (1988); Zhang et al, *Plant Cell Rep.* 7:379 (1988); Battraw and Hall, *Plant Sci.* 86:191-202 (1992); Christou et al, *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al, *Nature* 335:454-457 (1988); Marcotte et al, *Plant Cell* 1:523-532 (1989); McCarty et al, *Cell* 66:895-905 (1991); Hattori et al, *Genes Dev.* 6:609-618 (1992); Goff et al, *EMBO J.* 9:2517-2522 (1990)). Transient expression systems may be used to functionally dissect gene constructs (see generally, Mailga et al, *Methods in Plant Molecular Biology*, Cold Spring Harbor Press (1995)).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for expression or overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990); van der Krol et al., *Plant Cell* 2:291-299 (1990)). Cosuppression may result from stable transformation with a single copy nucleic acid molecule that is homologous to a nucleic acid sequence found with the cell (Prolls and Meyer, *Plant J.* 2:465-475 (1992)) or with multiple copies of a nucleic acid molecule that is homologous to a nucleic acid sequence found with the cell (Mittlesten et al., *Mol. Gen. Genet.* 244:325-330 (1994)). Genes, even though different, linked to homologous promoters may result in the cosuppression of the linked genes (Vaucheret, *C.R. Acad. Sci. III* 316:1471-1483 (1993); Flavell, *Proc. Natl. Acad. Sci.* (U.S.A.) 91:3490-3496 (1994)); van Blokland et al., *Plant J.* 6:861-877 (1994); Jorgensen, *Trends Biotechnol.* 8:340-344 (1990); Meins and Kunz, In: *Gene Inactivation and Homologous Recombination in Plants*, Paszkowski (ed.), pp. 335-348, Kluwer Academic, Netherlands (1994)).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.* 268:427-430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection can manipulate its specificity by selecting either unique regions of the target gene or regions where it shares homology to other related genes (Hiatt et al., In: *Genetic Engineering*, Setlow (ed.), Vol. 11, New York: Plenum 49-63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem.* 55:569-597 (1986)). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a protein in a plant cell may be reduced or depressed by growing a transformed plant cell containing a nucleic acid molecule whose non-transcribed strand encodes a protein or fragment thereof. Preferred proteins whose activity can be reduced or depressed, by any method, are MT1 and homogenistic acid dehydrogenase. In such an embodiment of the invention, it is preferred that the concentration of γ-tocopherol or γ-tocotrienol is increased.

Posttranscriptional gene silencing (PTGS) can result in virus immunity or gene silencing in plants. PTGS is induced by dsRNA and is mediated by an RNA-dependent RNA polymerase, present in the cytoplasm, which requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNase molecules hybridize to the endogene mRNA and cleave the single-stranded RNA adjacent to the hybrid. The cleaved single-stranded RNAs are further degraded by other host RNases because one will lack a capped 5' end and the other will lack a poly(A) tail (Waterhouse et al., *PNAS* 95: 13959-13964 (1998)).

It is understood that one or more of the nucleic acids of the invention may be introduced into a plant cell and transcribed using an appropriate promoter with such transcription resulting in the post transcriptional gene silencing of an endogenous transcript.

Antibodies have been expressed in plants (Hiatt et al., *Nature* 342:76-78 (1989); Conrad and Fielder, *Plant Mol. Biol.* 26:1023-1030 (1994)). Cytoplasmic expression of a scFv (single-chain Fv antibody) has been reported to delay infection by artichoke mottled crinkle virus. Transgenic plants that express antibodies directed against endogenous proteins may exhibit a physiological effect (Philips et al., *EMBO J.* 16:4489-4496 (1997); Marion-Poll, *Trends in Plant Science* 2:447-448 (1997)). For example, expressed anti-abscisic antibodies have been reported to result in a general perturbation of seed development (Philips et al., *EMBO J.* 16: 4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997); Baca et al., *Ann. Rev. Biophys. Biomol. Struct.* 26:461-493 (1997)). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289 and 5,194,585.

It is understood that any of the antibodies of the invention may be expressed in plants and that such expression can result in a physiological effect. It is also understood that any of the expressed antibodies may be catalytic.

The present invention also provides for parts of the plants, particularly reproductive or storage parts, of the present invention. Plant parts, without limitation, include seed, endosperm, ovule and pollen. In a particularly preferred embodiment of the present invention, the plant part is a seed. In one embodiment the seed is a constituent of animal feed.

In another embodiment, the plant part is a fruit, more preferably a fruit with enhanced shelf life. In another preferred embodiment, the fruit has increased levels of a tocopherol. In another preferred embodiment, the fruit has increased levels of a tocotrienol.

The present invention also provides a container of over about 10,000, more preferably about 20,000, and even more preferably about 40,000 seeds where over about 10%, more preferably about 25%, more preferably about 50% and even more preferably about 75% or 90% of the seeds are seeds derived from a plant of the present invention.

The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

Any of the plants or parts thereof of the present invention may be processed to produce a feed, meal, protein or oil preparation. A particularly preferred plant part for this purpose is a seed. In a preferred embodiment the feed, meal, protein or oil preparation is designed for ruminant animals. Methods to produce feed, meal, protein and oil preparations are known in the art. See, for example, U.S. Pat. Nos. 4,957, 748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g. cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g. Fehr, *Principles of Cultivar Development* Vol. 1, pp. 2-3 (1987))).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic known in the art. See, U.S. Pat. No. 5,811,636.

Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Particularly preferred bacteria are *agrobacterium tumefaciens* and *E. coli*.

Methods to transform such cells or organisms are known in the art (EP 0 238 023; Yelton et al., *Proc. Natl. Acad. Sci.* (U.S.A.), 81:1470-1474 (1984); Malardier et al., *Gene*, 78:147-156 (1989); Becker and Guarente, In: Abelson and Simon (eds.), *Guide to Yeast Genetics and Molecular Biology, Method Enzymol.*, Vol. 194, pp. 182-187, Academic Press, Inc., New York; Ito et al., *J. Bacteriology*, 153:163 (1983) Hinnen et al., *Proc. Natl. Acad. Sci.* (U.S.A.), 75:1920 (1978); Bennett and LaSure (eds.), *More Gene Manipulation in fungi*, Academic Press, CA (1991)). Methods to produce proteins of the present invention are also known (Kudla et al., *EMBO*, 9:1355-1364 (1990); Jarai and Buxton, *Current Genetics*, 26:2238-2244 (1994); Verdier, *Yeast*, 6:271-297 (1990; MacKenzie et al., *Journal of Gen. Microbiol.*, 139: 2295-2307 (1993); Hartl et al., *TIBS*, 19:20-25 (1994); Bergenron et al., *TIBS*, 19:124-128 (1994); Demolder et al., *J. Biotechnology*, 32:179-189 (1994); Craig, *Science*, 260: 1902-1903 (1993); Gething and Sambrook, *Nature*, 355:33-45 (1992); Puig and Gilbert, *J. Biol. Chem.*, 269:7764-7771 (1994); Wang and Tsou, *FASEB Journal*, 7:1515-1517 (1993); Robinson et al., *Bio/Technology*, 1:381-384 (1994); Enderlin and Ogrydziak, *Yeast*, 10:67-79 (1994); Fuller et al., *Proc. Natl. Acad. Sci.* (U.S.A.), 86:1434-1438 (1989); Julius et al., *Cell*, 37:1075-1089 (1984); Julius et al., *Cell* 32:839-852 (1983).

In a preferred embodiment, overexpression of a protein or fragment thereof of the present invention in a cell or organism provides in that cell or organism, relative to an untransformed cell or organism with a similar genetic background, an increased level of tocopherols.

In a preferred embodiment, overexpression of a protein or fragment thereof of the present invention in a cell or organism provides in that cell or organism, relative to an untransformed cell or organism with a similar genetic background, an increased level of α-tocopherols.

In a preferred embodiment, overexpression of a protein or fragment thereof of the present invention in a cell or organism provides in that cell or organism, relative to an untransformed cell or organism with a similar genetic background, an increased level of γ-tocopherols.

In another preferred embodiment, overexpression of a protein or fragment thereof of the present invention in a cell or organism provides in that cell or organism, relative to an untransformed cell or organism with a similar genetic background, an increased level of α-tocotrienols.

In another preferred embodiment, overexpression of a protein or fragment thereof of the present invention in a cell or organism provides in that cell or organism, relative to an untransformed cell or organism with a similar genetic background, an increased level of γ-tocotrienols.

Antibodies

One aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NOs: 19-31, 33-38, 39-41, and 46-49 or a fragment thereof. In another embodiment, the antibody specifically binds to a fusion protein comprising an amino acid sequence selected from the amino acid sequence set forth in SEQ ID NOs: 19-33 and 33-38 or a fragment thereof. In another embodiment the antibody specifically binds to a fusion protein comprising an amino acid sequence selected from the amino acid sequence set forth in SEQ ID NOs: 46-49 or a fragment thereof. Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

Nucleic acid molecules that encode all or part of the protein of the invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the invention may be expressed, via recombinant means, to yield proteins or peptides encoded by these nucleic acid molecules.

The antibodies that specifically bind proteins and protein fragments of the invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials that describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988)).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the invention permits the identification of mimetic compounds derived from those molecules. These mimetic compounds may contain a fragment of the protein or peptide or merely a structurally similar region and nonetheless exhibits an ability to specifically bind to antibodies directed against that compound.

Exemplary Uses

Nucleic acid molecules and fragments thereof of the invention may be employed to obtain other nucleic acid molecules from the same species (nucleic acid molecules from corn may be utilized to obtain other nucleic acid molecules from corn). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the invention may also be employed to obtain nucleic acid homologs. Such homologs include the nucleic acid molecules of plants and other organisms, including bacteria and fungi, including the nucleic acid molecules that encode, in whole or in part, protein homologues of other plant species or other organisms, sequences of genetic elements, such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those found in one or more of SEQ ID NOs: 2-17, 50, and 85 and complements thereof because complete complementarity is not needed for stable hybridization. The nucleic acid molecules of the invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (U.S.A.) 83:4143-4146 (1986); Goodchild et al., *Proc. Natl. Acad. Sci.* (U.S.A.) 85:5507-5511 (1988); Wickstrom et al., *Proc. Natl. Acad. Sci.* (U.S.A.) 85:1028-1032 (1988); Holt et al., *Molec. Cell. Biol.* 8:963-973 (1988); Gerwirtz et al., *Science* 242:1303-1306 (1988); Anfossi et al., *Proc. Natl. Acad. Sci.* (U.S.A.) 86:3379-3383 (1989); Becker et al., *EMBO J.* 8:3685-3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263-273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking," or inverse PCR may be used to obtain such sequences (Frohman et al., *Proc. Natl. Acad. Sci.* (U.S.A.) 85:8998-9002 (1988); Ohara et al., *Proc. Natl. Acad. Sci.* (U.S.A.) 86:5673-5677 (1989); Pang et al., *Biotechniques* 22:1046-1048 (1977); Huang et al., *Methods Mol.*

Biol. 69:89-96 (1997); Huang et al., *Method Mol. Biol.* 67:287-294 (1997); Benkel et al., *Genet. Anal.* 13:123-127 (1996); Hartl et al., *Methods Mol. Biol.* 58:293-301 (1996)). The term "chromosome walking" means a process of extending a genetic map by successive hybridization steps.

The nucleic acid molecules of the invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the invention includes nucleic acid molecules that are markers. The markers can be used in a number of conventional ways in the field of molecular genetics. Such markers include nucleic acid molecules SEQ ID NOs: 2-17, 50, and 85, complements thereof, and fragments of either that can act as markers and other nucleic acid molecules of the present invention that can act as markers.

Genetic markers of the invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a population may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39:144-147 (1987); Horn et al., PCT Patent Application WO 91/14003; Jeffreys, European Patent Application 370,719; Jeffreys, U.S. Pat. No. 5,175,082; Jeffreys et al., *Amer. J. Hum. Genet.* 39:11-24 (1986); Jeffreys et al., *Nature* 316:76-79 (1985); Gray et al., *Proc. R. Acad. Soc. Lond.* 243:241-253 (1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 124:783-789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" ("RFLPs") (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al., (PCT Application WO 90/13668; Uhlen, PCT Application WO 90/11369).

Polymorphisms can also be identified by Single Strand Conformation Polymorphism (SSCP) analysis (Elles, *Methods in Molecular Medicine: Molecular Diagnosis of Genetic Diseases*, Humana Press (1996)); Orita et al., *Genomics* 5:874-879 (1989)). A number of protocols have been described for SSCP including, but not limited to, Lee et al., *Anal. Biochem.* 205:289-293 (1992); Suzuki et al., *Anal. Biochem.* 192:82-84 (1991); Lo et al., *Nucleic Acids Research* 20:1005-1009 (1992); Sarkar et al., *Genomics* 13:441-443 (1992). It is understood that one or more of the nucleic acids of the invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407-4414 (1995)). This method allows for the specific co-amplification of high numbers of restriction fragments, which can be visualized by PCR without knowledge of the nucleic acid sequence. It is understood that one or more of the nucleic acids of the invention may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531-6535 (1990)) and cleavable amplified polymorphic sequences (CAPS) (Lyamichev et al., *Science* 260:778-783 (1993)). It is understood that one or more of the nucleic acid molecules of the invention, may be utilized as markers or probes to detect polymorphisms by RAPD or CAPS analysis.

Single Nucleotide Polymorphisms (SNPs) generally occur at greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and non-coding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980); Konieczny and Ausubel, *Plant J.* 4:403-410 (1993)), enzymatic and chemical mismatch assays (Myers et al., *Nature* 313:495-498 (1985)), allele-specific PCR (Newton et al., *Nucl. Acids Res.* 17:2503-2516 (1989); Wu et al., *Proc. Natl. Acad. Sci. USA* 86:2757-2760 (1989)), ligase chain reaction (Barany, *Proc. Natl. Acad. Sci. USA* 88:189-193 (1991)), single-strand conformation polymorphism analysis (Labrune et al., *Am. J. Hum. Genet.* 48: 1115-1120 (1991)), single base primer extension (Kuppuswamy et al., *Proc. Natl. Acad. Sci. USA* 88:1143-1147 (1991)), Goelet U.S. Pat. No. 6,004,744; Goelet U.S. Pat. No. 5,888,819), solid-phase ELISA-based oligonucleotide ligation assays (Nikiforov et al., *Nucl. Acids Res.* 22:4167-4175 (1994), dideoxy fingerprinting (Sarkar et al., *Genomics* 13:441-443 (1992)), oligonucleotide fluorescence-quenching assays (Livak et al., *PCR Methods Appl.* 4:357-362 (1995a)), 5'-nuclease allele-specific hybridization TaqMan™ assay (Livak et al., *Nature Genet.* 9:341-342 (1995)), template-directed dye-terminator incorporation (TDI) assay (Chen and Kwok, *Nucl. Acids Res.* 25:347-353 (1997)), allele-specific molecular beacon assay (Tyagi et al., *Nature Biotech.* 16: 49-53 (1998)), PinPoint assay (Haff and Smirnov, *Genome Res.* 7: 378-388 (1997)), dCAPS analysis (Neff et al., *Plant J.* 14:387-392 (1998)), pyrosequencing (Ronaghi et al, *Analytical Biochemistry* 267:65-71 (1999); Ronaghi et al PCT application WO 98/13523; Nyren et al PCT application WO 98/28440; www.pyrosequencing.com), using mass spectrometry, e.g. the Masscode™ system (Howbert et al PCT application, WO 99/05319; Howbert et al PCT application WO 97/27331; www.rapigene.com; Becker et al PCT application WO 98/26095; Becker et al PCT application; WO 98/12355; Becker et al PCT application WO 97/33000; Monforte et al U.S. Pat. No. 5,965,363), invasive cleavage of oligonucleotide probes (Lyamichev et al *Nature Biotechnology* 17:292-296; www.twt.com), and using high density oligonucleotide arrays (Hacia et al *Nature Genetics* 22:164-167; www.affymetrix.com).

Polymorphisms may also be detected using allele-specific oligonucleotides (ASO), which, can be for example, used in combination with hybridization based technology including southern, northern, and dot blot hybridizations, reverse dot blot hybridizations and hybridizations performed on microarray and related technology.

The stringency of hybridization for polymorphism detection is highly dependent upon a variety of factors, including length of the allele-specific oligonucleotide, sequence composition, degree of complementarity (i.e. presence or absence of base mismatches), concentration of salts and other factors such as formamide, and temperature. These factors are important both during the hybridization itself and during subsequent washes performed to remove target polynucleotide that is not specifically hybridized. In practice, the conditions of the final, most stringent wash are most critical. In addition, the amount of target polynucleotide that is able to hybridize to the allele-specific oligonucleotide is also governed by such factors as the concentration of both the ASO and the target polynucleotide, the presence and concentration of factors that act to "tie up" water molecules, so as to effectively concentrate the reagents (e.g., PEG, dextran, dextran sulfate, etc.), whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula: $T_m = 81.5 + 16.6 \times (\log 10[Na+]) + 0.41 \times (\% \, G+C) - 675/n$; where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target polynucleotide of the correct allele and a target polynucleotide of the incorrect allele. Preferably, there will be at least a two-fold differential between the signal produced by the ASO hybridizing to a target polynucleotide of the correct allele and the level of the signal produced by the ASO cross-hybridizing to a target polynucleotide of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target polynucleotide of the correct allele and the level of the signal produced by the ASO cross-hybridizing to a target polynucleotide of the incorrect allele.

While certain methods for detecting polymorphisms are described herein, other detection methodologies may be utilized. For example, additional methodologies are known and set forth, in Birren et al., *Genome Analysis*, 4:135-186, *A Laboratory Manual. Mapping Genomes*, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R. G. Landes Co., Georgetown, Tex., and Academic Press, San Diego, Calif.

(1996); *The Corn Handbook*, Freeling and Walbot, eds., Springer-Verlag, New York, N.Y. (1994); *Methods in Molecular Medicine: Molecular Diagnosis of Genetic Diseases*, Elles, ed., Humana Press, Totowa, N.J. (1996); Clark, ed., *Plant Molecular Biology: A Laboratory Manual*, Clark, ed., Springer-Verlag, Berlin, Germany (1997).

Factors for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185-199 (1989) and the interval mapping, based on maximum likelihood methods described by Lander and Botstein, *Genetics* 121:185-199 (1989) and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185-199 (1989) and further described by Arús and Moreno-González, *Plant Breeding*, Hayward et al., (eds.) Chapman & Hall, London, pp. 314-331 (1993).

In a preferred embodiment of the present invention the nucleic acid marker exhibits a LOD score of greater than 2.0, more preferably 2.5, even more preferably greater than 3.0 or 4.0 with the trait or phenotype of interest. In a preferred embodiment, the trait of interest is altered tocopherol levels or compositions or altered tocotrienol levels or compositions.

Additional models can be used. Many modifications and alternative approaches to interval mapping have been reported, including the use non-parametric methods (Kruglyak and Lander, *Genetics* 139:1421-1428 (1995)). Multiple regression methods or models can be also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447-1455 (1994), and Zeng, *Genetics* 136:1457-1468 (1994). Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng, *Genetics* 136:1457-1468 (1994)). These models can be extended to multi-environment experiments to analyze genotype-environment interactions (Jansen et al., *Theo. Appl. Genet.* 91:33-37 (1995)).

It is understood that one or more of the nucleic acid molecules of the invention may be used as molecular markers. It is also understood that one or more of the protein molecules of the invention may be used as molecular markers.

In a preferred embodiment, the polymorphism is present and screened for in a mapping population, e.g. a collection of plants capable of being used with markers such as polymorphic markers to map genetic position of traits. The choice of appropriate mapping population often depends on the type of marker systems employed (Tanksley et al., *J. P. Gustafson and R. Appels* (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large number of polymorphisms when compared to progeny in a narrow cross (adapted×adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather, Measurement of Linkage in Heredity: Methuen and Co., (1938)). In the case of dominant markers, progeny tests (e.g., $F_3$, $BCF_2$) are required to identify the heterozygotes, in order to classify the population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter. *Proc. Natl. Acad. Sci.* (U.S.A.) 89:1477-1481 (1992)). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (U.S.A.) 89:1477-1481 (1992)). Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as a mapping population. In mapping with NILs, only a portion of the polymorphic loci is expected to map to a selected region.

Bulk segregant analysis (BSA) is a method developed for the rapid identification of linkage between markers and traits of interest (Michelmore et al., *Proc. Natl. Acad. Sci U.S.A.* 88:9828-9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

In an aspect of the present invention, one or more of the nucleic molecules of the present invention are used to determine the level (i.e., the concentration of mRNA in a sample, etc.) in a plant (preferably canola, corn, *Brassica campestris*, oilseed rape, rapeseed, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether an Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. Derived from root, seed, flower, leaf, stem or pollen etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.* 101:477-484 (1984); Angerer et al., *Dev. Biol.* 112:157-166 (1985); Dixon et al., *EMBO J.* 10:1317-1324 (1991)). In situ hybridization may be used to measure the steady-state level of RNA accumulation (Hardin et al., *J. Mol. Biol.* 202:417-431 (1989)). A number of protocols have been devised for in situ hybridization, each with tissue preparation, hybridization and washing conditions (Meyerowitz, *Plant Mol. Biol. Rep.* 5:242-250 (1987); Cox and Goldberg, In: *Plant Molecular Biology: A Practical Approach*, Shaw (ed.), pp. 1-35, IRL Press, Oxford (1988); Raikhel et al., *In situ RNA hybridization in plant tissues, In: Plant Molecular Biology Manual*, vol. B9:1-32, Kluwer Academic Publisher, Dordrecht, Belgium (1989)).

In situ hybridization also allows for the localization of proteins within a tissue or cell (Wilkinson, *In Situ Hybridization*, Oxford University Press, Oxford (1992); Langdale, *In Situ Hybridization In: The Corn Handbook*, Freeling and Walbot (eds.), pp. 165-179, Springer-Verlag, New York (1994)). It is understood that one or more of the molecules of the invention, preferably one or more of the nucleic acid molecules or fragments thereof of the invention or one or more of the antibodies of the invention may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species (Griffor et al., *Plant Mol. Biol.* 17:101-109 (1991); Gustafson et al., *Proc. Natl. Acad. Sci.* (U.S.A.) 87:1899-1902 (1990); Mukai and Gill, *Genome* 34:448-452 (1991); Schwarzacher and Heslop-Harrison, *Genome* 34:317-323 (1991); Wang et al., *Jpn. J. Genet.* 66:313-316 (1991); Parra and Windle, *Nature Genetics* 5:17-21 (1993)). It is understood that the nucleic acid molecules of the invention may be used as probes or markers to localize sequences along a chromosome.

Another method to localize the expression of a molecule is tissue printing. Tissue printing provides a way to screen, at the same time on the same membrane many tissue sections from different plants or different developmental stages (Yomo and Taylor, *Planta* 112:35-43 (1973); Harris and Chrispeels, *Plant Physiol.* 56:292-299 (1975); Cassab and Varner, *J. Cell. Biol.* 105:2581-2588 (1987); Spruce et al., *Phytochemistry* 26:2901-2903 (1987); Barres et al., *Neuron* 5:527-544 (1990); Reid and Pont-Lezica, *Tissue Printing Tools for the Study of Anatomy, Histochemistry and Gene Expression*, Academic Press, New York, N.Y. (1992); Reid et al., *Plant Physiol.* 93:160-165 (1990); Ye et al., *Plant J.* 1:175-183 (1991)).

One skilled in the art can refer to general reference texts for detailed descriptions of known techniques discussed herein or equivalent techniques. These texts include *Current Protocols in Molecular Biology* Ausubel, et al., eds., John Wiley & Sons, N.Y. (1989), and supplements through September (1998), *Molecular Cloning, A Laboratory Manual*, Sambrook et al, 2$^{nd}$ Ed., Cold Spring Harbor Press, Cold Spring Harbor, N.Y. (1989), *Genome Analysis: A Laboratory Manual 1: Analyzing DNA*, Birren et al., Cold Spring Harbor Press, Cold Spring Harbor, N.Y. (1997); *Genome Analysis: A Laboratory Manual 2: Detecting Genes*, Birren et al., Cold Spring Harbor Press, Cold Spring Harbor, N.Y. (1998); *Genome Analysis: A Laboratory Manual 3: Cloning Systems*, Birren et al., Cold Spring Harbor Press, Cold Spring Harbor, N.Y. (1999); *Genome Analysis: A Laboratory Manual 4: Mapping Genomes*, Birren et al., Cold Spring Harbor Press, Cold Spring Harbor, N.Y. (1999); *Plant Molecular Biology: A Laboratory Manual*, Clark, Springer-Verlag, Berlin, (1997), *Methods in Plant Molecular Biology*, Maliga et al., Cold Spring Harbor Press, Cold Spring Harbor, N.Y. (1995). These texts can, of course, also be referred to in making or using an aspect of the invention. It is understood that any of the agents of the invention can be substantially purified and/or be biologically active and/or recombinant.

Having now generally described the invention, the same will be more readily understood through reference to the following examples that are provided by way of illustration, and are not intended to be limiting of the present invention, unless specified.

EXAMPLE 1

A DNA sequence of gamma-tocopherol methyltransferase from *Arabidopsis thaliana* (NCBI General Identifier Number 4106537) is used to search databases for plant sequences with homology to GMT using BLASTN (Altschul et al., *Nucleic Acids Res.* 25:3389-3402 (1997); see also www.ncbi.nlm.nih.gov/BLAST/). Results are shown in table 1, below.

TABLE 1

BLAST RESULTS FOR PLANT SEQUENCES ENCODING POLYPEPTIDES HOMOLOGOUS TO *ARABIDOPSIS* GAMMA-TOCOPHEROL METHYLTRANSFERASE

| Sequences producing significant alignments: | Score (bits) | E Value |
|---|---|---|
| *Arabidopsis thaliana* (Columbia ecotype) | 707 | 0.0 |
| *Brassica napus* S8 clone | 611 | e−179 |
| *Brassica napus* P4 clone | 605 | e−177 |
| cotton GMT | 459 | e−133 |
| soybeanGMT2 | 454 | e−132 |
| soybeanGMT1 | 453 | e−132 |
| soybeanGMT3 | 453 | e−131 |
| Marigold GMT (*Tagetes erecta*) | 446 | e−129 |
| tomato GMT | 441 | e−128 |
| *cuphea* GMT | 440 | e−127 |
| Rice GMT | 430 | e−124 |
| corn GMT | 428 | e−123 |
| *sorghum* bicolor GMT | 328 | 9e−94 |

The protein identity of these sequences compared to one another is listed in table 2.

TABLE 2

PROTEIN IDENTITY TABLE OF PLANT SEQUENCES ENCODING POLYPEPTIDES HOMOLOGOUS TO GAMMA-TOCOPHEROL METHYLTRANSFERASE

| | *Arabidopsis* GMT (gi 4106537) | *Arabidopsis* Columbia | *Brassica* S8 | *Brassica* P4 | *Cuphea pulcherrima* | *Gossypium hirsutum* | *Zea mays* | *Oryza sativa* | *Sorghum bicolor* | *Tagetes erecta* |
|---|---|---|---|---|---|---|---|---|---|---|
| *Arabidopsis* GMT (gi 4106537) | 100% 348/348 | | | | | | | | | |
| *Arabidopsis* Columbia GMT | 99% 347/348 | 100% 348/348 | | | | | | | | |
| *Brassica* S8 GMT | 88% 309/350 | 88% 308/350 | 100% 347/347 | | | | | | | |
| *Brassica* P4 GMT | 87% 304/349 | 86% 303/349 | 96% 335/348 | 100% 347/347 | | | | | | |
| *Cuphea pulcherrima* GMT | 72% 213/295 | 71% 212/295 | 68% 216/314 | 68% 213/313 | 100% 376/376 | | | | | |
| *Gossypium hirsutum* GMT | 67% 218/323 | 67% 219/323 | 71% 225/316 | 67% 231/342 | 71% 212/296 | 100% 345/345 | | | | |
| *Zea mays* GMT | 63% 210/333 | 62% 209/333 | 65% 217/332 | 63% 211/330 | 71% 208/290 | 67% 223/331 | 100% 352/352 | | | |
| *Oryza sativa* GMT | 63% 212/332 | 63% 212/332 | 67% 214/319 | 62% 220/352 | 70% 204/291 | 65% 226/347 | 76% 279/364 | 100% 364/364 | | |
| *Sorghum bicolor* GMT | 72% 154/212 | 72% 153/212 | 75% 159/212 | 73% 156/212 | 74% 157/212 | 78% 166/212 | 96% 208/215 | 91% 193/212 | 100% 215/215 | |
| *Tagetes erecta* GMT | 69% | 70% | 69% | 68% | 72% | 70% | 70% | 71% | 77% | 100% |

TABLE 2-continued

PROTEIN IDENTITY TABLE OF PLANT SEQUENCES ENCODING POLYPEPTIDES HOMOLOGOUS TO GAMMA-TOCOPHEROL METHYLTRANSFERASE

| | Arabidopsis GMT (gi 4106537) | Arabidopsis Columbia | Brassica S8 | Brassica P4 | Cuphea pulcherrima | Gossypium hirsutum | Zea mays | Oryza sativa | Sorghum bicolor | Tagetes erecta |
|---|---|---|---|---|---|---|---|---|---|---|
| Lycopersicon esculentum GMT | 218/312 68% | 219/312 | 214/309 | 211/310 | 210/291 | 209/297 | 216/305 | 219/308 | 165/212 | 310/310 |
| Glycine max GMT1 | 212/311 73% | | | | | | | | | |
| Glycine max GMT2 | 218/297 70% | | | | | | | | | |
| Glycine max GMT3 | 225/318 75% 220/290 | | | | | | | | | |

A protein sequence of the *Synechocystis* GMT (NCBI General Identifier Number 1001725) is used in a BlastP search against predicted ORFs from other cyanobacteria at the ERGO website (www.integratedgenomics.com/IGwit/).

Two sequences with substantial homology to the *Synechocystis* GMT are found from two cyanobacteria species. These sequences are annotated as having a function of delta (24)-sterol C-methyltransferase (EC 2.1.1.41).

| | E-Value | Score |
|---|---|---|
| Nostoc punctiforme | 1e-105 | 375 |
| Anabaena sp. | 1e-101 | 361 |

TABLE 3

CYANOBACTERIA GMT CLUSTAL W (1.8) MULTIPLE SEQUENCE ALIGNMENT

```
Nostoc punctiforme      ------------------------
MSATLYQQIQQFYDASSGLWEQIWGEHMHHG
Anabaena sp.            ------------------------
MSATLYQQIQQFYDASSGLWEEIWGEHMHHG
Synechocystis
MVYHVRPKHALFLAFYCYFSLLTMASATIASADLYEKINKNFYDDSSGLWEDVWGEHMHHG
                              ** **::*::***
******::********

Nostoc punctiforme YYGADGTQKKDRRQAQIDLIEELLNWAGVQAAED---
LDVGCGIGGSSLYLAQKFNAKA
Anabaena sp.       YYGADGTEQKNRRQAQIDLIEELLTWAGVQTAEN---
LDVGCGIGGSSLYLAGKLNAKA
Synechocystis
YGPHGTYRIDRRQAQIDLIKELLAWAVPQNSAKPRKILDLGCGIGGSSLYLAQQHQAEV
                 ***..** : :*********:*** **  *  :  .  ***:************ :
*:.

Nostoc punctiforme
GITLSPVQAARATERALEANLSLRTQFQVANAQAMPFADDSFDLVWSLESGEHMPDKTK
Anabaena sp.
GITLSPVQAARATERAKEAGLSGRSQFLVANAQAMPFDDNSFDLVWSLESGEHMPDKTK
Synechocystis
MGASLSPVQVERAGERARALGLGSTCQFQVANALDLPFASDSFDWVWSLESGEHMPNKAQ
          *  :*****. ** ***    .*.     ** ****  :**  .:***
**********.*::

Nostoc punctiforme FLQECYRVLKPGGKLIMVTWCHRPTD--
ESPLTADEEKHLQDIYRVYCLPYVISLPEYEA
Anabaena sp.       FLQECYRVLKPGGKLIMVTWCHRPTD--
KTPLTADEKKHLEDIYRVYCLPYVISLPEYEA
Synechocystis
FLQEAWRVLKPGGRLILATWCHRPIDPGNGPLTADERRHLQAIYDVYCLPYVVSLPDYEA
                 ****.:*******:**:.****** *   ******.:**: **
*******:***:***

Nostoc punctiforme
IAHQLPLHNIRTADWSTAVAPFWNVVIDSAFTPQALWGLLNAGWTTIQGALSLGLMRRGY
Anabaena ap.
IARQLPLNNIRTADWSQSVAQFWNIVIDSAFTPQAIFGLLRAGWTTIQGALSLGLMRRGY
Synechocystis
```

TABLE 3-continued

CYANOBACTERIA GMT CLUSTAL W (1.8) MULTIPLE SEQUENCE ALIGNMENT

```
IARECGFGEIKTADWSVAVAPFWDRVIESAFDPRVLWALGQAGPKIINAALCLRLMKWGY
             **::   : :*:*****  :** **:  **:***  *:.::.*  .** .  *:.**.* **:
**

Nostoc punctiforme  ERGLIRFGLLCGNK---  (SEQ ID NO: 39)
Anabaena sp.        ERGLIRFGLLCGDK---  (SEQ ID NO: 40)
Synechocystis       ERGLVRFGLLTGIKPLV  (SEQ ID NO: 41)
                    ****:***** * *
```

The sequence of the *Synechocystis* MT1 (NCBI General Identifier Number 1653572) is used in a blast search against ESTs of other cyanobacteria at the ERGO website (www.integratedgenomics.com/IGwit/).

Three sequences with substantial homology to the *Synechocystis* MT1 are found from three cyanobacteria species. These sequences are all annotated as having a function of DELTA(24)-STEROL C-METHYLTRANSFERASE (EC 2.1.1.41)

| BlastP | | SCORE |
|---|---|---|
| *Anabaena* sp. | 1e−144 | 504 |
| *Synechococcus* sp. | 6e−98 | 350 |
| *Prochlorococcus marinus* | 2e−84 | 304 |

EXAMPLE 2

Constructs are prepared to direct expression of the *Arabidopsis*, P4 and S8 *Brassica napus, Cuphea pulcherrima*, and *Gossypium hirsutum* GMT sequences in plants. The coding region of each GMT is amplified from either the appropriate EST clone or cDNA, as appropriate. Double stranded DNA sequence is obtained of all PCR products to verify that no errors are introduced by the PCR amplification.

An S8 *Brassica* GMT coding sequence is amplified from *Brassica napus* leaf cDNA as follows: PolyA$^+$ RNA is isolated from *Brassica napus* (var. Quantum) leaf tissue using an adapted biotin/streptavadin procedure based on the "mRNA Capture Kit" by Roche Molecular Biochemicals (Indianapolis, Ind.). Young leaf tissue is homogenized in CTAB buffer (50 mM Tris-HCl pH 9, 0.8M NaCl, 0.5% CTAB, 10 mM EDTA), extracted with chloroform, and pelleted. As specified

TABLE 4

CYANOBACTERIA MT1 CLUSTAL W (1.8) MULTIPLE SEQUENCE ALIGNMENT

```
Synechocystis     MPEYLLLLPAGLISLSLAIAAGLYLLTARGYQSSDSVANAYDQWTEDGILEYYWGDHIHLG
Anabaena          -MSWLFSTLVFFLTLLTAGIALYLITARRYQSSNSVANSYDQWTEDGILEFYWGEHIHLG
Synechococcus     ---MLGLLLLTGAAGATALLIWLQRDRRYHSSDSVAAAYDAWTDDQLLERLWGDHHIHLG
Prochlorococcus   MSIFLISSLVIFLTLLFSSLILWRINTRKYISSRTVATAYDSWTQDKLLERLWGEHIHLG
                          *      :      . ::    * * ** :**  :** **:*  :**    **:*:***

Synechocystis     HYGDPPVAKDFIQSKIDFVHAMAQWGGLDTLPPGTTVLDVGCGIGGSSRILAKDYGFNVT
Anabaena          HYGSPPQRKDFLVAKSDFVHEMVRWGGLDKLPPGTTLLDVGCGIGGSSRILARDYGFAVT
Synechococcus     HYGNPPGSVDFRQAKEAFVHELVRWSGLDQLPRGSRVLDVGCGIGGSARILARDYGLDVL
Prochlorococcus   FYP-LNKNIDFREAKVQFVHELVSWSGLDKLPRGSRILDVGCGIGGSSRILANYYGFNVT
                  .*      **  :*  ***  :. *.*** **  *:  :********** :****. **: *

Synechocystis     GITISPQQVKRATELTPPDVTAKFAVDDAMALSFPDGSFDVVWSVEAGPHMPDKAVFAKE
Anabaena          GITISPQQVQRAQELTPQELNAQFLVDDAMALSFPDNSFDVVWSIEAGPHMPDKAIFAKE
Synechococcus     GVSISPAQIRRATELTPAGLSCRFEVMDALNLQLPDRQFDAVWTVEAGPHMPDKQRFADE
Prochlorococcus   GITISPAQVKRAKELTPYECKDNFKVMDALDLKFEEGIFDGVWSVEAGAHMNNKTKFADQ
                  *::*** *::** ****     ...* * **: *.:  :  ** **:***.** :*  **.:

Synechocystis     LLRVVKPGGILVVADWNQRDDRQVPLNFWEKPVMRQLLDQWSHPAFASIEGFAENLEATG
Anabaena          LMRVLKPGGIMVLADWNQRDDRQKPLNFWEKPVMQQLLDQWSHPAFSSIEGFSELLAATG
Synechococcus     LLRVLRPGGCLAAADWNRRAPKDGAMNSTERWVMRQLLNQWAHPEFASISGFRANLEASP
Prochlorococcus   MLRTLRPGGYLALADWNSRDLQKQPPSMIEKIILKQLLEQWVHPKFISINEFSSILINNK
                  ::*.::***  :. ****  *   : .  . *: :::***:** ** **. *   *  .

Synechocystis     LVEGQVTTADWTVPTLPAWLDTIWQGIIRPQGWLQYGIRGFIKSVREVPTILLMRLAFGV
Anabaena          LVEGEVITADWTKQTLPSWLDSIWQGIVRPEGLVRGGLSGFIKSLREVPTLLLMRLAFGT
Synechococcus     HQRGLISTGDWTLATLPSWFDSIAEGLRRPWAVLGLGPKAVLQGLRETPTLLLMHWAFAT
Prochlorococcus   NSSGQVISSNWNSFTNPSWFDSIFEGMRRPNSILSLGPGAIIKSIREIPTILLMDWAPKK
                   *  :  :..*.  * *:*:*:*  :*: **  . :    *     ..::.:** **:***  **

Synechocystis     GLCRFGMFKAVRKNATQA-------------  (SEQ ID NO: 46)
Anabaena          GLCRFGMFRALRADTVRSSAEQTSAIKVAQK  (SEQ ID NO: 47)
Synechococcus     GLMQFGVFRLSR-------------------  (SEQ ID NO: 48)
Prochlorococcus   GLMEFGVYKCRG-------------------  (SEQ ID NO: 49)
                  ** .**:::
``` by the manufacturer's instructions, polyA+ RNA in the soluble fraction is hybridized to biotin-labeled oligo-dT, immobilized on streptavadin-coated PCR tubes and washed. First strand cDNA is synthesized using the "1$^{st}$ strand cDNA synthesis kit for RT-PCR" (Roche Molecular Biochemicals) in a 50 µl volume according to the manufacturer's protocol. Following the cDNA synthesis, the soluble contents of the tube are replaced with equal volume amplification reaction mixture. Components of the mixture at final concentration consisted of: 1× Buffer 2 (EXPAND High Fidelity PCR System, Roche Molecular Biochemicals), 200 µM dNTPs, 0.5 units RNAseH, 300 nM each synthetic oligonucleotide primers #16879 (SEQ ID NO: 51) and #16880 (SEQ ID NO: 52) and 0.4 µl EXPAND High Fidelity Polymerase (Roche Molecular Biochemicals).

A GMT gene is PCR amplified for 30 cycles using a "touchdown" cycling profile: 15 min pre-incubation at 37° C. followed by a 3 min pre-incubation at 94° C., during which EXPAND polymerase is spiked into the mix. The product is then amplified for 15 cycles consisting of denaturation at 94° C. for 30 sec, annealing at 65° C. for 30 sec, and elongation at 72° C. for 1.5 min. The annealing temperature is decreased by 1° C. per cycle for each of the previous 15 cycles. An additional 15 cycles followed, consisting of 94° C. for 30 sec, 50° C. for 30 sec, and 72° C. for 1.5 min, followed by a 7 min hold at 72° C.

Figure 2:
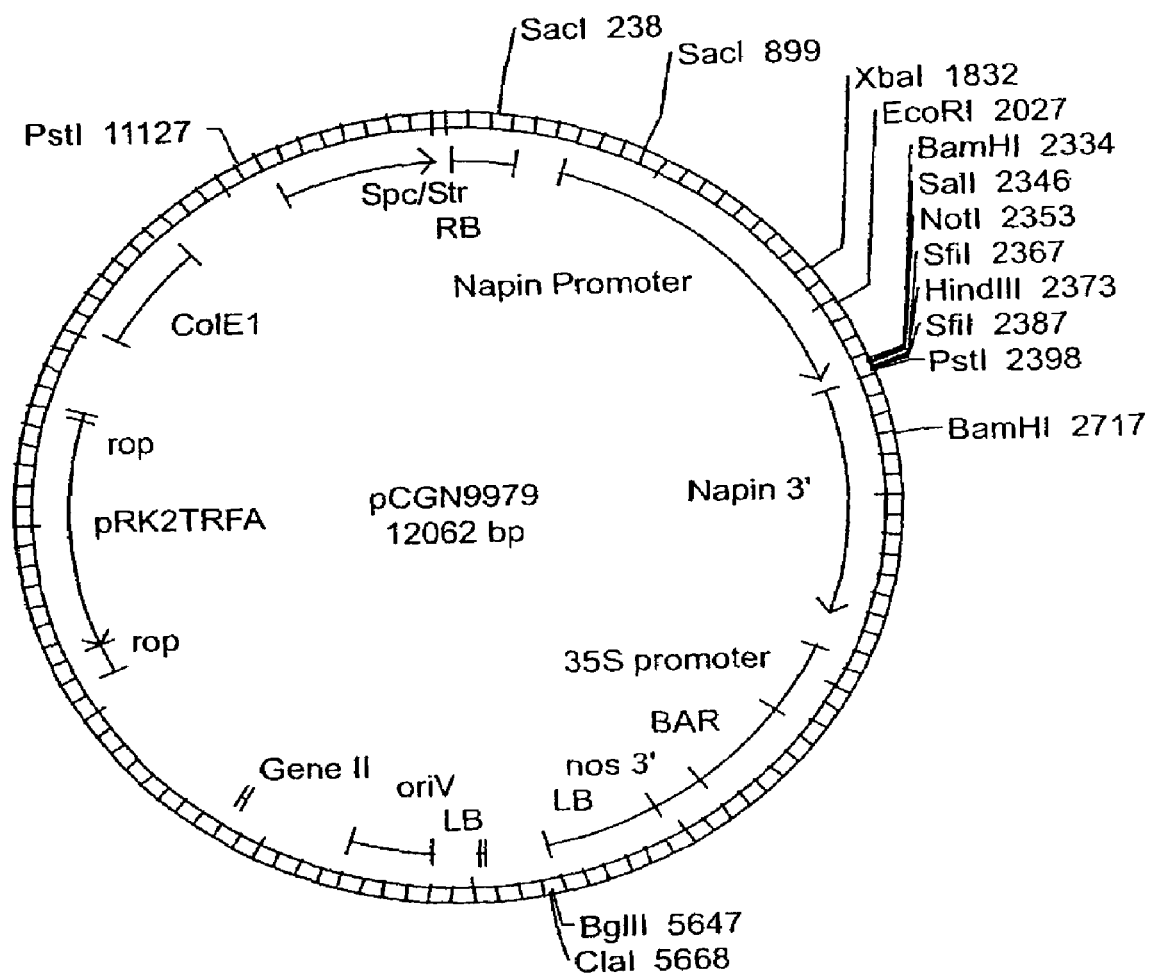
FIG. 2 is a schematic of construct pCGN9979.

The resulting PCR product is desalted using the Pharmacia "MICROSPIN S-400 HR Column" (Pharmacia, Uppsala, Sweden) then cloned into the vector pCR2.1 using the "TOPO TA Cloning® Kit" (Invitrogen, Carlsbad, Calif.) according to manufacturer's instructions. The resultant intermediate plasmid is named pMON67178 and confirmed by DNA sequencing. A pMON67178 intermediate plasmid is digested with the restriction endonucleases NotI and Sse83871 to liberate a S8 *Brassica* GMT insert, which is then gel-purified using the "QIAQUICK Gel Extraction Kit" (QIAGEN Inc., Valencia, Calif.). The vector pCGN9979 (FIG. 2) is prepared by digesting with NotI and Sse83871 endonucleases. Enzymes are subsequently removed using "StrataClean Resin™" (Stratagene, La Jolla, Calif.) followed by "MicroSpin S-400 HR Column" treatment (Pharmacia, Uppsala, Sweden). A GMT insert is ligated into the pCGN9979 vector, resulting in the formation of the binary construct pMON67170.

An *Arabidopsis* GMT coding sequence is amplified from *Arabidopsis thaliana*, ecotype Columbia using the same methodology as described above for the S8 *Brassica* GMT with the exceptions that RNAseH is not added to the amplification reaction mixture, and the synthetic oligonucleotide primers are #16562 (SEQ ID NO: 75) and #16563 (SEQ ID NO: 76). The resulting PCR product is desalted using the Pharmacia "MICROSPIN S-400 HR Column" (Pharmacia, Uppsala, Sweden) then cloned into the vector pCR2.1 using the "TOPO TA Cloning® Kit" (Invitrogen, Carlsbad, Calif.) according to manufacturer's instructions. The resultant intermediate plasmid is named pMON67155 and confirmed by DNA sequencing. The pMON67155 intermediate plasmid is digested with the restriction endonucleases NotI and Sse83871 to liberate an *Arabidopsis thaliana* GMT insert, which is then gel-purified using the "QIAQUICK Gel Extraction Kit" (QIAGEN Inc., Valencia, Calif.). The vector pCGN9979 is prepared by digesting with NotI and Sse83871 endonucleases. Enzymes are subsequently removed using "StrataClean Resin™" (Stratagene, La Jolla, Calif.) followed by "MICROSPIN S-400 HR Column" treatment (Pharmacia, Uppsala, Sweden). A GMT insert is ligated into the pCGN9979 vector, resulting in the formation of the binary construct pMON67156.

A P4 *Brassica* GMT coding sequence is amplified from *Brassica napus* leaf cDNA using the same methodology as described above for the S8 *Brassica* GMT with the exceptions that RNAseH is not added to the amplification reaction mixture, and the synthetic oligonucleotide primers are #16655 (SEQ ID NO: 53) and #16654 (SEQ ID NO: 54). A "touchdown" cycling conditions consisted of a pre-incubation for 3 min at 94° C., during which 0.4 µl EXPAND polymerase is spiked into the mix. The product is then amplified with 15 cycles of denaturation at 94° C. for 30 sec, annealing at 60° C. for 30 sec, and elongation at 72° C. for 1.5 min. The annealing temperature is decreased by 1° C. per cycle for each of the previous 15 cycles. An additional 15 cycles followed, consisting of 94° C. for 30 sec, 45° C. for 30 sec, and 72° C. for 1.5 min, followed by a 7 min hold at 72° C.

The resulting PCR product is desalted using the Pharmacia "MicroSpin™ S-400 HR Column" (Pharmacia, Uppsala, Sweden) then cloned into the GATEWAY vector pDONR™201 using the "PCR Cloning System with GATEWAY Technology" (Life Technologies, a Division of Invitrogen Corporation, Rockville, Md.), according to the manufacturer's instructions. The ensuing plasmid pMON68751 is confirmed by DNA sequencing.

A P4 *Brassica* GMT is then cloned from the pMON68751 donor vector into the pMON67150 destination vector, which is the GATEWAY-compatible version of the pCGN9979 Napin binary. The "*E. coli* Expression Systems with GATEWAY Technology" kit (Life Technologies, a Division of Invitrogen Corporation, Rockville, Md.) is used according to the manufacturer's instructions to create the expression clone pMON67159.

A *Cuphea pulcherrima* GMT coding sequence is amplified from the EST clone LIB3792-031-Q1-K1-F3 using the synthetic oligonucleotide primers #16658 (SEQ ID NO: 55) and #16659 (SEQ ID NO: 56). 1.01 µl of EST template is used for the *Cuphea* GMT amplification reaction. Otherwise, amplification conditions and cycling parameters are identical to those of P4 *Brassica* GMT.

Using the same GATEWAY procedure as described above for the P4 *Brassica* GMT coding region, a *Cuphea* GMT PCR product is cloned into the pDONR™201 vector to create pMON68752, then subcloned into the Napin expression vector pMON67150 to create pMON67158.

A *Gossypium hirsutum* GMT coding sequence is amplified from the EST clone LIB3584-003-P1-K1-A1 using the synthetic oligonucleotide primers #16681 (SEQ ID NO: 57) and #16682 (SEQ ID NO: 58). 0.5 µl of EST template is used for the *Gossypium* GMT amplification reaction. Otherwise, amplification conditions and cycling parameters are identical to those of P4 *Brassica* GMT.

Using the same GATEWAY procedure as described above for the P4 *Brassica* GMT coding region, a *Gossypium* GMT PCR product is cloned into the pDONR™201 vector to create pMON67161, then subcloned into a napin expression vector pMON67150 to create pMON67160.

The napin cassette derived from pCGN3223 (described in U.S. Pat. No. 5,639,790) is used to drive the expression of GMT sequences in seeds. GMT sequences are cloned into the multiple cloning site of the napin cassette using either a NotI/Sse83871 digest (pMON67178) or the gateway cloning system (Gibco BRL) in a binary vector suitable for plant transformation (pCGN9979).

The resulting plasmids containing the gene of interest in the plant binary transformation vector under the control of the napin promoter are labeled as follows pMON67156 (*Arabidopsis thaliana*, Columbia ecotype), pMON67170 (S8 *Brassica napus* GMT), pMON67159 (P4 *Brassica napus* GMT), pMON 67158 (*Cuphea pulcherrima* GMT), and pMON 67160 (*Gossypium hirsutum* GMT).

Figure 23:
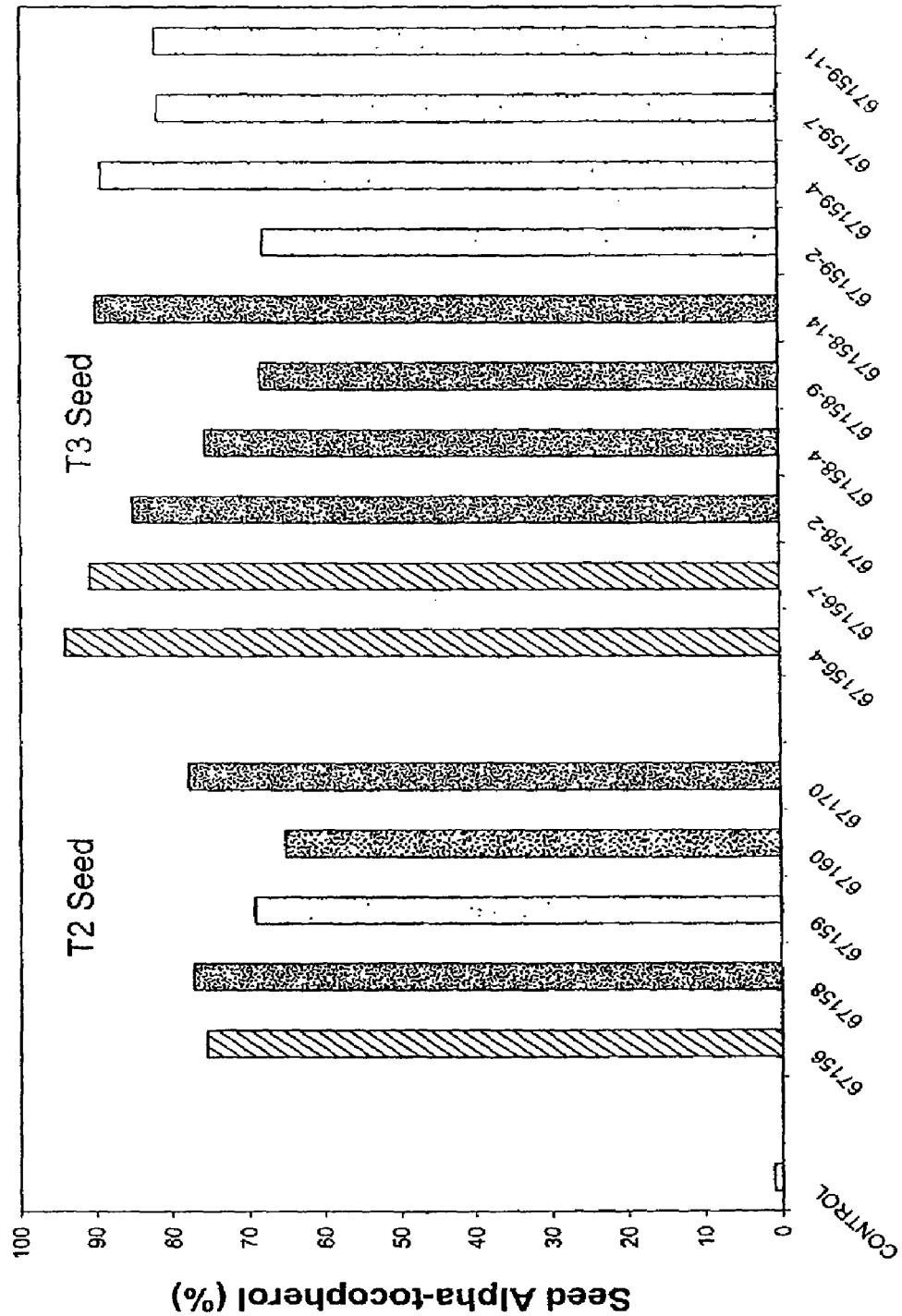
FIG. 23 is a graph representing the average seed γ-tocopherol level in transformed *Arabidopsis* plants harboring expression constructs for the *Arabidopsis thaliana* ecotype Columbia GMT (67156), the *cuphea* GMT (67158), the *Brassica* P4 GMT (67159), the cotton GMT (67160), and the *Brassica* S8 GMT (67170).

The plant binary constructs described above are used in *Arabidopsis thaliana* plant transformation to direct the expression of the gamma-methyltransferases in the embryo. Binary vector constructs are transformed into ABI strain *Agrobacterium* cells by the method of Holsters et al. *Mol. Gen. Genet.* 163:181-187 (1978). Transgenic *Arabidopsis thaliana* plants are obtained by *Agrobacterium*-mediated transformation as described by Valverkens et al., *Proc. Nat. Acad. Sci.* 85:5536-5540 (1988), Bent et al., *Science* 265: 1856-1860 (1994), and Bechtold et al., *CR. Acad. Sci., Life Sciences* 316:1194-1199 (1993). Transgenic plants are selected by sprinkling the transformed $T_1$ seeds directly onto soil and then vernalizing them at 4° C. in the absence of light for 4 days. The seeds are then transferred to 21° C., 16 hours light and sprayed with a 1:200 dilution of FINALE (Basta) at 7 days and 14 days after seeding. Transformed plants are grown to maturity and the $T_2$ seed that is produced is analyzed for tocopherol content. FIGS. 21*a*, 21*b*, 22*a*, and 22*b* show the tocopherol analysis from T2 seed of transgenic *Arabidopsis thaliana* plants expressing GMTs from different sources under the control of the napin seed-specific promoter. FIG. 23 is a graph showing average seed α-tocopherol levels for various lines of transformed plants. In FIG. 23, the plant lines shown have the following GMT sequence origins: 67156=*Arabidopsis* GMT, 67158=*Cuphea* GMT, 67159=*Brassica* (P4)GMT, 67160=Cotton GMT, and 67170=*Brassica* (S8) GMT. Table 5 below gives specific tocopherol level results for various transformed and control plant lines.

TABLE 5

| ng α toco/mg seed | ng β toco/mg seed | ng γ toco/mg seed | ng δ toco/mg seed | ng total toco/mg seed | Line Number | A. description | Gen. | % Alpha | Avg. Alpha % |
|---|---|---|---|---|---|---|---|---|---|
| 6.64 | 15.28 | 494.91 | 13.16 | 529.99 | 9979-36 | 9979 = vector control | | 1.3 | 1.3 |
| 6.07 | 15.69 | 490.82 | 13.66 | 526.23 | 9979-37 | 9979 = vector control | | 1.2 | |
| 6.57 | 16.79 | 492.59 | 12.37 | 528.32 | 9979-38 | 9979 = vector control | | 1.2 | |
| 7.76 | 17.16 | 513.41 | 15.76 | 554.09 | 9979-39 | 9979 = vector control | | 1.4 | |
| 8.44 | 15.62 | 508.64 | 15.94 | 548.64 | 9979-40 | 9979 = vector control | | 1.5 | |
| 291.45 | 21.86 | 180.41 | 4.96 | 498.69 | 67156-8 | 67156 = napin GMT arab | T2 | 58.4 | 75.5 |
| 275.80 | 20.49 | 141.25 | 3.05 | 440.59 | 67156-6 | 67156 = napin GMT arab | T2 | 62.6 | |
| 289.41 | 21.00 | 138.56 | 3.73 | 452.70 | 67156-12 | 67156 = napin GMT arab | T2 | 63.9 | |
| 312.57 | 22.56 | 128.32 | 2.91 | 466.36 | 67156-5 | 67156 = napin GMT arab | T2 | 67.0 | |
| 302.71 | 20.69 | 113.96 | 2.53 | 439.89 | 67156-3 | 67156 = napin GMT arab | T2 | 68.8 | |
| 329.09 | 24.38 | 118.80 | 3.37 | 475.65 | 67156-1 | 67156 = napin GMT arab | T2 | 69.2 | |
| 352.00 | 21.78 | 128.75 | 3.54 | 506.08 | 67156-9 | 67156 = napin GMT arab | T2 | 69.6 | |
| 304.60 | 19.54 | 110.64 | 2.65 | 437.43 | 67156-11 | 67156 = napin GMT arab | T2 | 69.6 | |
| 337.70 | 24.25 | 109.93 | 2.86 | 474.74 | 67156-15 | 67156 = napin GMT arab | T2 | 71.1 | |
| 359.35 | 20.72 | 39.85 | 0.31 | 420.23 | 67156-13 | 67156 = napin GMT arab | T2 | 85.5 | |
| 367.77 | 22.54 | 35.41 | 0.35 | 426.08 | 67156-14 | 67156 = napin GMT arab | T2 | 86.3 | |
| 373.10 | 22.67 | 27.93 | 0.11 | 423.82 | 67156-10 | 67156 = napin GMT arab | T2 | 88.0 | |
| 383.43 | 23.64 | 24.00 | 0.26 | 431.33 | 67156-2 | 67156 = napin GMT arab | T2 | 88.9 | |
| 385.72 | 22.61 | 10.77 | 0.00 | 419.10 | 67156-4 | 67156 = napin GMT arab | T2 | 92.0 | |
| 412.47 | 27.18 | 13.00 | 0.21 | 452.86 | 67156-7 | 67156 = napin GMT arab | T2 | 91.1 | |
| 296.50 | 23.38 | 163.93 | 7.58 | 491.39 | 67159-3 | 67159 = brassica P4 GMT | T2 | 60.3 | 69.1 |
| 327.29 | 3.46 | 192.06 | 9.38 | 532.18 | 67159-13 | *Brassica* P4 GMT | T2 | 61.5 | |
| 294.64 | 18.61 | 148.42 | 6.93 | 468.60 | 67159-2 | 67159 = brassica P4 GMT | T2 | 62.9 | |
| 309.72 | 21.32 | 152.46 | 6.20 | 489.70 | 67159-7 | 67159 = brassica P4 GMT | T2 | 63.2 | |
| 300.73 | 21.11 | 142.66 | 5.67 | 470.18 | 67519-1 | 67159 = brassica P4 GMT | T2 | 64.0 | |
| 305.37 | 20.25 | 141.83 | 7.85 | 475.29 | 67159-10 | 67159 = brassica P4 GMT | T2 | 64.2 | |
| 311.90 | 20.92 | 145.60 | 6.91 | 485.33 | 67159-5 | 67159 = brassica P4 GMT | T2 | 64.3 | |
| 289.83 | 19.63 | 128.07 | 6.33 | 443.86 | 67159-12 | 67159 = brassica P4 GMT | T2 | 65.3 | |
| 302.93 | 17.84 | 127.91 | 5.36 | 454.03 | 67159-6 | 67159 = brassica P4 GMT | T2 | 66.7 | |
| 348.38 | 19.53 | 103.12 | 7.50 | 478.53 | 67159-9 | 67159 = brassica P4 GMT | T2 | 72.8 | |
| 329.10 | 20.27 | 78.65 | 4.28 | 432.30 | 67159-15 | 67159 = brassica P4 GMT | T2 | 76.1 | |
| 359.15 | 23.04 | 70.61 | 4.95 | 457.76 | 67159-11 | 67159 = brassica P4 GMT | T2 | 78.5 | |
| 358.83 | 19.79 | 68.26 | 4.79 | 451.67 | 67159-14 | 67159 = brassica P4 GMT | T2 | 79.4 | |
| 398.21 | 19.29 | 32.82 | 3.20 | 453.52 | 67159-4 | 67159 = brassica P4 GMT | T2 | 87.8 | |
| 3.97 | 0.00 | 494.67 | 15.15 | 513.79 | 9979-81 | control | | 0.8 | 0.8 |
| 3.32 | 0.00 | 501.58 | 18.47 | 523.37 | 9979-82 | control | | 0.6 | |
| 4.00 | 0.00 | 492.08 | 15.31 | 511.38 | 9979-83 | control | | 0.8 | |
| 4.19 | 0.00 | 541.20 | 18.42 | 563.81 | 9979-84 | control | | 0.7 | |
| 5.23 | 0.00 | 541.75 | 20.12 | 567.10 | 9979-85 | control | | 0.9 | |
| 251.34 | 10.02 | 216.55 | 6.77 | 484.68 | 67158-8 | napin *Cuphea* GMT | T2 | 51.9 | 77.3 |
| 325.52 | 10.51 | 156.76 | 5.32 | 498.11 | 67158-11 | napin *Cuphea* GMT | T2 | 65.4 | |
| 338.00 | 10.58 | 155.40 | 5.35 | 509.33 | 67158-12 | napin *Cuphea* GMT | T2 | 66.4 | |
| 322.09 | 8.99 | 139.84 | 4.74 | 475.66 | 67158-5 | napin *Cuphea* GMT | T2 | 67.7 | |
| 348.47 | 12.70 | 132.54 | 5.14 | 498.85 | 67158-10 | napin *Cuphea* GMT | T2 | 69.9 | |
| 369.43 | 14.85 | 135.94 | 4.49 | 524.71 | 67158-15 | napin *Cuphea* GMT | T2 | 70.4 | |
| 324.99 | 9.08 | 123.23 | 3.95 | 461.25 | 67158-4 | napin *Cuphea* GMT | T2 | 70.5 | |
| 358.91 | 8.49 | 108.56 | 3.76 | 479.72 | 67158-9 | napin *Cuphea* GMT | T2 | 74.8 | |
| 363.29 | 14.16 | 84.19 | 3.45 | 465.09 | 67158-3 | napin *Cuphea* GMT | T2 | 78.1 | |
| 375.18 | 9.78 | 46.59 | 2.39 | 433.94 | 67158-1 | napin *Cuphea* GMT | T2 | 86.5 | |
| 425.61 | 13.14 | 39.87 | 2.71 | 481.32 | 67158-13 | napin *Cuphea* GMT | T2 | 88.4 | |
| 415.44 | 13.75 | 33.16 | 2.01 | 464.35 | 67158-7 | napin *Cuphea* GMT | T2 | 89.5 | |
| 452.35 | 15.65 | 21.65 | 3.46 | 493.10 | 67158-2 | napin *Cuphea* GMT | T2 | 91.7 | |
| 430.11 | 20.33 | 9.67 | 0.00 | 460.11 | 67158-14 | napin *Cuphea* GMT | T2 | 93.5 | |

TABLE 5-continued

| ng α toco/mg seed | ng β toco/mg seed | ng γ toco/mg seed | ng δ toco/mg seed | ng total toco/mg seed | Line Number | A. description | Gen. | % Alpha | Avg. Alpha % |
|---|---|---|---|---|---|---|---|---|---|
| 408.68 | 13.89 | 7.13 | 1.22 | 430.92 | 67158-6 | napin *Cuphea* GMT | T2 | 94.8 | |
| 6.18 | 0.00 | 510.97 | 19.47 | 536.62 | 9979-86 | control | | 1.2 | 0.9 |
| 4.33 | 0.00 | 547.85 | 21.06 | 573.24 | 9979-87 | control | | 0.8 | |
| 6.28 | 0.00 | 503.21 | 19.67 | 529.17 | 9979-88 | control | | 1.2 | |
| 4.35 | 0.00 | 538.55 | 21.08 | 563.98 | 9979-89 | control | | 0.8 | |
| 3.45 | 0.00 | 523.43 | 19.31 | 546.19 | 9979-90 | control | | 0.6 | |
| 5.52 | 0.47 | 478.70 | 17.54 | 502.23 | 67160-7 | napin cotton GMT | T2 | 1.1 | 65.1 |
| 8.11 | 0.00 | 552.24 | 21.34 | 581.69 | 67160-15 | napin cotton GMT | T2 | 1.4 | |
| 324.58 | 7.93 | 177.97 | 7.70 | 518.18 | 67160-9 | napin cotton GMT | T2 | 62.6 | |
| 338.02 | 7.43 | 160.27 | 9.11 | 514.82 | 67160-1 | napin cotton GMT | T2 | 65.7 | |
| 345.35 | 9.94 | 159.12 | 7.51 | 521.92 | 67160-5 | napin cotton GMT | T2 | 66.2 | |
| 355.54 | 9.65 | 155.73 | 6.95 | 527.87 | 67160-14 | napin cotton GMT | T2 | 67.4 | |
| 371.70 | 14.34 | 142.80 | 6.58 | 535.43 | 67160-2 | napin cotton GMT | T2 | 69.4 | |
| 355.35 | 5.96 | 135.17 | 9.11 | 505.59 | 67160-11 | napin cotton GMT | T2 | 70.3 | |
| 360.43 | 7.03 | 136.83 | 7.76 | 512.05 | 67160-6 | napin cotton GMT | T2 | 70.4 | |
| 373.32 | 9.65 | 138.68 | 7.74 | 529.39 | 67160-4 | napin cotton GMT | T2 | 70.5 | |
| 374.20 | 10.97 | 89.34 | 4.57 | 479.07 | 67160-3 | napin cotton GMT | T2 | 78.1 | |
| 435.98 | 16.16 | 67.09 | 4.81 | 524.03 | 67160-8 | napin cotton GMT | T2 | 83.2 | |
| 446.18 | 13.59 | 44.43 | 3.54 | 507.74 | 67160-12 | napin cotton GMT | T2 | 87.9 | |
| 420.34 | 13.54 | 26.74 | 2.51 | 463.12 | 67160-10 | napin cotton GMT | T2 | 90.8 | |
| 465.41 | 15.32 | 21.78 | 2.69 | 505.21 | 67160-13 | napin cotton GMT | T2 | 92.1 | |
| 3.98 | 0.00 | 502.78 | 15.54 | 522.30 | 9979-94 | control | | 0.8 | 0.8 |
| 4.27 | 0.00 | 510.20 | 17.15 | 531.62 | 9979-93 | control | | 0.8 | |
| 4.42 | 0.00 | 549.18 | 18.50 | 572.10 | 9979-91 | control | | 0.8 | |
| 4.43 | 0.00 | 480.59 | 14.35 | 499.38 | 9979-95 | control | | 0.9 | |
| 5.22 | 0.00 | 538.48 | 19.08 | 562.78 | 9979-92 | control | | 0.9 | |
| 306.93 | 7.18 | 193.74 | 7.25 | 515.10 | 67170-3 | *Brassica* S8 GMT | T2 | 59.6 | 77.8 |
| 364.13 | 8.20 | 151.34 | 5.92 | 529.59 | 67170-6 | *Brassica* S8 GMT | T2 | 68.8 | |
| 355.93 | 6.18 | 137.59 | 5.36 | 505.06 | 67170-2 | *Brassica* S8 GMT | T2 | 70.5 | |
| 381.42 | 8.51 | 142.79 | 6.09 | 538.82 | 67170-14 | *Brassica* S8 GMT | T2 | 70.8 | |
| 372.06 | 5.24 | 130.94 | 4.04 | 512.28 | 67170-9 | *Brassica* S8 GMT | T2 | 72.6 | |
| 368.24 | 7.38 | 108.85 | 4.32 | 488.79 | 67170-1 | *Brassica* S8 GMT | T2 | 75.3 | |
| 374.71 | 5.53 | 97.22 | 3.29 | 480.75 | 67170-15 | *Brassica* S8 GMT | T2 | 77.9 | |
| 419.64 | 11.39 | 88.39 | 4.20 | 523.61 | 67170-5 | *Brassica* S8 GMT | T2 | 80.1 | |
| 408.32 | 3.44 | 88.98 | 6.94 | 507.68 | 67170-11 | *Brassica* S8 GMT | T2 | 80.4 | |
| 438.52 | 10.27 | 55.07 | 3.73 | 507.59 | 67170-8 | *Brassica* S8 GMT | T2 | 86.4 | |
| 452.28 | 12.04 | 49.76 | 2.65 | 516.72 | 67170-7 | *Brassica* S8 GMT | T2 | 87.5 | |
| 461.35 | 10.82 | 51.41 | 2.62 | 526.20 | 67170-4 | *Brassica* S8 GMT | T2 | 87.7 | |
| 458.39 | 10.45 | 17.75 | 1.16 | 487.76 | 67170-12 | *Brassica* S8 GMT | T2 | 94.0 | |
| 5.31 | 0.00 | 528.79 | 20.48 | 554.59 | 1 | 9979 | | 1.0 | 1.1 |
| 5.91 | 0.00 | 543.96 | 21.53 | 571.40 | 2 | 9979 | | 1.0 | |
| 5.26 | 0.00 | 515.35 | 18.45 | 539.07 | 3 | 9979 | | 1.0 | |
| 6.52 | 0.00 | 509.65 | 19.20 | 535.37 | 4 | 9979 | | 1.2 | |
| 7.70 | 0.00 | 537.19 | 22.97 | 567.87 | 5 | 9979 | | 1.4 | |
| 5.21 | 0.00 | 511.12 | 19.85 | 536.17 | 6 | 9979 | | 1.0 | |
| 301.07 | 4.48 | 125.80 | 7.99 | 439.34 | 2-8 | 67159 = brassica P4 GMT | T3 | 68.5 | 68.1 |
| 306.33 | 3.22 | 169.37 | 8.75 | 487.68 | 2-3 | 67159 = brassica P4 GMT | T3 | 62.8 | |
| 320.26 | 6.05 | 167.87 | 8.65 | 502.84 | 2-4 | 67159 = brassica P4 GMT | T3 | 63.7 | |
| 329.45 | 7.12 | 169.63 | 9.21 | 515.41 | 2-2 | 67159 = brassica P4 GMT | T3 | 63.9 | |
| 329.53 | 5.80 | 152.26 | 8.99 | 496.59 | 2-5 | 67159 = brassica P4 GMT | T3 | 66.4 | |
| 334.46 | 5.82 | 145.10 | 8.16 | 493.54 | 2-6 | 67159 = brassica P4 GMT | T3 | 67.8 | |
| 335.46 | 4.25 | 141.18 | 8.39 | 489.28 | 2-7 | 67159 = brassica P4 GMT | T3 | 68.6 | |
| 344.53 | 8.17 | 145.61 | 9.24 | 507.54 | 2-1 | 67159 = brassica P4 GMT | T3 | 67.9 | |
| 401.15 | 5.41 | 68.31 | 8.01 | 482.88 | 2-9 | 67159 = brassica P4 GMT | T3 | 83.1 | |
| 345.21 | 3.07 | 161.54 | 11.71 | 521.53 | 4-2 | 67159 = brassica P4 GMT | T3 | 66.2 | 89.2 |
| 431.50 | 6.46 | 56.16 | 6.72 | 500.83 | 4-9 | 67159 = brassica P4 GMT | T3 | 86.2 | |
| 445.25 | 5.69 | 20.55 | 7.24 | 478.73 | 4-8 | 67159 = brassica P4 GMT | T3 | 93.0 | |
| 445.71 | 5.48 | 20.58 | 6.60 | 478.36 | 4-3 | 67159 = brassica P4 GMT | T3 | 93.2 | |
| 446.77 | 7.74 | 14.86 | 5.03 | 474.41 | 4-7 | 67159 = brassica P4 GMT | T3 | 94.2 | |
| 452.65 | 8.96 | 49.76 | 7.52 | 518.89 | 4-4 | 67159 = brassica P4 GMT | T3 | 87.2 | |
| 454.02 | 8.09 | 14.05 | 5.10 | 481.26 | 4-6 | 67159 = brassica P4 GMT | T3 | 94.3 | |
| 467.24 | 9.65 | 11.93 | 4.93 | 493.75 | 4-1 | 67159 = brassica P4 GMT | T3 | 94.6 | |
| 517.68 | 12.95 | 13.39 | 5.10 | 549.12 | 4-5 | 67159 = brassica P4 GMT | T3 | 94.3 | |
| 347.03 | 2.66 | 155.38 | 8.28 | 513.35 | 7-5 | 67159 = brassica P4 GMT | T3 | 67.6 | 81.9 |
| 350.32 | 0.48 | 132.12 | 8.20 | 491.12 | 7-7 | 67159 = brassica P4 GMT | T3 | 71.3 | |
| 352.48 | 1.50 | 141.14 | 8.26 | 503.37 | 7-2 | 67159 = brassica P4 GMT | T3 | 70.0 | |
| 367.65 | 1.04 | 134.34 | 7.75 | 510.78 | 7-8 | 67159 = brassica P4 GMT | T3 | 72.0 | |
| 372.23 | 0.00 | 125.08 | 7.40 | 504.71 | 7-6 | 67159 = brassica P4 GMT | T3 | 73.8 | |
| 454.16 | 7.27 | 10.99 | 3.38 | 475.80 | 7-4 | 67159 = brassica P4 GMT | T3 | 95.5 | |
| 464.63 | 6.08 | 10.50 | 3.10 | 484.31 | 7-9 | 67159 = brassica P4 GMT | T3 | 95.9 | |
| 467.40 | 6.99 | 11.11 | 3.82 | 489.32 | 7-1 | 67159 = brassica P4 GMT | T3 | 95.5 | |
| 474.28 | 8.23 | 11.61 | 4.65 | 498.77 | 7-3 | 67159 = brassica P4 GMT | T3 | 95.1 | |
| 324.79 | 0.00 | 179.06 | 11.83 | 515.68 | 11-7 | 67159 = brassica P4 GMT | T3 | 63.0 | 82.2 |
| 334.92 | 0.00 | 175.60 | 11.84 | 522.35 | 11-2 | 67159 = brassica P4 GMT | T3 | 64.1 | |
| 352.84 | 0.00 | 170.23 | 12.16 | 535.22 | 11-5 | 67159 = brassica P4 GMT | T3 | 65.9 | |

TABLE 5-continued

| ng α toco/mg seed | ng β toco/mg seed | ng γ toco/mg seed | ng δ toco/mg seed | ng total toco/mg seed | Line Number | A. description | Gen. | % Alpha | Avg. Alpha % |
|---|---|---|---|---|---|---|---|---|---|
| 425.54 | 4.66 | 49.26 | 5.84 | 485.30 | 11-3 | 67159 = brassica P4 GMT | T3 | 87.7 | |
| 427.09 | 5.61 | 61.10 | 6.38 | 500.18 | 11-4 | 67159 = brassica P4 GMT | T3 | 85.4 | |
| 448.32 | 6.34 | 12.02 | 4.67 | 471.35 | 11-6 | 67159 = brassica P4 GMT | T3 | 95.1 | |
| 462.49 | 7.21 | 42.46 | 7.43 | 519.59 | 11-1 | 67159 = brassica P4 GMT | T3 | 89.0 | |
| 464.30 | 4.97 | 12.86 | 5.43 | 487.55 | 11-9 | 67159 = brassica P4 GMT | T3 | 95.2 | |
| 469.00 | 4.57 | 16.21 | 5.08 | 494.86 | 11-8 | 67159 = brassica P4 GMT | T3 | 94.8 | |
| 427.19 | 7.33 | 43.05 | 4.39 | 481.96 | 4-9 | 67156 = napin GMT arab | T3 | 88.6 | 94.0 |
| 429.83 | 3.85 | 47.80 | 3.09 | 484.57 | 4-8 | 67156 = napin GMT arab | T3 | 88.7 | |
| 442.62 | 8.97 | 45.02 | 3.71 | 500.32 | 4-4 | 67156 = napin GMT arab | T3 | 88.5 | |
| 449.25 | 4.88 | 13.31 | 2.54 | 469.99 | 4-2 | 67156 = napin GMT arab | T3 | 95.6 | |
| 454.35 | 6.96 | 2.91 | 2.58 | 466.79 | 4-5 | 67156 = napin GMT arab | T3 | 97.3 | |
| 459.55 | 7.20 | 2.75 | 1.43 | 470.94 | 4-6 | 67156 = napin GMT arab | T3 | 97.6 | |
| 467.64 | 9.17 | 5.77 | 2.51 | 485.09 | 4-3 | 67156 = napin GMT arab | T3 | 96.4 | |
| 469.22 | 7.89 | 9.04 | 3.43 | 489.58 | 4-1 | 67156 = napin GMT arab | T3 | 95.8 | |
| 476.93 | 6.07 | 3.18 | 2.68 | 488.85 | 4-7 | 67156 = napin GMT arab | T3 | 97.6 | |
| 341.52 | 0.00 | 152.78 | 6.96 | 501.27 | 7-1 | 67156 = napin GMT arab | T3 | 68.1 | 90.7 |
| 426.76 | 3.74 | 55.93 | 7.18 | 493.62 | 7-2 | 67156 = napin GMT arab | T3 | 86.5 | |
| 427.82 | 2.42 | 36.53 | 3.79 | 470.56 | 7-7 | 67156 = napin GMT arab | T3 | 90.9 | |
| 448.96 | 3.62 | 8.76 | 3.29 | 464.62 | 7-9 | 67156 = napin GMT arab | T3 | 96.6 | |
| 455.79 | 5.26 | 12.41 | 3.45 | 476.91 | 7-6 | 67156 = napin GMT arab | T3 | 95.6 | |
| 457.18 | 6.56 | 21.53 | 2.89 | 488.16 | 7-5 | 67156 = napin GMT arab | T3 | 93.7 | |
| 461.11 | 6.33 | 8.82 | 3.36 | 479.62 | 7-8 | 67156 = napin GMT arab | T3 | 96.1 | |
| 462.08 | 7.10 | 16.36 | 3.59 | 489.14 | 7-4 | 67156 = napin GMT arab | T3 | 94.5 | |
| 466.01 | 7.72 | 15.40 | 4.54 | 493.68 | 7-3 | 67156 = napin GMT arab | T3 | 94.4 | |
| 5.09 | 0.00 | 535.79 | 19.35 | 560.22 | 9979-81:@.0005. | Control | | 0.9 | |
| 5.37 | 0.00 | 534.93 | 21.47 | 561.77 | 9979-81:@.0006. | Control | | 1.0 | |
| 327.76 | 22.52 | 156.62 | 9.37 | 516.27 | 67158-2:@.0002. | napin *Cuphea* GMT | T3 | 63.5 | 85.2 |
| 384.99 | 24.97 | 92.36 | 7.82 | 510.14 | 67158-2:@.0001. | napin *Cuphea* GMT | T3 | 75.5 | |
| 406.19 | 27.74 | 3.42 | 2.12 | 439.47 | 67158-2:@.0006. | napin *Cuphea* GMT | T3 | 92.4 | |
| 424.62 | 22.33 | 34.40 | 6.92 | 488.27 | 67158-2:@.0009. | napin *Cuphea* GMT | T3 | 87.0 | |
| 432.70 | 25.03 | 52.96 | 8.60 | 519.29 | 67158-2:@.0004. | napin *Cuphea* GMT | T3 | 83.3 | |
| 443.67 | 25.50 | 46.41 | 8.22 | 523.80 | 67158-2:@.0003. | napin *Cuphea* GMT | T3 | 84.7 | |
| 449.38 | 26.25 | 4.06 | 2.34 | 482.03 | 67158-2:@.0005. | napin *Cuphea* GMT | T3 | 93.2 | |
| 449.63 | 25.26 | 2.17 | 1.84 | 478.89 | 67158-2:@.0008. | napin *Cuphea* GMT | T3 | 93.9 | |
| 451.00 | 25.32 | 6.56 | 2.74 | 485.63 | 67158-2:@.0007. | napin *Cuphea* GMT | T3 | 92.9 | |
| 312.62 | 22.03 | 153.68 | 6.73 | 495.05 | 67158-4:@.0007. | napin *Cuphea* GMT | T3 | 63.1 | 75.7 |
| 326.50 | 23.50 | 131.44 | 6.54 | 487.99 | 67158-4:@.0001. | napin *Cuphea* GMT | T3 | 66.9 | |
| 327.91 | 22.51 | 143.83 | 7.42 | 501.67 | 67158-4:@.0005. | napin *Cuphea* GMT | T3 | 65.4 | |
| 331.65 | 24.40 | 137.74 | 7.20 | 500.98 | 67158-4:@.0009. | napin *Cuphea* GMT | T3 | 66.2 | |
| 345.95 | 24.75 | 134.17 | 6.75 | 511.62 | 67158-4:@.0006. | napin *Cuphea* GMT | T3 | 67.6 | |
| 355.47 | 24.91 | 120.77 | 6.50 | 507.65 | 67158-4:@.0003. | napin *Cuphea* GMT | T3 | 70.0 | |
| 448.67 | 24.98 | 0.92 | 1.97 | 476.54 | 67158-4:@.0004. | napin *Cuphea* GMT | T3 | 94.2 | |
| 453.62 | 25.23 | 0.98 | 1.59 | 481.42 | 67158-4:@.0008. | napin *Cuphea* GMT | T3 | 94.2 | |
| 456.45 | 27.19 | 1.34 | 1.92 | 486.91 | 67158-4:@.0002. | napin *Cuphea* GMT | T3 | 93.7 | |
| 6.39 | 0.00 | 498.67 | 24.65 | 529.71 | 9979-81:@.0007. | Control | | 1.2 | |
| 6.65 | 0.00 | 520.22 | 19.20 | 546.08 | 9979--81:@.0008. | Control | | 1.2 | |
| 325.71 | 19.95 | 154.88 | 8.09 | 508.64 | 67158-9:@.0007. | napin *Cuphea* GMT | T3 | 64.0 | 68.4 |
| 330.27 | 21.90 | 154.36 | 8.08 | 514.61 | 67158-9:@.0005. | napin *Cuphea* GMT | T3 | 64.2 | |
| 347.97 | 22.33 | 129.57 | 6.54 | 506.41 | 67158-9:@.0004. | napin *Cuphea* GMT | T3 | 68.7 | |
| 351.68 | 22.59 | 122.64 | 6.96 | 503.87 | 67158-9:@.0006. | napin *Cuphea* GMT | T3 | 69.8 | |
| 353.74 | 22.51 | 118.23 | 6.90 | 501.38 | 67158--9:@.0001. | napin *Cuphea* GMT | T3 | 70.6 | |
| 354.17 | 23.30 | 137.47 | 7.50 | 522.44 | 67158--9:@.0002. | napin *Cuphea* GMT | T3 | 67.8 | |
| 358.21 | 21.84 | 132.99 | 6.76 | 519.80 | 67158-9:@.0009. | napin *Cuphea* GMT | T3 | 68.9 | |
| 362.74 | 22.40 | 114.96 | 6.69 | 506.79 | 67158-9:@.0008. | napin *Cuphea* GMT | T3 | 71.6 | |
| 362.98 | 24.28 | 124.73 | 6.50 | 518.49 | 67158-9:@.0003. | napin *Cuphea* GMT | T3 | 70.0 | |
| 403.35 | 26.19 | 33.39 | 3.08 | 466.02 | 67158-14:@.0003. | napin *Cuphea* GMT | T3 | 86.6 | 90.0 |
| 416.91 | 26.96 | 34.74 | 3.21 | 481.83 | 67158-14:@.0002. | napin *Cuphea* GMT | T3 | 86.5 | |
| 423.10 | 22.19 | 36.04 | 3.17 | 484.50 | 67158-14:@.0008. | napin *Cuphea* GMT | T3 | 87.3 | |
| 424.87 | 26.52 | 4.48 | 1.62 | 457.49 | 67158--14:@.0004. | napin *Cuphea* GMT | T3 | 92.9 | |
| 428.75 | 23.34 | 24.92 | 5.13 | 482.14 | 67158-14:@.0009. | napin *Cuphea* GMT | T3 | 88.9 | |
| 433.96 | 30.08 | 5.32 | 2.24 | 471.61 | 67158--14:@.0001. | napin *Cuphea* GMT | T3 | 92.0 | |
| 434.51 | 29.70 | 20.34 | 1.90 | 486.44 | 67158-14:@.0005. | napin *Cuphea* GMT | T3 | 89.3 | |
| 435.86 | 23.44 | 3.27 | 1.75 | 464.33 | 67158-14:@.0006. | napin *Cuphea* GMT | T3 | 93.9 | |
| 440.46 | 23.40 | 10.67 | 2.27 | 476.80 | 67158-14:@.0007. | napin *Cuphea* GMT | T3 | 92.4 | |

EXAMPLE 3

Computer programs are used to predict the chloroplast targeting peptide cleavage sites of the plant GMT proteins. The predictions of CTPs by using two programs:

| 1) Program: Predotar | | | |
|---|---|---|---|
| Sequence ID | Score | Cut Site | P-Value |
| Gossypium | 4.56 | 49 * 50 | 3.0496E+07 |
| Brassica | 2.27 | 51 * 52 | 2.3192E+05 |
| Cuphea | 1.96 | undetermined | 2.7934E−01 |

| 2) chloroplast target peptide prediction results Number of query sequences: 5 | | | | | |
|---|---|---|---|---|---|
| Name | Length | Score | cTP | CS-score | cTP-length |
| Arabidopsis | 348 | 0.587 | Y | 7.834 | 50 |
| Gossypium | 345 | 0.580 | Y | 4.116 | 48 |
| Brassica | 347 | 0.581 | Y | 8.142 | 51 |
| Cuphea | 376 | 0.573 | Y | 1.746 | 64 |
| Zea mays | 352 | 0.560 | Y | 4.808 | 48 |

Based on this information GMT proteins from plant sources are engineered to remove the predicted chloroplast target peptides to allow for the expression of the mature protein in *E. coli*. In order for these proteins to be expressed in a prokaryotic expression system, an amino terminal methionine is required. This can be accomplished, for example, by the addition of a 5' ATG. A methionine is added to each of the following amino acid sequences, which are expressed in *E. coli* with detectable GMT activity (SEQ ID NOs: 33-38 each have the added methionine as the first amino acid in the sequence): Mature S8 *Brassica napus* GMT protein as expressed in *E. coli* (SEQ ID NO: 33); Mature P4 *Brassica napus* GMT protein as expressed in *E. coli* (SEQ ID NO: 34); Mature *Cuphea pulcherrima* GMT protein as expressed in *E. coli* (SEQ ID NO: 35); Mature *Gossypium hirsutum* GMT protein as expressed in *E. coli* (SEQ ID NO: 36); Mature *Tagetes erecta* (Marigold) GMT protein as expressed in *E. coli* (SEQ ID NO:37); Mature *Zea mays* (Corn) GMT protein as expressed in *E. coli* (SEQ ID NO: 38).

Constructs are prepared to direct expression of the mature P4 and S8 *Brassica napus, Cuphea pulcherrima, Gossypium hirsutum, Tagetes erecta*, and *Zea mays* GMT sequences in a prokaryotic expression vector. The mature protein-coding region of each GMT with the aminoterminal methionine, as described previously, is amplified from plasmid DNA using the following species specific oligonucleotide primers in the polymerase chain reaction (PCR). Components of each 100 µl PCR reaction at final concentration consisted of: 1.0 µl genomic DNA or 1.0 µl plasmid DNA diluted 1:20 with water, as appropriate, 1×Buffer 2 (EXPAND High Fidelity PCR System, Roche Molecular Biochemicals), 200 µM dNTPs, 300 nM each, synthetic oligonucleotide primers, and 0.8 µl EXPAND High Fidelity Polymerase (Roche Molecular Biochemicals, Indianapolis, Ind.).

"Touchdown" cycling conditions consisted of a pre-incubation for 3 min at 94° C., during which the EXPAND polymerase is spiked into the mix. The product is then amplified with 15 cycles of denaturation at 94° C. for 45 sec, annealing at 70° C. for 30 sec, and elongation at 72° C. for 1.5 min. The annealing temperature is decreased by 1° C. per cycle for each of the previous 15 cycles. An additional 15 cycles followed, consisting of 94° C. for 45 sec, 55° C. for 30 sec, and 72° C. for 1.5 min, followed by a 7 min hold at 72° C.

A mature S8 *Brassica* GMT coding sequence is amplified from pMON67170 using the synthetic oligonucleotide primers: #16765 (SEQ ID NO: 59) and #16654 (SEQ ID NO: 60).

A mature P4 *Brassica* GMT coding sequence is amplified from pMON67159 using the synthetic oligonucleotide primers: #16765 (SEQ ID NO: 59) and #16654 (SEQ ID NO: 60).

A mature *Cuphea pulcherrima* GMT coding sequence is amplified from pMON67158 using the synthetic oligonucleotide primers: #16763 (SEQ ID NO: 61) and #16659 (SEQ ID NO: 62).

A mature *Gossypium hirsutum* GMT coding sequence is amplified from pMON67160 using the synthetic oligonucleotide primers: #16764 (SEQ ID NO: 63) and #16682 (SEQ ID NO: 64).

A mature *Tagetes erecta* GMT coding sequence is amplified from the EST clone LIB3100-001-Q1-M1-E2 using the synthetic oligonucleotide primers: #16766 (SEQ ID NO: 65) and #16768 (SEQ ID NO: 66).

A mature *Zea mays* GMT coding region is amplified from the EST clone LIB3689-262-Q1-K1-D6 using the synthetic oligonucleotide primers: 5'GGG GAC AAG TTT GTA CAA AAA AGC AGG CTT AGA AGG AGA TAG AAC CAT GGC CTC GTC GAC GGC TCA GGC CC3' (SEQ ID NO: 73) and 5'GGG GAC CAC TTT GTA CAA GAA AGC TGG GTC CTG CAG GCT ACG CGG CTC CAG GCT TGC GAC AG (SEQ ID NO: 74).

A GMT coding region from *Nostoc punctiforme* (ATCC 29133) is amplified from genomic DNA. Genomic DNA is isolated from 3 day cultures of the cyanobacteria according to the procedure of Chisholm (CYANONEWS, Vol. 6. No. 3 (1990)). Cultures are centrifuged and the supernatant discarded. Pellets are suspended in 400 µl TES (TES: 2.5 ml of 1 M Tris, pH 8.5; 5 ml of 5 M NaCl; 5 ml of 500 mM EDTA, bring volume to 500 ml.) To the suspended pellet, 100 µl lysozyme (50 mg/ml) is added and the suspension incubated for 15 minutes at 37° C. with occasional mixing. To this, 50 µl sarkosyl (10%) is added. Protein is extracted by adding 600 µl phenol and incubating at room temperature with gentle shaking. The phases are separated by centrifugation and the aqueous phase is transferred to a new tube. RNase is added to a final concentration of 1.0 mg/ml and the solution is incubated for 15 minutes at 37° C. To this solution 100 µl NaCl (5 M), 100 µl CTAB/NaCl (CTAB/NaCl: To 80 ml of water, add 4.1 g of NaCl, then 10 g CTAB, heat to 65° C. to dissolve, bring volume to 100 ml), and 600 µl chloroform are added and the solution incubated 15 minutes at room temperature with gentle shaking. The phases are separated by centrifugation and the aqueous phase is transferred to a new tube. 700 µl isopropanol is added to precipitate DNA. The sample is centrifuged for 15 minutes at 14,000 rpms in a micro-centrifuge to pellet genomic DNA. The pellet is rinsed with 70% ethanol, dried briefly in a SPEEDVAC and the genomic DNA is suspended in 100 µl TE. DNA concentration, as determined by spectrophotometry, is 79 µg/ml.

*Nostoc* GMT amplification reactions contained 79 ng genonic DNA, 2.5 µl 20×dNTPs 2.5 µl of each of the following primers: 5'GGG GAC AAG TTT GTA CAA AAA AGC AGG CTT AGA AGG AGA TAG AAC CAT GAG TGC AAC ACT TTA CCA GCA AAT TC 3' (SEQ ID NO: 67) and 5'GGG GAC CAC TTT GTA CAA GAA AGC TGG GTC CTA CTA CTT ATT GCC GCA CAG TAA GC 3' (SEQ ID NO: 68), 5 µl 10×PCR buffer 2 or 3, and 0.75 µl EXPAND High Fidelity DNA Polymerase. PCR conditions for amplification are as follows: 1 cycle of 94° C. for 2 minutes, 10 cycles of 94° C.-15 seconds; 55° C.-30 seconds; and 72° C.-1.5 minutes, 15 cycles of 94° C.-15 seconds; 55° C.-30 seconds; and 72° C.-1.5 minutes adding 5 seconds to the 72° C. extension with each cycle, 1 cycle of 72° C. for 7 minutes. After amplification, samples are purified using a Qiagen PCR cleanup column, suspended in 30 µl water and 10 µl are visualized on an agarose gel.

GMT and MT1 coding sequences are amplified from genomic DNA from the cyanobacterium *Anabaena* species (ATCC 27893). DNA used for PCR amplification of *Anabaena* GMT and MT1 is isolated by collecting pellets from 3 day old cyanobacteria cultures by centrifugation. The pellet is washed with 1 ml PBS to remove media. The suspension is centrifuged and the supernatent is discarded. The pellet is resuspended in 1 ml of water and boiled for 10 minutes. *Anabaena* amplification reactions contained 10 µl boiled *Anabaena* extract, 2.5 µl 20× dNTPs 2.5 µl of each primer, 5 µl 10× PCR buffer 2 or 3, and 0.75 µl EXPAND High Fidelity DNA Polymerase. PCR conditions for amplification are as follows: 1 cycle of 94° C. for 2 minutes, 10 cycles of 94° C.-15 seconds; 55° C.-30 seconds; and 72° C.-1.5 minutes, 15 cycles of 94° C.-15 seconds; 55° C.-30 seconds; and 72° C.-1.5 minutes adding 5 seconds to the 72° C. extension with each cycle, 1 cycle of 72° C. for 7 minutes. After amplification, samples are purified using a Qiagen PCR cleanup column, suspended in 30 µl water and 10 µl are visualized on an agarose gel.

*Anabaena* species GMT coding sequence is amplified using the synthetic oligonucleotide primers: 5'GGG GAC AAG TTT GTA CAA AAA AGC AGG CTT AGA AGG AGA TAG AAC CAT GAG TGC AAC ACT TTA CCA ACA AAT TCA G 3' (SEQ ID NO: 69) and 5'GGG GAC CAC TTT GTA CAA GAA AGC TGG GTC CTA TCA CTT ATC CCC ACA AAG CAA CC 3' (SEQ ID NO: 70).

*Anabaena* species MT1 coding sequence is amplified using the synthetic oligonucleotide primers: 5'GGG GAC AAG TTT GTA CAA AAA AGC AGG CTT AGA AGG AGA TAG AAC CAT GAG TTG GTT GTT TTC TAC ACT GG 3' (SEQ ID NO: 71) and 5'GGG GAC CAC TTT GTA CAA GAA AGC TGG GTC CTA TTA CTT TTG AGC AAC CTT GAT CG3' (SEQ ID NO: 72).

The resulting PCR products are subcloned into pDONR™201 (Life Technologies, A Division of Invitrogen Corp., Rockville, Md.) using the GATEWAY cloning system (Life Technologies, A Division of Invitrogen Corp., Rockville, Md.) and labeled pMON67180 (mature S8 *Brassica napus* GMT), pMON68757 (mature P4 *Brassica napus* GMT), pMON68755 (mature *Cuphea pulcherrima* GMT), pMON68756 (mature *Gossypium hirsulum* GMT), pMON68758 (mature *Tagetes erecta* GMT), pMON67182 (mature *Zea mays* GMT), pMON67520 (*Nostoc punctiforme* GMT), pMON67518 (*Anabaena* species GMT), and pMON67517 (*Anabaena* species MT1). Double stranded DNA sequence is obtained to verify that no errors are introduced by the PCR amplification.

For functional testing GMT and MT1 sequences are then recombined behind the T7 promoter in the prokaryotic expression vector pET-DEST42 (FIG. 1) (Life Technologies, A Division of Invitrogen Corp., Rockville, Md.) using the GATEWAY cloning system (Life Technologies, A Division of Invitrogen Corp., Rockville, Md.) according to the manufacturer's protocol. The resulting expression vectors are labeled pMON67181 (mature S8 *Brassica napus* GMT), pMON67172 (mature P4 *Brassica napus* GMT), pMON67173 (mature *Cuphea pulcherrima* GMT), pMON67171 (mature *Gossypium hirsutum* GMT), pMON67177 (mature *Tagetes erecta* GMT), pMON67176 (*Nostoc punctiforme* GMT), pMON67175 (Anabaena species GMT), pMON67174 (*Anabaena* species MT1), and pMON67183 (*Zea mays* GMT) (see also table 6).

TABLE 6

Bacterial expression vectors for functional testing of methyltransferases

| Construct I.D. | Gene | Source of Gene | Modifications |
|---|---|---|---|
| pMON67171 | GMT | *Gossypium hirsutum* | Mature protein |
| pMON67172 | GMT | *Brassica napus* P4 | Mature protein |
| pMON67173 | GMT | *Cuphea pulcherrima* | Mature protein |
| pMON67174 | MT1 | *Anabaena* | |
| pMON67175 | GMT | *Anabaena* | |
| pMON67176 | GMT | *Nostoc* | |
| pMON67177 | GMT | *Tagetes erecta* | Mature protein |
| pMON67181 | GMT | *Brassica napus* S8 | Mature protein |
| pMON67183 | GMT | *Zea mays* | Mature protein |

EXAMPLE 4

Bacterial expression plasmids listed in Table 6 are transformed into expression host cells (BL21 (DE3) (Stratagene, La Jolla, Calif.)) prior to growth and induction. A 100 mL LB-culture with the appropriate selection antibiotic (mg/mL carbenicillin) is inoculated with an overnight starter culture of cell transformants to an $OD_{600}$ of 0.1 and grown at 25° C., 250 rpm to an $OD_{600}$ of 0.6. The cells are then induced by adding IPTG to a final concentration of 0.4 mM and incubating for three hours at 25° C. and 200 rpm. Cultures are transferred to 250 mL polypropylene centrifuge tubes, chilled on ice for five minutes, and harvested by centrifugation at 5000×g for ten minutes. The cell pellet is stored at −80° C. after thoroughly aspirating off the supernatant.

Methyltransferase activity is measured in vitro using a modification of the method described by d'Harlingue et al., 1985 d'Harlingue and Camara, *J. Biol. Chem.* 260(28):15200-3 (1985). The cell pellet is thawed on ice and resuspended in 4 mL of extraction buffer (10 mM HEPES-KOH pH 7.8, 5 mM DTT (dithiothriotol), 1 mM AEBSF (4-(2-aminoethyl)benzenesulfonyl fluoride), 0.1 µM aprotinin, 1 µg/mL leupeptin). Cells are disrupted using a French press. Each cell suspension is run through the pressure cell twice at 20,000 psi. Triton x-100 is added to a final concentration of 1% and the cell homogenate is incubated on ice for one hour before centrifugation at 5000 g for ten minutes at 4° C. The supernatant is transferred to fresh eppendorf tubes for methyltransferase activity analysis.

Enzyme assays are performed in assay buffer containing 50 mM Tris-HCl pH 7.0 (pH 8.0 for MT1), 5 mM DTT, 100 µM substrate (γ-tocopherol or γ-tocotrienol for GMT (Calbiochem-Novabiochem Corporation, San Diego, Calif.); 2-methylphytylplastoquinol (racemic mixture) (2-methylphytylplastoquinol and 2,3-dimethyl-5-phytylplastoquinol are synthesized as described by Soll and Schultz 1980 (Soll, J., Schultz, G., 1980, 2-methyl-6-phytylplastoquinol and 2,3-dimethyl-5-phytylplastoquinol as precursors of tocopherol synthesis in spinach chloroplasts, Phytochemistry 19:215-218) for MT1 and TMT2), 0.1 µCi $^{14}$C-SAM (48 µCi/µmole, ICN Biomedicals, Aurora, Ohio), and 0.5% TWEEN 80 (for substrate solubility) in a final volume of 1 mL. Reactions are prepared in 10 mL polypropylene culture tubes by first adding the substrate from concentrated stocks dissolved in hexane and evaporating off the hexane under nitrogen gas flow. TWEEN 80 is added directly to the substrate before adding the remainder of the assay buffer less the SAM. Crude cell extract is added to the assay mix in 50 μL volumes and the timed reactions are initiated by adding SAM. Reactions are vortexed thoroughly to dissolve all of the detergent into the mix and then incubated at 30° C. in the dark for 30 minutes.

The reactions are transferred to 15 mL screw-capped glass tubes with teflon-coated caps prior to quenching and phase extracting with 4 mL of 2:1 chloroform/methanol containing 1 mg/mL of butylated hydroxytoluene (BHT for stability of the end product). These are then vortexed for at least 30 seconds and centrifuged at 800×g for 5 minutes to separate the layers. If necessary, 1 mL of 0.9% NaCl is added to improve the phase separation (emulsions may form because the enzyme is added as a crude extract). The organic phase (bottom layer) of each phase extraction is transferred to a fresh 15 mL glass tube and evaporated completely under nitrogen gas flow. The reaction products are then dissolved in 200 μL of ethanol containing 1% pyrogalol and vortexed for at least 30 seconds. This is filtered through a 0.2 μm filter (WHATMAN PTFE) into glass inserts contained within light protected LC vials for HPLC analysis.

The HPLC (HP 1100) separation is carried out using a normal phase column (Agilent ZORBAX Sil, 5 μm, 4.6×250 mm) with 1.5 mL/minute isocratic flow of 10% methyl-t-butyl-ether in hexane over a period of 14 minutes. Samples are injected onto the column in 50 μl volumes. Quantitation of $^{14}C$-labeled reaction products is performed using a flow scintillation counter (Packard 500TR). Methyltransferase activities are calculated based on a standard curve of D-α-[5-methyl-$^{14}C$]-tocopherol (Amersham-Pharmacia, 57 mCi/mmol).

Figure 17:
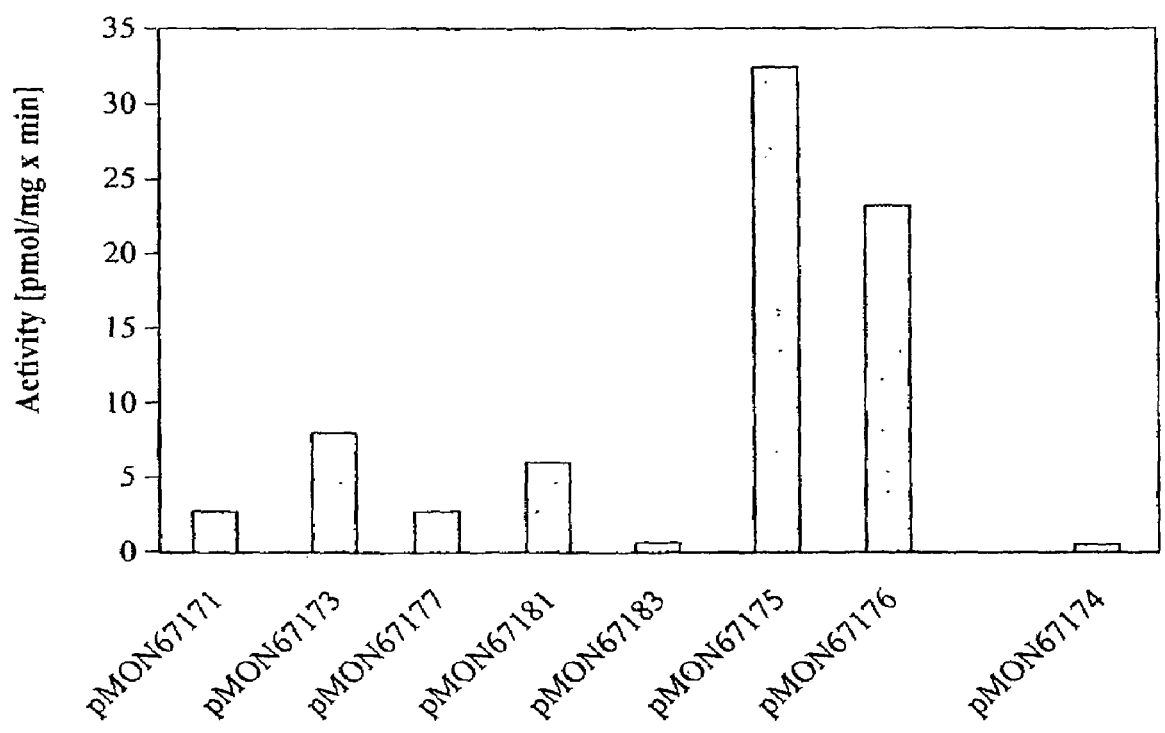
FIG. 17 is a graph representing the enzyme activities of various gamma-methyltransferases (GMT) and a tocopherol methyl transferase 1 (MT1) in recombinant *E. coli* crude extract preparations. Enzyme activities are expressed as either pmol α-tocopherol (GMT) or 2,3-dimethyl-5-phytylplastoquinol (MT1) formation per mg protein per min. Vector designations stand for the following recombinant genes: pMON67171, mature cotton GMT; pMON67173, mature *Cuphea pulcherrima* GMT; pMON67177, mature marigold GMT; pMON67181, mature *Brassica napus* S8 GMT; pMON67183, *Zea mays* GMT; pMON67175, *Anabaena* GMT; pMON67176, Nostoc GMT; and pMON67174, *Anabaena* MT1.

The assay results confirm γ-tocopherol methyltransferase activity for all GMT gene candidates listed in table 6, except for the *Brassica* P4 gene (FIG. 17).

Figure 18:
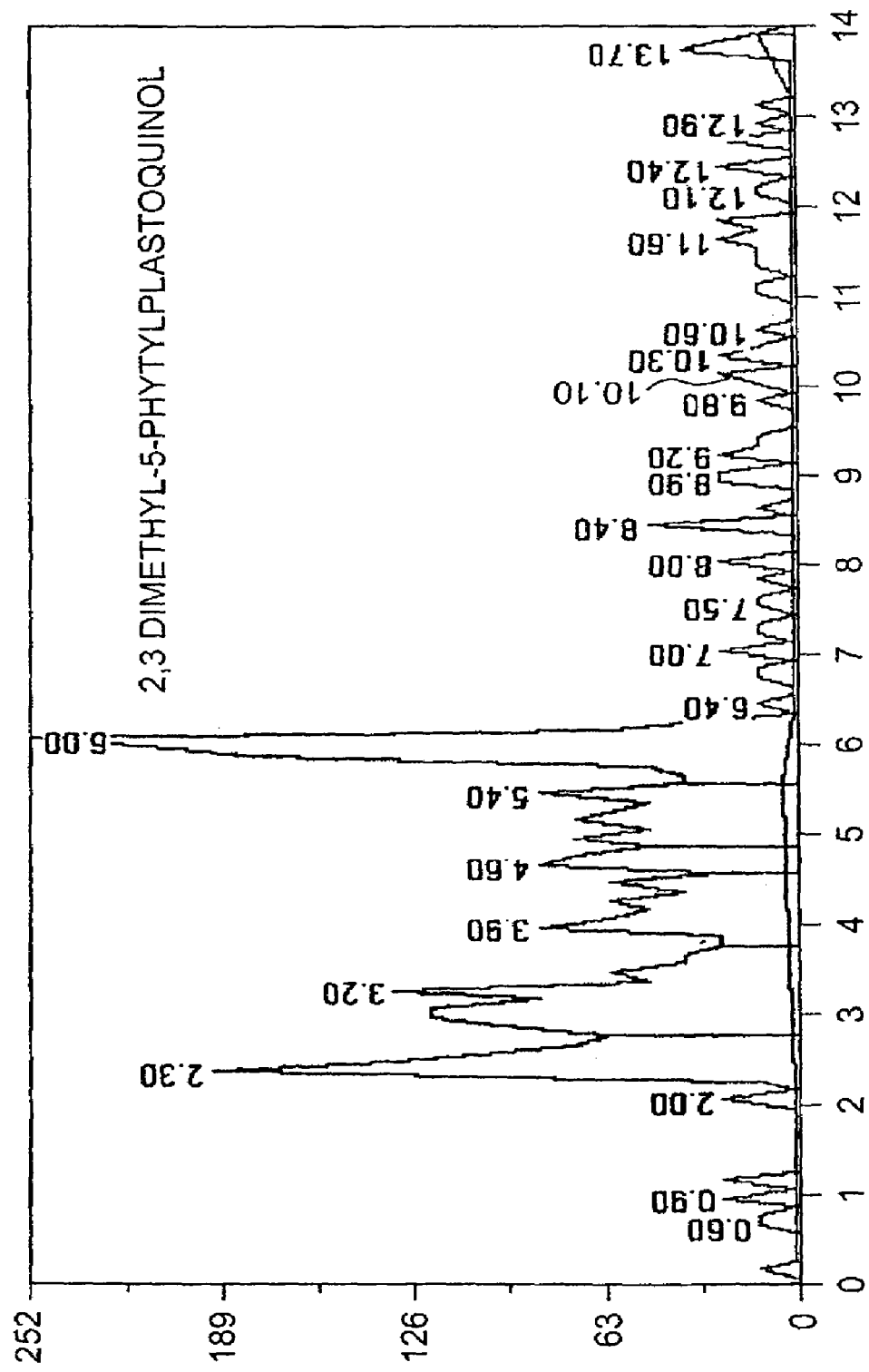
FIG. 18 is an HPLC chromatogram, representing the methyltransferase activity of recombinant expressed *Anabaena* methyltransferase 1. Enzyme activity is monitored on crude cell extracts from *E. coli* harboring pMON67174.
Figure 19:
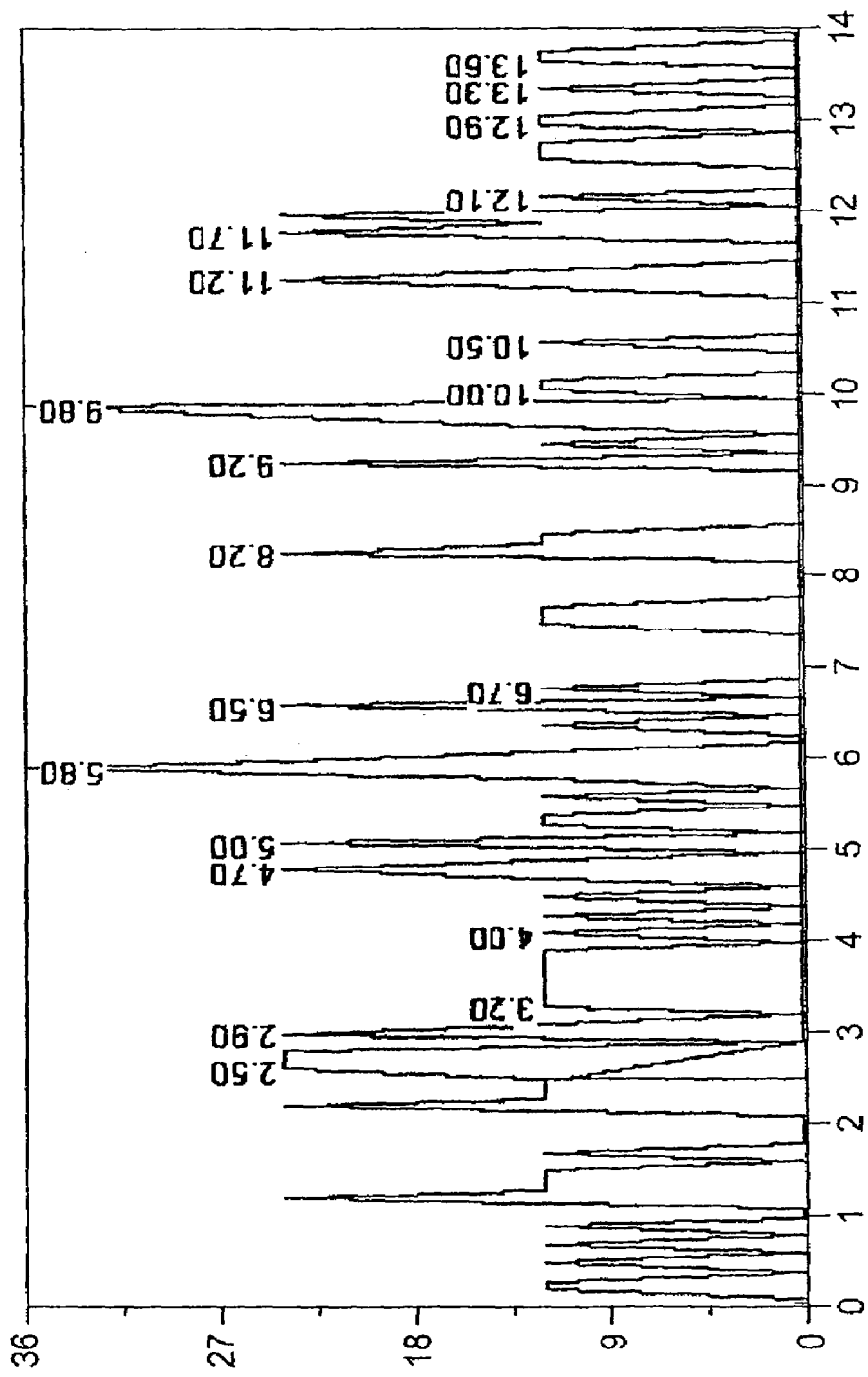
FIG. 19 is an HPLC chromatogram, representing the Methyltransferase activity of recombinant expressed *Anabaena* methyltransferase 1 without 2-methylphytylplastoquinol substrate (negative control). Enzyme activity is monitored on crude cell extracts from *E. coli* harboring pMON67174.
Figure 20:
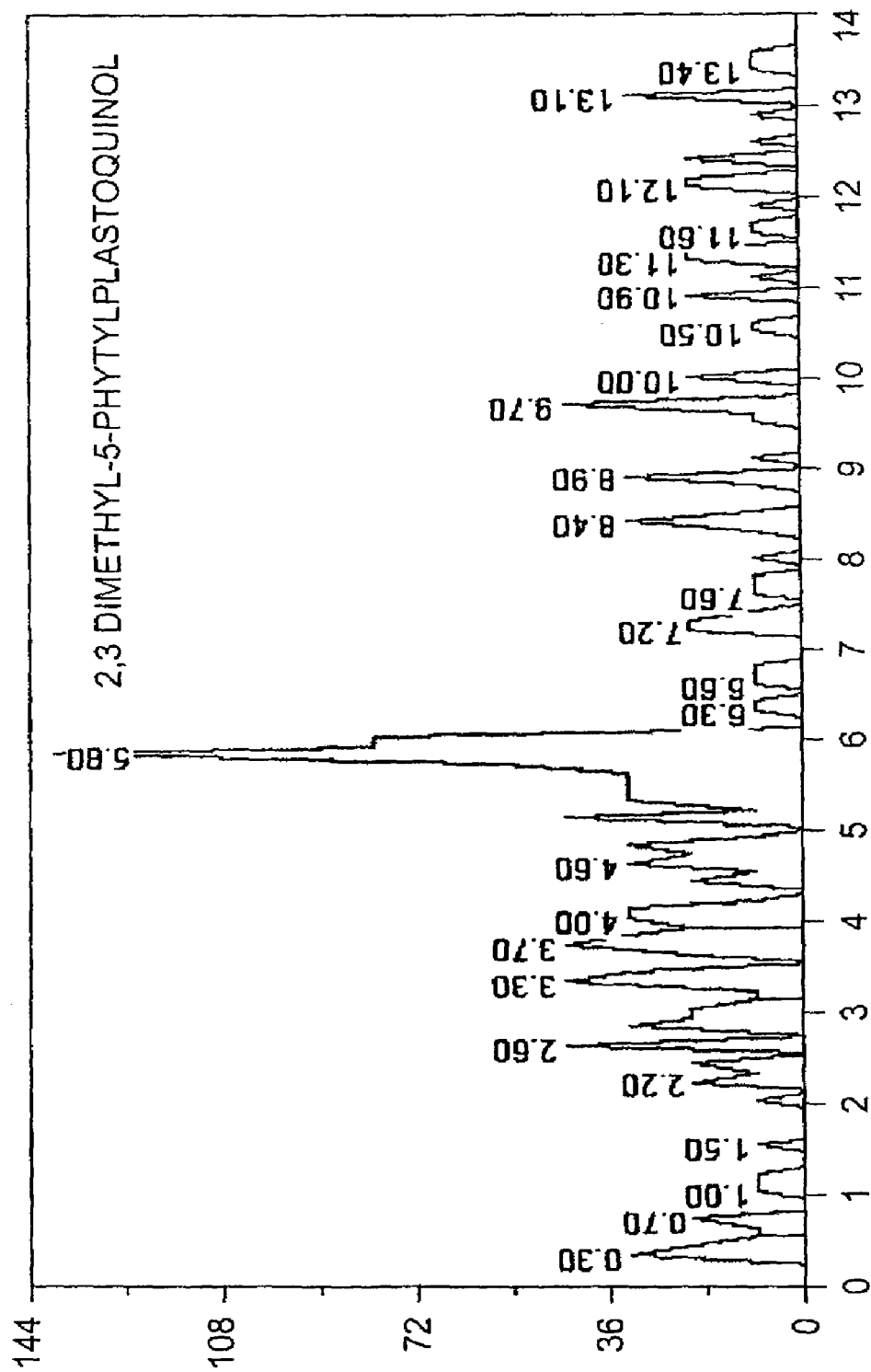
FIG. 20 is an HPLC chromatogram, representing the methyltransferase 1 activity in isolated pea chloroplasts (positive control).
Figure 21A:
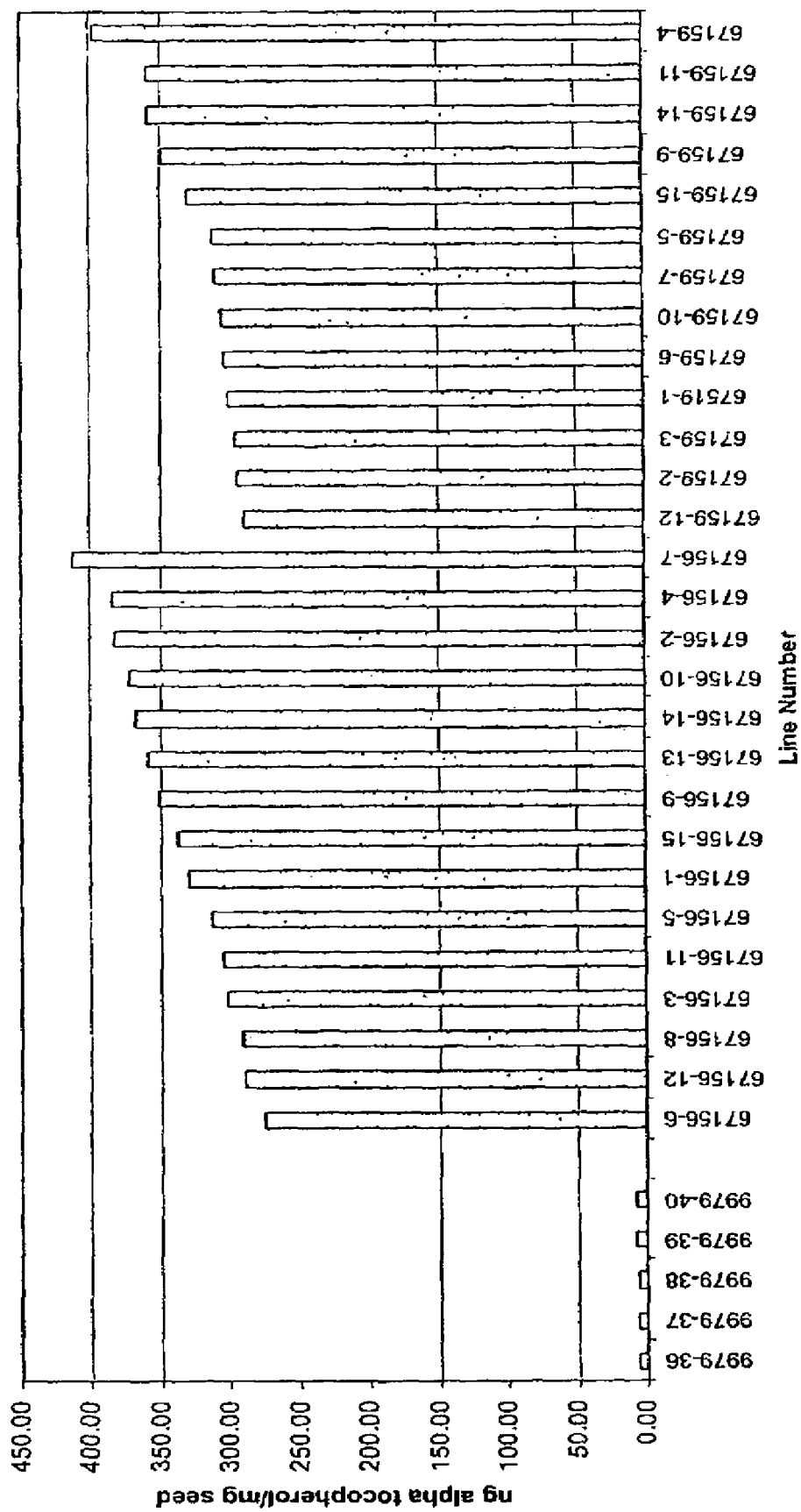
FIGS. 21A and 21B are graphs representing the α and γ-tocopherol levels in *Arabidopsis* $T_2$ seed from 5 transgenic control plants containing the napin binary vector (9979), 15 transgenic plants expressing the *Arabidopsis thaliana* GMT gene (Columbia ecotype) under the control of the napin promoter (67156) and 13 transgenic plants expressing the *Brassica napus* P4 GMT under the control of the napin promoter (67159).
Figure 21B:
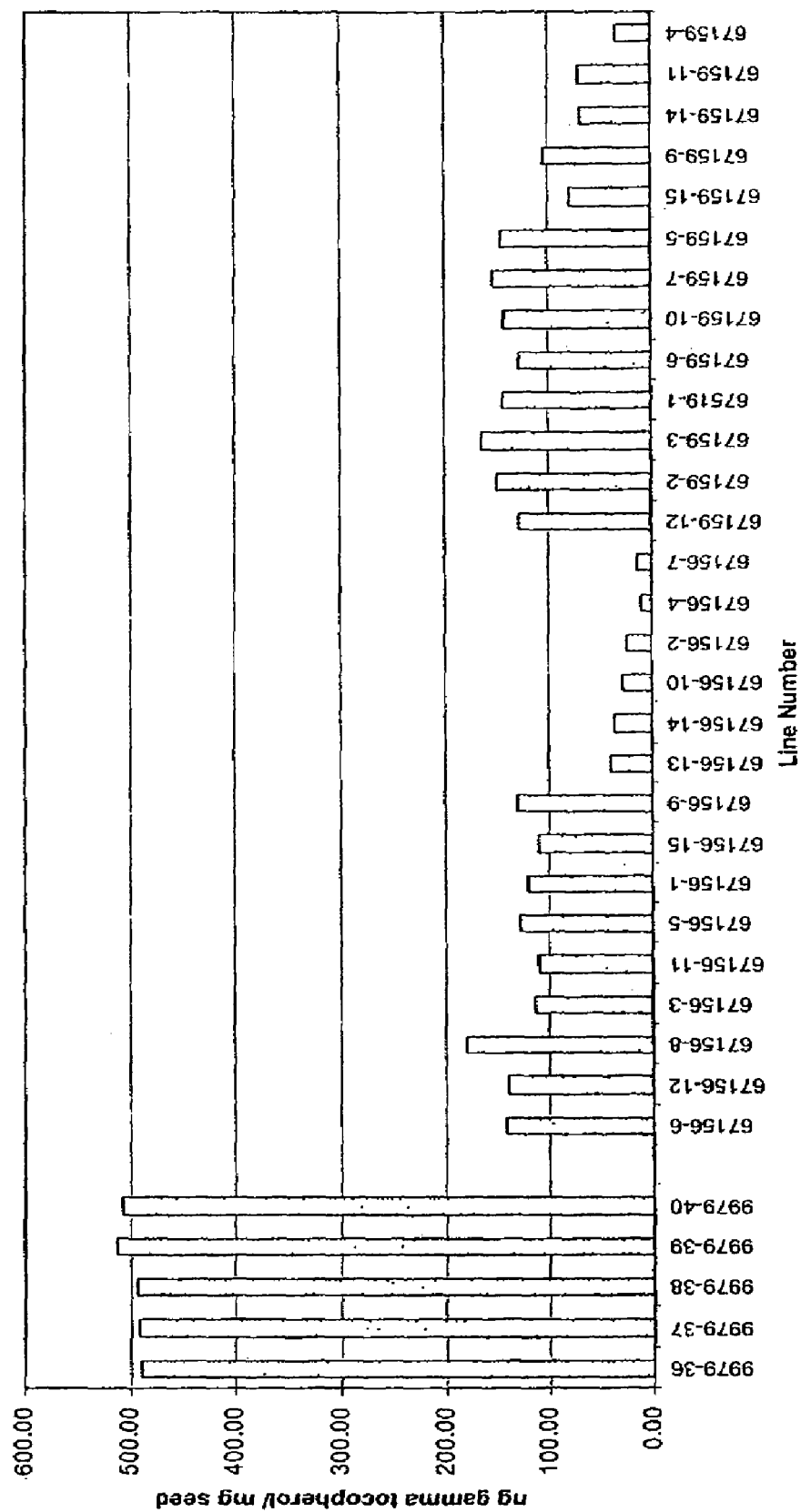
Figure 22A:
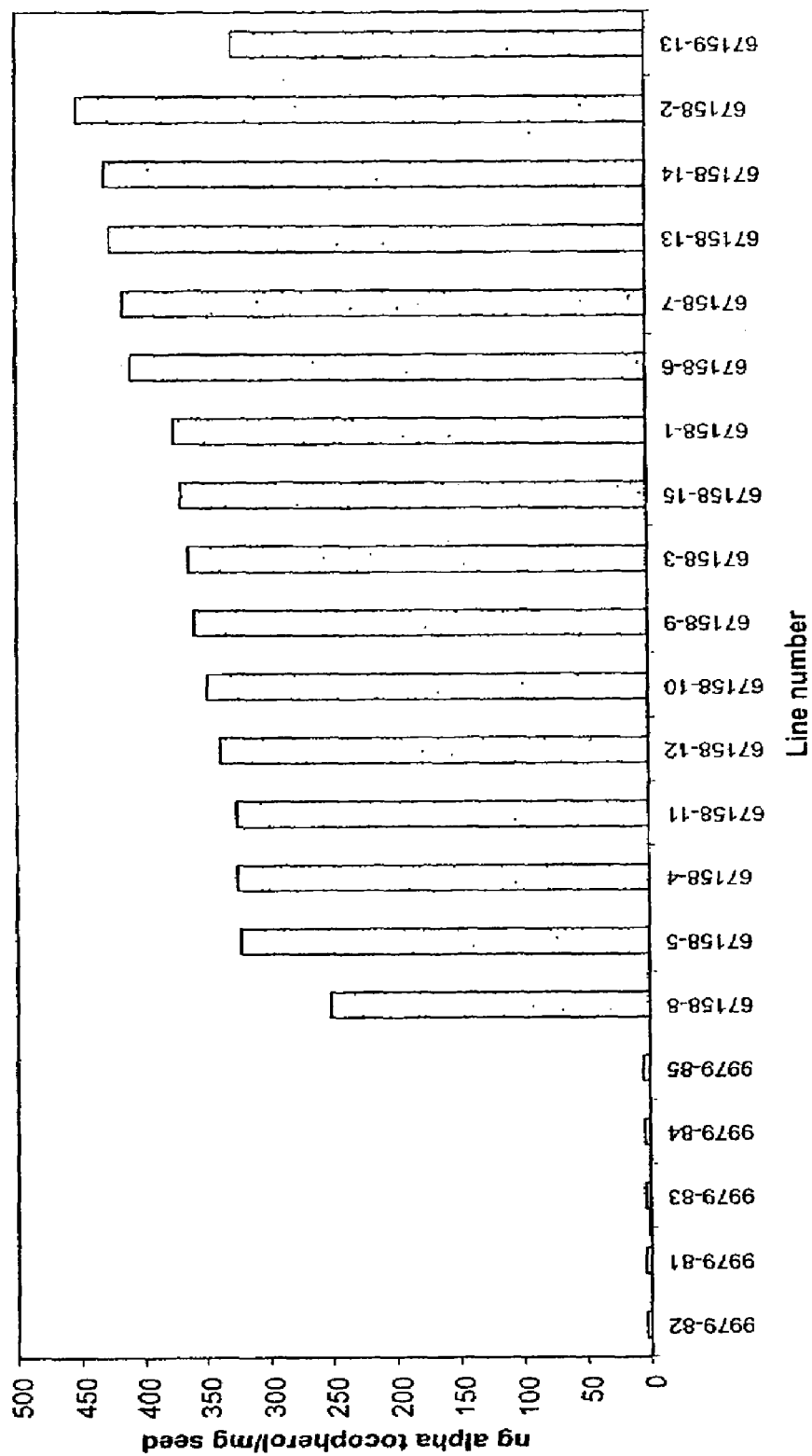
FIGS. 22A and 22B are graphs representing the α and γ-tocopherol levels in *Arabidopsis* $T_2$ seeds from 5 transgenic plants containing the napin binary vector (9979), 15 transgenic plants expressing the *Cuphea pulcherrima* GMT gene under the control of the napin promoter (67158) and 1 transgenic plant expressing the *Brassica napus* P4 GMT under the control of the napin promoter (67159).
Figure 22B:
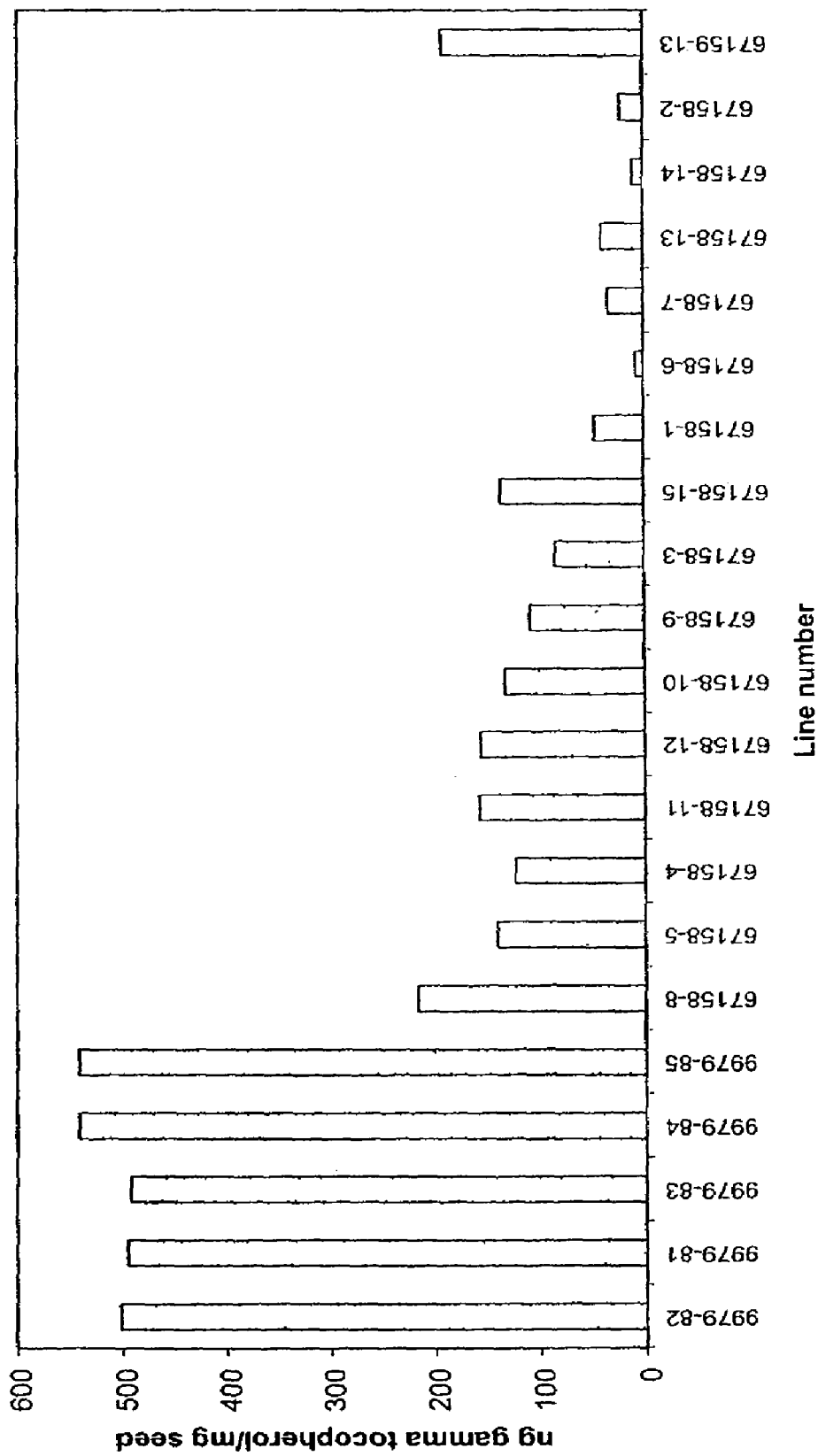
Figure 33:
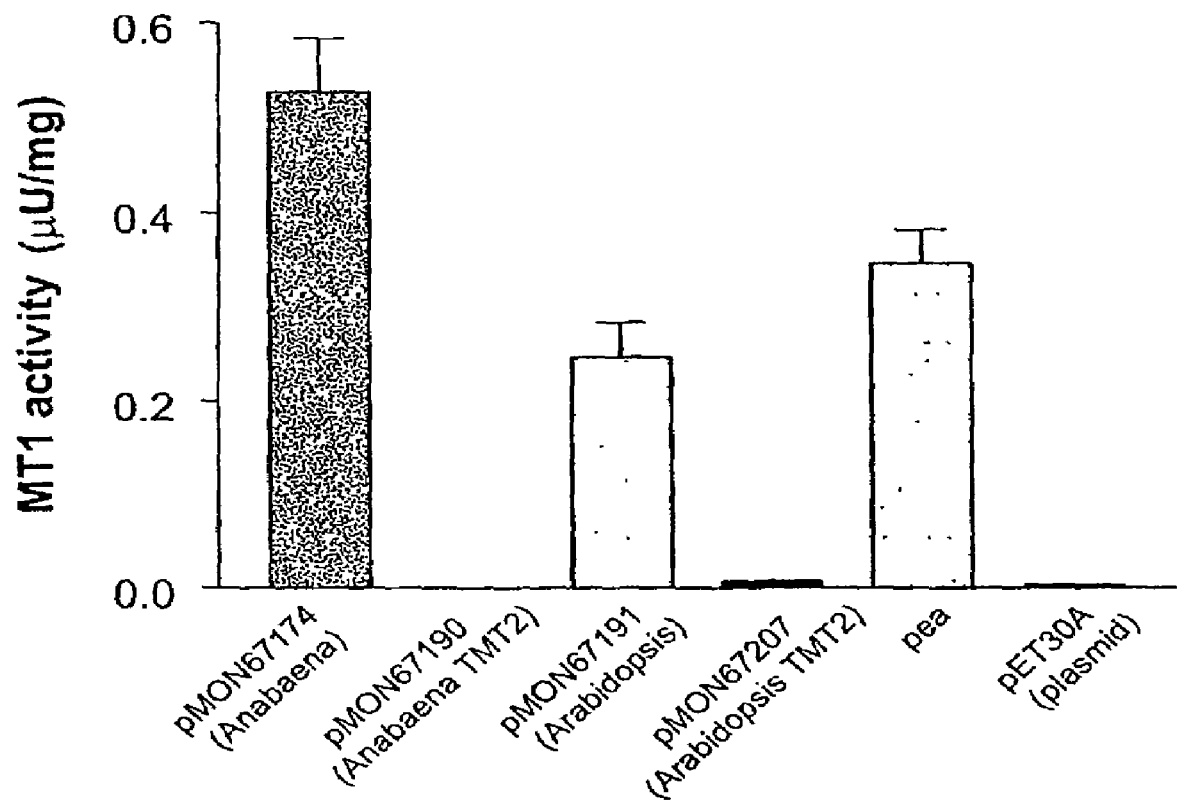
FIG. 33 is a graph showing 2-Methylphytylplastoquinol methyltransferase activity obtained with recombinant proteins and a pea chloroplast control. Data are obtained with recombinant proteins from microbial and plant sources.

The MT1 assay results (FIG. 33) indicated 2-methylphytylplastoquinol methyltransferase activity with the *Anabaena* MT1 expression product. FIGS. 18, 19, and 20 represent HPLC chromatograms of the MT1 assay carried out with recombinant expressed *Anabaena* MT1, with recombinant *Anabaena* MT1 without 2-methylphytylplastoquinol substrate, and an assay performed with pea chloroplast extract as a positive control for the MT1 assay, respectively.

Figure 34:
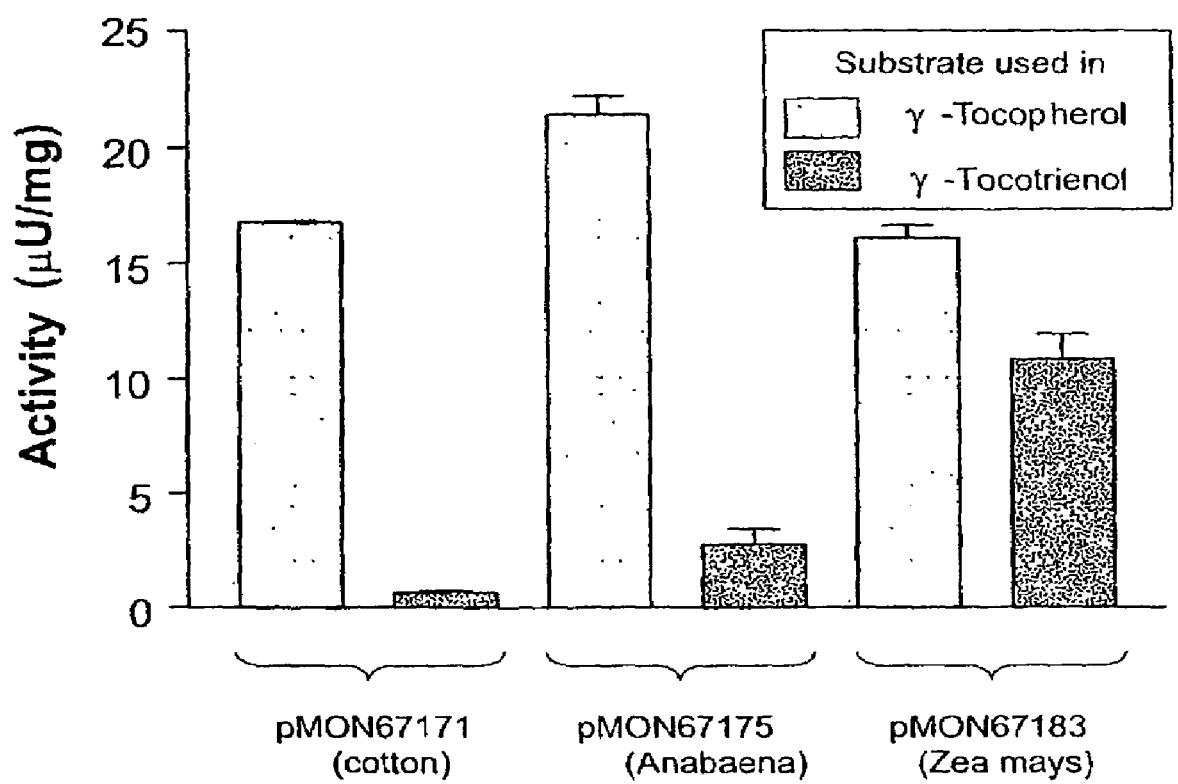
FIG. 34 is a graph showing GMT substrate specificity for gamma-tocopherols versus gamma-tocotrienols. GMT activity is measured with recombinant expressed gamma methyltransferases from cotton, *Anabaena*, and corn, using gamma tocopherol or gamma-tocotrienol and S-adenosylmethionine as a substrate.

The *Anabaena*, corn, and cotton GMTs are chosen for the purpose of comparing enzymes from microbial and monocotyledon sources versus dicotyledon plant sources for methyltransferase activity with γ-tocotrienol. Assays are run in duplicate with γ-tocopherol assays run in parallel as controls. In both cases 100 μM of substrate is used, with the substrate as the only difference in assay conditions. The monocot GMT showed comparable methyltransferase activity with γ-tocopherol and γ-tocotrienol. In contrast the bacterial and the dicot GMT are substantially less active with γ-tocotrienol. The results of this experiment are summarized in FIG. 34.

EXAMPLE 5

Seed specific expression of GMT in *Brassica* is obtained by linking the *Arabidopsis thaliana*, ecotype Columbia gene to the napin promoter as described here. Poly A+ RNA is isolated from *Arabidopsis thaliana*, ecotype Columbia using an adapted biotin/streptavadin procedure based on a mRNA Capture Kit" (Roche Molecular Biochemicals, Indianapolis, Ind.). Young leaf tissue is homogenized in CTAB buffer (50 mM Tris-HCl pH9, 0.8M NaCl, 0.5% CTAB, 10 mM EDTA), extracted with chloroform and pelleted. As set forth in the manufacturer's instructions, the soluble phase is hybridized to biotin-labeled oligo-dT, immobilized on streptavadin-coated PCR tubes and washed. First strand cDNA is synthesized using the "$1^{st}$ strand cDNA synthesis kit for RT-PCR" (Roche Molecular Biochemicals, Indianapolis, Ind.). cDNA synthesis is performed according to the manufacturer's protocol and followed by RNase digestion (0.5 units RNase in 48 μl for 30 min.).

*Arabidopsis thaliana*, ecotype Columbia is amplified using primers #16562 Arab GMT Forward-Not 5' GCG GCC GCA CAA TGA AAG CAA CTC TAG CAG CAC CCT C3' (SEQ ID NO: 77) and #16563 Arab GMT Reverse-Sse 5' CCT GCA GGT TAG AGT GGC TTC TGG CAA GTG ATG 3' (SEQ ID NO: 78) and the "EXPAND High Fidelity PCR System (Roche Molecular Biochemicals, Indianapolis, Ind.). A GMT gene is PCR-amplified for 30 cycles using a "touchdown" cycling profile: 3 min incubation at 94° C., followed by 15 cycles of 45 seconds denaturation at 94° C., 30 seconds annealing at 60° C. and 2 min extensions at 72° C. Primers are designed to add a NotI/Kozak site and a 3' Sse83871 site.

Figure 13:
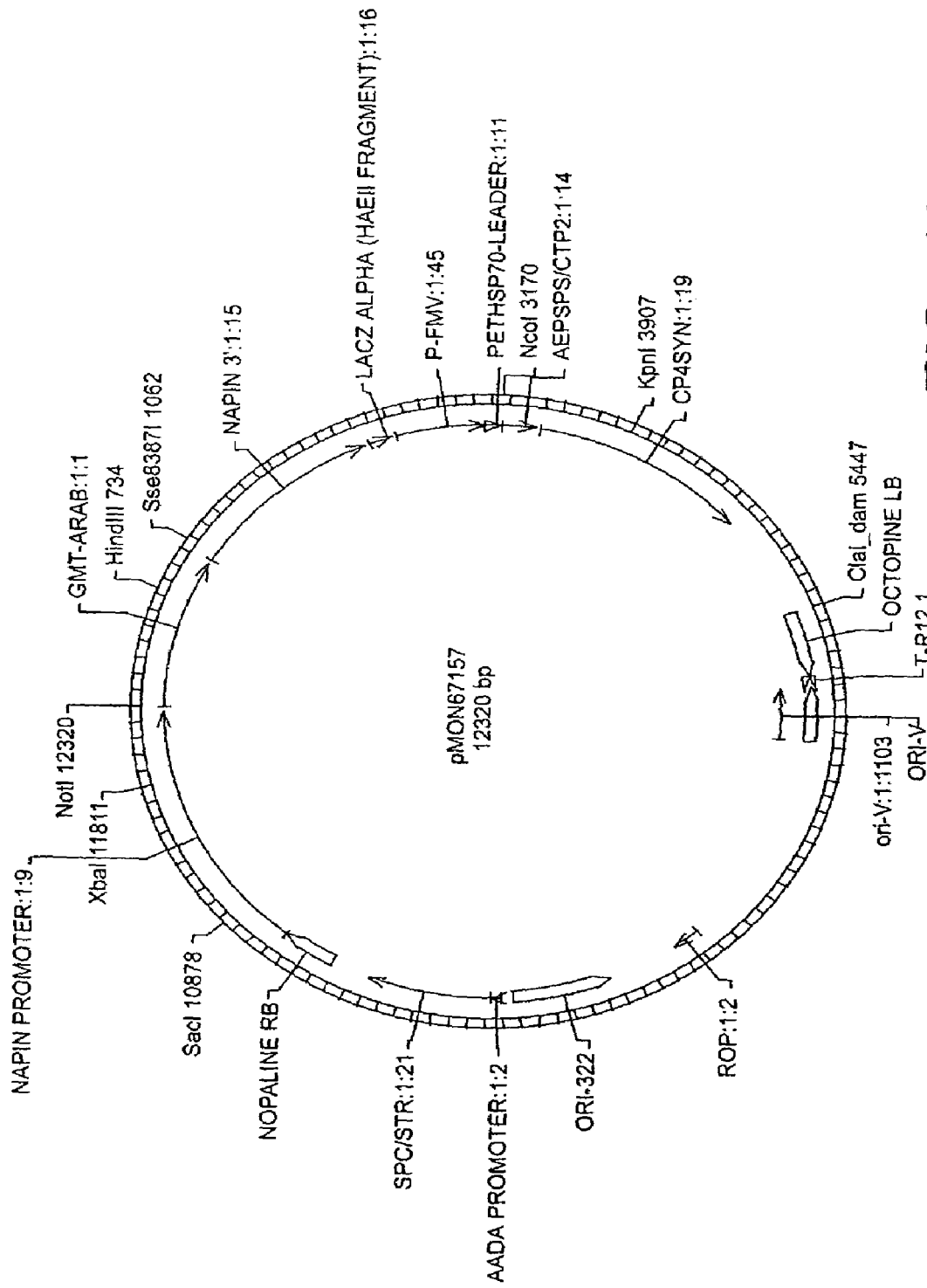
FIG. 13 is a schematic of construct pMON67157.

The PCR product is desalted using a Pharmacia Microspin S-400 HR Column (Pharmacia, Uppsala, Sweden). The purified fragment is inserted into pCR2.1 using a TOPO TA Cloning Kit (Invitrogen, Carlsbad, Calif.) resulting in the formation of pMON67155. The nucleotide sequence of the insert, *Arabidopsis thaliana*, ecotype Columbia GMT is confirmed by DNA sequencing. The GMT insert is excised from pMON67155 by NotI/Sse8371 digestion. Restriction enzymes are removed using StrataClean Resin (Stratagene, La Jolla, Calif.) and passed through a Microspin S-400 HR Column (Pharmacia, Uppsala, Sweden). The fragment is ligated into NotI/Sse83871 digested, identically treated pMON11307, resulting in the formation of the binary vector pMON67157 (FIG. 13).

The plant binary construct described above is used in *Brassica napus* plant transformation to direct the expression of the gamma-methyltransferases in the embryo. The vector is transformed into ABI strain *Agrobacterium* cells by the method of Holsters et al., *Mol. Gen. Genet.* 163:181-187 (1978). *Brassica* plants may be obtained by *Agrobacterium*-mediated transformation as described by Radke et al. *Plant Cell Reports* 11: 499-505 (1992) and WO 00/61771. The tocopherol level and composition of the seed from transgenic plants is analyzed using the method set forth in example 6.

Figure 24:
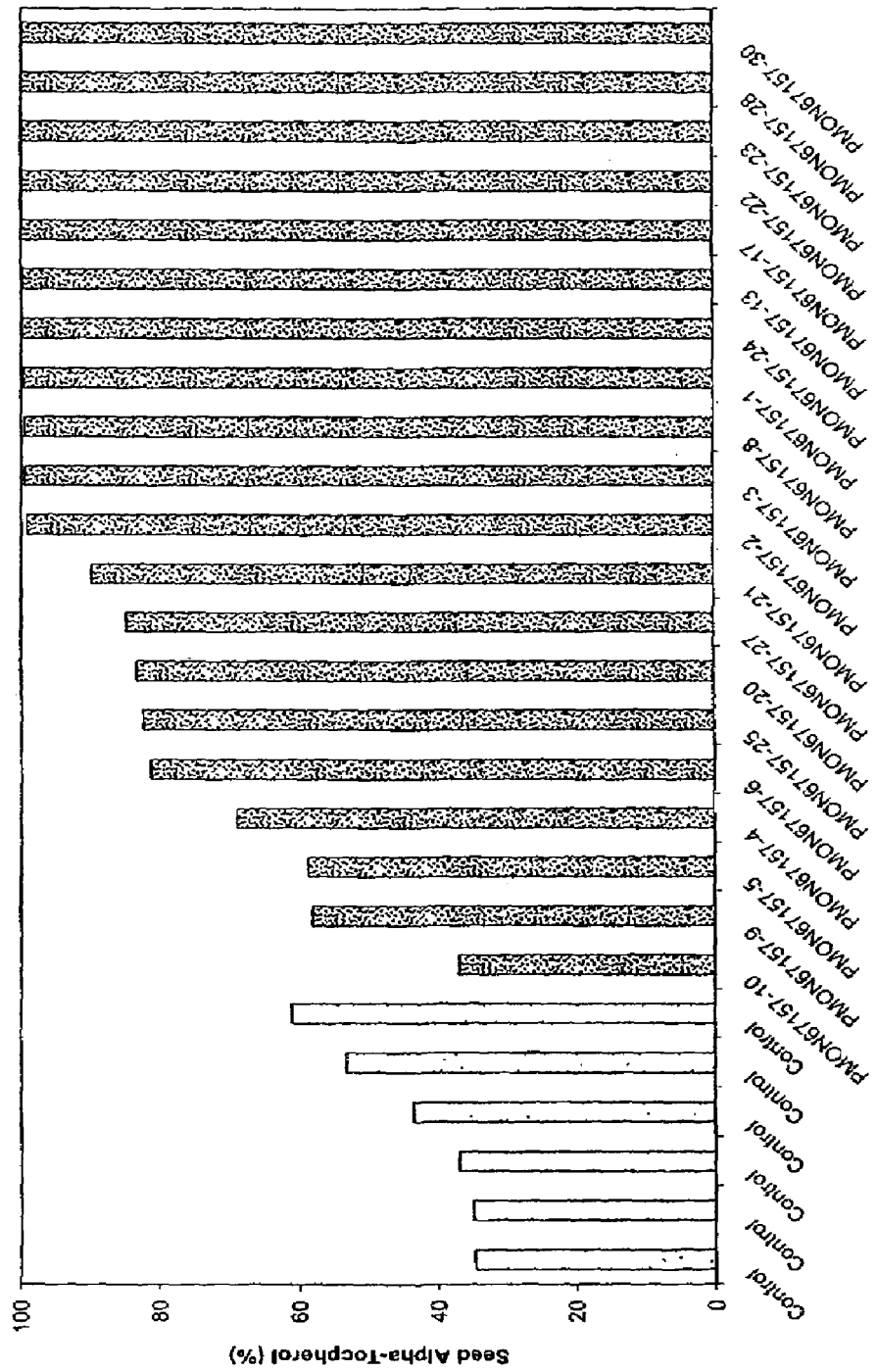
FIG. 24 is a graph representing the average seed α-tocopherol level in transformed *Brassica* plants.

Results of *Brassica* transformation are shown in FIG. 24, which is a graph representing the seed α-tocopherol levels for various transformants. Table 7 represents transformation data from various lines.

TABLE 7

| ng α toco./mg seed | ng β toco./mg seed | ng γ toco./mg seed | ng δ toco./mg seed | ng total toco./mg seed | Line Number | | % Alpha | Avg. % Alpha | Description |
|---|---|---|---|---|---|---|---|---|---|
| 165.07 | 0.00 | 139.34 | 5.33 | 309.74 | Control - Empty Vector | R1 | 53.3 | 44.1 | Control |
| 102.41 | 0.00 | 189.34 | 3.76 | 295.50 | Control | R1 | 34.7 | | Control |
| 126.90 | 0.00 | 229.27 | 6.64 | 362.81 | Control | R1 | 35.0 | | Control |

TABLE 7-continued

| ng α toco./mg seed | ng β toco./mg seed | ng γ toco./mg seed | ng δ toco./mg seed | ng total toco./mg seed | Line Number | | % Alpha | Avg. % Alpha | Description |
|---|---|---|---|---|---|---|---|---|---|
| 139.09 | 0.00 | 230.64 | 5.97 | 375.70 | Control | R1 | 37.0 | | Control |
| 137.88 | 0.00 | 173.73 | 4.36 | 315.97 | Control | R1 | 43.6 | | Control |
| 203.16 | 0.00 | 126.41 | 2.74 | 332.31 | Control | R1 | 61.1 | | Control |
| 113.75 | 0.00 | 187.68 | 5.86 | 307.29 | *Arabidopsis* GMT in Canola | R1 | 37.0 | 87.1 | PMON67157-10 |
| 197.02 | 0.00 | 137.48 | 4.50 | 338.99 | *Arabidopsis* GMT in Canola | R1 | 58.1 | | PMON67157-9 |
| 201.11 | 0.00 | 134.65 | 6.52 | 342.28 | *Arabidopsis* GMT in Canola | R1 | 58.8 | | PMON67157-5 |
| 212.78 | 0.00 | 92.97 | 3.36 | 309.11 | *Arabidopsis* GMT in Canola | R1 | 68.8 | | PMON67157-4 |
| 240.49 | 0.00 | 53.44 | 1.77 | 295.70 | *Arabidopsis* GMT in Canola | R1 | 81.3 | | PMON67157-6 |
| 231.63 | 0.00 | 49.46 | 0.00 | 281.09 | *Arabidopsis* GMT in Canola | R1 | 82.4 | | PMON67157-25 |
| 234.90 | 0.00 | 45.91 | 1.03 | 281.84 | *Arabidopsis* GMT in Canola | R1 | 83.3 | | PMON67157-20 |
| 334.07 | 0.00 | 57.69 | 1.65 | 393.41 | *Arabidopsis* GMT in Canola | R1 | 84.9 | | PMON67157-27 |
| 345.00 | 0.00 | 36.75 | 2.23 | 383.99 | *Arabidopsis* GMT in Canola | R1 | 89.8 | | PMON67157-21 |
| 286.02 | 0.00 | 1.04 | 1.61 | 288.67 | *Arabidopsis* GMT in Canola | R1 | 99.1 | | PMON67157-2 |
| 387.23 | 0.00 | 0.16 | 1.64 | 389.03 | *Arabidopsis* GMT in Canola | R1 | 99.5 | | PMON67157-3 |
| 322.59 | 0.00 | 0.68 | 0.66 | 323.93 | *Arabidopsis* GMT in Canola | R1 | 99.6 | | PMON67157-8 |
| 331.27 | 0.00 | 0.46 | 0.61 | 332.34 | *Arabidopsis* GMT in Canola | R1 | 99.7 | | PMON67157-1 |
| 322.34 | 0.00 | 0.00 | 0.62 | 322.97 | *Arabidopsis* GMT in Canola | R1 | 99.8 | | PMON67157-24 |
| 316.73 | 0.00 | 0.51 | 0.00 | 317.24 | *Arabidopsis* GMT in Canola | R1 | 99.8 | | PMON67157-13 |
| 357.05 | 0.00 | 0.24 | 0.00 | 357.29 | *Arabidopsis* GMT in Canola | R1 | 99.9 | | PMON67157-17 |
| 310.97 | 0.00 | 0.17 | 0.00 | 311.13 | *Arabidopsis* GMT in Canola | R1 | 99.9 | | PMON67157-22 |
| 324.07 | 0.00 | 0.00 | 0.00 | 324.07 | *Arabidopsis* GMT in Canola | R1 | 100.0 | | PMON67157-23 |
| 367.84 | 0.00 | 0.00 | 0.00 | 367.84 | *Arabidopsis* GMT in Canola | R1 | 100.0 | | PMON67157-28 |
| 438.54 | 0.00 | 0.00 | 0.00 | 438.54 | *Arabidopsis* GMT in Canola | R1 | 100.0 | | PMON67157-30 |

EXAMPLE 6

Seed specific expression of GMT in soy is obtained by linking the *Arabidopsis thaliana*, ecotype Columbia GMT gene with different types of seed specific promoters as described here. Total RNA is isolated from *Arabidopsis* leaf tissue (ecotype Columbia) using the Qiagen "RNEASY plant mini kit" (Qiagen Inc., Valencia, Calif.). First strand cDNA synthesized using the "$1^{st}$ strand cDNA synthesis kit for RT-PCR" from Boehringer Mannheim. RNA isolation and cDNA synthesis is performed according to the manufacturer protocols.

The *Arabidopsis* GMT is amplified using primers "GMT-ara 5' CAT GCC ATG GGA ATG AAA GCA ACT CTA GCA G" (SEQ ID NO: 75) and "GMT-ara 3' GTC AGA ATT CTT ATT AGA GTG GCT TCT GGC AAG" (SEQ ID NO: 76) and the Boehringer Mannheim "EXPAND High Fidelity PCR System". The GMT gene is PCR-amplified by 30 cycles under the following conditions: 5 min incubation at 95° C., followed by 30 cycles of 1 min at 95° C., 1 min annealing at 58° C. and 2 min extension at 72° C. These reactions are followed by 5 min incubation at 72° C. The primers are designed to add a methionine and a glycin to the N-terminus of the GMT protein.

Figure 3:
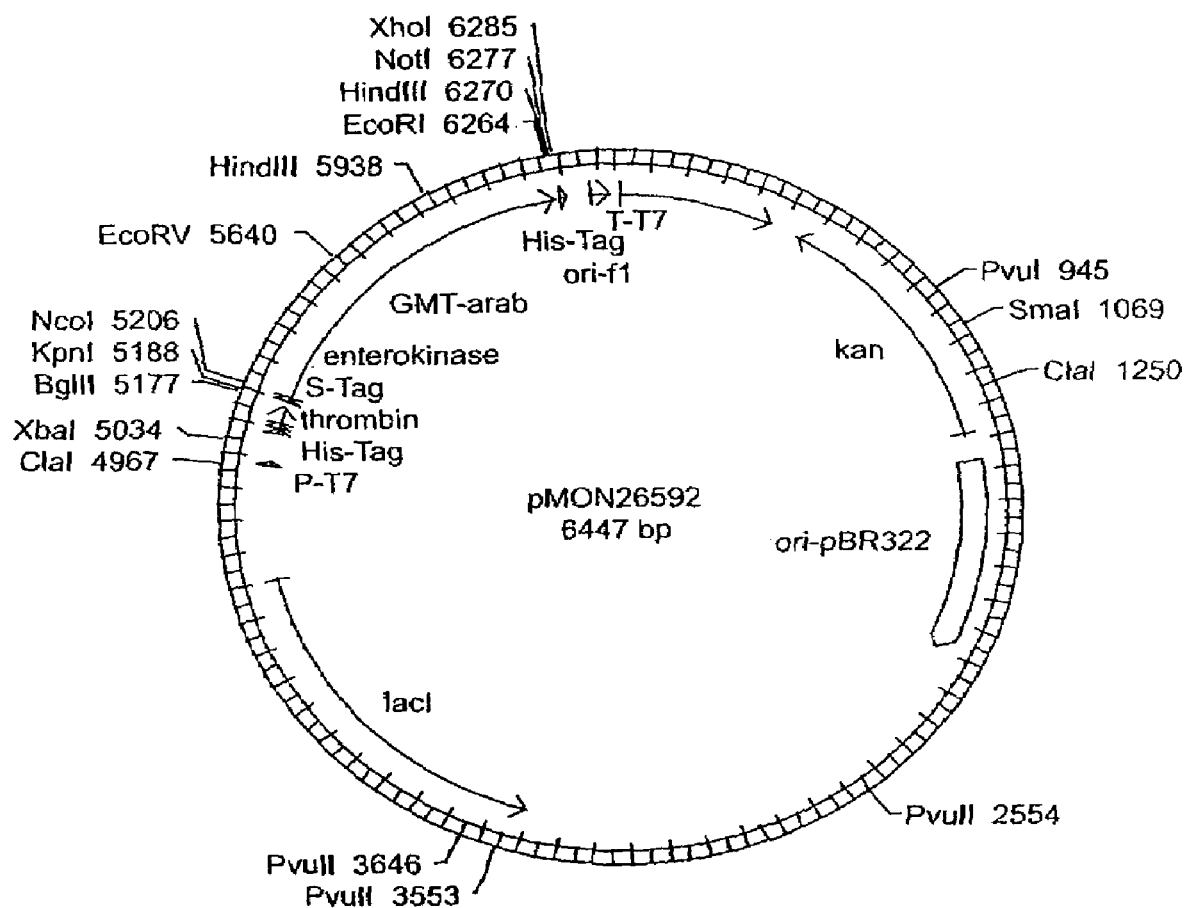
FIG. 3 is a schematic of construct pMON26592.
Figure 4:
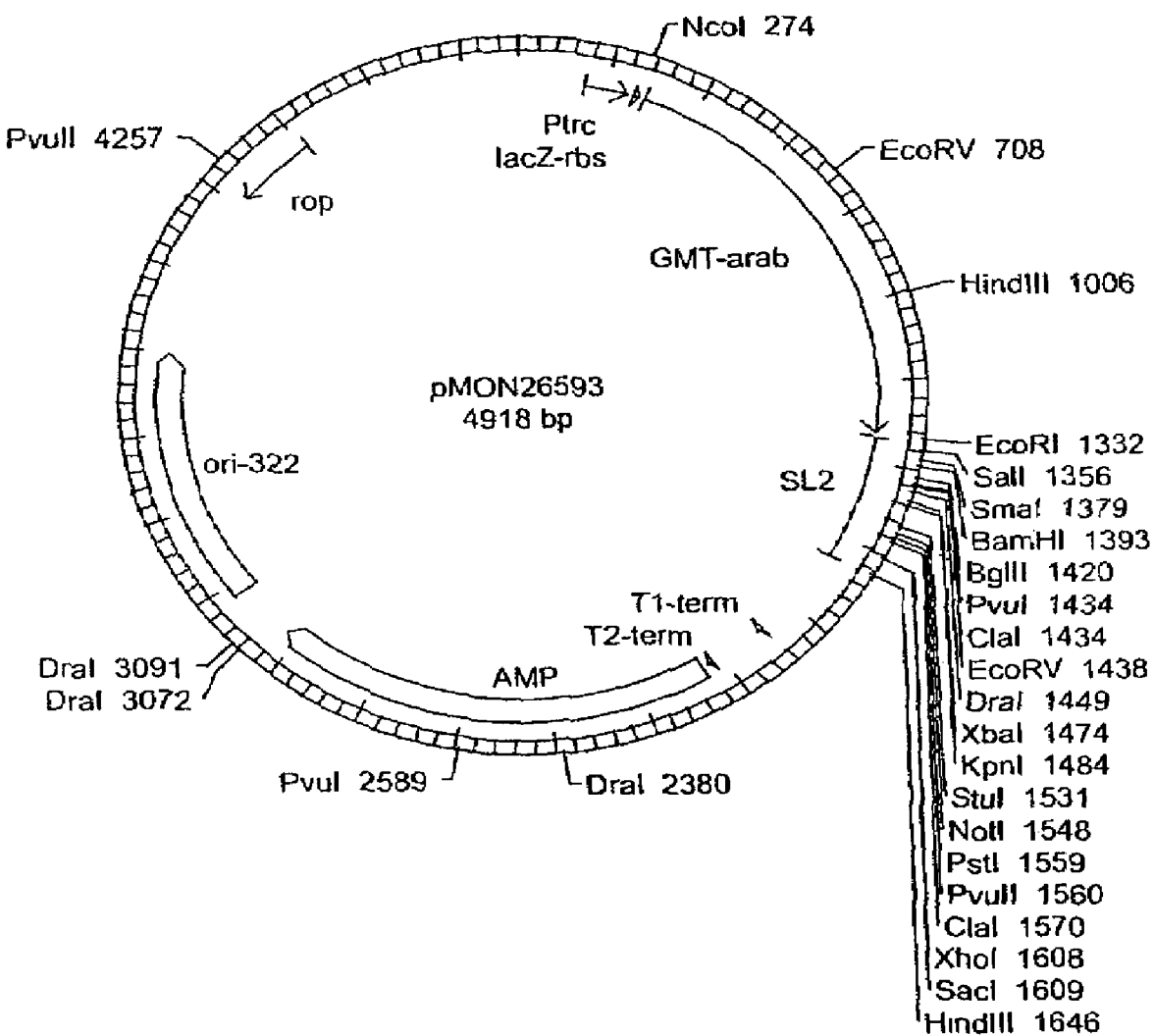
FIG. 4 is a schematic of construct pMON26593.

The PCR products are EcoRI and NcoI digested and gel purified using the Qiagen "QIAQUICK Gel Extraction Kit" (Qiagen Inc., Valencia, Calif.). Purified fragments are ligated into EcoRI/NocI digested and gel purified pET30 (Novagen, Madison, Wis.) and pSE280 (Invitrogen, Carlsbad, Calif.) resulting in the formation of pMON26592 (FIG. 3) and pMON26593 (FIG. 4), respectively. Subsequently the *Arabidopsis* GMT sequence is confirmed. During the sequencing procedure it is found that the cloned sequence from the Columbia ecotype exhibited two nucleotide changes compared to the *Arabidopsis thaliana* GMT sequence published in WO 99/04622 (position 345, change from C to T; position 523, substitution from T to G). While the first substitution is a silent mutation, the second nucleotide change resulted in an amino acid change from serine to alanine.

Figure 6:
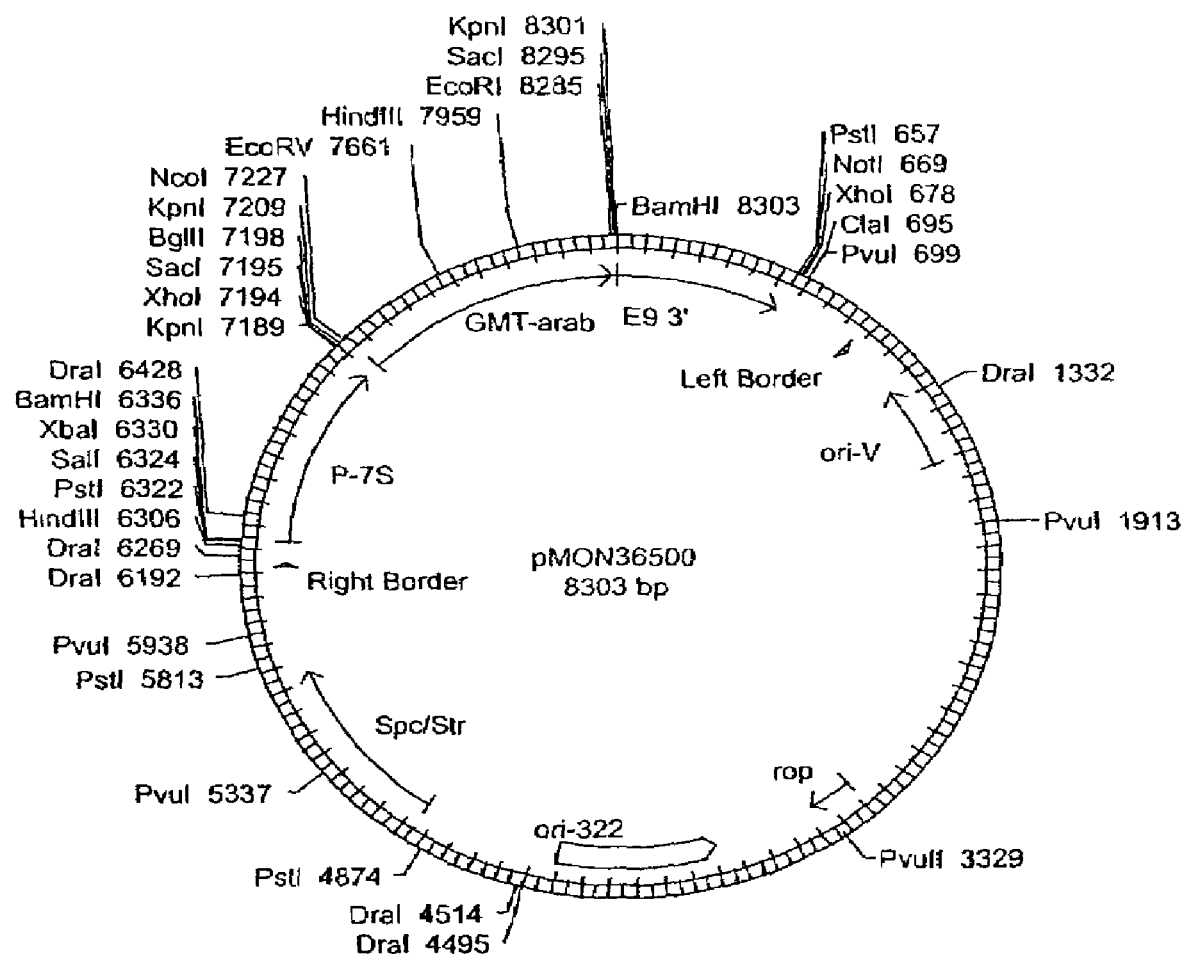
FIG. 6 is a schematic of construct pMON36500.

For generation of a GMT plant transformation vector under p7S promoter control, a GMT is excised as a BglII/EcoRI fragment from pMON26592, gel purified, and cloned into a BglII/EcoRI digested and gel purified vector containing a p7S expression cassette resulting in the formation of the shuttle vector pMON36500 (FIG. 6). The p7S::$GMT_{At}$ expression cassette is excised from pMON36500 by PstI digest, the ends are filled in by T4 DNA polymerase treatment, gel purified, and cloned into SmaI digested, alkaline phosphatase treated and gel purified pMON38207R, resulting in the formation of the binary vector pMON36503.

An NcoI/EcoRI digested, gel purified GMT excised from pMON26592 is ligated into an NcoI/EcoRI digested vector harboring a pARC5-1 expression cassette, resulting in the formation of the shuttle vector pMON36502. The pARC5-1::GMTAt expression cassette is excised from pMON35502 by NotI digest, blunt ends are generated by treatment with Klenow fragment, the fragment is gel purified, and ligated into Sma I digested, alkaline phosphatase treated and gel purified pMON38207R. The resulting binary vector is designated pMON36505.

Figure 5:
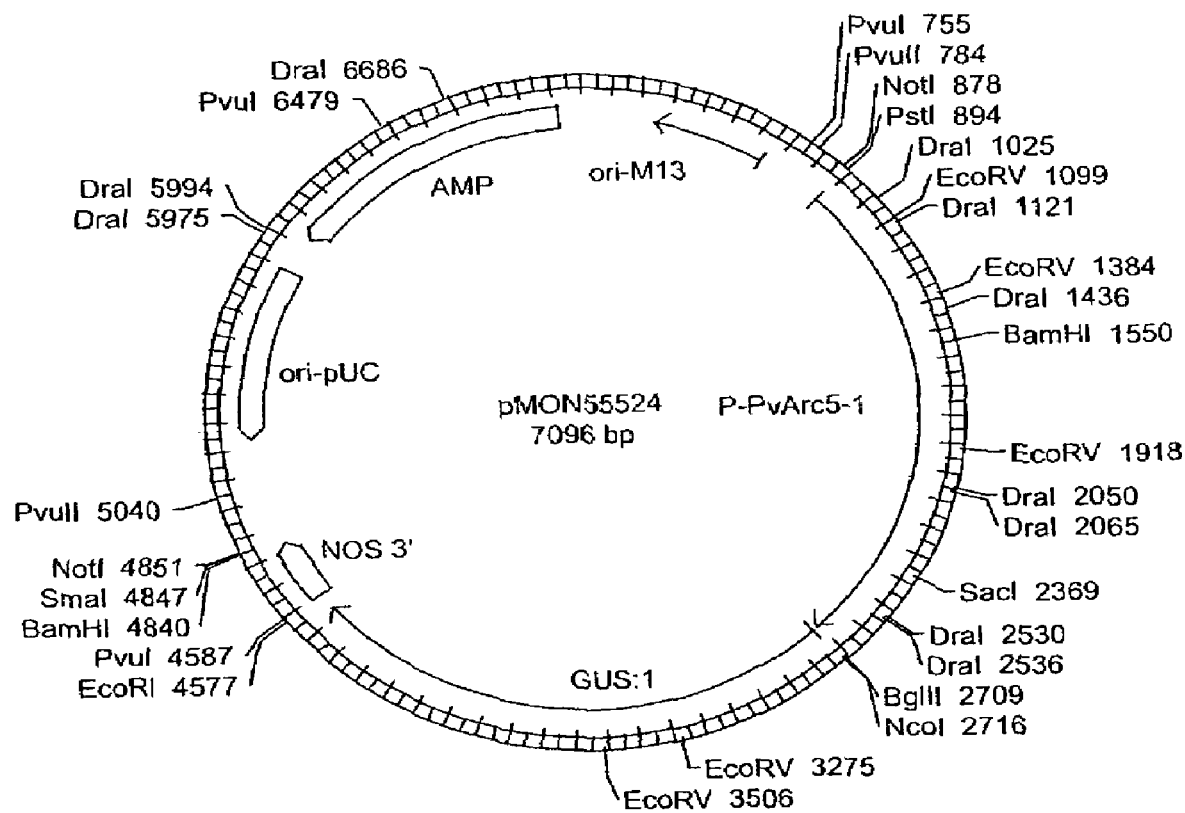
FIG. 5 is a schematic of construct pMON55524.
Figure 7:
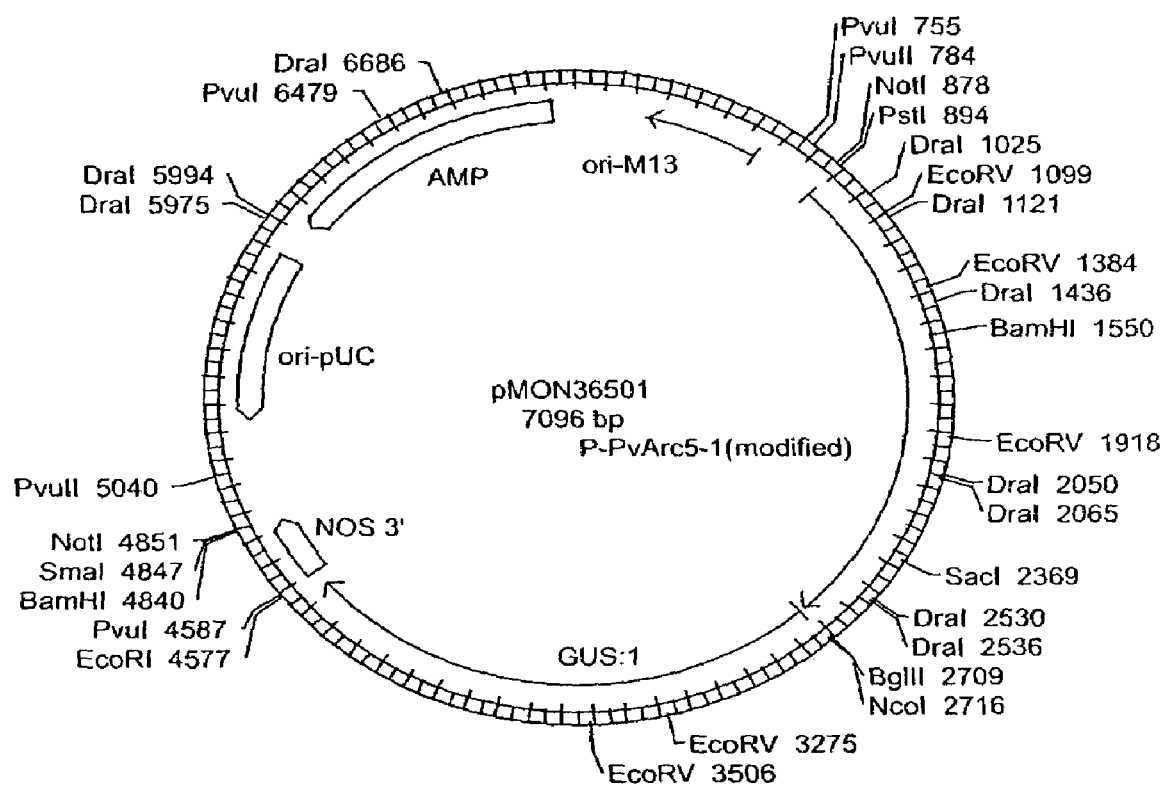
FIG. 7 is a schematic of construct pMON36501.
Figure 8:
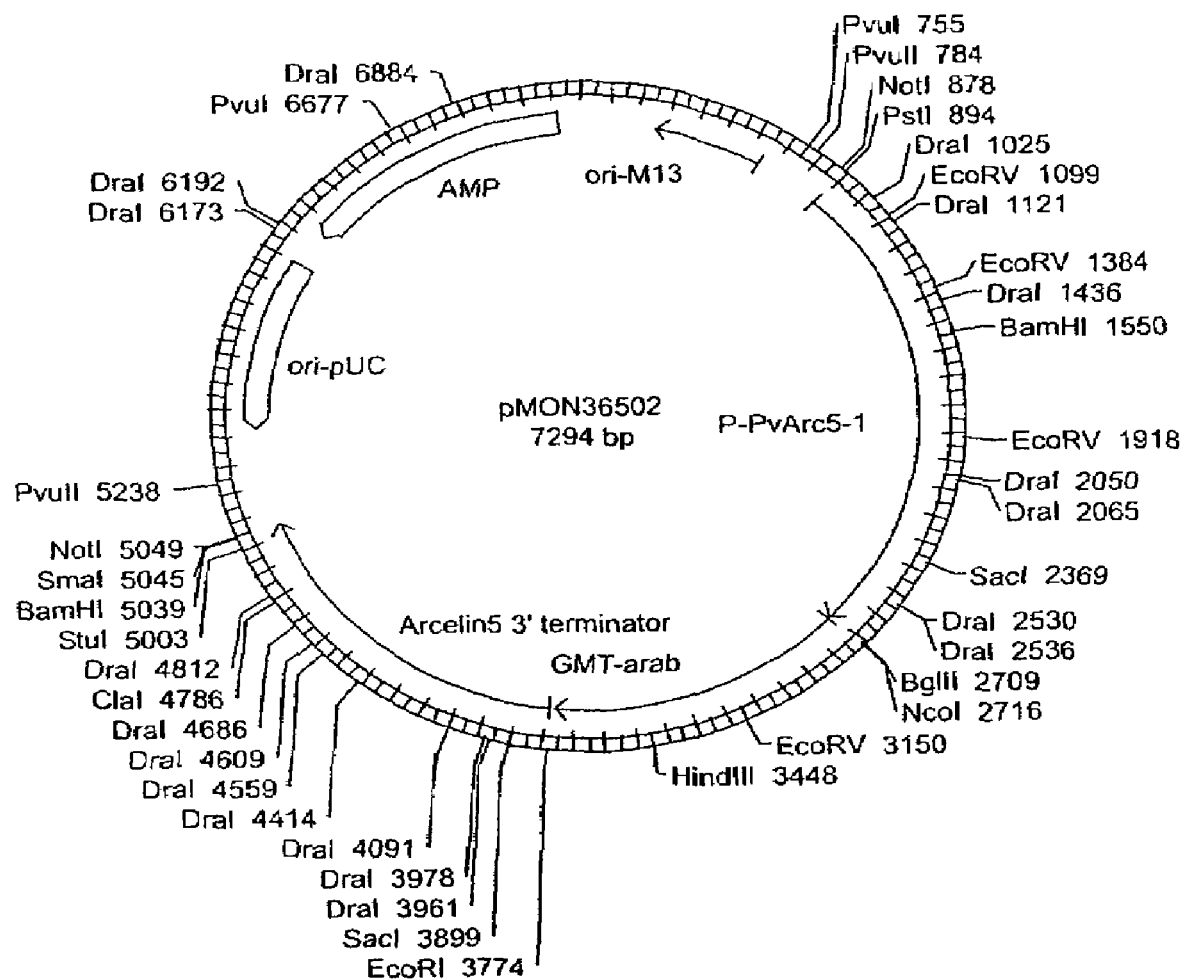
FIG. 8 is a schematic of construct pMON36502.
Figure 10:
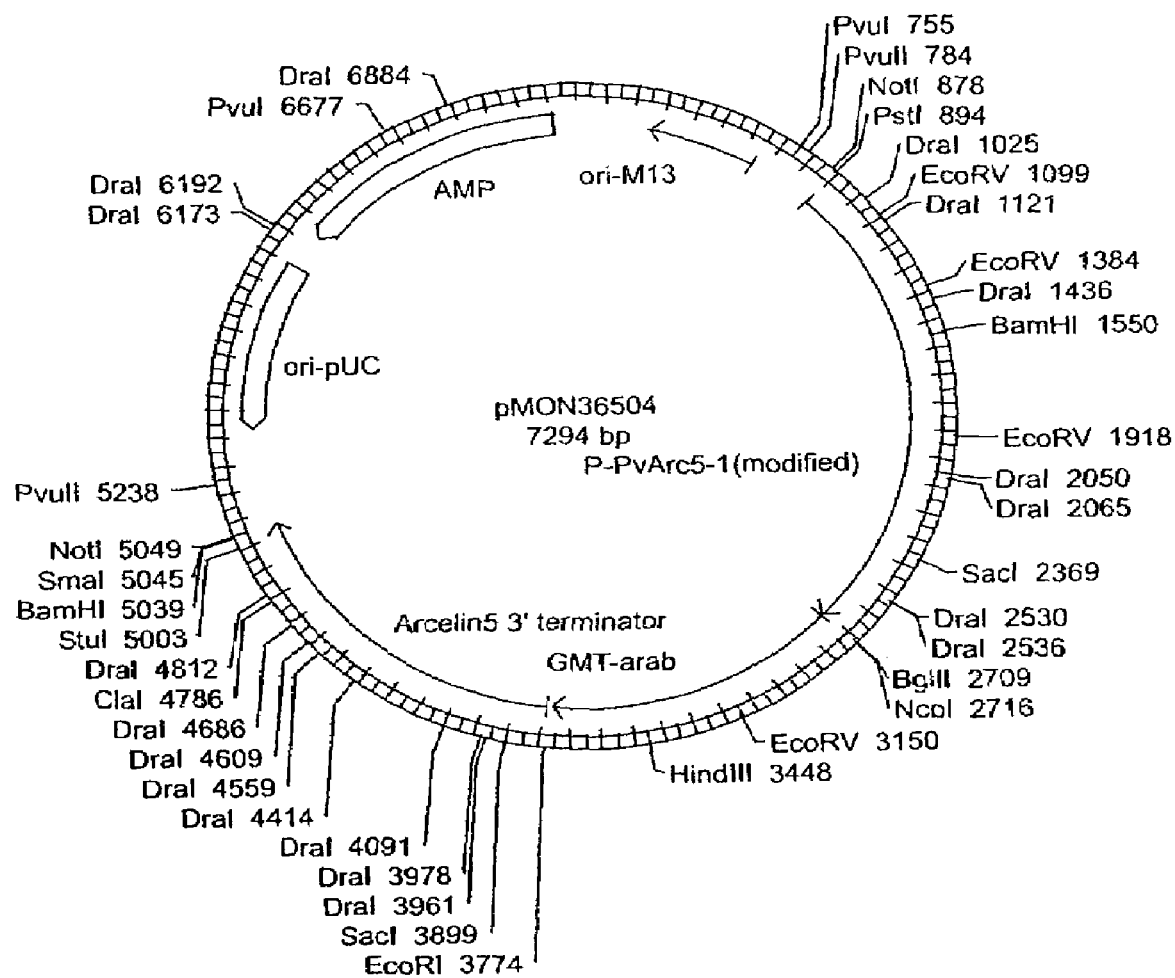
FIG. 10 is a schematic of construct pMON36504.

An arcelin 5 promoter harbors 6 ATG start codons at the 5' sequence located in different reading frames (Goosens et al., *Plant Physiol*. (1999), 120(4), 1095-1104, Goosens et al., *FEBS Lett*. (1999), 456(1), 160-164.). To decrease the risk of interference of these start codons during gene expression, 4 of these putative translational start sites are deleted. Deletion of 4 ATG codons is achieved by PCR, using primers Parc5' (5'-CCA CGT GAG CTC CTT CCT CTT CCC-3') (SEQ ID NO: 79) and Parc3' (5'-GTG CCA TGG CAG ATC TGA TGA TGG ATT GAT GGA-3') (SEQ ID NO: 80). Primer Parc3' is designed to hybridize to the Arcelin 5 promoter sequence at the translational start site and delete 4 of the 6 ATG codons. PCR is performed using pMON55524 (FIG. 5) as template DNA and the Boehringer Mannheim PCR Core Kit in 30 PCR cycles under the following conditions: 5 min incubation at 95° C., followed by 30 cycles of 1 min at 95° C., 1 min annealing at 60° C. and 40 second extension at 72° C. These reactions are followed by 5 min incubation at 72° C. The resulting approximately 360 bp PCR product is digested with Sa/I and NcoI, gel purified and cloned into SalI/NcoI digested and gel purified pMON55524, resulting in the formation of pMON36501 (FIG. 7). A DNA sequence of the cloned PCR product is confirmed by DNA sequencing. A GMT expression cassette using the modified promoter is assembled by ligating the backbone of SmaI/NcoI digested and gel purified pMON36501 with a GMTAt::Arcelin 5 3' terminator fusion obtained from SmaI/NcoI digested gel purified pMON36502 (FIG. 8). The resulting shuttle vector is designated pMON36504 (FIG. 10). A binary vector (pMON36506) harboring a GMT expression cassette under the control of the modified arcelin 5 promoter is generated by cloning the NotI digested, Klenow fragment treated (for blunt end generation), gel purified GMT expression cassette into gel purified SmaI digested alkaline phosphatase treated, and gel purified pMON38207R vector backbone (5'-GAG TG<u>ATGG</u> TTA <u>ATG</u> C<u>ATG</u>AATGC <u>ATG</u> ATC AGA TCT GCC <u>ATG</u> GTC CGT CCT-3' (SEQ ID NO: 81) (original DNA sequence at the translational start site of the Arcelin 5 promoter—pARC5-1) (5'-GAG TG<u>ATG</u>G TTA <u>ATC</u> C<u>ATC</u>A<u>ATCC</u> <u>ATC</u> <u>ATC</u> AGA TCT GCC <u>ATG</u> GTC CGT CCT-3') (SEQ ID NO: 82) (DNA sequence at the translational start site of the mutated Arcelin 5 promoter—pARC5-1M))

Figure 9:
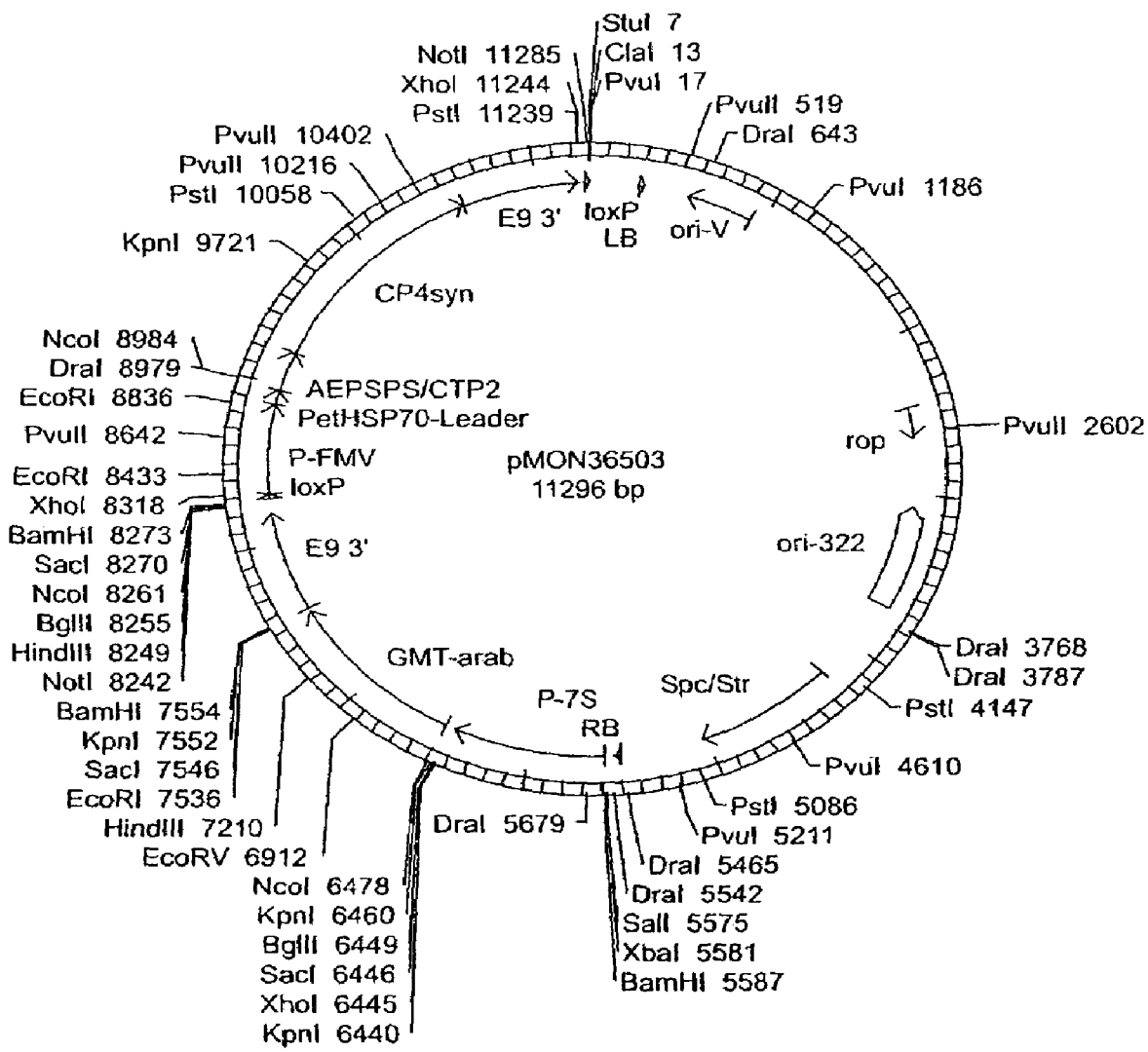
FIG. 9 is a schematic of construct pMON36503.
Figure 11:
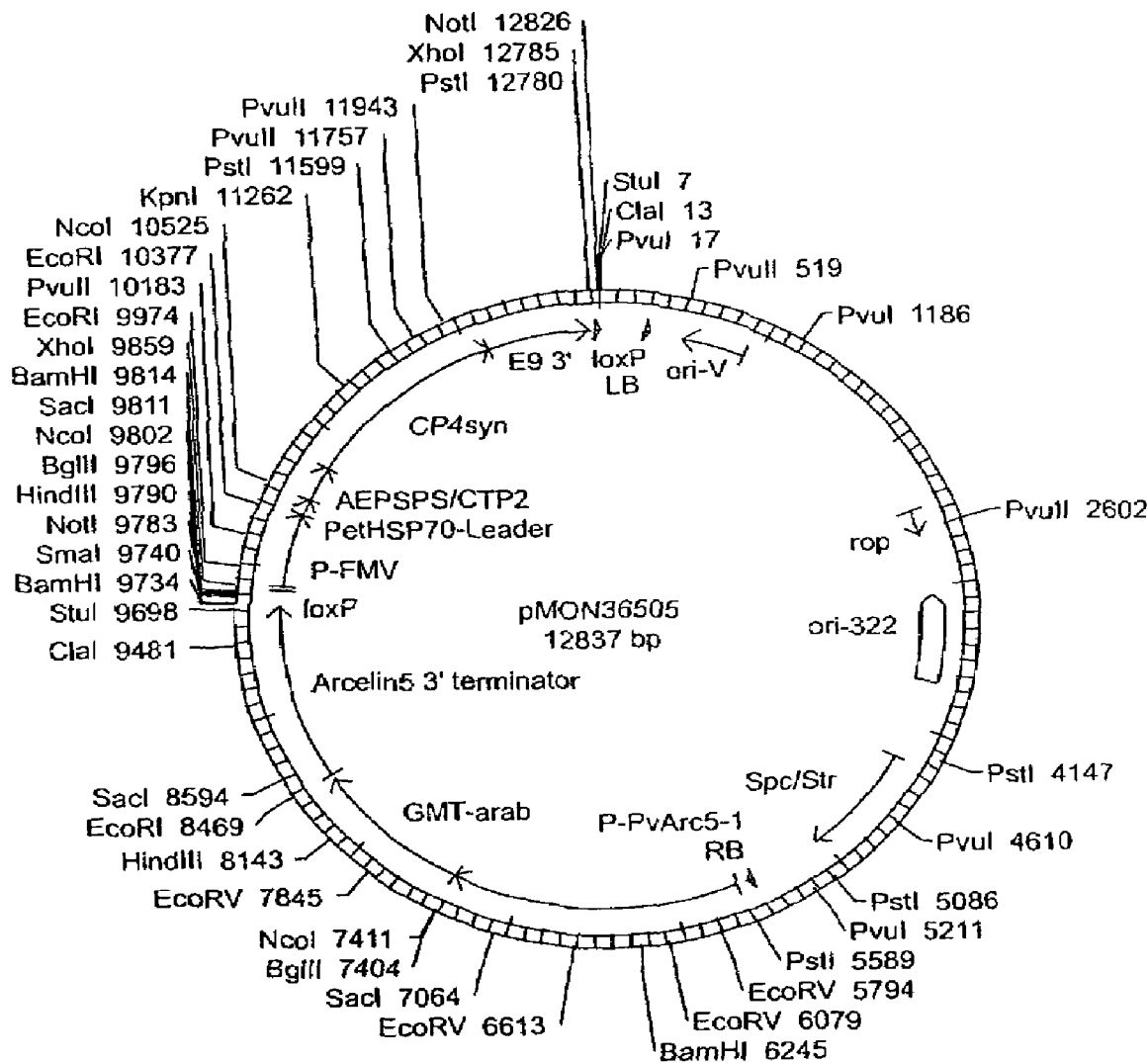
FIG. 11 is a schematic of construct pMON36505.
Figure 12:
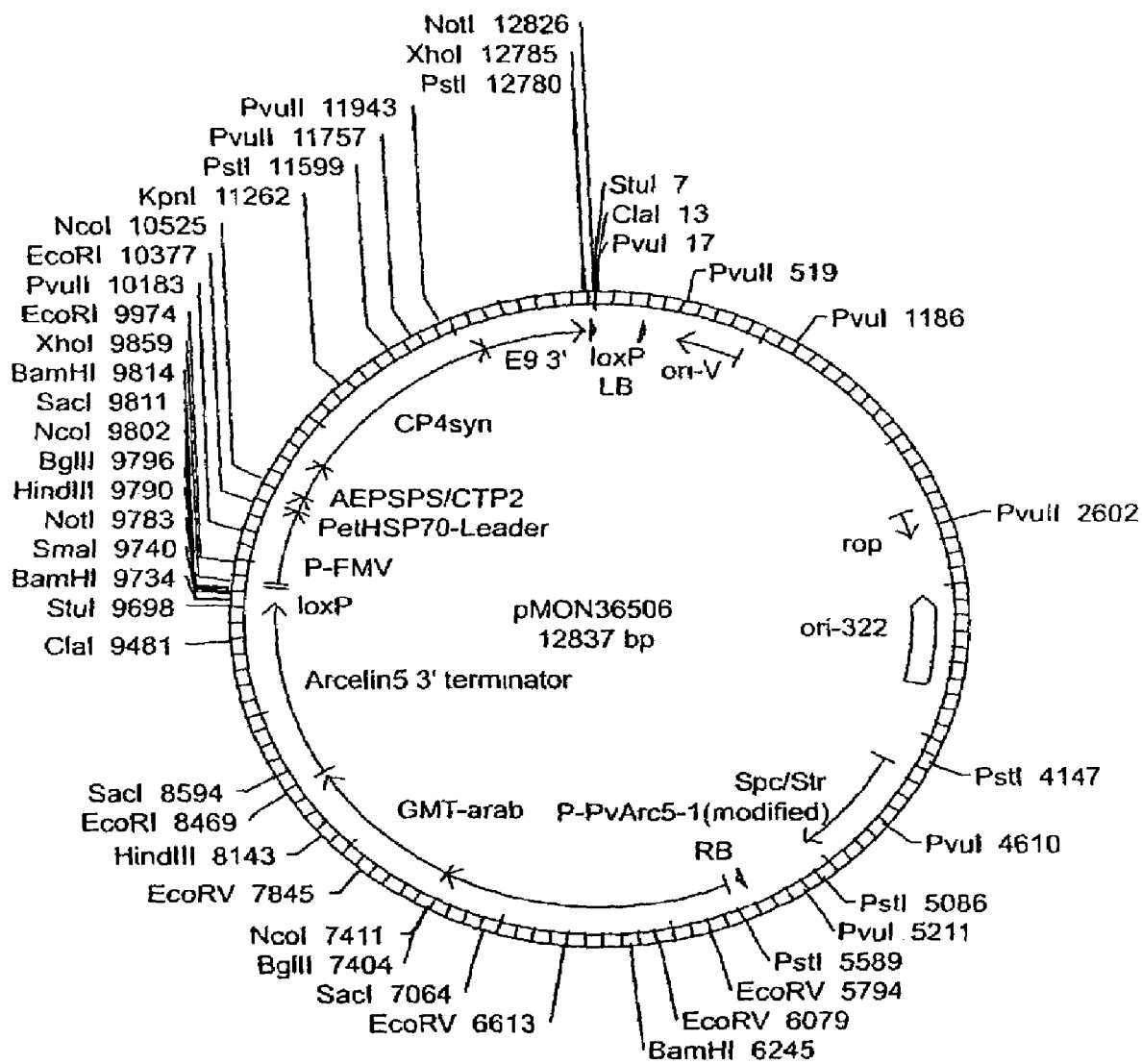
FIG. 12 is a schematic of construct pMON36506.
Figure 14:
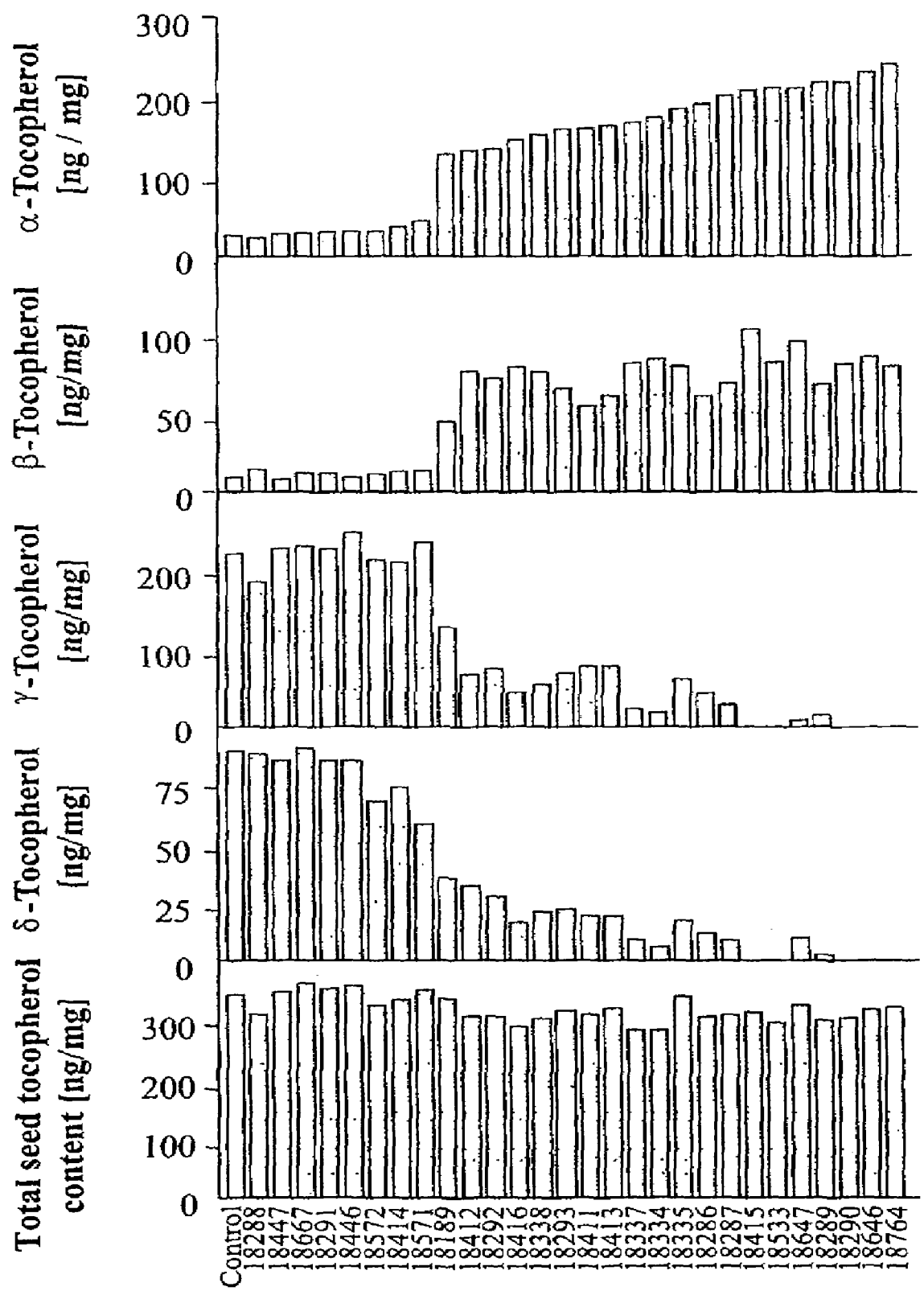
FIG. 14 is a graph depicting the soy seed tocopherol content and composition from pooled seed of the R1 generation of plants transformed with pMON36503. This construct expresses an *A. thaliana* GMT under p7S promoter control.
Figure 15:
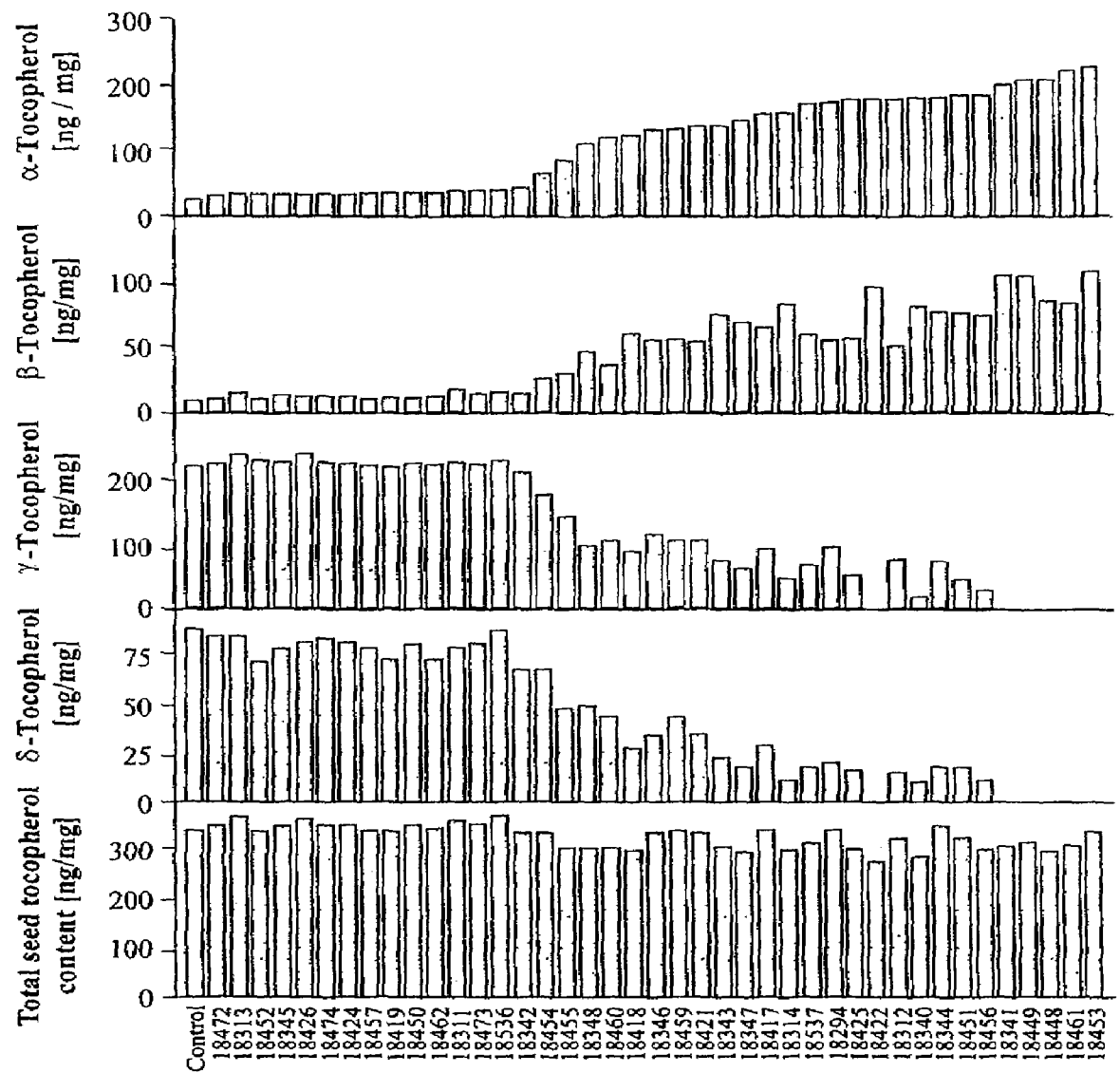
FIG. 15 is a graph depicting the soy seed tocopherol content and composition from pooled seed of the R1 generation of plants transformed with pMON36505. This construct expresses an *A. thaliana* GMT under arcelin5 promoter control.
Figure 16:
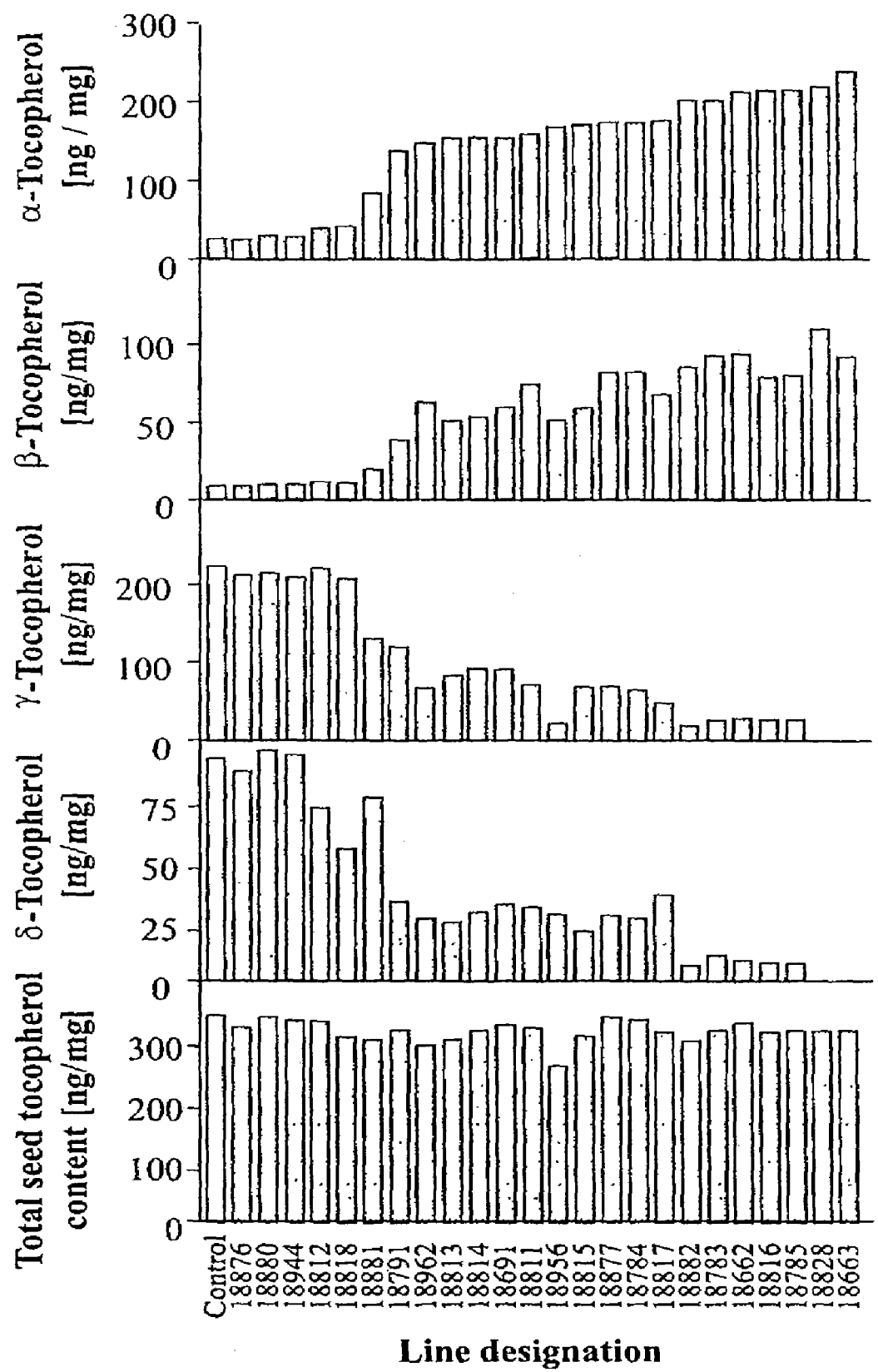
FIG. 16 is a graph depicting the soy seed tocopherol content and composition from pooled seed of the R1 generation of plants transformed with pMON36506. This construct expresses an *A. thaliana* GMT under the control of the modified arcelin 5 promoter.

GMT expression vectors pMON36503 (FIG. 9), pMON36505 (FIG. 11) and pMON36506 (FIG. 12) are transformed into the soybean line A3244 using *Agrobacterium* mediated transformation. See, for example the methods described by Fraley et al., *Bio/Technology* 3:629-635 (1985) and Rogers et al., *Methods Enzymol.* 153: 253-277 (1987). Ten bulked seeds from the $R_1$ generation are ground and the resulting soy meal is used for tocopherol analysis. Twenty five to forty mg of the soy meal is weighed into a 2 mL micro tube, and 500 µl 1% pyrogallol (Sigma Chemicals, St. Louis, Mo.) in ethanol containing 5 µg/mL tocol, is added to the tube. The sample is shaken twice for 45 seconds in a FAST-PREP (Bio101/Savant) using speed 6.5. The extract is then filtered (Gelman PTFE acrodisc 0.2 µm, 13 mm syringe filters, Pall Gelman Laboratory Inc, Ann Arbor, Mich.) into an autosampler tube. HPLC is performed on a ZORBAX silica HPLC column, 4.6 mm×250 mm (5 µm) with a fluorescent detection using a Hewlett Packard HPLC (Agilent Technologies). Sample excitation is performed at 290 nm, and emission is monitored at 336 nm. Tocopherols are separated with a hexane methyl-t-butyl ether gradient using an injection volume of 20 µl, a flow rate of 1.5 ml/min, and a run time of 12 min (40° C.). Tocopherol concentration and composition is calculated based on standard curves for $\alpha$, $\beta$, $\gamma$ and $\delta$-tocopherol using Chemstation software (Agilent Technologies, Palo Alto, Calif.). As shown in FIGS. 14-16, several lines from each construct completely or substantially converted $\delta$ and $\gamma$-tocopherol, leaving $\alpha$ and $\beta$-tocopherol as the only detectable tocopherol isomers.

EXAMPLE 7

Canola, *Brassica napus*, or soybean plants are transformed with a variety of DNA constructs using *Agrobacterium* mediated transformation. Two sets of DNA constructs are produced. The first set of constructs are "single gene constructs". Each of the following genes is inserted into a separate plant DNA construct under the control of a seed specific promoter such as the arcelin 5, 7S α or napin promoter (Kridl et al., *Seed Sci. Res.* 1:209:219 (1991) (Keegstra, *Cell* 56(2):247-53 (1989); Nawrath, et al., *Proc. Natl. Acad. Sci. U.S.A.* 91:12760-12764 (1994)): a bifunctional prephenate dehydrogenase such as the *E. herbicola* or the *E. coli* tyrA gene (Xia et al., *J. Gen. Microbiol.* 138:1309-1316 (1992)), a phytyl-prenyltransferase such as the slr1736 (in Cyanobase (www.kazusa.or.jp/cyanobase)) or the ATPT2 gene (Smith et al., *Plant J.* 11: 83-92 (1997)), a 1-deoxyxylulose 5-phosphate synthase such as the *E. coli* dxs gene (Lois et al., *Proc. Natl. Acad. Sci. U.S.A.* 95 (5):2105-2110 (1998)), a 1-deoxyxylulose 5-phosphate reductoisomerase (dxr) gene (Takahashi et al. *Proc. Natl. Acad. Sci. U.S.A.* 95 (17), 9879-9884 (1998)), a p-hydroxyphenylpyruvate dioxygenase, such as the *Arabidopsis thaliana* HPPD gene (Norris et al., *Plant Physiol.* 117:1317-1323 (1998)), a geranylgeranylpyrophosphate synthase gene such as the *Arabidopsis thaliana* GGPPS gene (Bartley and Scolnik, *Plant Physiol.* 104:1469-1470 (1994)), a transporter such as the AANT1 gene (Saint Guily, et al., *Plant Physiol,* 100(2):1069-1071 (1992)), a GMT gene, an MT 1 gene, and a tocopherol cyclase such as the slr1737 gene (in Cyanobase (www.kazusa.or.jp/cyanobase) or its *Arabidopsis* ortholog (PIR_T04448)), a isopentenylpyrophosphate isomerase gene (IDI), and an antisense construct for homogentisic acid dioxygenase (Sato et al., *J. DNA Res.* 7 (1):31-63 (2000))). The products of the genes are targeted to the plastid by natural plastid target peptides present in the trans gene, or by an encoded plastid target peptide such as CTP1. Each construct is transformed into at least one canola, *Brassica napus* and soybean plant. Plants expressing each of these genes are selected to participate in additional crosses. Crosses are carried out for each species to generate transgenic plants having one or more of the following combination of introduced genes: tyrA, slr1736, ATPT2, dxs, dxr, GGPPS, HPPD, GMT, MT1, AANT1, slr1737, IDI, and an antisense construct for homogentisic acid dioxygenase.

The tocopherol composition and level in each plant generated by the crosses (including all intermediate crosses) is also analyzed. Progeny of the transformants from these constructs will be crossed with each other to stack the additional genes to reach the desired level of tocopherol.

A second set of DNA constructs is generated and referred to as the "multiple gene constructs." The multiple gene constructs contain multiple genes each under the control of a seed specific promoter such as the arcelin 5, 7S α or napin promoter (Kridl et al., *Seed Sci. Res.* 1:209:219 (1991) (Keegstra, *Cell* 56(2):247-53 (1989); Nawrath, et al., *Proc. Natl. Acad. Sci. U.S.A.* 91:12760-12764 (1994)) and the gene products of each of the genes are targeted to the plastid by an encoded plastid target peptide. The multiple gene construct can have two or more of the following genes: tyrA, slr1736, or ATPT2, dxs, dxr, GGPPS, HPPD, GMT, MT1, AANT1, slr1737, or its plant ortholog, IDI, and an antisense construct for homogentisic acid dioxygenase.

Each construct is then transformed into at least one canola, *Brassica napus* or soybean plant. The tocopherol composition and level in each plant is also analyzed using the method set forth in example 6. Progeny of the transformants from these constructs are crossed with each other to stack the additional genes to reach the desired level of tocopherol.

EXAMPLE 8

Expression of the *Anabaena* MT1 coding sequence in *Arabidopsis* is carried out. The *Anabaena* putative-MT1 coding sequence is amplified from genomic DNA derived from 3-day old *Anabaena* sp. (ATCC 27893) cultures. To isolate DNA, cultures are spun and the pellet washed with 1 ml PBS to remove media. Subsequently, the suspension is centrifuged and the supernatant is discarded. The resulting pellet is resuspended in 1 ml of water and is boiled for 10 minutes. *Anabaena* DNA amplification reactions contain 10 µL boiled *Anabaena* extract, the EXPAND High Fidelity PCR System and the oligonucleotide primers: 5' GGG GAC AAG TTT GTA CAA AAA AGC AGG CTT AGA AGG AGA TAG AAC CAT GAG TTG GTT GTT TTC TAC ACT GG 3' (SEQ ID NO: 83) and 5' GGG GAC CAC TTT GTA CAA GAA AGC TGG GTC CTA TTA CTT TTG AGC AAC CTT GAT CG3' (SEQ ID NO: 84). The reaction mix is pre-incubated for 5 minutes at 95° C., during which time the polymerase is spiked in. The product is then amplified for 15 cycles of 94° C. for 30 sec, 60° C. for 30 sec, and 72° C. for 1.5 minutes each. During the cycling, the annealing temperature is decreased by 1° C. per cycle for each of the 15 cycles. An additional 15 cycles follow, consisting of 94° C. for 30 seconds, 45° C. for 30 seconds, and 72° C. for 1.5 minute, each followed by a 7 minute hold at 72° C.

After amplification, PCR products are purified using a Qiagen PCR cleanup column (Qiagen Company, Valencia, Calif.) and subcloned into PDONR™201 using the GATEWAY cloning system (Life Technologies, Rockville, Md.) to generate pMON67517. Sequences are confirmed by DNA sequencing using standard methodologies and then cloned into the napin cassette derived from pCGN3223 (Kridl et al., *Seed Sci. Res.* 1:209-219 (1991)) in a GATEWAY compatible binary destination vector containing the BAR selectable marker under the control of the 35S promoter. The MT1 gene is cloned in as a translational fusion with the encoded plastid target peptide CTP1 (WO 00/61771) to target this protein to the plastid from pMON16600. The resultant expression vector (pMON67211) is electroporated into ABI strain *Agrobacterium* cells and grown under standard conditions (McBride et al., *Proc. Natl. Acad. Sci. USA* 91:7301-7305 (1994)) and vector fidelity is reconfirmed by restriction analysis. Transformation of pMON67211 into wild-type *Arabidopsis*, accession Columbia, as well as three high δ-tocopherol mutant lines (hdt2, hdt10, hdt16) is accomplished using the dipping method (Clough and Bent, *Plant J.* 16(6):735-43 (1998)) and $T_0$ plants are grown in a growth chamber under 16 h light, 19° C. $T_1$ seeds are sprinkled directly onto soil, vernalized at 4° C. in the absence of light for 4 days, then transferred to 21° C., 16 hours light. Transgenic plants are selected by spraying with a 1:200 dilution of Finale (AgrEvo Environmental Health, Montvale, N.J.) at 7 days and 14 days after seeding. Transformed plants are grown to maturity and the $T_2$ seed is analyzed for tocopherol content using normal phase HPLC (Savidge, B. et al., *Plant Physiology* 129:321-332 (2002)).

Two lines of pMON67211 in the hdt2 mutant line (67211-6 and 67211-12) are taken forward to the next generation for examination of phenotype in $T_3$ seed. In doing so, $T_2$ seeds are sprinkled directly onto soil, vernalized at 4° C. in the absence of light for 4 days, then transferred to 21° C., 16 hours light. Transgenic plants are selected by spraying with a 1:200 dilution of Finale (AgrEvo Environmental Health, Montvale, N.J.) at 7 days and 14 days after seeding. Transformed plants are grown to maturity (9 plants from line 6, 9 plants from line 12, and 4 hdt2 mutant controls in one flat) and the $T_3$ seed is analyzed for tocopherol content using normal phase HPLC.

Figure 25:
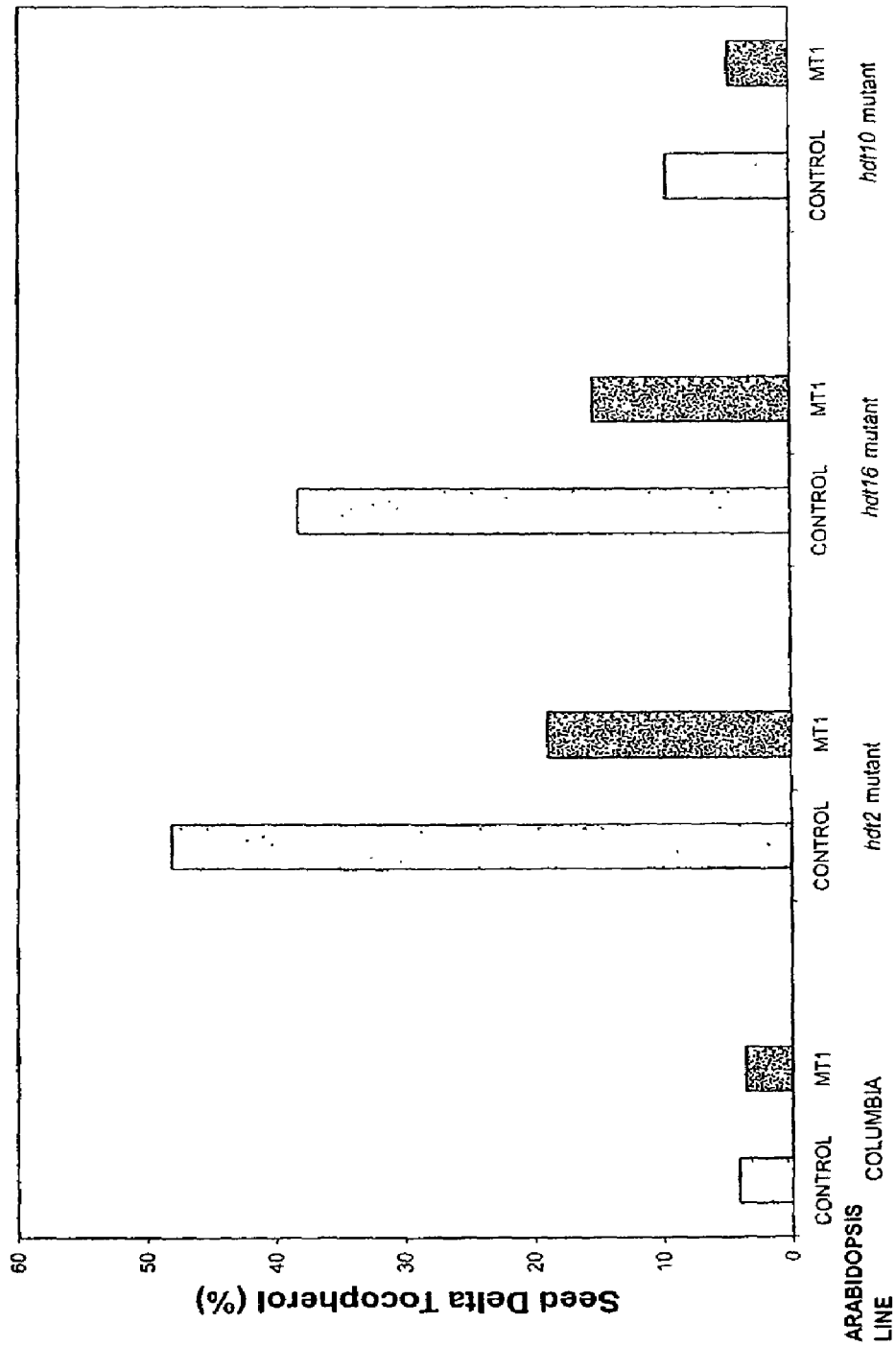
FIG. 25 shows the percent of seed δ-tocopherol in *Arabidopsis* T2 seed from lines expressing MT1 under the control of the napin promoter.

FIG. 25 shows the percent of seed δ-tocopherol in *Arabidopsis* T2 seed from lines expressing MT1 under the control of the napin promoter.

Table 8 below represents various data resulting from the above transformants.

TABLE 8

Alpha strategy $R_2$ *Arabidopsis* seed: CTP-MT1
HPLC sequence and data folder SR022602

| Sample Name | Sample wt. (mg) | Ng α toco./mg seed | ng γ toco./mg seed | ng δ toco./mg seed | ng total toco./mg seed | Serial Number | Pedigree | Gen | % Delta | Avg. Delta % |
|---|---|---|---|---|---|---|---|---|---|---|
| 77 | 14 | 3.42 | 459.72 | 20.17 | 483.31 | 9979-AT00002-54:@.0008. | 9979 | For 67211s | 4.2 | 4.1 |
| 78 | 15 | 2.59 | 461.87 | 19.26 | 483.73 | 9979-AT00002-54:@.0009. | 9979 | For 67211s | 4.0 | |
| 89 | 13 | 4.78 | 459.21 | 16.34 | 480.33 | AT_G193:@. | PMON67211 | T2 | 3.4 | 3.6 |
| 90 | 14 | 5.50 | 475.59 | 17.27 | 498.35 | AT_G194:@. | PMON67211 | T2 | 3.5 | |
| 86 | 13 | 5.64 | 476.70 | 18.13 | 500.46 | AT_G190:@. | PMON67211 | T2 | 3.6 | |
| 82 | 13 | 6.19 | 476.84 | 18.10 | 501.13 | AT_G186:@. | PMON67211 | T2 | 3.6 | |
| 88 | 14 | 7.13 | 477.51 | 19.27 | 503.91 | AT_G192:@. | PMON67211 | T2 | 3.8 | |
| 95 | 13 | 6.45 | 478.90 | 18.78 | 504.13 | AT_G199:@. | PMON67211 | T2 | 3.7 | |
| 85 | 11 | 5.67 | 480.31 | 19.62 | 505.60 | AT_G189:@. | PMON67211 | T2 | 3.9 | |
| 96 | 13 | 10.08 | 480.68 | 18.69 | 509.45 | AT_G200:@. | PMON67211 | T2 | 3.7 | |
| 84 | 13 | 6.34 | 487.23 | 18.47 | 512.04 | AT_G188:@. | PMON67211 | T2 | 3.6 | |
| 91 | 12 | 7.18 | 487.68 | 19.42 | 514.28 | AT_G195:@. | PMON67211 | T2 | 3.8 | |
| 87 | 14 | 4.45 | 492.16 | 19.92 | 516.52 | AT_G191:@. | PMON67211 | T2 | 3.9 | |
| 93 | 13 | 7.07 | 492.17 | 18.19 | 517.43 | AT_G197:@. | PMON67211 | T2 | 3.5 | |
| 92 | 13 | 7.12 | 493.27 | 19.77 | 520.15 | AT_G196:@. | PMON67211 | T2 | 3.8 | |
| 94 | 13 | 8.28 | 494.79 | 18.04 | 521.11 | AT_G198:@. | PMON67211 | T2 | 3.5 | |
| 80 | 13 | 8.70 | 498.94 | 18.71 | 526.36 | AT_G184:@. | PMON67211 | T2 | 3.6 | |
| 83 | 14 | 6.49 | 502.75 | 18.16 | 527.40 | AT_G187:@. | PMON67211 | T2 | 3.4 | |
| 81 | 12 | 6.75 | 505.87 | 18.84 | 531.45 | AT_G185:@. | PMON67211 | T2 | 3.5 | |
| 9 | 12 | 3.66 | 277.61 | 265.61 | 546.88 | hdt2:0001. | | M5 | 48.6 | 48.1 |
| 10 | 10 | 5.62 | 268.82 | 239.24 | 513.69 | hdt2:0002. | | M5 | 46.6 | |
| 11 | 13 | 4.80 | 266.70 | 250.79 | 522.29 | hdt2:0003. | | M5 | 48.0 | |
| 12 | 12 | 6.34 | 281.87 | 271.70 | 559.90 | hdt2:0004. | | M5 | 48.5 | |
| 13 | 12 | 4.75 | 277.59 | 266.87 | 549.21 | hdt2:0005. | | M5 | 48.6 | |
| 18 | 13 | 4.38 | 410.93 | 146.44 | 561.74 | 67211-HDT2:0005. | | T2 | 26.1 | 18.9 |
| 20 | 12 | 5.53 | 421.63 | 133.57 | 560.73 | 67211-HDT2:0007. | | T2 | 23.8 | |
| 22 | 11 | 4.39 | 413.42 | 116.94 | 534.75 | 67211-HDT2:0009. | | T2 | 21.9 | |
| 17 | 12 | 5.31 | 425.83 | 114.16 | 545.30 | 67211-HDT2:0004. | | T2 | 20.9 | |
| 15 | 12 | 4.97 | 402.64 | 105.62 | 513.23 | 67211-HDT2:0002. | | T2 | 20.6 | |

TABLE 8-continued

Alpha strategy R₂ *Arabidopsis* seed: CTP-MT1
HPLC sequence and data folder SR022602

| Sample Name | Sample wt. (mg) | Ng α toco./mg seed | ng γ toco./mg seed | ng δ toco./mg seed | ng total toco./mg seed | Serial Number | Pedigree | Gen | % Delta | Avg. Delta % |
|---|---|---|---|---|---|---|---|---|---|---|
| 27 | 13 | 4.74 | 434.37 | 112.96 | 552.07 | 67211-HDT2:0014. | | T2 | 20.5 | |
| 16 | 13 | 5.98 | 416.73 | 108.13 | 530.84 | 67211-HDT2:0003. | | T2 | 20.4 | |
| 14 | 12 | 7.07 | 431.05 | 107.70 | 545.81 | 67211-HDT2:0001. | | T2 | 19.7 | |
| 23 | 10 | 4.74 | 436.59 | 106.91 | 548.24 | 67211-HDT2:0010. | | T2 | 19.5 | |
| 26 | 12 | 6.89 | 424.31 | 104.39 | 535.59 | 67211-HDT2:0013. | | T2 | 19.5 | |
| 21 | 11 | 4.91 | 441.50 | 104.57 | 550.98 | 67211-HDT2:0008. | | T2 | 19.0 | |
| 28 | 12 | 4.40 | 493.29 | 87.63 | 585.32 | 67211-HDT2:0015. | | T2 | 15.0 | |
| 24 | 13 | 4.20 | 452.86 | 74.83 | 531.89 | 67211-HDT2:0011. | | T2 | 14.1 | |
| 25 | 13 | 5.20 | 510.41 | 72.70 | 588.31 | 67211-HDT2:0012. | | T2 | 12.4 | |
| 19 | 11 | 5.58 | 545.61 | 67.86 | 619.05 | 67211-HDT2:0006. | | T2 | 11.0 | |
| 3 | 12.5 | 3.36 | 262.76 | 180.18 | 446.30 | hdt16:@.0007. | Control | M5 | 40.4 | 38.2 |
| 2 | 9.6 | 2.54 | 305.52 | 178.20 | 486.25 | hdt16:@.0005. | Control | M5 | 36.6 | |
| 1 | 11.9 | 3.36 | 290.12 | 177.76 | 471.24 | hdt16:@.0003. | Control | M5 | 37.7 | |
| 11 | 10.1 | 2.02 | 255.50 | 169.29 | 426.81 | AT_G58:@. | PMON67211 | T2 | 39.7 | 15.3 |
| 12 | 12.4 | 5.28 | 352.67 | 100.76 | 458.71 | AT_G59:@. | PMON67211 | T2 | 22.0 | |
| 24 | 12.5 | 3.60 | 392.97 | 78.20 | 474.77 | AT_G71:@. | PMON67211 | T2 | 16.5 | |
| 14 | 12 | 3.90 | 380.29 | 72.98 | 457.18 | AT_G61:@. | PMON67211 | T2 | 16.0 | |
| 22 | 12.6 | 2.06 | 370.66 | 68.50 | 441.22 | AT_G69:@. | PMON67211 | T2 | 15.5 | |
| 18 | 12.2 | 3.52 | 379.38 | 70.29 | 453.19 | AT_G65:@. | PMON67211 | T2 | 15.5 | |
| 15 | 13 | 5.67 | 386.12 | 71.61 | 463.39 | AT_G62:@. | PMON67211 | T2 | 15.5 | |
| 21 | 11.3 | 3.86 | 405.98 | 74.54 | 484.39 | AT_G68:@. | PMON67211 | T2 | 15.4 | |
| 25 | 12.6 | 6.42 | 408.38 | 74.56 | 489.36 | AT_G72:@. | PMON67211 | T2 | 15.2 | |
| 19 | 12.5 | 3.95 | 412.64 | 72.24 | 488.84 | AT_G66:@. | PMON67211 | T2 | 14.8 | |
| 20 | 12.7 | 2.99 | 431.01 | 65.65 | 499.66 | AT_G67:@. | PMON67211 | T2 | 13.1 | |
| 17 | 12.3 | 5.77 | 423.19 | 48.73 | 477.70 | AT_G64:@. | PMON67211 | T2 | 10.2 | |
| 23 | 11.3 | 2.35 | 408.24 | 45.41 | 456.00 | AT_G70:@. | PMON67211 | T2 | 10.0 | |
| 10 | 11.9 | 7.81 | 443.06 | 43.58 | 494.45 | AT_G57:@. | PMON67211 | T2 | 8.8 | |
| 13 | 12.6 | 3.64 | 421.06 | 38.53 | 463.23 | AT_G60:@. | PMON67211 | T2 | 8.3 | |
| 16 | 12.9 | 3.76 | 430.69 | 37.10 | 471.56 | AT_G63:@. | PMON67211 | T2 | 7.9 | |
| 33 | 13.2 | 4.32 | 356.41 | 71.85 | 432.59 | hdt10:@.0001. | Control | M6 | 16.6 | 9.6 |
| 34 | 13.1 | 5.73 | 469.11 | 12.79 | 487.62 | hdt10:@.0002. | Control | M6 | 2.6 | |
| 56 | 13.3 | 4.77 | 361.67 | 63.37 | 429.82 | AT_G48:@. | PMON67211 | T2 | 14.7 | 4.7 |
| 61 | 8.1 | 2.70 | 351.84 | 50.96 | 405.50 | AT_G54:@. | PMON67211 | T2 | 12.6 | |
| 54 | 12.2 | 5.66 | 432.55 | 41.60 | 479.81 | AT_G46:@. | PMON67211 | T2 | 8.7 | |
| 59 | 13.9 | 5.18 | 416.88 | 38.34 | 460.40 | AT_G52:@. | PMON67211 | T2 | 8.3 | |
| 51 | 13 | 3.99 | 430.18 | 22.41 | 456.58 | AT_G43:@. | PMON67211 | T2 | 4.9 | |
| 58 | 12.2 | 4.88 | 463.37 | 21.72 | 489.97 | AT_G51:@. | PMON67211 | T2 | 4.4 | |
| 52 | 13.4 | 5.34 | 442.72 | 18.24 | 466.31 | AT_G44:@. | PMON67211 | T2 | 3.9 | |
| 64 | 12.6 | 5.50 | 477.62 | 10.72 | 493.84 | AT_G117:@. | PMON67211 | T2 | 2.2 | |
| 57 | 12.7 | 6.27 | 467.48 | 9.12 | 482.88 | AT_G50:@. | PMON67211 | T2 | 1.9 | |
| 50 | 13.1 | 4.83 | 450.16 | 7.94 | 462.93 | AT_G42:@. | PMON67211 | T2 | 1.7 | |
| 63 | 12.8 | 4.78 | 445.42 | 7.81 | 458.00 | AT_G56:@. | PMON67211 | T2 | 1.7 | |
| 55 | 12.6 | 8.32 | 460.07 | 7.58 | 475.98 | AT_G47:@. | PMON67211 | T2 | 1.6 | |
| 53 | 13.3 | 6.43 | 417.71 | 6.76 | 430.91 | AT_G45:@. | PMON67211 | T2 | 1.6 | |
| 62 | 12.6 | 5.36 | 473.04 | 6.88 | 485.28 | AT_G55:@. | PMON67211 | T2 | 1.4 | |
| 60 | 12.9 | 4.87 | 463.45 | 5.68 | 474.00 | AT_G53:@. | PMON67211 | T2 | 1.2 | |

Figure 26:
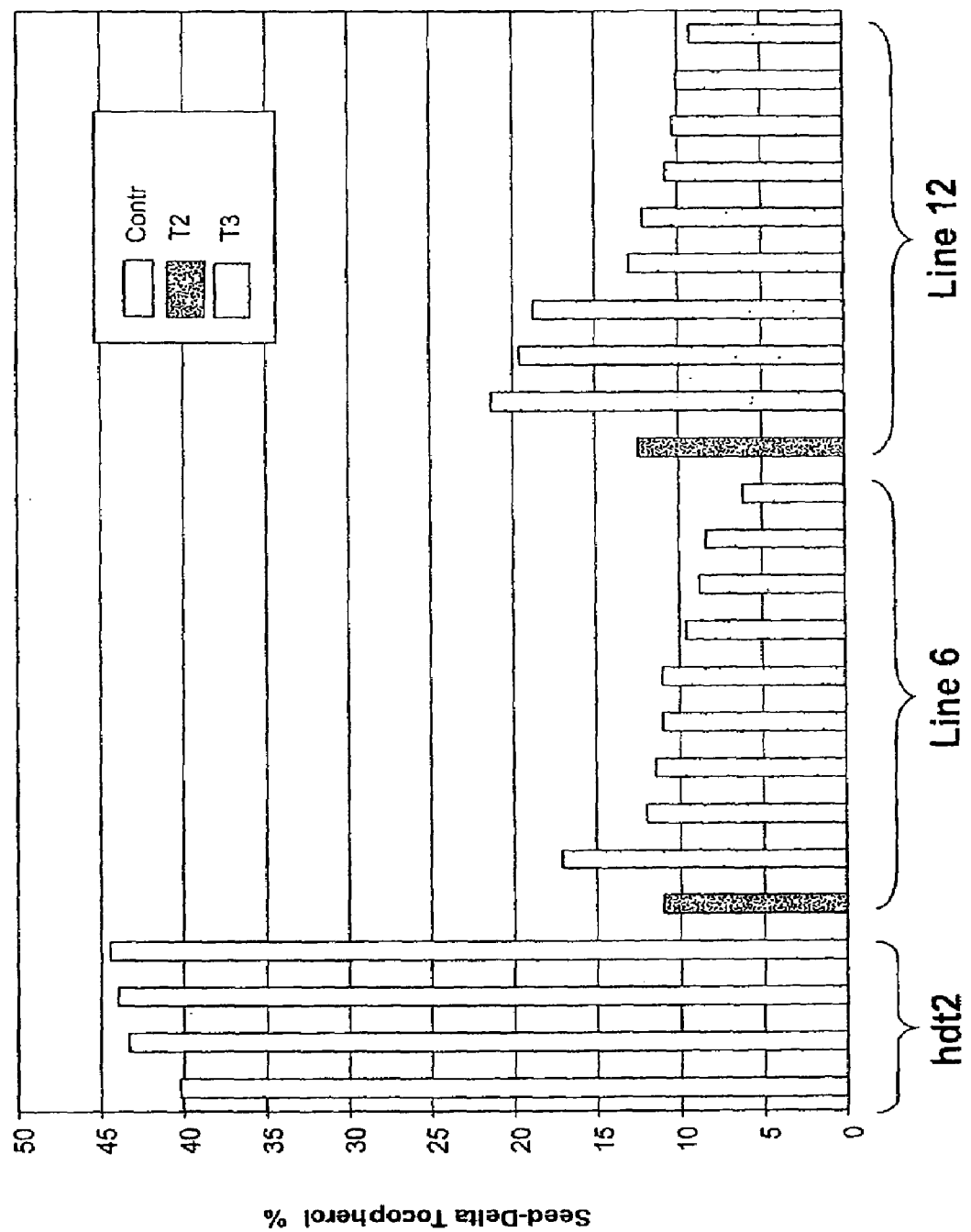
FIG. 26 shows $T_3$ seed δ-tocopherol levels in two lines expressing MT1 under the control of the napin promoter.

FIG. 26 shows T₃ seed δ-tocopherol percentage from two lines expressing MT1 under the control of the napin promoter (pMON67211). Table 9 below shows T₃ seed data from hdt2 mutant lines transformed with pMON67211.

TABLE 9

| Crop | Biotype | Pedigree | mp:aT | mp:gT | mp:dT | total toco. | % delta | Gen |
|---|---|---|---|---|---|---|---|---|
| AT | SEED | hdt2:@.0001.0001. | 2 | 280 | 190 | 472 | 40.3 | M7 |
| AT | SEED | hdt2:@.0001.0003. | 4 | 263 | 204 | 471 | 43.3 | M7 |
| AT | SEED | hdt2:@.0001.0002. | 3 | 262 | 208 | 473 | 44.0 | M7 |
| AT | SEED | hdt2:@.0001.0004. 67211-6 | 4 | 271 | 220 | 495 | 44.4 11.0 | M7 R2 |
| AT | SEED | 67211-HDT2:0006.0005. | 4 | 398 | 83 | 485 | 17.1 | R3 |
| AT | SEED | 67211-HDT2:0006.0001. | 3 | 438 | 60 | 501 | 12.0 | R3 |
| AT | SEED | 67211-HDT2:0006.0008. | 4 | 453 | 59 | 516 | 11.4 | R3 |
| AT | SEED | 67211-HDT2:0006.0002. | 3 | 448 | 56 | 507 | 11.0 | R3 |
| AT | SEED | 67211-HDT2:0006.0004. | 2 | 417 | 52 | 471 | 11.0 | R3 |
| AT | SEED | 67211-HDT2:0006.0007. | 3 | 468 | 50 | 521 | 9.6 | R3 |
| AT | SEED | 67211-HDT2:0006.0006. | 4 | 464 | 45 | 513 | 8.8 | R3 |
| AT | SEED | 67211-HDT2:0006.0009. | 5 | 456 | 42 | 503 | 8.3 | R3 |
| AT | SEED | 67211-HDT2:0006.0003. | 4 | 456 | 30 | 490 | 6.1 | R3 |

TABLE 9-continued

| Crop | Biotype | Pedigree | mp:aT | mp:gT | mp:dT | total toco. | % delta | Gen |
|---|---|---|---|---|---|---|---|---|
| | | 67211-12 | | | | | 12.4 | R2 |
| AT | SEED | 67211-HDT2:0012.0002. | 4 | 373 | 102 | 479 | 21.3 | R3 |
| AT | SEED | 67211-HDT2:0012.0009. | 3 | 399 | 98 | 500 | 19.6 | R3 |
| AT | SEED | 67211-HDT2:0012.0003. | 3 | 397 | 92 | 492 | 18.7 | R3 |
| AT | SEED | 67211-HDT2:0012.0001. | 4 | 440 | 66 | 510 | 12.9 | R3 |
| AT | SEED | 67211-HDT2:0012.0008. | 2 | 469 | 65 | 536 | 12.1 | R3 |
| AT | SEED | 67211-HDT2:0012.0006. | 4 | 438 | 53 | 495 | 10.7 | R3 |
| AT | SEED | 67211-HDT2:0012.0004. | 5 | 465 | 54 | 524 | 10.3 | R3 |
| AT | SEED | 67211-HDT2:0012.0005. | 5 | 460 | 52 | 517 | 10.1 | R3 |
| AT | SEED | 67211-HDT2:0012.0007. | 3 | 458 | 47 | 508 | 9.3 | R3 |

EXAMPLE 9

The CTP-MT1 gene described in example 8 is cloned behind the napin promoter into a binary vector with the ATPT2 gene from *Arabidopsis* and in another double construct with the prenyltransferase (PT) gene (SLR1736 ORF) from *Synechocystis* (described in PCT application WO 0063391).

Figure 27:
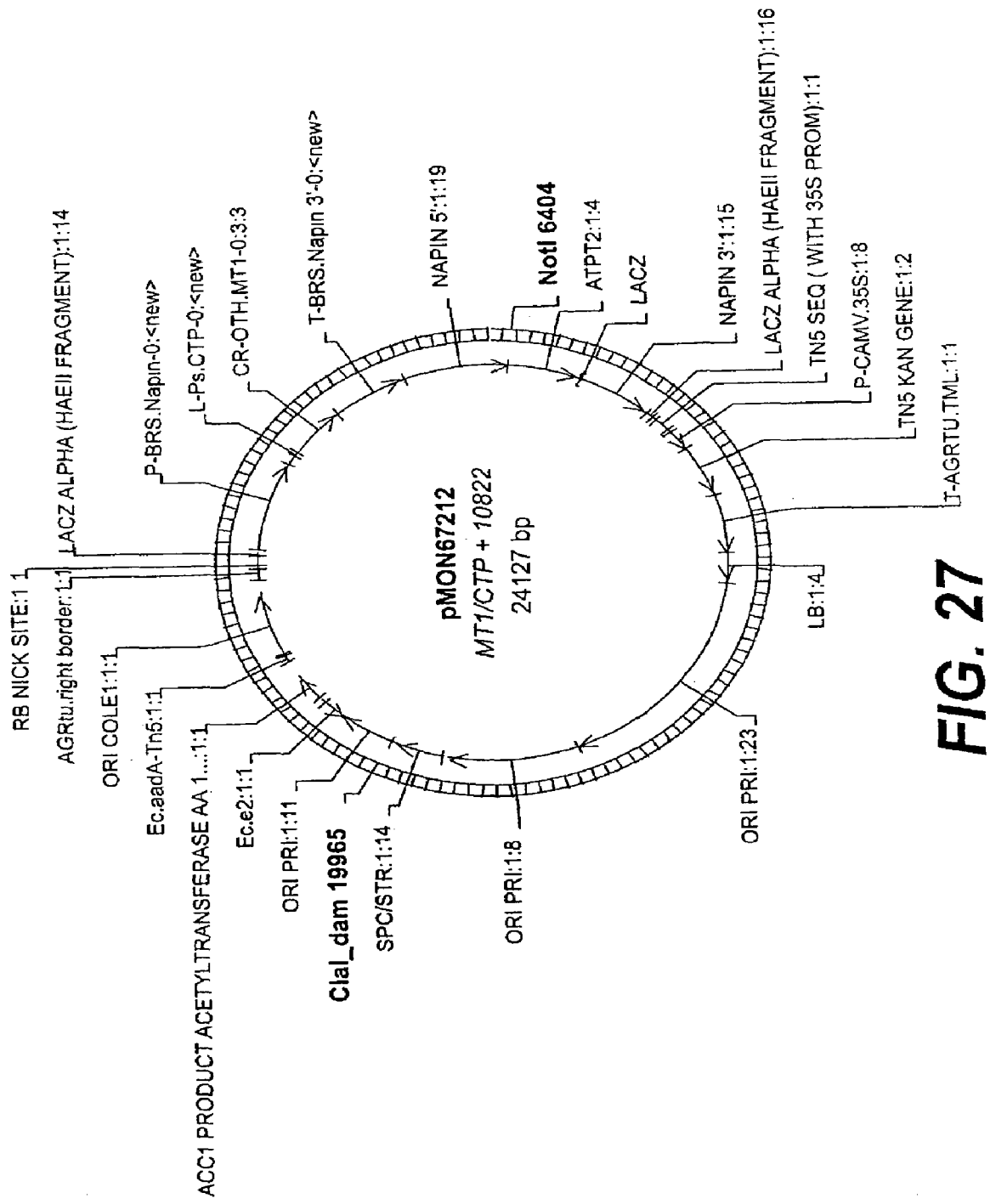
FIG. 27 represents pMON67212.
Figure 28:
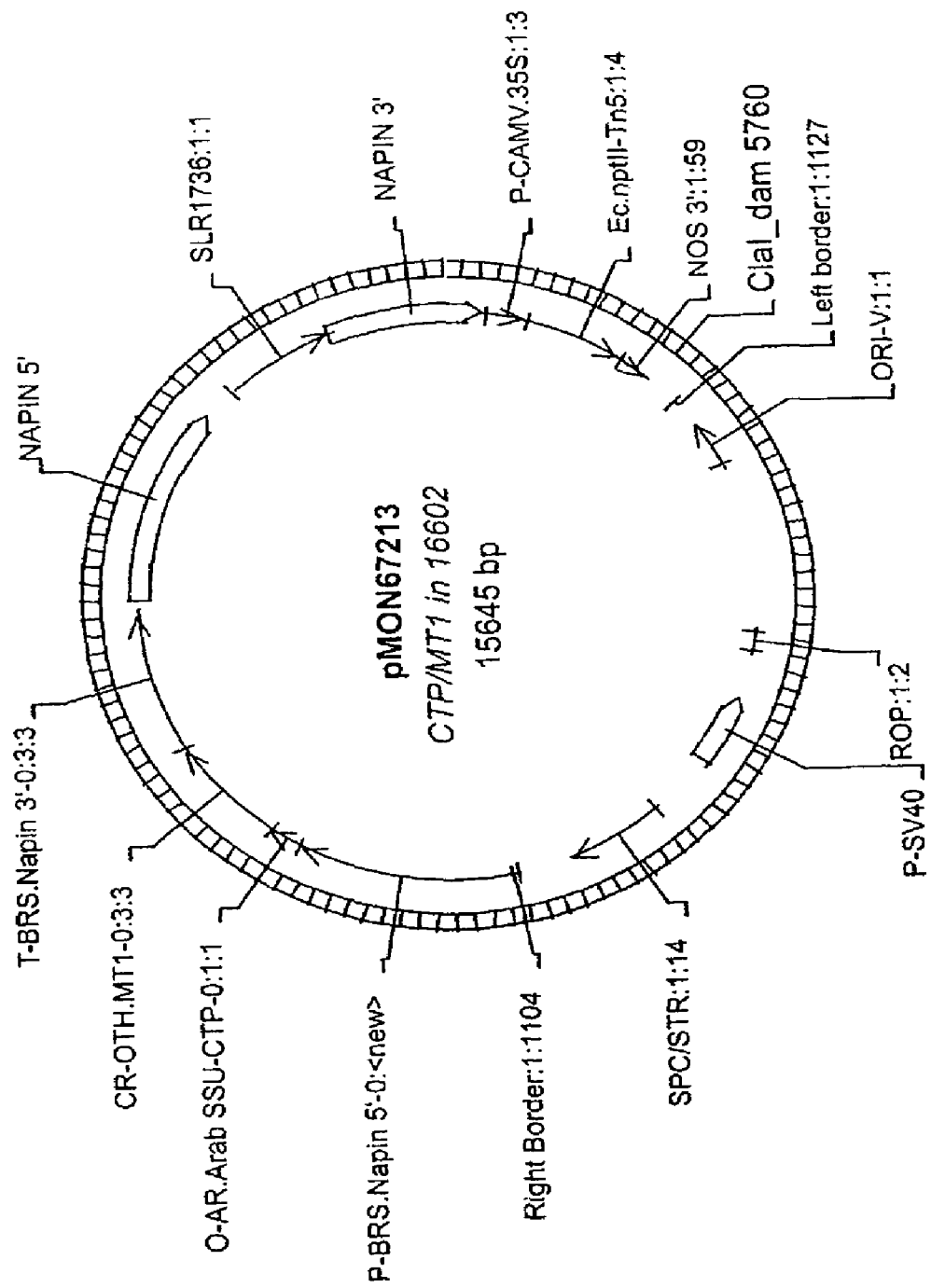
FIG. 28 represents pMON67213.
Figure 29:
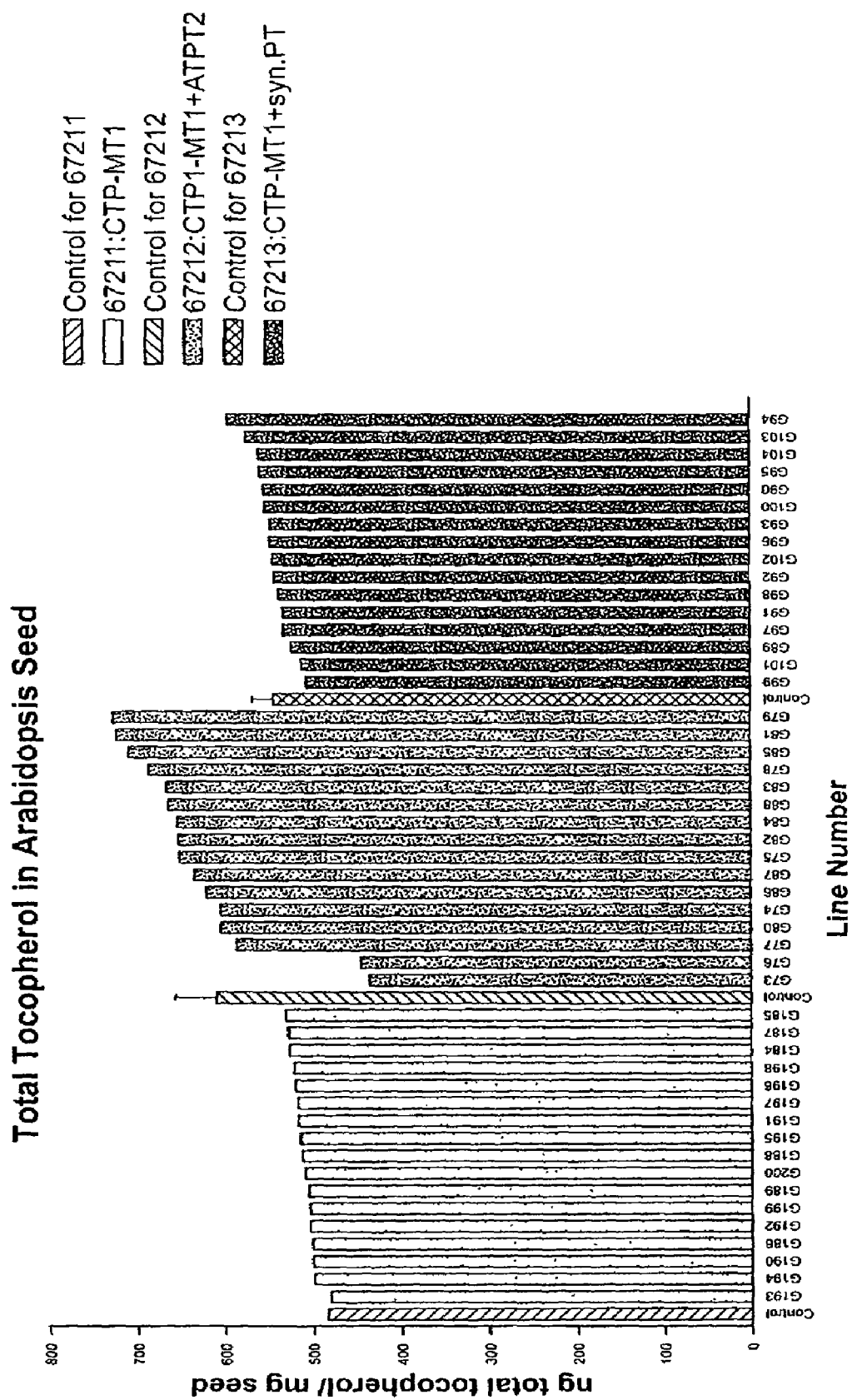
FIG. 29 shows total tocopherol level for *Arabidopsis* transformed with an MT1 and prenyltransferase double construct.
Figure 30:
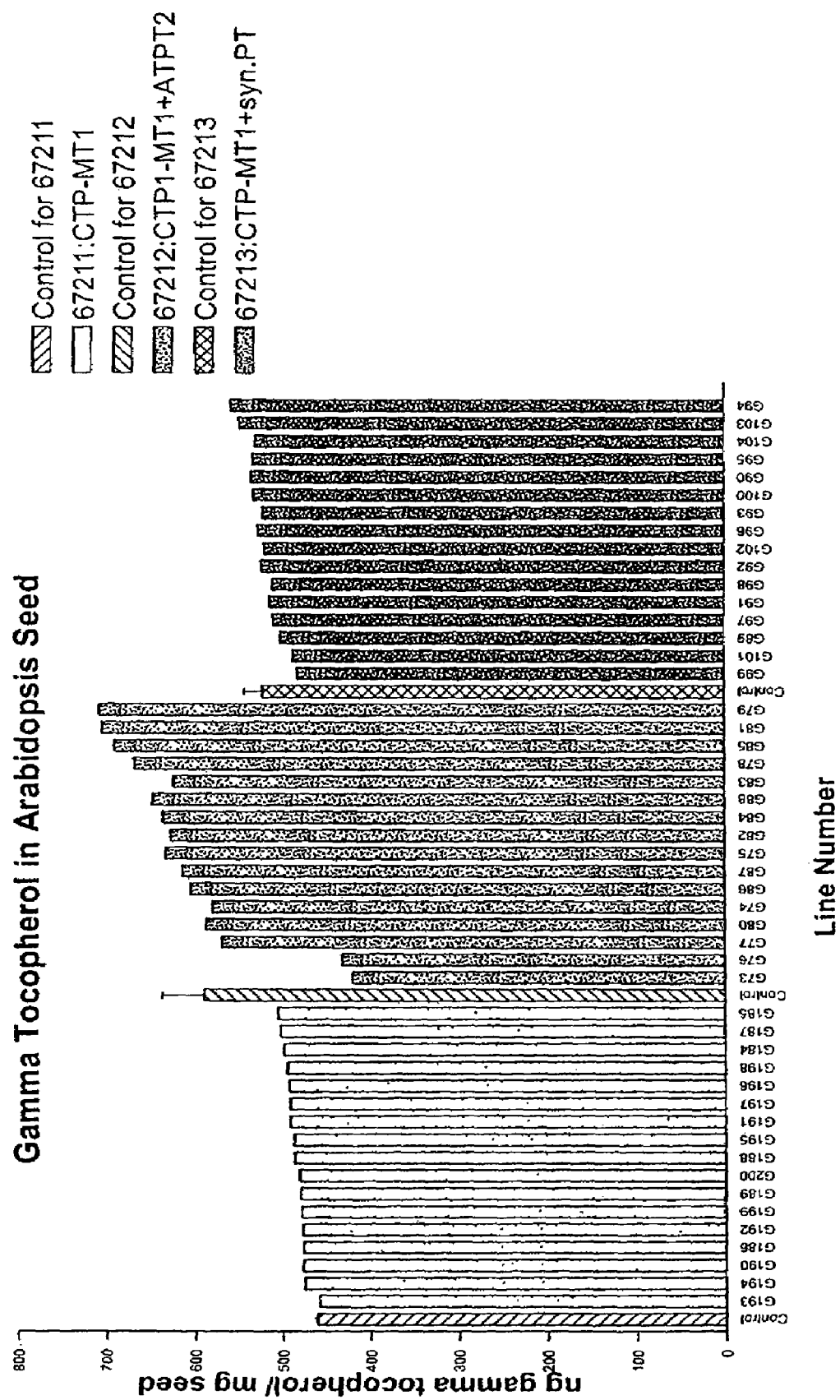
FIG. 30 shows γ tocopherol level for *Arabidopsis* transformed with an MT1 and prenyltransferase double construct.
Figure 31:
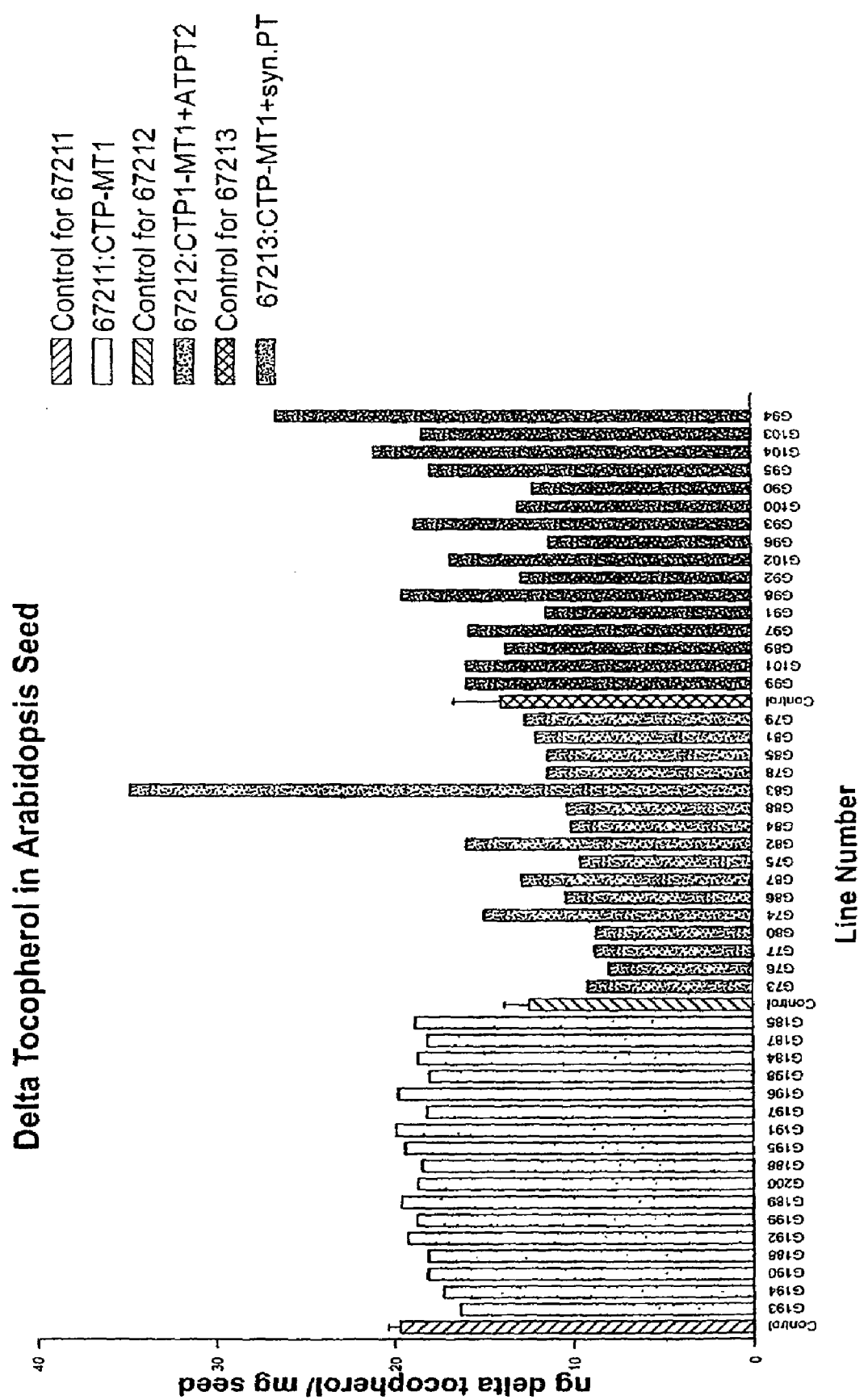
FIG. 31 shows δ-tocopherol level for *Arabidopsis* transformed with an MT1 and prenyltransferase double construct.
Figure 32:
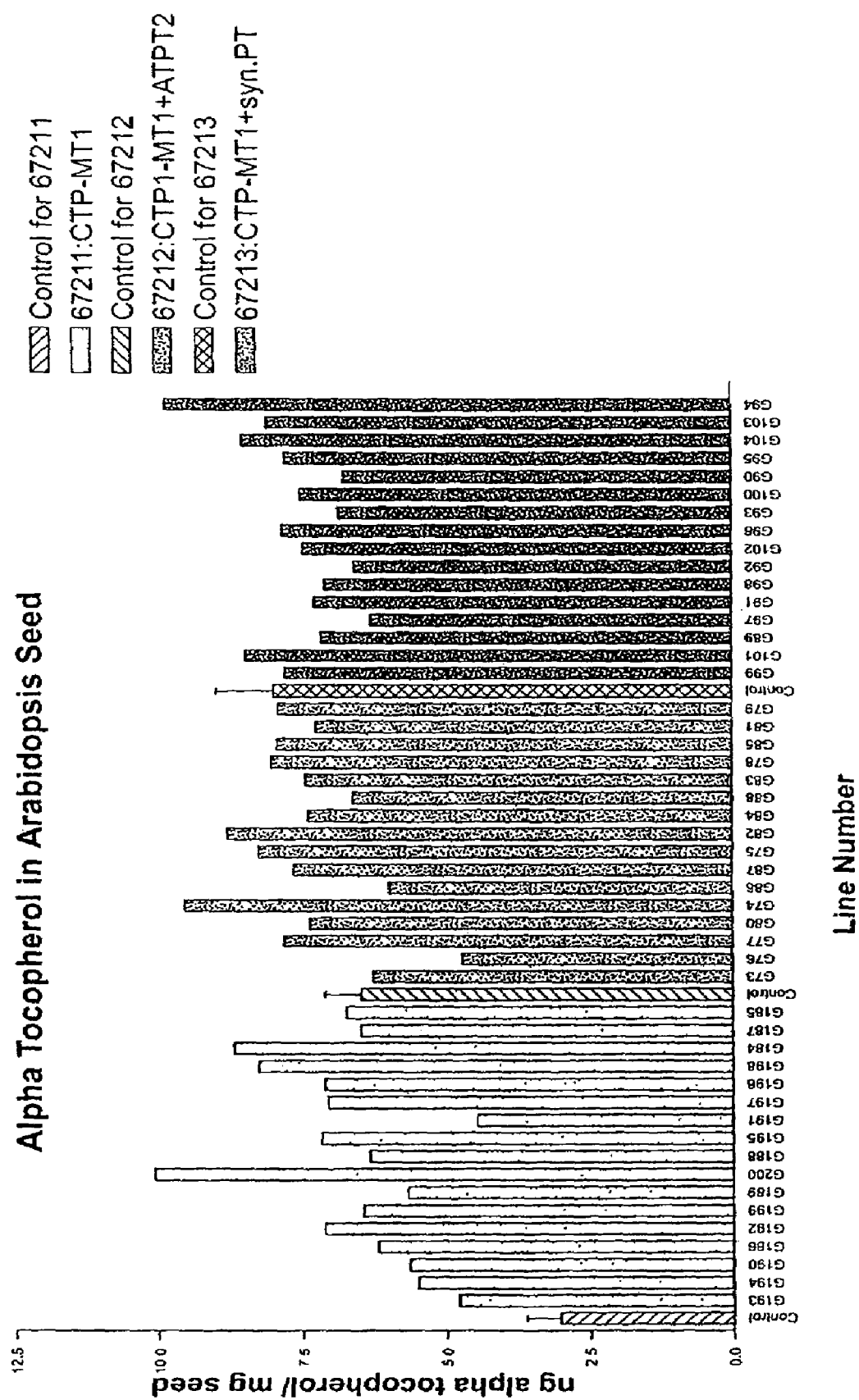
FIG. 32 shows α-tocopherol level for *Arabidopsis* transformed with an MT1 and prenyltransferase double construct.

The MT1 gene is cut out of vector pMON67517 using the restriction enzymes BspHI/PstI and cloned into the PstI/NcoI digested vector backbone of the napin shuttle vector pMON16600, resulting in the formation of pMON67210. The napin cassette from pMON67210, containing the MT1 gene as a translational fusion with the encoded plastid target peptide CTP1 (WO 00/61771) is then cut from this vector with Not I and the ends filled in with dNTPs using a Klenow procedure. The resulting fragment is inserted into vectors pMON16602 (digested with PmeI) and pCGN10822 (digested with SnaBI) to make pMON67213 and pMON67212, respectively (FIGS. 27 and 28). Vectors pMON 16602 and pCGN10822 are described in PCT application WO 0063391.

These double constructs express the MT1 gene and the homogentisate prenyltransferase from either *Arabidopsis* or *Synechocystis* under the control of the napin seed-specific promoter. The double gene constructs are used to transform *Arabidopsis* and transformed plants are grown to maturity as detailed in Example 2. The resulting $T_2$ seed is analyzed for total tocopherol content and composition using analytical procedures described in Example 2. FIGS. 29-32 show total, γ-, δ-, and α-tocopherol levels for various transformed plant lines. Table 10 provides further data from the above-described transformations.

TABLE 10

| ng α toco./mg seed | ng γ toco./mg seed | ng δ toco./mg seed | ng total toco./mg seed | serial number | Pedigree | Construct | |
|---|---|---|---|---|---|---|---|
| 6.28 | 520.72 | 13.30 | 540.30 | 69000157657 | AT00002:@.0321. | Control | For 67212s |
| 5.83 | 612.04 | 10.36 | 628.24 | 69000157645 | AT00002:@.0322. | Control | For 67212s |
| 7.34 | 621.17 | 12.62 | 641.14 | 69000157633 | AT00002:@.0323. | Control | For 67212s |
| 6.48 | 609.23 | 13.41 | 629.12 | 69000157621 | AT00002:@.0324. | Control | For 67212s |
| 6.28 | 421.10 | 9.19 | 436.56 | 69000157710 | AT_G73:@. | PMON67212 | |
| 4.72 | 433.54 | 7.99 | 446.24 | 69000157746 | AT_G76:@. | PMON67212 | |
| 7.83 | 570.77 | 8.77 | 587.37 | 69000157758 | AT_G77:@. | PMON67212 | |
| 7.38 | 588.65 | 8.70 | 604.74 | 69000157784 | AT_G80:@. | PMON67212 | |
| 9.56 | 580.79 | 14.93 | 605.28 | 69000157722 | AT_G74:@. | PMON67212 | |
| 5.99 | 605.44 | 10.38 | 621.82 | 69000157847 | AT_G86:@. | PMON67212 | |
| 7.66 | 615.03 | 12.84 | 635.53 | 69000157859 | AT_G87:@. | PMON67212 | |
| 8.29 | 634.10 | 9.58 | 651.97 | 69000157734 | AT_G75:@. | PMON67212 | |
| 8.82 | 628.29 | 15.95 | 653.06 | 69000157809 | AT_G82:@. | PMON67212 | |
| 7.41 | 636.96 | 10.07 | 654.45 | 69000157823 | AT_G84:@. | PMON67212 | |
| 6.64 | 648.21 | 10.25 | 665.10 | 69000157861 | AT_G88:@. | PMON67212 | |
| 7.46 | 624.59 | 34.85 | 666.91 | 69000157811 | AT_G83:@. | PMON67212 | |
| 8.07 | 668.83 | 11.37 | 688.27 | 69000157760 | AT_G78:@. | PMON67212 | |
| 7.96 | 691.84 | 11.38 | 711.18 | 69000157835 | AT_G85:@. | PMON67212 | |
| 7.26 | 705.18 | 12.01 | 724.44 | 69000157796 | AT_G81:@. | PMON67212 | |
| 7.95 | 708.29 | 12.64 | 728.88 | 69000157772 | AT_G79:@. | PMON67212 | |
| 6.95 | 508.05 | 11.25 | 526.25 | 69000157582 | AT00002:@.0328. | Control | For 67213s |
| 8.16 | 513.84 | 14.12 | 536.11 | 69000157619 | AT00002:@.0325. | Control | For 67213s |
| 8.94 | 547.41 | 16.60 | 572.95 | 69000157607 | AT00002:@.0326. | Control | For 67213s |
| 7.83 | 483.85 | 15.95 | 507.63 | 69000157974 | AT_G99:@. | PMON67213 | |
| 8.50 | 488.67 | 15.92 | 513.09 | 69000157671 | AT_G101:@. | PMON67213 | |
| 7.18 | 503.50 | 13.74 | 524.42 | 69000157873 | AT_G89:@. | PMON67213 | |
| 6.31 | 511.87 | 15.83 | 534.01 | 69000157950 | AT_G97:@. | PMON67213 | |
| 7.30 | 515.26 | 11.47 | 534.02 | 69000157897 | AT_G91:@. | PMON67213 | |
| 7.11 | 512.25 | 19.56 | 538.92 | 69000157962 | AT_G98:@. | PMON67213 | |
| 6.61 | 525.17 | 12.82 | 544.60 | 69000157900 | AT_G92:@. | PMON67213 | |
| 7.50 | 521.38 | 16.85 | 545.73 | 69000157683 | AT_G102:@. | PMON67213 | |
| 7.87 | 529.25 | 11.29 | 548.41 | 69000157948 | AT_G96:@. | PMON67213 | |
| 6.88 | 523.01 | 18.83 | 548.72 | 69000157912 | AT_G93:@. | PMON67213 | |
| 7.56 | 534.21 | 13.03 | 554.80 | 69000157669 | AT_G100:@. | PMON67213 | |
| 6.79 | 536.89 | 12.17 | 555.86 | 69000157885 | AT_G90:@. | PMON67213 | |
| 7.83 | 535.00 | 17.97 | 560.80 | 69000157936 | AT_G95:@. | PMON67213 | |

TABLE 10-continued

| ng α toco./mg seed | ng γ toco./mg seed | ng δ toco./mg seed | ng total toco./mg seed | serial number | Pedigree | Construct |
|---|---|---|---|---|---|---|
| 8.57 | 532.53 | 21.13 | 562.23 | 69000157708 | AT_G104:@. | PMON67213 |
| 8.15 | 550.66 | 18.42 | 577.23 | 69000157695 | AT_G103:@. | PMON67213 |
| 9.91 | 560.45 | 26.66 | 597.02 | 69000157924 | AT_G94:@. | PMON67213 |

The invention claimed is:

1. A substantially purified nucleic acid molecule comprising a nucleic acid sequence that encodes a polypeptide with gamma-tocopherol methyltransferase activity and is selected from the group consisting of
   (a) a nucleic acid sequence comprising from 90% to 100% identity to SEQ ID NO:7; and
   (b) a nucleic acid sequence that encodes the polypeptide sequence of SEQ ID NO:34 or a homolog thereof with at least 95% identity to the polypeptide sequence of SEQ ID NO:34.

2. The substantially purified nucleic acid molecule of claim 1, wherein said molecule comprises a nucleic acid sequence that encodes the polypeptide sequence of SEQ ID NO:34.

3. The substantially purified nucleic acid molecule of claim 1, wherein said molecule is operably linked to a promoter region which functions in a plant cell.

4. The nucleic acid molecule of claim 3, further comprising a 3' non-translated sequence that functions in said plant cell to cause termination of transcription and polyA addition.

5. A transformed plant comprising an exogenous nucleic acid molecule comprising the nucleic acid sequence of claim 1.

6. The transformed plant according to claim 5, wherein said plant is selected from the group consisting of canola, corn, *Brassica campestris, Brassica napus*, oilseed rape, rapeseed, soybean, crambe, mustard, castor bean, peanut, sesame, cottonseed, linseed, safflower, oil palm, flax and sunflower.

7. The transformed plant according to claim 6, wherein said plant is canola or oilseed rape.

8. The transformed plant according to claim 6, wherein said plant is soybean or soybean line A3244.

9. The transformed plant according to claim 5, wherein said nucleic acid molecule is operably linked to a promoter.

10. The transformed plant according to claim 9, wherein said promoter is a seed specific promoter.

11. The transformed plant according to claim 10, wherein said promoter is the p7S or Arcelin 5 promoter.

12. The transformed plant according to claim 11, wherein said promoter comprises the nucleic acid molecule of SEQ ID NO: 81.

13. The transformed plant according to claim 11, wherein said promoter comprises the nucleic acid molecule of SEQ ID NO: 82.

14. A method of producing a plant having a seed with an increased α-tocopherol or increased α-tocotrienol level relative to a seed with the same genetic background comprising: (A) transforming said plant with a nucleic acid molecule, wherein said nucleic acid molecule comprises the nucleic acid molecule of claim 1; and (B) growing said transformed plant.

15. The method according to claim 14, wherein said plant is selected from the group consisting of canola, rapeseed, corn, *Brassica campestris, Brassica napus*, oilseed rape, soybean, crambe, mustard, castor bean, peanut, sesame, cottonseed, linseed, safflower, oil palm, flax and sunflower.

16. The method according to claim 15, wherein said plant is canola, soybean or oilseed rape.

17. A seed from a transformed plant comprising the nucleic acid molecule of claim 1, wherein the seed comprises said nucleic acid molecule.

18. The seed of claim 17, wherein the nucleic acid molecule encodes the polypeptide of SEQ ID NO:34.

19. A host cell comprising the nucleic acid molecule of claim 1.

20. The host cell according to claim 19, wherein said cell is a bacterial cell, plant cell.

21. The host cell according to claim 19, wherein said cell is an *Agrobacterium tumefaciens* or *E. coli* cell.

22. The nucleic acid molecule of claim 1 comprising SEQ ID NO:7.

23. The nucleic acid molecule of claim 1, wherein said molecule is operably linked to a nucleic acid encoding a chloroplast transit peptide.

24. The nucleic acid molecule of claim 1, wherein said molecule is operably linked to a nucleic acid encoding a heterologous chloroplast transit peptide.

* * * * *

SEQUENCE LISTING

<160> NUMBER OF SEQ ID NOS: 85

<210> SEQ ID NO 1
<211> LENGTH: 1047
<212> TYPE: DNA
<213> ORGANISM: Arabidopsis thaliana

<400> SEQUENCE: 1

```
atgaaagcaa ctctagcagc accctcttct ctcacaagcc tcccttatcg aaccaactct      60
tctttcggct caaagtcatc gcttctcttt cggtctccat cctcctcctc ctcagtctct     120
atgacgacaa cgcgtggaaa cgtggctgtg gcggctgctg ctacatccac tgaggcgcta     180
agaaaaggaa tagcggagtt ctacaatgaa acttcgggtt tgtgggaaga gatttgggga     240
gatcatatgc atcatggctt ttatgaccct gattcttctg ttcaactttc tgattctggt     300
cacaaggaag ctcagatccg tatgattgaa gagtctctcc gtttcgccgg tgttactgat     360
gaagaggagg agaaaaagat aaagaaagta gtggatgttg ggtgtgggat tggaggaagc     420
tcaagatatc ttgcctctaa atttggagct gaatgcattg gcattactct cagccctgtt     480
caggccaaga gagccaatga tctcgcggct gctcaatcac tctctcataa ggcttccttc     540
caagttgcgg atgcgttgga tcagccattc gaagatggaa aattcgatct agtgtggtcg     600
atggagagtg gtgagcatat gcctgacaag gccaagtttg taaaagagtt ggtacgtgtg     660
gcggctccag gaggtaggat aataatagtg acatggtgcc atagaaatct atctgcgggg     720
gaggaagctt tgcagccgtg ggagcaaaac atcttggaca aaatctgtaa gacgttctat     780
ctcccggctt ggtgctccac cgatgattat gtcaacttgc ttcaatccca ttctctccag     840
gatattaagt gtgcggattg gtcagagaac gtagctcctt tctggcctgc ggttatacgg     900
actgcattaa catggaaggg ccttgtgtct ctgcttcgta gtggtatgaa aagtattaaa     960
ggagcattga caatgccatt gatgattgaa ggttacaaga aaggtgtcat taagtttggt    1020
atcatcactt gccagaagcc actctaa                                        1047
```

<210> SEQ ID NO 2
<211> LENGTH: 1047
<212> TYPE: DNA
<213> ORGANISM: Arabidopsis thaliana

<400> SEQUENCE: 2

```
atgaaagcaa ctctagcagc accctcttct ctcacaagcc tcccttatcg aaccaactct      60
tctttcggct caaagtcatc gcttctcttt cggtctccat cctcctcctc ctcagtctct     120
atgacgacaa cgcgtggaaa cgtggctgtg gcggctgctg ctacatccac tgaggcgcta     180
agaaaaggaa tagcggagtt ctacaatgaa acttcgggtt tgtgggaaga gatttgggga     240
gatcatatgc atcatggctt ttatgaccct gattcttctg ttcaactttc tgattctggt     300
```

```
cacaaggaag ctcagatccg tatgattgaa gagtctctcc gttttgccgg tgttactgat    360
gaagaggagg agaaaaagat aaagaaagta gtggatgttg ggtgtgggat tggaggaagc    420
tcaagatatc ttgcctctaa atttggagct gaatgcattg gcattactct cagccctgtt    480
caggccaaga gagccaatga tctcgcggct gctcaatcac tcgctcataa ggcttccttc    540
caagttgcgg atgcgttgga tcagccattc gaagatggaa aattcgatct agtgtggtcg    600
atggagagtg gtgagcatat gcctgacaag gccaagtttg taaaagagtt ggtacgtgtg    660
gcggctccag gaggtaggat aataatagtg acatggtgcc atagaaatct atctgcgggg    720
gaggaagctt tgcagccgtg ggagcaaaac atcttggaca aaatctgtaa gacgttctat    780
ctcccggctt ggtgctccac cgatgattat gtcaacttgc ttcaatccca ttctctccag    840
gatattaagt gtgcggattg gtcagagaac gtagctcctt tctggcctgc ggttatacgg    900
actgcattaa catggaaggg ccttgtgtct ctgcttcgta gtggtatgaa agtattaaa     960 ggagcattga caatgccatt gatgattgaa ggttacaaga aggtgtcat taagtttggt   1020 atcatcactt gccagaagcc actctaa                                       1047

<210> SEQ ID NO 3
<211> LENGTH: 1095
<212> TYPE: DNA
<213> ORGANISM: Oryza sativa

<400> SEQUENCE: 3
atggcccacg ccgccgcggc cacgggcgca ctggcaccgc tgcatccact gctccgctgc     60
acgagccgtc atctctgcgc ctcggcttcc cctcgcgccg gcctctgcct ccaccaccac    120
cgccgccgcc gccgcagcag ccggaggacg aaactcgccg tgcgcgcgat ggcaccgacg    180
ttgtcctcgt cgtcgacggc ggcggcagct cccccgggc tgaaggaggg catcgcgggg    240
ctctacgacg agtcgtccgg cgtgtgggag agcatctggg cgagcacat gcaccacggc    300 ttctacgacg ccggcgaggc cgcctccatg tccgaccacc gccgcgccca gatccgcatg    360
atcgaggaat ccctcgcctt cgccgccgtc cccggtgcag atgatgcgga agagaaaccc    420
aaaagtgtag ttgatgttgg ctgtggcatt ggtggtagct caagatactt ggcgaacaaa    480
tacggagcgc aatgctacgg catcacgttg agtccggtgc aggctgaaag aggaaatgcc    540
ctcgcggcag agcaagggtt atcagacaag gtgcgtattc aagttggtga tgcattggag    600
cagccttttc ctgatgggca gtttgatctt gtctggtcca tggagagtgg cgagcacatg    660
ccagacaaac ggcagtttgt aagcgagctg gcacgcgtcg cagctcctgg ggcgagaata    720
atcattgtga cctggtgcca taggaaactc gagccatccg aagagtccct gaaacctgat    780
gagctgaatc tcctgaaaag gatatgcgat gcatattatc tcccagactg gtgctctcct    840
tctgattatg tcaaaattgc cgagtcactg tctcttgagg atataaggac agctgattgg    900
tcagagaacg tcgccccatt ctggcctgcg gttataaaat cagcattgac atggaaaggt    960
ttaacttctc tgctaagaag tgggtggaag acgataagag gtgcaatggt gatgcctctg   1020
atgatcgaag gatacaagaa agggctcatc aaattcacca tcatcacctg tcgcaagccc   1080
gaaacaacgc agtag                                                   1095

<210> SEQ ID NO 4
<211> LENGTH: 1038
<212> TYPE: DNA
<213> ORGANISM: Gossypium hirsutum

<400> SEQUENCE: 4
```

```
atggctgccg cgttacaatt acaaacacac ccttgcttcc atggcacgtg ccaactctca    60
cctccgccac gaccttccgt ttccttccct tcttcctccc gctcgtttcc atctagcaga   120
cgttccctgt ccgcgcatgt gaaggcggcg gcgtcgtctt tgtccaccac caccttgcag   180
gaagggatag cggagtttta cgatgagtcg tcggggattt gggaagacat atgggtgac    240
catatgcacc atggatatta cgagccgggt tccgatattt cgggttcaga tcatcgtgcc   300
gctcagattc gaatggtcga agaatcgctc cgttttgctg gaatatcaga ggacccagca   360
aacaggccca agagaatagt tgatgttggg tgtgggatag gaggcagttc taggtatcta   420
gcaaggaaat atggggcaaa atgccaaggc attactttga gccctgttca agctggaaga   480
gccaatgctc ttgctaatgc tcaaggacta gcagaacagg tttgttttga agttgcagat   540
gccttgaacc aaccattccc tgatgaccaa tttgatcttg tttggtctat ggaaagcgga   600
gaacacatgc ctgacaaacc caagtttgtt aaagagctgg tgcgagtggc agctccagga   660
ggcacaataa tagtagtgac atggtgccat agggatcttg gtccatctga agagtctttg   720
cagccatggg agcaaaagct tttaaacaga atatgtgatg cttactattt accagagtgg   780
tgttctactt ctgattatgt caaattattt cagtccctat ctctccagga tataaaggca   840
ggagactgga ctgagaatgt agcacccttt tggccagcag tgatacgttc agcattgaca   900
tggaagggct tcacatcgct gctacgaagt ggattaaaaa caataaaagg tgcactggtg   960
atgccattga tgatcgaagg tttccagaaa ggggtgataa agtttgccat cattgcttgc  1020
cggaagccag ctgagtag                                                1038

<210> SEQ ID NO 5
<211> LENGTH: 1131
<212> TYPE: DNA
<213> ORGANISM: Cuphea pulcherrima

<400> SEQUENCE: 5
atgccgataa catctatttc cgcaaaccaa aggccattct tcccctcacc ttatagaggc    60
agctccaaga acatggcacc gcccgaactg gctcagtcgc aagtacctat ggaagtaac    120
aagagcaaca agaaccacgg cttggtcggt tcggtttctg gttggagaag gatgtttggg   180
acatgggcta ctgccgacaa gactcagagt accgatacgt ctaatgaagg cgtggttagt   240
tacgatactc aggtcttgca gaagggtata gcggagttct atgacgagtc gtcgggtata   300
tgggaggata tatggggaga tcacatgcat catggctact atgatggttc cactcctgtc   360
tccctcccag accatcgctc tgcgcagatc cgaatgattg acgaggctct ccgctttgcc   420
tcggttcctt caggagaaga agatgagtcc aagtctaaga ttccaaagag gatagtggat   480
gtcgggtgtg ggatagggg aagctccaga tacctggcta gaaaatatgg cgccgagtgt   540
cggggcatca ctctcagtcc tgtccaggct gagaggggca attcacttgc acggtctcaa   600
ggtctttctg acaaggtctc ctttcaagtc gccgatgctt tggcacagcc atttcccgat   660
ggacagtttg atttggtctg gtccatggag agcggggaac acatgcccga caagagcaag   720
tttgtcaatg agctagtaag agtagcagct ccgggtggca cgataataat tgtcacatgg   780
tgccatagag atctcaggga agacgaagat gcgctgcagc ctcgggagaa agagatattg   840
gacaagatat gcaaccccct ttatcttccc gcctggtgtt ctgctgccga ctatgttaag   900
ttgctccagt cacttgatgt cgaggacatt aaatctgcgg actggactcc atatgttgcc   960
ccatttggc cagctgtgct gaagtccgct ttcactataa agggcttcgt gtctctattg  1020
```

```
aggagcggaa tgaagaccat aaagggagca tttgcaatgc cgctgatgat cgaaggatac    1080
aagaaaggtg tcatcaagtt ttccatcatc acatgccgta agcccgaata g             1131

<210> SEQ ID NO 6
<211> LENGTH: 2045
<212> TYPE: DNA
<213> ORGANISM: Brassica napus

<400> SEQUENCE: 6
atgaaagcga ctctcgcacc ctcctctctc ataagcctcc ccaggcacaa agtatcttct      60
ctccgttcac cgtcgcttct ccttcagtcc aacggccat cctcagcctt aatgacgacg     120
acgacggcat cacgtggaag cgtggctgtg acggctgctg ctacctcctc cgttgaggcg     180
ctgcgggaag gaatagcgga attctacaac gagacgtcgg gattatggga ggagatttgg     240
ggagatcata tgcatcacgg cttctacgat cctgattcct ctgttcaact ttcagattcc     300
ggtcaccggg aagctcagat ccggatgatc gaagagtctc tacgtttcgc cggcgttact     360
ggttcgcttc tcatgctata cagttagagt ttgattcgtt gtttgttatg aatgataaac     420
ctacacatga acactttcta gatttattat aaacattctt tttgaactta tattataaac     480
aattcttaca acaaaatgc tctttgaact cttaaaaata tataacaatg gtttagtttt      540
gatttgtcgg taagagaaat gagtagggat gtttgaagcc agataaagcc tttcttttat     600
ccctggggag aggcttacag taagccacgt cccatccaga agcagaccca ttccctaact     660
aggctggatg atgataaata agttcttcct catttcaaga ttaagaaaac aatctaaact     720
gaaataataa cgcgcagtcg gtgaaaatat ctttatgctt gggattgttg ttgttattat     780
taatttatat tataaacaca tgacctttt aaagaagagg agaaaaagat aaagagagta      840
gtggatgttg ggtgtgggat cggcggaagc tcaaggtata ttgcctctaa atttggtgcc     900
gaatgcattg gcatcacact cagtcccgtt caagccaaga gagccaatga tctcgccgcc     960
gctcaatcac tctctcataa ggtgtcttct tgtacattcg accattttt tctgcggaat     1020 ctgagctaac tgagacgcca ctggaccagg tttccttcca agttgcagat gcactggagc     1080
aaccatttga agatggtata ttcgatcttg tgtggtcaat ggaaagcggt gagcatatgc     1140
ctgacaaggc caaggtatac tacctagctc accataatct ttatactaga tttagtagac     1200
aatatccatc tttttggatgt caatgatgtc cattaatttt taaataaaca aaataaaaaa     1260
tgagagtaaa attttttttt gtcaaactta tctaataaat attatgtaat aataccacgt     1320
ttttctattt aattatggca tggtttcttt ttttttttgtc taaaaaaaat tgtagtatct     1380
gttagaaaac agaatctaag tatgatattt tgaaactca ttcagtcttc gttgtggaag     1440
tatatttacc gtgtgtgcga atgagtgta gttcgtgaag gaattggtac gtgtggcggc      1500
tccaggagga aggataataa tagtgacatg gtgccacaga atctatctc caggggaaga    1560 ggctttgcag ccatgggagc agaacctctt ggacagaatc tgcaaaacat tttatctccc    1620
agcctggtgc tccacctcgg attatgtcga tttgcttcag tccctctcgc tccaggttat    1680
tatatttctc acgctccaat tgctaaaatt agtacttgga gctagttaag tagtgtctca    1740
aatatatgtg tgtttgtagg atattaagtg tgcagattgg tcagagaacg tagctccttt    1800
ctggccggcg ttatacgaa ccgcattaac gtggaagggc cttgtgtctc tgcttcgtag     1860
tggtatgttt ccgcaatgtt gttcacattc atgattttta taagattaga actaaggttg    1920
ttgggtgtcg gaaacgcaca ggtatgaaga gtataaaagg agcattgaca atgccattga    1980
tgattgaagg gtacaagaaa ggtgtcatta agtttggcat catcacttgc cagaagcctc    2040
``` tctaa                                                                    2045

<210> SEQ ID NO 7
<211> LENGTH: 2973
<212> TYPE: DNA
<213> ORGANISM: Brassica napus

<400> SEQUENCE: 7
atgaaagcga cactcgcacc accctcctct ctcataagcc tccccaggca caaagtatct    60
tccctccgtt caccgtcgct tctccttcag tcccaacggc gatcctcagc cttaatgacg   120
acgacggcat cacgtggaag cgtggctgtg acggctgctg ctacctcctc cgctgaggcg   180
ctgcgagaag gaatagcgga attctacaac gagacgtcgg gattatggga ggagatttgg   240
ggagatcata tgcatcacgg cttctacgat cccgattcct ctgttcaact ttcagattcc   300
ggtcaccggg aagctcagat ccggatgatt gaagagtctc tacgtttcgc cggcgttact   360
ggttcgcttc tcatgctcta cacttgagtt tgatacgttg tttattataa acattttttt   420
gaacttttat tataaacaat tcttacaaac aaattactct ttgaactctt taaaatctat   480
aacaaaggtt tagttttact ttttatttgt tgttggtaac agaaatgagt agggatgttt   540
gaagtcagat atagccttc tgtttatccc ttgggaagaa aggcttacag taagccacgt   600
cccatccaga agcagaccca ttccctaact aatcattttt atgaacaatt tgtaacacta   660
ttattcctag atattttttt tttacgttta gttaccctaa ctctttgtat ataagacaag   720
aggtgatttt tcacattata tatcaaaaca tagacatagt ttttttgaga aaatatatca   780
tacatagttg taacttagaa ttatatattt ttgagaaaaa aactcagtaa taattttctt   840
ataattattc atagttttat atttattaat aataagattt tgtaagctct ttttgaaact   900
attatggata tgaataagt tccccatttc aagattaaga aaacaattta aactgaaata   960
ataatgcgca ttcggtgaaa atatctttct gcttgggatt gttgttgtta atctatatta  1020
ttaaaactga agtacatttt ggtactgttt ggaaacttag atagtagatt aaatgaaaat  1080
tgtttggaaa caaggatagc agattaaata tttttttatt tacatatttta gtcactgtat  1140
ttctttctca tttacagatt ctgtcgtttg gaaacttgga tagcagatta aatgaaaaat  1200
gtttggaaac acagttaaca tattaaatat ctatttttat ttcatattta gccattgcat  1260
ttctttctta tttacaaatc tgccacttca cttaaaataa aaaaattaaa ttaattacaa  1320
tgaattgtta tttctttttg ctgaaaataa aaacgcaaac tgcaatatat agtatatatt  1380
aatctgctac aatacaattt tcaagaaaac caaatatcat aaaattaata ataatttata  1440
aaaacctaca gtaaaaaaat aaatcatttt taaataaata aacaaaaaaa atcaataggt  1500
tgatatatga atattacaat tacatcaaat tgcatcaagt tataaaatta taaatataat  1560
attacgtaca aataaaaatt attatcaaac atctatttta taatataata tattctactc  1620
taaatatatt tacaaaacat aaaaatataa atggacattt tataaaatca atggtttata  1680
agttacatt gaacgcaagt taaattccaa catccgcgcg gggcgcgggt caagatctag  1740
tattaattta tattataaac acatgacttt ttttaaagaa gaggagaaaa agataaagag  1800
agtggtggat gttgggtgtg ggatcggagg aagctcaagg tatattgcct ctaaatttgg  1860
tgccgaatgc attggcatca cactcagtcc cgttcaagcc aagagagcaa atgatctcgc  1920
caccgctcaa tcactctctc ataaggtgtc ttctcgtaca ttcgaccatt ctttctgcgg  1980
ataatctgat ctaactgaga cgccattgga ccaggtttcc ttccaagttg cagatgcatt  2040

```
ggaccaacca tttgaagatg gtatatccga tcttgtttgg tcaatggaaa gcggtgagca    2100
tatgcctgac aaggccaagg tatactagct cagcataact tttatactag atttactaga    2160
caatatctat cttttcatgt caatgatgtc caataatttt aaaataaaca aaagaaggat    2220
gtgagggtaa aattttgtca aatttatata acaacacgtt ttctatttag ttatgtcatg    2280
gtttcttttt gtctaaaaaa ttttaggcag agtttacaaa aagaaaattg tagtatctgt    2340
tcgaaaacag aatcttagtg tggtatttta gaaactcatt cagtcttcct tgtggaagca    2400
tatttactgt gtgtgcgaaa tgagtgtagt tcgtgaagga attggtacgt gtgacggctc    2460
caggaggaag ataataata gtgacatggt gccacagaaa tctatctcaa ggggaagaat    2520
ctttgcagcc atgggagcag aacctcttgg acagaatctg caaaacattt tatctcccgg    2580
cctggtgctc caccactgat tatgtcgagt tgcttcaatc cctctcgctc caggttatta    2640
tatttctcac gctccgatgc taaaatcagt aagtattgtc tcaaatatat gtgtgtttgt    2700
aggatattaa gtatgcagat tggtcagaga acgtagctcc tttctggccg gcggttatac    2760
gaaccgcatt aacgtggaag ggccttgtgt ctctgcttcg tagtggtatg tttccgcaat    2820
gttgtttaca ttcatgattc caaatgttta agattaga aacatacagg tatgaagagt    2880
ataaaaggag cattgacaat gccattgatg attgaagggt acaagaaagg tgtcattaag    2940
tttggcatca tcacttgcca gaagcctcta taa                                2973

<210> SEQ ID NO 8
<211> LENGTH: 1044
<212> TYPE: DNA
<213> ORGANISM: Brassica napus

<400> SEQUENCE: 8
atgaaagcga ctctcgcacc ctcctctctc ataagcctcc ccaggcacaa agtatcttct      60
ctccgttcac cgtcgcttct ccttcagtcc caacggccat cctcagcctt aatgacgacg     120
acgacggcat cacgtggaag cgtggctgtg acggctgctg ctacctcctc cgttgaggcg     180
ctgcgggaag gaatagcgga attctacaac gagacgtcgg gattatggga ggagatttgg     240
ggagatcata tgcatcacgg cttctacgat cctgattcct ctgttcaact ttcagattcc     300
ggtcaccggg aagctcagat ccggatgatc gaagagtctc tacgtttcgc cggcgttact     360
gaagaggaga aaagataaa gagagtagtg gatgttgggt gtgggatcgg cggaagctca     420
aggtatattg cctctaaatt tggtgccgaa tgcattggca tcacactcag tcccgttcaa     480
gccaagagag ccaatgatct cgccgccgct caatcactct ctcataaggt ttccttccaa     540
gttgcagatg cactggagca accatttgaa gatggtatat tcgatcttgt gtggtcaatg     600
gaaagcggtg agcatatgcc tgacaaggcc aagttcgtga aggaattggt acgtgtggcg     660
gctccaggag gaaggataat aatagtgaca tggtgccaca gaaatctatc tccaggggaa     720
gaggctttgc agccatggga gcagaacctc ttggacagaa tctgcaaaac atttatctc      780 ccagcctggt gctccacctc ggattatgtc gatttgcttc agtccctctc gctccaggat     840
attaagtgtg cagattggtc agagaacgta gctcctttct ggccggcggt tatacgaacc     900
gcattaacgt ggaagggcct tgtgtctctg cttcgtagtg gtatgaagag tataaaagga     960
gcattgacaa tgccattgat gattgaaggg tacaagaaag gtgtcattaa gtttggcatc    1020
atcacttgcc agaagcctct ctaa                                           1044

<210> SEQ ID NO 9
<211> LENGTH: 1044
```

<212> TYPE: DNA
<213> ORGANISM: Brassica napus

<400> SEQUENCE: 9

```
atgaaagcga cactcgcacc accctcctct ctcataagcc tccccaggca caaagtatct    60
tccctccgtt caccgtcgct tctccttcag tcccaacggc gatcctcagc cttaatgacg   120
acgacggcat cacgtggaag cgtggctgtg acggctgctg ctacctcctc cgctgaggcg   180
ctgcgagaag gaatagcgga attctacaac gagacgtcgg gattatggga ggagatttgg   240
ggagatcata tgcatcacgg cttctacgat cccgattcct ctgttcaact ttcagattcc   300
ggtcaccggg aagctcagat ccggatgatt gaagagtctc tacgtttcgc cggcgttact   360
gaagaggaga aaaagataaa gagagtggtg gatgttgggt gtgggatcgg aggaagctca   420
aggtatattg cctctaaatt tggtgccgaa tgcattggca tcacactcag tcccgttcaa   480
gccaagagag caaatgatct cgccaccgct caatcactct ctcataaggt ttccttccaa   540
gttgcagatg cattggacca accatttgaa gatggtatat ccgatcttgt ttggtcaatg   600
gaaagcggtg agcatatgcc tgacaaggcc aagttcgtga aggaattggt acgtgtgacg   660
gctccaggag gaaggataat aatagtgaca tggtgccaca gaaatctatc tcaaggggaa   720
gaatctttgc agccatggga gcagaacctc ttggacagaa tctgcaaaac attttatctc   780
ccggcctggt gctccaccac tgattatgtc gagttgcttc agtccctctc gctccaggat   840
attaagtatg cagattggtc agagaacgta gctccttcct ggccggcggt tatacgaacc   900
gcattaacgt ggaagggcct tgtgtctctg cttcgtagtg gtatgaagag tataaaagga   960
gcattgacaa tgccattgat gattgaaggg tacaagaaag gtgtcattaa gtttggcatc  1020
atcacttgcc agaagcctct ctaa                                         1044
```

<210> SEQ ID NO 10
<211> LENGTH: 933
<212> TYPE: DNA
<213> ORGANISM: Lycopersicon esculentum

<400> SEQUENCE: 10

```
atggctagtg ttgctgcgat gaatgctgtg tcttcgtcat ctgtagaagt tggaatacag    60
aatcaacagg agctgaaaaa aggaattgca gatttatatg atgagtcttc tgggatttgg   120
gaagatattt ggggtgacca tatgcatcat ggatattatg aacctaaatc ctctgtggaa   180
ctttcagatc atcgtgctgc tcagatccgt atgattgaac aggctctaag ttttgctgct   240
atttctgaag atccagcgaa gaaaccaacg tccatagttg atgttggatg tggcatcggt   300
ggcagttcta ggtaccttgc aaagaaatat ggcgctacag ctaaaggtat cactttgagt   360
cctgtacaag cagagagggc tcaagctctt gctgatgctc aaggattagg tgataaggtt   420
tcatttcaag tagcagacgc cttgaatcag ccttttccag atgggcaatt cgacttggtt   480
tggtccatgg agagtggaga acacatgccg aacaaagaaa gtttgttgg cgaattagct   540
cgagtggcag caccaggagg cacaatcatc cttgtcacat ggtgccacag ggacctttcc   600
ccttcggagg aatctctgac tccagaggag aaagagctgt taaataagat atgcaaagcc   660
ttctatcttc cggcttggtg ttccactgct gattatgtga gttacttca atccaattct   720
cttcaggata tcaaggcaga agactggtct gagaatgttg ctccatttg gccagcagtc   780
ataaagtcag cactgacatg gaagggcttc acatcagtac tacgcagtgg atggaagaca   840
atcaaagctg cactggcaat gccactgatg attgaaggat acaagaaagg tctcatcaaa   900
```

```
tttgccatca tcacatgtcg aaaacctgaa taa                            933
```

<210> SEQ ID NO 11
<211> LENGTH: 909
<212> TYPE: DNA
<213> ORGANISM: Glycine max

<400> SEQUENCE: 11

```
atgtcggtgg agcagaaagc agcagggaag gaggaggagg gaaaactgca gaagggaatt     60
gcagagttct acgacgagtc gtctggcata tgggagaaca tttggggcga tcacatgcac    120
cacggctttt atgacccgga ttccaccgtt tctgttttctg atcatcgcgc tgctcagatc    180
cgaatgatcc aagaatctct tcgttttgcc tctctgcttt ctgagaaccc ttctaaatgg    240
cccaagagta tagttgatgt tgggtgtggc atagggggca gctccagata cctgccaag     300
aaatttggag caacgagcgt aggcattact ctgagtcctg ttcaagctca aagagcaaat    360
gctcttgctg ctgctcaagg attggctgat aaggtttcct ttcaggttgc tgacgctcta    420
cagcaaccat tctctgacgg ccagtttgat ctggtgtggt ccatggagag tggagagcat    480
atgcctgaca agctaagtt tgttggagag ttagctcggg tagcagcacc aggtgccact    540
ataataatag taacatggtg ccacagggat cttgccctg acgaacaatc cttacatcca    600
tgggagcaag atctcttaaa gaagatttgc gatgcatatt acctccctgc tggtgctca    660
acttctgatt atgttaagtt gctccaatcc ctgtcacttc aggacatcaa gtcagaagat    720
tggtctcgct ttgttgctcc atttttggcca gcagtgatac gctcagcctt cacatggaag    780
ggtctaactt cactcttgag cagtggacaa aaaacgataa aaggagctt ggctatgcca     840
ttgatgatag agggatacaa gaaagatcta attaagtttg ccatcattac atgtcgaaaa    900
cctgaataa                                                            909
```

<210> SEQ ID NO 12
<211> LENGTH: 1053
<212> TYPE: DNA
<213> ORGANISM: Glycine max

<400> SEQUENCE: 12

```
atggccaccg tggtgaggat cccaacaatc tcatgcatcc acatccacac gttccgttcc     60
caatcccctc gcactttcgc cagaatccgg gtcggaccca ggtcgtgggc tcctattcgg    120
gcatcggcag cgagctcgga gagggggag atagtattgg agcagaagcc gaagaaggag    180
gaggaggga aactgcagaa gggaatcgca gagttctacg acgagtcgtc tggcttatgg    240
gagaacattt ggggcgacca catgcaccat ggcttttatg acccggattc cactgtttct    300
gtttctgatc atcgcgctgc tcagatccga atgatccaag agtctcttcg ctttgcctct    360
gtttctgagg agcgtagtaa atggcccaag agtatagttg atgttgggtg tggcataggt    420
ggcagctcca gatacctggc caagaaattt ggagcaacca gcgtaggcat tactctgagt    480
cctgttcaag ctcaaagagc aaatgctctt gctgctgctc aaggattggc tgataaggtt    540
tcctttcagg ttgctgacgc tctacagcaa ccattctctg acggccagtt tgatctggtg    600
tggtccatgg agagtggaga gcatatgcct gacaaagcta gtttgttgg agagttagct     660
cgggtagcag caccaggtgc cactataata atagtaacat ggtgccacag ggatcttggc    720
cctgacgaac aatccttaca tccatgggag caagatctct taaagaagat ttgcgatgca    780
tattaccttc ctgcctggtg ctcaacttct gattatgtta agttgctcca atccctgtca    840
cttcaggaca tcaagtcaga agattggtct cgctttgttg ctccattttg gccagcagtg    900
```

```
atacgctcag ccttcacatg aagggtcta acttcactct tgagcagtgg acttaaaacc      960
ataaaaggag ctttggctat gccattgatg atagagggat acaagaaaga tctaattaag    1020
tttgccatca ttacatgtcg aaaacctgaa taa                                  1053

<210> SEQ ID NO 13
<211> LENGTH: 1053
<212> TYPE: DNA
<213> ORGANISM: Glycine max

<400> SEQUENCE: 13
atggccaccg tggtgaggat cccaacaatc tcatgcatcc acatccacac gttccgttcc      60
caatcccctc gcactttcgc cagaatccgg gtcggaccca gtcgtgggc tcctattcgg     120 gcatcggcag cgagctcgga gagggggag atagtattgg agcagaagcc gaagaaggat      180
gacaaggaga aactgcagaa gggaatcgca gagttttacg acgagtcttc tggcttatgg     240
gagaacattt ggggcgacca catgcaccat ggcttttatg acccggattc cactgtttcg     300
ctttcggatc atcgtgctgc tcagatccga atgatccaag agtctcttcg ctttgccctct    360 gtttctgagg agcgtagtaa atggcccaag agtatagttg atgttgggtg tggcataggt     420
ggcagctcca gatacctggc caagaaattt ggagcaacca gtgtaggcat cactctgagt     480
cctgttcaag ctcaaagagc aaatgctctt gctgctgctc aaggattggc tgataaggtt     540
tcctttcagg ttgctgacgc tctacagcaa ccattctctg acggccagtt tgatctggtg     600
tggtccatgg agagtggaga gcatatgcct gacaaagcta agtttgttgg agagttagct     660
cgggtagcag caccaggtgc cactataata tagtaacat ggtgccacag ggatcttggc      720
cctgacgaac aatccttaca tccatgggag caagatctct taaagaagat ttgcgatgca     780
tattacctcc ctgcctggtg ctcaacttct gattatgtta agttgctcca atccctgtca     840
cttcaggaca tcaagtcaga agattggtct cgctttggtg ctccattttg gccagcagtg     900
atacgctcag ccttcacatg gaagggtcta acttcactct tgagcagtgg ccaaaaaacg     960
ataaaaggag ctttggctat gccattgatg atagagggat acaagaaaga tctaattaag    1020
tttgccatca ttacatgtcg aaaacctgaa taa                                  1053

<210> SEQ ID NO 14
<211> LENGTH: 933
<212> TYPE: DNA
<213> ORGANISM: Tagetes erecta

<400> SEQUENCE: 14
gcccttagcg tggtcgcggc cgaggtacca gttacggtta ctccggcgac gacgaaggcg      60
gaggatgtgg agctgaagaa aggaattgca gagttctacg atgaatcgtc ggagatgtgg     120
gagaatatat ggggagaaca catgcatcat ggatactata acactaatgc cgttgttgaa     180
ctctccgatc atcgttctgc tcagatccgt atgattgaac aagccctact tttcgcatct     240
gtttcagatg atccagtaaa gaaacctaga agcatcgttg atgttgggtg tggcataggt     300
ggtagctcaa ggtatctggc aaagaaatac gaagctgaat gccatggaat cactctcagc     360
cctgtgcaag ctgagagagc tcaagctcta gctgctgctc aaggattggc cgataaggct     420
tcatttcaag ttgctgatgc tttagaccaa ccatttcctg atggaaagtt tgatctggtc     480
tggtcaatgg agagtggtga acacatgcct gacaaactaa agtttgttag tgagttggtt     540
cgggttgctg ccccaggagc cacgattatc atagttacat ggtgccatag ggatcttttct    600
```

```
cctggtgaaa agtcccttcg acccgatgaa gaaaaaatct tgaaaaagat ttgttccagc      660
ttttatcttc ctgcttggtg ttcaacatct gattatgtaa aattactaga gtccctttct      720
cttcaggaca tcaaagctgc agactggtca gcaaacgtgg ctccattttg gcctgctgta      780
ataaaaacag cattatcttg aagggcatt acttcgctac ttcgtagtgg atggaagtca       840
ataagagggg caatggtaat gccattgatg attgaaggat ttaagaagga tataatcaaa      900
ttctccatca tcacatgcaa aaagcctgaa taa                                   933
```

<210> SEQ ID NO 15
<211> LENGTH: 1230
<212> TYPE: DNA
<213> ORGANISM: Sorghum bicolor

<400> SEQUENCE: 15

```
cgaacggcga gcagcaggag ggcgtcgcga acccttgggc ggcggatcgg tacccgtagg       60
cagccactac tactaccgcg ccccttcgca cgtcccgcgc cgctcccgcc cccgcggacg      120
cggcggcgtc gtcagcctgc gtccgatggc ctcgtcgacg gcggctcagc ccccgcgcc      180 ggcgccccg ggcctgaagg agggcatcgc ggggctgtac gacgagtctt cggggctgtg      240
ggagaacatc tggggcgacc acatgcacca cggcttctac gactcgggcg aggccgcgtc      300 catgccgac caccgacgcg cccagatccg catgatcgag gaggcgctcg ccttcgccgc      360
cgtcccatcc ccagatgatc cggagaaggc accaaaaacc atagtagatg ttggatgtgg      420
cattggtggt agctcaaggt acttggctaa gaaatacgga gcacagtgca agggatcac      480 attgagccct gttcaagctg aaagaggaaa tgctcttgct acagcgcagg ggttgtcgga      540
tcaggttact ctgcaagttg ctgatgctct ggagcaaccg tttcctgatg gcagtttga      600 tctggtatgg tccatggaga gtggcgagca catgccggac aagagaaagt tgttagtga      660 gctggcacgc gtcgctgctc ctggagggac aataatcatc gtgacatggt gccataggaa      720
cctcgaacca tctgagactt cgctaaaacc cgatgaactg agtctcttga agaggatttg      780
cgatgcgtac tacctcccag actggtgctc accttcagac tatgtgaaca tcgccaaatc      840
actgtctctg gaggatatca aggcagctga ttggtcagag aatgtggccc catttttggcc     900 cgctgtgata aaatcagcac taacatggaa gggcctcacc tctctactga caagcggatg      960
gaagacgatc agaggggcga tggtgatgcc gctgatgatc caaggttaca agaagggct      1020 catcaaattc accatcatca cctgtcgcaa gcctgggagca gcgtaggtga ccaaggggca      1080
gaagttactg tcaaagcacc tctgctaagt ccaataatgt agatccatgg ccccatcacc      1140
gtctattgta ctgtactgta ctgtaccaga tgaacagtc tcctgggaca tgttttccaa      1200
ttgccatgac atgtcaaatg atcttctacc                                      1230
```

<210> SEQ ID NO 16
<211> LENGTH: 843
<212> TYPE: DNA
<213> ORGANISM: Nostoc punctiforme

<400> SEQUENCE: 16

```
atgagtgcaa cactttacca gcaaattcag caattttacg atgcttcatc tggtctgtgg       60
gaacagatat ggggcgaaca catgcaccac ggctattacg cgctgatgg tacccagaaa      120 aaagaccgcc gtcaggctca aattgattta atcgaagaat tgcttaattg gcaggggta      180 caagcagcag aagatatact agatgtgggt tgtggaattg gcgtagttc tttataccctg     240 gcgcaaaagt ttaatgctaa agctacaggg attacattga gtcctgtaca agctgcaaga      300
```

```
gcaacagaac gcgcattgga agctaatttg agtctgagaa cacagttcca agtcgctaat    360
gctcaagcaa tgccctttgc tgacgattct tttgacttgg tttggtcgct ggaaagtggc    420
gaacacatgc cagataaaac caagtttctt caggagtgct atcgagtact gaagcctggt    480
ggcaagttaa ttatggtgac ttggtgtcat cgaccaactg atgaatctcc attaacggca    540
gatgaggaaa agcacttgca ggatatttat cgggtgtatt gtttgcctta tgtgatttct    600
ttgccagagt atgaagcgat cgcacatcaa ctaccattac ataatatccg cactgctgat    660
tggtcaactg ctgtcgcccc cttttggaat gtggtaattg attctgcatt cactccccaa    720
gcgctttggg gtttactaaa tgctggttgg actaccattc aagggggatt atcactggga    780
ttaatgcgtc gcggttatga acgtgggtta attcggtttg cttactgtg cggcaataag    840 tag                                                                   843
```

<210> SEQ ID NO 17
<211> LENGTH: 843
<212> TYPE: DNA
<213> ORGANISM: Anabaena sp.

<400> SEQUENCE: 17

```
atgagtgcaa cactttacca acaaattcag caattttacg atgcttcctc tgggctgtgg     60
gaagagattt ggggcgaaca tatgcaccac ggctattatg gtgcagacgg tactgaacaa    120
aaaaaccgcc gtcaggcgca aattgattta attgaagaat tactcacttg gcaggagta    180 caaacagcag aaaatatact agatgtgggt tgtggtattg tggtagttc tctgtatttg    240 gcaggaaagt tgaatgctaa agctacagga attaccctga gtccagtgca agccgctaga    300
gccacagaaa gagccaagga agctggttta agtggtagaa gtcagttttt agtggcaaat    360
gcccaagcaa tgccttttga tgataattct tttgacttgg tgtggtcgct agaaagtggc    420
gaacatatgc cagataaaac caagttttg caagagtgtt atcgagtctt gaacccgggc    480
ggtaagttaa tcatggtgac atggtgtcat cgtcccactg ataaaacacc actgacggct    540
gatgaaaaaa acacactaga agatatttat cgggtgtatt gtttgcctta tgtaattcg    600 ttgccggagt atgaagcgat cgcacgtcaa ctaccattaa ataatatccg caccgccgac    660
tggtcgcaat ccgtcgccca ttttggaac atagtcatcg attccgcctt taccccccaa    720
gcaatattcg gcttactccg cgcaggttgg actaccatcc aaggagcctt atcactaggc    780
ttaatgcgtc gcggctatga gcgcgggtta attcggtttg ggttgctttg tggggataag    840
tga                                                                   843
```

<210> SEQ ID NO 18
<211> LENGTH: 348
<212> TYPE: PRT
<213> ORGANISM: Arabidopsis thaliana

<400> SEQUENCE: 18

```
Met Lys Ala Thr Leu Ala Ala Pro Ser Ser Leu Thr Ser Leu Pro Tyr
  1               5                  10                  15

Arg Thr Asn Ser Ser Phe Gly Ser Lys Ser Ser Leu Leu Phe Arg Ser
                 20                  25                  30

Pro Ser Ser Ser Ser Val Ser Met Thr Thr Thr Arg Gly Asn Val
             35                  40                  45

Ala Val Ala Ala Ala Ala Thr Ser Thr Glu Ala Leu Arg Lys Gly Ile
         50                  55                  60
```

Ala Glu Phe Tyr Asn Glu Thr Ser Gly Leu Trp Glu Ile Trp Gly
 65                  70                  75                  80

Asp His Met His His Gly Phe Tyr Asp Pro Asp Ser Ser Val Gln Leu
                 85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
        115                 120                 125

Lys Val Val Asp Val Gly Cys Gly Ile Gly Gly Ser Ser Arg Tyr Leu
130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Ala Gln Ser Leu Ser His
                165                 170                 175

Lys Ala Ser Phe Gln Val Ala Asp Ala Leu Asp Gln Pro Phe Glu Asp
            180                 185                 190

Gly Lys Phe Asp Leu Val Trp Ser Met Glu Ser Gly Glu His Met Pro
        195                 200                 205

Asp Lys Ala Lys Phe Val Lys Glu Leu Val Arg Val Ala Ala Pro Gly
    210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Asp Tyr Val Asn
            260                 265                 270

Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
    290                 295                 300

Trp Lys Gly Leu Val Ser Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
            340                 345

<210> SEQ ID NO 19
<211> LENGTH: 348
<212> TYPE: PRT
<213> ORGANISM: Arabidopsis thaliana

<400> SEQUENCE: 19

Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
                20                  25                  30

Pro Ser Ser Ser Ser Val Ser Met Thr Thr Thr Arg Gly Asn Val
            35                  40                  45

Ala Val Ala Ala Ala Thr Ser Thr Glu Ala Leu Arg Lys Gly Ile
        50                  55                  60

Ala Glu Phe Tyr Asn Glu Thr Ser Gly Leu Trp Glu Ile Trp Gly
 65                  70                  75                  80

Asp His Met His His Gly Phe Tyr Asp Pro Asp Ser Ser Val Gln Leu
                 85                  90                  95

-continued

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
        115                 120                 125

Lys Val Val Asp Val Gly Cys Gly Ile Gly Gly Ser Ser Arg Tyr Leu
130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Gln Ser Leu Ala His
            165                 170                 175

Lys Ala Ser Phe Gln Val Ala Asp Ala Leu Asp Gln Pro Phe Glu Asp
                180                 185                 190

Gly Lys Phe Asp Leu Val Trp Ser Met Glu Ser Gly Glu His Met Pro
            195                 200                 205

Asp Lys Ala Lys Phe Val Lys Glu Leu Val Arg Val Ala Ala Pro Gly
    210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Asp Tyr Val Asn
            260                 265                 270

Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
    290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
            340                 345

<210> SEQ ID NO 20
<211> LENGTH: 364
<212> TYPE: PRT
<213> ORGANISM: Oryza sativa

<400> SEQUENCE: 20

Met Ala His Ala Ala Ala Ala Thr Gly Ala Leu Ala Pro Leu His Pro
1               5                   10                  15

Leu Leu Arg Cys Thr Ser Arg His Leu Cys Ala Ser Ala Ser Pro Arg
            20                  25                  30

Ala Gly Leu Cys Leu His His His Arg Arg Arg Arg Ser Ser Arg
        35                  40                  45

Arg Thr Lys Leu Ala Val Arg Ala Met Ala Pro Thr Leu Ser Ser Ser
    50                  55                  60

Ser Thr Ala Ala Ala Ala Pro Pro Gly Leu Lys Glu Gly Ile Ala Gly
65                  70                  75                  80

Leu Tyr Asp Glu Ser Ser Gly Val Trp Glu Ser Ile Trp Gly Glu His
                85                  90                  95

Met His His Gly Phe Tyr Asp Ala Gly Glu Ala Ala Ser Met Ser Asp
            100                 105                 110

His Arg Arg Ala Gln Ile Arg Met Ile Glu Glu Ser Leu Ala Phe Ala

```
                115                 120                 125
Ala Val Pro Gly Ala Asp Ala Glu Lys Pro Lys Ser Val Val
        130                 135                 140

Asp Val Gly Cys Gly Ile Gly Gly Ser Ser Arg Tyr Leu Ala Asn Lys
145                 150                 155                 160

Tyr Gly Ala Gln Cys Tyr Gly Ile Thr Leu Ser Pro Val Gln Ala Glu
                165                 170                 175

Arg Gly Asn Ala Leu Ala Ala Glu Gln Gly Leu Ser Asp Lys Val Arg
            180                 185                 190

Ile Gln Val Gly Asp Ala Leu Glu Gln Pro Phe Pro Asp Gly Gln Phe
        195                 200                 205

Asp Leu Val Trp Ser Met Glu Ser Gly Glu His Met Pro Asp Lys Arg
    210                 215                 220

Gln Phe Val Ser Glu Leu Ala Arg Val Ala Ala Pro Gly Ala Arg Ile
225                 230                 235                 240

Ile Ile Val Thr Trp Cys His Arg Asn Leu Glu Pro Ser Glu Glu Ser
                245                 250                 255

Leu Lys Pro Asp Glu Leu Asn Leu Leu Lys Arg Ile Cys Asp Ala Tyr
            260                 265                 270

Tyr Leu Pro Asp Trp Cys Ser Pro Ser Asp Tyr Val Lys Ile Ala Glu
        275                 280                 285

Ser Leu Ser Leu Glu Asp Ile Arg Thr Ala Asp Trp Ser Glu Asn Val
    290                 295                 300

Ala Pro Phe Trp Pro Ala Val Ile Lys Ser Ala Leu Thr Trp Lys Gly
305                 310                 315                 320

Leu Thr Ser Leu Leu Arg Ser Gly Trp Lys Thr Ile Arg Gly Ala Met
                325                 330                 335

Val Met Pro Leu Met Ile Glu Gly Tyr Lys Lys Gly Leu Ile Lys Phe
            340                 345                 350

Thr Ile Ile Thr Cys Arg Lys Pro Glu Thr Thr Gln
        355                 360

<210> SEQ ID NO 21
<211> LENGTH: 352
<212> TYPE: PRT
<213> ORGANISM: Zea mays

<400> SEQUENCE: 21

Met Ala His Ala Ala Leu Leu His Cys Ser Gln Ser Ser Arg Ser Leu
1               5                   10                  15

Ala Ala Cys Arg Arg Gly Ser His Tyr Arg Ala Pro Ser His Val Pro
                20                  25                  30

Arg His Ser Arg Arg Leu Arg Arg Ala Val Val Ser Leu Arg Pro Met
            35                  40                  45

Ala Ser Ser Thr Ala Gln Ala Pro Ala Thr Ala Pro Pro Gly Leu Lys
        50                  55                  60

Glu Gly Ile Ala Gly Leu Tyr Asp Glu Ser Ser Gly Leu Trp Glu Asn
65                  70                  75                  80

Ile Trp Gly Asp His Met His Gly Phe Tyr Asp Ser Ser Glu Ala
                85                  90                  95

Ala Ser Met Ala Asp His Arg Arg Ala Gln Ile Arg Met Ile Glu Glu
            100                 105                 110

Ala Leu Ala Phe Ala Gly Val Pro Ala Ser Asp Asp Pro Glu Lys Thr
        115                 120                 125
```

```
Pro Lys Thr Ile Val Asp Val Gly Cys Gly Ile Gly Ser Ser Arg
    130                 135                 140

Tyr Leu Ala Lys Lys Tyr Gly Ala Gln Cys Thr Gly Ile Thr Leu Ser
145                 150                 155                 160

Pro Val Gln Ala Glu Arg Gly Asn Ala Leu Ala Ala Gln Gly Leu
                165                 170                 175

Ser Asp Gln Val Thr Leu Gln Val Ala Asp Ala Leu Glu Gln Pro Phe
                180                 185                 190

Pro Asp Gly Gln Phe Asp Leu Val Trp Ser Met Glu Ser Gly Glu His
                195                 200                 205

Met Pro Asp Lys Arg Lys Phe Val Ser Glu Leu Ala Arg Val Ala Ala
    210                 215                 220

Pro Gly Gly Thr Ile Ile Ile Val Thr Trp Cys His Arg Asn Leu Asp
225                 230                 235                 240

Pro Ser Glu Thr Ser Leu Lys Pro Asp Glu Leu Ser Leu Leu Arg Arg
                245                 250                 255

Ile Cys Asp Ala Tyr Tyr Leu Pro Asp Trp Cys Ser Pro Ser Asp Tyr
                260                 265                 270

Val Asn Ile Ala Lys Ser Leu Ser Leu Glu Asp Ile Lys Thr Ala Asp
                275                 280                 285

Trp Ser Glu Asn Val Ala Pro Phe Trp Pro Ala Val Ile Lys Ser Ala
    290                 295                 300

Leu Thr Trp Lys Gly Phe Thr Ser Leu Leu Thr Thr Gly Trp Lys Thr
305                 310                 315                 320

Ile Arg Gly Ala Met Val Met Pro Leu Met Ile Gln Gly Tyr Lys Lys
                325                 330                 335

Gly Leu Ile Lys Phe Thr Ile Ile Thr Cys Arg Lys Pro Gly Ala Ala
                340                 345                 350

<210> SEQ ID NO 22
<211> LENGTH: 345
<212> TYPE: PRT
<213> ORGANISM: Gossypium hirsutum

<400> SEQUENCE: 22

Met Ala Ala Ala Leu Gln Leu Gln Thr His Pro Cys Phe His Gly Thr
1               5                   10                  15

Cys Gln Leu Ser Pro Pro Arg Pro Ser Val Ser Phe Pro Ser Ser
                20                  25                  30

Ser Arg Ser Phe Pro Ser Ser Arg Arg Ser Leu Ser Ala His Val Lys
            35                  40                  45

Ala Ala Ala Ser Ser Leu Ser Thr Thr Thr Leu Gln Glu Gly Ile Ala
    50                  55                  60

Glu Phe Tyr Asp Glu Ser Ser Gly Ile Trp Glu Asp Ile Trp Gly Asp
65                  70                  75                  80

His Met His His Gly Tyr Tyr Glu Pro Gly Ser Asp Ile Ser Gly Ser
                85                  90                  95

Asp His Arg Ala Ala Gln Ile Arg Met Val Glu Glu Ser Leu Arg Phe
                100                 105                 110

Ala Gly Ile Ser Glu Asp Pro Ala Asn Arg Pro Lys Arg Ile Val Asp
            115                 120                 125

Val Gly Cys Gly Ile Gly Gly Ser Ser Arg Tyr Leu Ala Arg Lys Tyr
    130                 135                 140

Gly Ala Lys Cys Gln Gly Ile Thr Leu Ser Pro Val Gln Ala Gly Arg
145                 150                 155                 160
```

```
Ala Asn Ala Leu Ala Asn Ala Gln Gly Leu Ala Glu Gln Val Cys Phe
                165                 170                 175

Glu Val Ala Asp Ala Leu Asn Gln Pro Phe Pro Asp Asp Gln Phe Asp
            180                 185                 190

Leu Val Trp Ser Met Glu Ser Gly Glu His Met Pro Asp Lys Pro Lys
        195                 200                 205

Phe Val Lys Glu Leu Val Arg Val Ala Ala Pro Gly Gly Thr Ile Ile
    210                 215                 220

Val Val Thr Trp Cys His Arg Asp Leu Gly Pro Ser Glu Glu Ser Leu
225                 230                 235                 240

Gln Pro Trp Glu Gln Lys Leu Leu Asn Arg Ile Cys Asp Ala Tyr Tyr
                245                 250                 255

Leu Pro Glu Trp Cys Ser Thr Ser Asp Tyr Val Lys Leu Phe Gln Ser
            260                 265                 270

Leu Ser Leu Gln Asp Ile Lys Ala Gly Asp Trp Thr Glu Asn Val Ala
        275                 280                 285

Pro Phe Trp Pro Ala Val Ile Arg Ser Ala Leu Thr Trp Lys Gly Phe
    290                 295                 300

Thr Ser Leu Leu Arg Ser Gly Leu Lys Thr Ile Lys Gly Ala Leu Val
305                 310                 315                 320

Met Pro Leu Met Ile Glu Gly Phe Gln Lys Gly Val Ile Lys Phe Ala
                325                 330                 335

Ile Ile Ala Cys Arg Lys Pro Ala Glu
            340                 345

<210> SEQ ID NO 23
<211> LENGTH: 376
<212> TYPE: PRT
<213> ORGANISM: Cuphea pulcherrima

<400> SEQUENCE: 23

Met Pro Ile Thr Ser Ile Ser Ala Asn Gln Arg Pro Phe Phe Pro Ser
1               5                   10                  15

Pro Tyr Arg Gly Ser Ser Lys Asn Met Ala Pro Glu Leu Ala Gln
            20                  25                  30

Ser Gln Val Pro Met Gly Ser Asn Lys Ser Asn Lys Asn His Gly Leu
        35                  40                  45

Val Gly Ser Val Ser Gly Trp Arg Arg Met Phe Gly Thr Trp Ala Thr
    50                  55                  60

Ala Asp Lys Thr Gln Ser Thr Asp Thr Ser Asn Glu Gly Val Val Ser
65                  70                  75                  80

Tyr Asp Thr Gln Val Leu Gln Lys Gly Ile Ala Glu Phe Tyr Asp Glu
                85                  90                  95

Ser Ser Gly Ile Trp Glu Asp Ile Trp Gly Asp His Met His His Gly
            100                 105                 110

Tyr Tyr Asp Gly Ser Thr Pro Val Ser Leu Pro Asp His Arg Ser Ala
        115                 120                 125

Gln Ile Arg Met Ile Asp Glu Ala Leu Arg Phe Ala Ser Val Pro Ser
    130                 135                 140

Gly Glu Glu Asp Glu Ser Lys Ser Lys Ile Pro Lys Arg Ile Val Asp
145                 150                 155                 160

Val Gly Cys Gly Ile Gly Gly Ser Ser Arg Tyr Leu Ala Arg Lys Tyr
                165                 170                 175

Gly Ala Glu Cys Arg Gly Ile Thr Leu Ser Pro Val Gln Ala Glu Arg
```

-continued

```
                180                 185                 190
Gly Asn Ser Leu Ala Arg Ser Gln Gly Leu Ser Asp Lys Val Ser Phe
            195                 200                 205

Gln Val Ala Asp Ala Leu Ala Gln Pro Phe Pro Asp Gly Gln Phe Asp
        210                 215                 220

Leu Val Trp Ser Met Glu Ser Gly Glu His Met Pro Asp Lys Ser Lys
225                 230                 235                 240

Phe Val Asn Glu Leu Val Arg Val Ala Ala Pro Gly Gly Thr Ile Ile
                245                 250                 255

Ile Val Thr Trp Cys His Arg Asp Leu Arg Glu Asp Glu Asp Ala Leu
            260                 265                 270

Gln Pro Arg Glu Lys Glu Ile Leu Asp Lys Ile Cys Asn Pro Phe Tyr
        275                 280                 285

Leu Pro Ala Trp Cys Ser Ala Ala Asp Tyr Val Lys Leu Leu Gln Ser
    290                 295                 300

Leu Asp Val Glu Asp Ile Lys Ser Ala Asp Trp Thr Pro Tyr Val Ala
305                 310                 315                 320

Pro Phe Trp Pro Ala Val Leu Lys Ser Ala Phe Thr Ile Lys Gly Phe
                325                 330                 335

Val Ser Leu Leu Arg Ser Gly Met Lys Thr Ile Lys Gly Ala Phe Ala
            340                 345                 350

Met Pro Leu Met Ile Glu Gly Tyr Lys Lys Gly Val Ile Lys Phe Ser
        355                 360                 365

Ile Ile Thr Cys Arg Lys Pro Glu
    370                 375

<210> SEQ ID NO 24
<211> LENGTH: 347
<212> TYPE: PRT
<213> ORGANISM: Brassica napus

<400> SEQUENCE: 24

Met Lys Ala Thr Leu Ala Pro Ser Ser Leu Ile Ser Leu Pro Arg His
1               5                   10                  15

Lys Val Ser Ser Leu Arg Ser Pro Ser Leu Leu Gln Ser Gln Arg
            20                  25                  30

Pro Ser Ser Ala Leu Met Thr Thr Thr Ala Ser Arg Gly Ser Val
        35                  40                  45

Ala Val Thr Ala Ala Thr Ser Ser Val Glu Ala Leu Arg Glu Gly
    50                  55                  60

Ile Ala Glu Phe Tyr Asn Glu Thr Ser Gly Leu Trp Glu Glu Ile Trp
65                  70                  75                  80

Gly Asp His Met His His Gly Phe Tyr Asp Pro Asp Ser Ser Val Gln
                85                  90                  95

Leu Ser Asp Ser Gly His Arg Glu Ala Gln Ile Arg Met Ile Glu Glu
            100                 105                 110

Ser Leu Arg Phe Ala Gly Val Thr Glu Glu Lys Lys Ile Lys Arg
        115                 120                 125

Val Val Asp Val Gly Cys Gly Ile Gly Gly Ser Ser Arg Tyr Ile Ala
    130                 135                 140

Ser Lys Phe Gly Ala Glu Cys Ile Gly Ile Thr Leu Ser Pro Val Gln
145                 150                 155                 160

Ala Lys Arg Ala Asn Asp Leu Ala Ala Ala Gln Ser Leu Ser His Lys
                165                 170                 175
```

```
Val Ser Phe Gln Val Ala Asp Ala Leu Glu Gln Pro Phe Glu Asp Gly
            180                 185                 190

Ile Phe Asp Leu Val Trp Ser Met Glu Ser Gly Glu His Met Pro Asp
            195                 200                 205

Lys Ala Lys Phe Val Lys Glu Leu Val Arg Val Ala Pro Gly Gly
        210                 215                 220

Arg Ile Ile Ile Val Thr Trp Cys His Arg Asn Leu Ser Pro Gly Glu
225                 230                 235                 240

Glu Ala Leu Gln Pro Trp Glu Gln Asn Leu Leu Asp Arg Ile Cys Lys
                245                 250                 255

Thr Phe Tyr Leu Pro Ala Trp Cys Ser Thr Ser Asp Tyr Val Asp Leu
            260                 265                 270

Leu Gln Ser Leu Ser Leu Gln Asp Ile Lys Cys Ala Asp Trp Ser Glu
            275                 280                 285

Asn Val Ala Pro Phe Trp Pro Ala Val Ile Arg Thr Ala Leu Thr Trp
290                 295                 300

Lys Gly Leu Val Ser Leu Leu Arg Ser Gly Met Lys Ser Ile Lys Gly
305                 310                 315                 320

Ala Leu Thr Met Pro Leu Met Ile Glu Gly Tyr Lys Lys Gly Val Ile
                325                 330                 335

Lys Phe Gly Ile Ile Thr Cys Gln Lys Pro Leu
                340                 345

<210> SEQ ID NO 25
<211> LENGTH: 347
<212> TYPE: PRT
<213> ORGANISM: Brassica napus

<400> SEQUENCE: 25

Met Lys Ala Thr Leu Ala Pro Pro Ser Ser Leu Ile Ser Leu Pro Arg
1               5                   10                  15

His Lys Val Ser Ser Leu Arg Ser Pro Ser Leu Leu Gln Ser Gln
            20                  25                  30

Arg Arg Ser Ser Ala Leu Met Thr Thr Thr Ala Ser Arg Gly Ser Val
            35                  40                  45

Ala Val Thr Ala Ala Ala Thr Ser Ser Ala Glu Ala Leu Arg Glu Gly
        50                  55                  60

Ile Ala Glu Phe Tyr Asn Glu Thr Ser Gly Leu Trp Glu Glu Ile Trp
65                  70                  75                  80

Gly Asp His Met His His Gly Phe Tyr Asp Pro Asp Ser Ser Val Gln
                85                  90                  95

Leu Ser Asp Ser Gly His Arg Glu Ala Gln Ile Arg Met Ile Glu Glu
            100                 105                 110

Ser Leu Arg Phe Ala Gly Val Thr Glu Glu Lys Lys Ile Lys Arg
            115                 120                 125

Val Val Asp Val Gly Cys Gly Ile Gly Gly Ser Ser Arg Tyr Ile Ala
        130                 135                 140

Ser Lys Phe Gly Ala Glu Cys Ile Gly Ile Thr Leu Ser Pro Val Gln
145                 150                 155                 160

Ala Lys Arg Ala Asn Asp Leu Ala Thr Ala Gln Ser Leu Ser His Lys
                165                 170                 175

Val Ser Phe Gln Val Ala Asp Ala Leu Asp Gln Pro Phe Glu Asp Gly
            180                 185                 190

Ile Ser Asp Leu Val Trp Ser Met Glu Ser Gly Glu His Met Pro Asp
            195                 200                 205
```

```
Lys Ala Lys Phe Val Lys Glu Leu Val Arg Val Thr Ala Pro Gly Gly
        210                 215                 220

Arg Ile Ile Ile Val Thr Trp Cys His Arg Asn Leu Ser Gln Gly Glu
225                 230                 235                 240

Glu Ser Leu Gln Pro Trp Glu Gln Asn Leu Leu Asp Arg Ile Cys Lys
                245                 250                 255

Thr Phe Tyr Leu Pro Ala Trp Cys Ser Thr Thr Asp Tyr Val Glu Leu
            260                 265                 270

Leu Gln Ser Leu Ser Leu Gln Asp Ile Lys Tyr Ala Asp Trp Ser Glu
        275                 280                 285

Asn Val Ala Pro Phe Trp Pro Ala Val Ile Arg Thr Ala Leu Thr Trp
    290                 295                 300

Lys Gly Leu Val Ser Leu Leu Arg Ser Gly Met Lys Ser Ile Lys Gly
305                 310                 315                 320

Ala Leu Thr Met Pro Leu Met Ile Glu Gly Tyr Lys Lys Gly Val Ile
                325                 330                 335

Lys Phe Gly Ile Ile Thr Cys Gln Lys Pro Leu
            340                 345

<210> SEQ ID NO 26
<211> LENGTH: 310
<212> TYPE: PRT
<213> ORGANISM: Lycopersicon esculentum

<400> SEQUENCE: 26

Met Ala Ser Val Ala Ala Met Asn Ala Val Ser Ser Ser Ser Val Glu
1               5                   10                  15

Val Gly Ile Gln Asn Gln Gln Glu Leu Lys Lys Gly Ile Ala Asp Leu
            20                  25                  30

Tyr Asp Glu Ser Ser Gly Ile Trp Glu Asp Ile Trp Gly Asp His Met
        35                  40                  45

His His Gly Tyr Tyr Glu Pro Lys Ser Ser Val Glu Leu Ser Asp His
    50                  55                  60

Arg Ala Ala Gln Ile Arg Met Ile Glu Gln Ala Leu Ser Phe Ala Ala
65                  70                  75                  80

Ile Ser Glu Asp Pro Ala Lys Lys Pro Thr Ser Ile Val Asp Val Gly
                85                  90                  95

Cys Gly Ile Gly Gly Ser Ser Arg Tyr Leu Ala Lys Lys Tyr Gly Ala
            100                 105                 110

Thr Ala Lys Gly Ile Thr Leu Ser Pro Val Gln Ala Glu Arg Ala Gln
        115                 120                 125

Ala Leu Ala Asp Ala Gln Gly Leu Gly Asp Lys Val Ser Phe Gln Val
    130                 135                 140

Ala Asp Ala Leu Asn Gln Pro Phe Pro Asp Gly Gln Phe Asp Leu Val
145                 150                 155                 160

Trp Ser Met Glu Ser Gly Glu His Met Pro Asn Lys Glu Lys Phe Val
                165                 170                 175

Gly Glu Leu Ala Arg Val Ala Ala Pro Gly Gly Thr Ile Ile Leu Val
            180                 185                 190

Thr Trp Cys His Arg Asp Leu Ser Pro Ser Glu Glu Ser Leu Thr Pro
        195                 200                 205

Glu Glu Lys Glu Leu Leu Asn Lys Ile Cys Lys Ala Phe Tyr Leu Pro
    210                 215                 220

Ala Trp Cys Ser Thr Ala Asp Tyr Val Lys Leu Leu Gln Ser Asn Ser
```

```
                225                 230                 235                 240
Leu Gln Asp Ile Lys Ala Glu Asp Trp Ser Glu Asn Val Ala Pro Phe
                    245                 250                 255

Trp Pro Ala Val Ile Lys Ser Ala Leu Thr Trp Lys Gly Phe Thr Ser
                260                 265                 270

Val Leu Arg Ser Gly Trp Lys Thr Ile Lys Ala Ala Leu Ala Met Pro
            275                 280                 285

Leu Met Ile Glu Gly Tyr Lys Lys Gly Leu Ile Lys Phe Ala Ile Ile
        290                 295                 300

Thr Cys Arg Lys Pro Glu
305                 310

<210> SEQ ID NO 27
<211> LENGTH: 302
<212> TYPE: PRT
<213> ORGANISM: Glycine max

<400> SEQUENCE: 27

Met Ser Val Glu Gln Lys Ala Ala Gly Lys Glu Glu Gly Lys Leu
1               5                   10                  15

Gln Lys Gly Ile Ala Glu Phe Tyr Asp Glu Ser Ser Gly Ile Trp Glu
                20                  25                  30

Asn Ile Trp Gly Asp His Met His His Gly Phe Tyr Asp Pro Asp Ser
            35                  40                  45

Thr Val Ser Val Ser Asp His Arg Ala Ala Gln Ile Arg Met Ile Gln
    50                  55                  60

Glu Ser Leu Arg Phe Ala Ser Leu Leu Ser Glu Asn Pro Ser Lys Trp
65                  70                  75                  80

Pro Lys Ser Ile Val Asp Val Gly Cys Gly Ile Gly Gly Ser Ser Arg
                85                  90                  95

Tyr Leu Ala Lys Lys Phe Gly Ala Thr Ser Val Gly Ile Thr Leu Ser
                100                 105                 110

Pro Val Gln Ala Gln Arg Ala Asn Ala Leu Ala Ala Ala Gln Gly Leu
            115                 120                 125

Ala Asp Lys Val Ser Phe Gln Val Ala Asp Ala Leu Gln Gln Pro Phe
130                 135                 140

Ser Asp Gly Gln Phe Asp Leu Val Trp Ser Met Glu Ser Gly Glu His
145                 150                 155                 160

Met Pro Asp Lys Ala Lys Phe Val Gly Glu Leu Ala Arg Val Ala Ala
                165                 170                 175

Pro Gly Ala Thr Ile Ile Ile Val Thr Trp Cys His Arg Asp Leu Gly
            180                 185                 190

Pro Asp Glu Gln Ser Leu His Pro Trp Glu Gln Asp Leu Leu Lys Lys
        195                 200                 205

Ile Cys Asp Ala Tyr Tyr Leu Pro Ala Trp Cys Ser Thr Ser Asp Tyr
    210                 215                 220

Val Lys Leu Leu Gln Ser Leu Ser Leu Gln Asp Ile Lys Ser Glu Asp
225                 230                 235                 240

Trp Ser Arg Phe Val Ala Pro Phe Trp Pro Ala Val Ile Arg Ser Ala
                245                 250                 255

Phe Thr Trp Lys Gly Leu Thr Ser Leu Leu Ser Ser Gly Gln Lys Thr
            260                 265                 270

Ile Lys Gly Ala Leu Ala Met Pro Leu Met Ile Glu Gly Tyr Lys Lys
        275                 280                 285
```

```
Asp Leu Ile Lys Phe Ala Ile Ile Thr Cys Arg Lys Pro Glu
    290             295                 300
```

<210> SEQ ID NO 28
<211> LENGTH: 350
<212> TYPE: PRT
<213> ORGANISM: Glycine max

<400> SEQUENCE: 28

```
Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ser Ser Glu Arg
        35                  40                  45

Gly Glu Ile Val Leu Glu Gln Lys Pro Lys Glu Glu Gly Lys
50                  55                  60

Leu Gln Lys Gly Ile Ala Glu Phe Tyr Asp Ser Ser Gly Leu Trp
65                  70                  75                  80

Glu Asn Ile Trp Gly Asp His Met His His Gly Phe Tyr Asp Pro Asp
                85                  90                  95

Ser Thr Val Ser Val Ser Asp His Arg Ala Ala Gln Ile Arg Met Ile
            100                 105                 110

Gln Glu Ser Leu Arg Phe Ala Ser Val Ser Glu Glu Arg Ser Lys Trp
        115                 120                 125

Pro Lys Ser Ile Val Asp Val Gly Cys Gly Ile Gly Gly Ser Ser Arg
130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
210                 215                 220

Pro Gly Ala Thr Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285

Trp Ser Arg Phe Val Ala Pro Phe Trp Pro Ala Val Ile Arg Ser Ala
290                 295                 300

Phe Thr Trp Lys Gly Leu Thr Ser Leu Leu Ser Ser Gly Leu Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
            340                 345                 350
```

<210> SEQ ID NO 29

<211> LENGTH: 350
<212> TYPE: PRT
<213> ORGANISM: Glycine max

<400> SEQUENCE: 29

```
Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ser Ser Glu Arg
        35                  40                  45

Gly Glu Ile Val Leu Glu Gln Lys Pro Lys Asp Lys Glu Lys
    50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His Gly Phe Tyr Asp Pro Asp
                85                  90                  95

Ser Thr Val Ser Leu Ser Asp His Arg Ala Ala Gln Ile Arg Met Ile
            100                 105                 110

Gln Glu Ser Leu Arg Phe Ala Ser Val Ser Glu Arg Ser Lys Trp
        115                 120                 125

Pro Lys Ser Ile Val Asp Val Gly Cys Gly Ile Gly Gly Ser Ser Arg
130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Thr Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285

Trp Ser Arg Phe Gly Ala Pro Phe Trp Pro Ala Val Ile Arg Ser Ala
    290                 295                 300

Phe Thr Trp Lys Gly Leu Thr Ser Leu Leu Ser Ser Gly Gln Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
            340                 345                 350
```

<210> SEQ ID NO 30
<211> LENGTH: 310
<212> TYPE: PRT
<213> ORGANISM: Tagetes erecta

<400> SEQUENCE: 30

```
Ala Leu Ser Val Val Ala Glu Val Pro Val Thr Val Thr Pro Ala
1               5                   10                  15

Thr Thr Lys Ala Glu Asp Val Glu Leu Lys Lys Gly Ile Ala Glu Phe
            20                  25                  30

Tyr Asp Glu Ser Ser Glu Met Trp Glu Asn Ile Trp Gly Glu His Met
            35                  40                  45

His His Gly Tyr Tyr Asn Thr Asn Ala Val Val Glu Leu Ser Asp His
        50                  55                  60

Arg Ser Ala Gln Ile Arg Met Ile Glu Gln Ala Leu Leu Phe Ala Ser
65                  70                  75                  80

Val Ser Asp Asp Pro Val Lys Lys Pro Arg Ser Ile Val Asp Val Gly
                85                  90                  95

Cys Gly Ile Gly Gly Ser Ser Arg Tyr Leu Ala Lys Lys Tyr Glu Ala
                100                 105                 110

Glu Cys His Gly Ile Thr Leu Ser Pro Val Gln Ala Glu Arg Ala Gln
            115                 120                 125

Ala Leu Ala Ala Ala Gln Gly Leu Ala Asp Lys Ala Ser Phe Gln Val
    130                 135                 140

Ala Asp Ala Leu Asp Gln Pro Phe Pro Asp Gly Lys Phe Asp Leu Val
145                 150                 155                 160

Trp Ser Met Glu Ser Gly Glu His Met Pro Asp Lys Leu Lys Phe Val
                165                 170                 175

Ser Glu Leu Val Arg Val Ala Ala Pro Gly Ala Thr Ile Ile Ile Val
            180                 185                 190

Thr Trp Cys His Arg Asp Leu Ser Pro Gly Glu Lys Ser Leu Arg Pro
        195                 200                 205

Asp Glu Glu Lys Ile Leu Lys Lys Ile Cys Ser Ser Phe Tyr Leu Pro
    210                 215                 220

Ala Trp Cys Ser Thr Ser Asp Tyr Val Lys Leu Leu Glu Ser Leu Ser
225                 230                 235                 240

Leu Gln Asp Ile Lys Ala Ala Asp Trp Ser Ala Asn Val Ala Pro Phe
                245                 250                 255

Trp Pro Ala Val Ile Lys Thr Ala Leu Ser Trp Lys Gly Ile Thr Ser
            260                 265                 270

Leu Leu Arg Ser Gly Trp Lys Ser Ile Arg Gly Ala Met Val Met Pro
        275                 280                 285

Leu Met Ile Glu Gly Phe Lys Lys Asp Ile Ile Lys Phe Ser Ile Ile
    290                 295                 300

Thr Cys Lys Lys Pro Glu
305             310

<210> SEQ ID NO 31
<211> LENGTH: 354
<212> TYPE: PRT
<213> ORGANISM: Sorghum bicolor

<400> SEQUENCE: 31

Glu Arg Arg Ala Ala Gly Gly Arg Arg Glu Pro Leu Gly Gly Gly Ser
1               5                   10                  15

Val Pro Val Gly Ser His Tyr Tyr Arg Ala Pro Ser His Val Pro
            20                  25                  30

Arg Arg Ser Arg Pro Arg Gly Arg Gly Val Val Ser Leu Arg Pro
            35                  40                  45

Met Ala Ser Ser Thr Ala Ala Gln Pro Pro Ala Pro Ala Pro Pro Gly
```

```
            50                  55                  60
Leu Lys Glu Gly Ile Ala Gly Leu Tyr Asp Glu Ser Ser Gly Leu Trp
 65                  70                  75                  80

Glu Asn Ile Trp Gly Asp His Met His His Gly Phe Tyr Asp Ser Gly
                 85                  90                  95

Glu Ala Ala Ser Met Ala Asp His Arg Arg Ala Gln Ile Arg Met Ile
            100                 105                 110

Glu Glu Ala Leu Ala Phe Ala Ala Val Pro Ser Pro Asp Asp Pro Glu
        115                 120                 125

Lys Ala Pro Lys Thr Ile Val Asp Val Gly Cys Gly Ile Gly Gly Ser
130                 135                 140

Ser Arg Tyr Leu Ala Lys Lys Tyr Gly Ala Gln Cys Lys Gly Ile Thr
145                 150                 155                 160

Leu Ser Pro Val Gln Ala Glu Arg Gly Asn Ala Leu Ala Thr Ala Gln
                165                 170                 175

Gly Leu Ser Asp Gln Val Thr Leu Gln Val Ala Asp Ala Leu Glu Gln
            180                 185                 190

Pro Phe Pro Asp Gly Gln Phe Asp Leu Val Trp Ser Met Glu Ser Gly
        195                 200                 205

Glu His Met Pro Asp Lys Arg Lys Phe Val Ser Glu Leu Ala Arg Val
210                 215                 220

Ala Ala Pro Gly Gly Thr Ile Ile Ile Val Thr Trp Cys His Arg Asn
225                 230                 235                 240

Leu Glu Pro Ser Glu Thr Ser Leu Lys Pro Asp Glu Leu Ser Leu Leu
                245                 250                 255

Lys Arg Ile Cys Asp Ala Tyr Tyr Leu Pro Asp Trp Cys Ser Pro Ser
            260                 265                 270

Asp Tyr Val Asn Ile Ala Lys Ser Leu Ser Leu Glu Asp Ile Lys Ala
        275                 280                 285

Ala Asp Trp Ser Glu Asn Val Ala Pro Phe Trp Pro Ala Val Ile Lys
290                 295                 300

Ser Ala Leu Thr Trp Lys Gly Leu Thr Ser Leu Leu Thr Ser Gly Trp
305                 310                 315                 320

Lys Thr Ile Arg Gly Ala Met Val Met Pro Leu Met Ile Gln Gly Tyr
                325                 330                 335

Lys Lys Gly Leu Ile Lys Phe Thr Ile Thr Cys Arg Lys Pro Gly
            340                 345                 350
Ala Ala

<210> SEQ ID NO 32
<211> LENGTH: 92
<212> TYPE: PRT
<213> ORGANISM: Pisum sativum

<400> SEQUENCE: 32

Met Ala Ser Ser Met Leu Ser Ser Ala Thr Met Val Ala Ser Pro Ala
 1               5                  10                  15

Gln Ala Thr Met Val Ala Pro Phe Asn Gly Leu Lys Ser Ser Ala Ala
                 20                  25                  30

Phe Pro Ala Thr Arg Lys Ala Asn Asn Asp Ile Thr Ser Ile Thr Ser
            35                  40                  45

Asn Gly Gly Arg Val Asn Cys Met Gln Val Trp Pro Pro Ile Gly Lys
        50                  55                  60

Lys Lys Phe Glu Thr Leu Ser Tyr Leu Pro Asp Leu Thr Asp Ser Gly
```

```
                65                  70                  75                  80
Gly Arg Val Asn Cys Met Gln Ala Asn Asn Asn
                85                  90
```

<210> SEQ ID NO 33
<211> LENGTH: 301
<212> TYPE: PRT
<213> ORGANISM: Brassica napus

<400> SEQUENCE: 33

```
Met Val Ala Val Thr Ala Ala Thr Ser Ser Val Glu Ala Leu Arg
  1               5                  10                  15

Glu Gly Ile Ala Glu Phe Tyr Asn Glu Thr Ser Gly Leu Trp Glu
                 20                  25                  30

Ile Trp Gly Asp His Met His Gly Phe Tyr Asp Pro Asp Ser Ser
                 35                  40                  45

Val Gln Leu Ser Asp Ser Gly His Arg Glu Ala Gln Ile Arg Met Ile
                 50                  55                  60

Glu Glu Ser Leu Arg Phe Ala Gly Val Thr Glu Glu Lys Lys Ile
 65                  70                  75                  80

Lys Arg Val Val Asp Val Gly Cys Gly Ile Gly Gly Ser Ser Arg Tyr
                 85                  90                  95

Ile Ala Ser Lys Phe Gly Ala Glu Cys Ile Gly Ile Thr Leu Ser Pro
                100                 105                 110

Val Gln Ala Lys Arg Ala Asn Asp Leu Ala Ala Ala Gln Ser Leu Ser
                115                 120                 125

His Lys Val Ser Phe Gln Val Ala Asp Ala Leu Glu Gln Pro Phe Glu
                130                 135                 140

Asp Gly Ile Phe Asp Leu Val Trp Ser Met Glu Ser Gly Glu His Met
145                 150                 155                 160

Pro Asp Lys Ala Lys Phe Val Lys Glu Leu Val Arg Val Ala Ala Pro
                165                 170                 175

Gly Gly Arg Ile Ile Ile Val Thr Trp Cys His Arg Asn Leu Ser Pro
                180                 185                 190

Gly Glu Glu Ala Leu Gln Pro Trp Glu Gln Asn Leu Leu Asp Arg Ile
                195                 200                 205

Cys Lys Thr Phe Tyr Leu Pro Ala Trp Cys Ser Thr Ser Asp Tyr Val
                210                 215                 220

Asp Leu Leu Gln Ser Leu Ser Leu Gln Asp Ile Lys Cys Ala Asp Trp
225                 230                 235                 240

Ser Glu Asn Val Ala Pro Phe Trp Pro Ala Val Ile Arg Thr Ala Leu
                245                 250                 255

Thr Trp Lys Gly Leu Val Ser Leu Leu Arg Ser Gly Met Lys Ser Ile
                260                 265                 270

Lys Gly Ala Leu Thr Met Pro Leu Met Ile Glu Gly Tyr Lys Lys Gly
                275                 280                 285

Val Ile Lys Phe Gly Ile Ile Thr Cys Gln Lys Pro Leu
                290                 295                 300
```

<210> SEQ ID NO 34
<211> LENGTH: 301
<212> TYPE: PRT
<213> ORGANISM: Brassica napus

<400> SEQUENCE: 34

Met Val Ala Val Thr Ala Ala Ala Thr Ser Ser Ala Glu Ala Leu Arg

```
                1               5                   10                  15
        Glu Gly Ile Ala Glu Phe Tyr Asn Glu Thr Ser Gly Leu Trp Glu Glu
                        20                  25                  30

Ile Trp Gly Asp His Met His His Gly Phe Tyr Asp Pro Asp Ser Ser
                    35                  40                  45

Val Gln Leu Ser Asp Ser Gly His Arg Glu Ala Gln Ile Arg Met Ile
                50                  55                  60

Glu Glu Ser Leu Arg Phe Ala Gly Val Thr Glu Glu Lys Lys Ile
        65                  70                  75                  80

Lys Arg Val Val Asp Val Gly Cys Gly Ile Gly Gly Ser Ser Arg Tyr
                        85                  90                  95

Ile Ala Ser Lys Phe Gly Ala Glu Cys Ile Gly Ile Thr Leu Ser Pro
                        100                 105                 110

Val Gln Ala Lys Arg Ala Asn Asp Leu Ala Thr Ala Gln Ser Leu Ser
                        115                 120                 125

His Lys Val Ser Phe Gln Val Ala Asp Ala Leu Asp Gln Pro Phe Glu
                        130                 135                 140

Asp Gly Ile Ser Asp Leu Val Trp Ser Met Glu Ser Gly Glu His Met
        145                 150                 155                 160

Pro Asp Lys Ala Lys Phe Val Lys Glu Leu Val Arg Val Thr Ala Pro
                        165                 170                 175

Gly Gly Arg Ile Ile Ile Val Thr Trp Cys His Arg Asn Leu Ser Gln
                        180                 185                 190

Gly Glu Glu Ser Leu Gln Pro Trp Glu Gln Asn Leu Leu Asp Arg Ile
                        195                 200                 205

Cys Lys Thr Phe Tyr Leu Pro Ala Trp Cys Ser Thr Thr Asp Tyr Val
                        210                 215                 220

Glu Leu Leu Gln Ser Leu Ser Leu Gln Asp Ile Lys Tyr Ala Asp Trp
        225                 230                 235                 240

Ser Glu Asn Val Ala Pro Phe Trp Pro Ala Val Ile Arg Thr Ala Leu
                        245                 250                 255

Thr Trp Lys Gly Leu Val Ser Leu Leu Arg Ser Gly Met Lys Ser Ile
                        260                 265                 270

Lys Gly Ala Leu Thr Met Pro Leu Met Ile Glu Gly Tyr Lys Lys Gly
                        275                 280                 285

Val Ile Lys Phe Gly Ile Ile Thr Cys Gln Lys Pro Leu
                        290                 295                 300

<210> SEQ ID NO 35
<211> LENGTH: 315
<212> TYPE: PRT
<213> ORGANISM: Cuphea pulcherrima

<400> SEQUENCE: 35

Met Ala Thr Ala Asp Lys Thr Gln Ser Thr Asp Thr Ser Asn Glu Gly
1               5                   10                  15

Val Val Ser Tyr Asp Thr Gln Val Leu Gln Lys Gly Ile Ala Glu Phe
                20                  25                  30

Tyr Asp Glu Ser Ser Gly Ile Trp Glu Asp Ile Trp Gly Asp His Met
                35                  40                  45

His His Gly Tyr Tyr Asp Gly Ser Thr Pro Val Ser Leu Pro Asp His
                50                  55                  60

Arg Ser Ala Gln Ile Arg Met Ile Asp Glu Ala Leu Arg Phe Ala Ser
65                  70                  75                  80
```

```
Val Pro Ser Gly Glu Glu Asp Glu Ser Lys Ser Lys Ile Pro Lys Arg
            85                  90                  95

Ile Val Asp Val Gly Cys Gly Ile Gly Gly Ser Ser Arg Tyr Leu Ala
                100                 105                 110

Arg Lys Tyr Gly Ala Glu Cys Arg Gly Ile Thr Leu Ser Pro Val Gln
            115                 120                 125

Ala Glu Arg Gly Asn Ser Leu Ala Arg Ser Gln Gly Leu Ser Asp Lys
        130                 135                 140

Val Ser Phe Gln Val Ala Asp Ala Leu Ala Gln Pro Phe Pro Asp Gly
145                 150                 155                 160

Gln Phe Asp Leu Val Trp Ser Met Glu Ser Gly Glu His Met Pro Asp
                165                 170                 175

Lys Ser Lys Phe Val Asn Glu Leu Val Arg Val Ala Ala Pro Gly Gly
            180                 185                 190

Thr Ile Ile Val Thr Trp Cys His Arg Asp Leu Arg Glu Asp Glu
        195                 200                 205

Asp Ala Leu Gln Pro Arg Glu Lys Glu Ile Leu Asp Lys Ile Cys Asn
        210                 215                 220

Pro Phe Tyr Leu Pro Ala Trp Cys Ser Ala Ala Asp Tyr Val Lys Leu
225                 230                 235                 240

Leu Gln Ser Leu Asp Val Glu Asp Ile Lys Ser Ala Asp Trp Thr Pro
                245                 250                 255

Tyr Val Ala Pro Phe Trp Pro Ala Val Leu Lys Ser Ala Phe Thr Ile
                260                 265                 270

Lys Gly Phe Val Ser Leu Leu Arg Ser Gly Met Lys Thr Ile Lys Gly
            275                 280                 285

Ala Phe Ala Met Pro Leu Met Ile Glu Gly Tyr Lys Lys Gly Val Ile
        290                 295                 300

Lys Phe Ser Ile Ile Thr Cys Arg Lys Pro Glu
305                 310                 315

<210> SEQ ID NO 36
<211> LENGTH: 299
<212> TYPE: PRT
<213> ORGANISM: Gossypium hirsutum

<400> SEQUENCE: 36

Met Val Lys Ala Ala Ala Ser Ser Leu Ser Thr Thr Thr Leu Gln Glu
1               5                   10                  15

Gly Ile Ala Glu Phe Tyr Asp Glu Ser Ser Gly Ile Trp Glu Asp Ile
            20                  25                  30

Trp Gly Asp His Met His His Gly Tyr Tyr Glu Pro Gly Ser Asp Ile
        35                  40                  45

Ser Gly Ser Asp His Arg Ala Ala Gln Ile Arg Met Val Glu Glu Ser
    50                  55                  60

Leu Arg Phe Ala Gly Ile Ser Glu Asp Pro Ala Asn Arg Pro Lys Arg
65              70                  75                  80

Ile Val Asp Val Gly Cys Gly Ile Gly Gly Ser Ser Arg Tyr Leu Ala
                85                  90                  95

Arg Lys Tyr Gly Ala Lys Cys Gln Gly Ile Thr Leu Ser Pro Val Gln
            100                 105                 110

Ala Gly Arg Ala Asn Ala Leu Ala Asn Ala Gln Gly Leu Ala Glu Gln
        115                 120                 125

Val Cys Phe Glu Val Ala Asp Ala Leu Asn Gln Pro Phe Pro Asp Asp
        130                 135                 140
```

```
Gln Phe Asp Leu Val Trp Ser Met Glu Ser Gly Glu His Met Pro Asp
145                 150                 155                 160

Lys Pro Lys Phe Val Lys Glu Leu Val Val Ala Ala Pro Gly Gly Thr
                165                 170                 175

Ile Ile Val Val Thr Trp Cys His Arg Asp Leu Gly Pro Ser Glu Glu
            180                 185                 190

Ser Leu Gln Pro Trp Glu Gln Lys Leu Leu Asn Arg Ile Cys Asp Ala
        195                 200                 205

Tyr Tyr Leu Pro Glu Trp Cys Ser Thr Ser Asp Tyr Val Lys Leu Phe
    210                 215                 220

Gln Ser Leu Ser Leu Gln Asp Ile Lys Ala Gly Asp Trp Thr Glu Asn
225                 230                 235                 240

Val Ala Pro Phe Trp Pro Ala Val Ile Arg Ser Ala Leu Thr Trp Lys
                245                 250                 255

Gly Phe Thr Ser Leu Leu Arg Ser Gly Leu Lys Thr Ile Lys Gly Ala
            260                 265                 270

Leu Val Met Pro Leu Met Ile Glu Gly Phe Gln Lys Gly Val Ile Lys
        275                 280                 285

Phe Ala Ile Ile Ala Cys Arg Lys Pro Ala Glu
    290                 295

<210> SEQ ID NO 37
<211> LENGTH: 311
<212> TYPE: PRT
<213> ORGANISM: Tagetes erecta

<400> SEQUENCE: 37

Met Ala Leu Ser Val Val Ala Ala Glu Val Pro Val Thr Val Thr Pro
1               5                   10                  15

Ala Thr Thr Lys Ala Glu Asp Val Glu Leu Lys Lys Gly Ile Ala Glu
                20                  25                  30

Phe Tyr Asp Glu Ser Ser Glu Met Trp Glu Asn Ile Trp Gly Glu His
            35                  40                  45

Met His His Gly Tyr Tyr Asn Thr Asn Ala Val Val Glu Leu Ser Asp
        50                  55                  60

His Arg Ser Ala Gln Ile Arg Met Ile Glu Gln Ala Leu Leu Phe Ala
65                  70                  75                  80

Ser Val Ser Asp Asp Pro Val Lys Lys Pro Arg Ser Ile Val Asp Val
                85                  90                  95

Gly Cys Gly Ile Gly Gly Ser Ser Arg Tyr Leu Ala Lys Lys Tyr Glu
            100                 105                 110

Ala Glu Cys His Gly Ile Thr Leu Ser Pro Val Gln Ala Glu Arg Ala
        115                 120                 125

Gln Ala Leu Ala Ala Ala Gln Gly Leu Ala Asp Lys Ala Ser Phe Gln
    130                 135                 140

Val Ala Asp Ala Leu Asp Gln Pro Phe Pro Asp Gly Lys Phe Asp Leu
145                 150                 155                 160

Val Trp Ser Met Glu Ser Gly Glu His Met Pro Asp Lys Leu Lys Phe
                165                 170                 175

Val Ser Glu Leu Val Arg Val Ala Ala Pro Gly Ala Thr Ile Ile Ile
            180                 185                 190

Val Thr Trp Cys His Arg Asp Leu Ser Pro Gly Glu Lys Ser Leu Arg
        195                 200                 205

Pro Asp Glu Glu Lys Ile Leu Lys Lys Ile Cys Ser Ser Phe Tyr Leu
```

```
            210                 215                 220
Pro Ala Trp Cys Ser Thr Ser Asp Tyr Val Lys Leu Leu Glu Ser Leu
225                 230                 235                 240

Ser Leu Gln Asp Ile Lys Ala Ala Asp Trp Ser Ala Asn Val Ala Pro
                245                 250                 255

Phe Trp Pro Ala Val Ile Lys Thr Ala Leu Ser Trp Lys Gly Ile Thr
            260                 265                 270

Ser Leu Leu Arg Ser Gly Trp Lys Ser Ile Arg Gly Ala Met Val Met
                275                 280                 285

Pro Leu Met Ile Glu Gly Phe Lys Lys Asp Ile Ile Lys Phe Ser Ile
            290                 295                 300

Ile Thr Cys Lys Lys Pro Glu
305                 310

<210> SEQ ID NO 38
<211> LENGTH: 305
<212> TYPE: PRT
<213> ORGANISM: Zea mays

<400> SEQUENCE: 38

Met Ala Ser Ser Thr Ala Gln Ala Pro Ala Thr Ala Pro Pro Gly Leu
1               5                   10                  15

Lys Glu Gly Ile Ala Gly Leu Tyr Asp Glu Ser Ser Gly Leu Trp Glu
            20                  25                  30

Asn Ile Trp Gly Asp His Met His His Gly Phe Tyr Asp Ser Ser Glu
        35                  40                  45

Ala Ala Ser Met Ala Asp His Arg Arg Ala Gln Ile Arg Met Ile Glu
    50                  55                  60

Glu Ala Leu Ala Phe Ala Gly Val Pro Ala Ser Asp Asp Pro Glu Lys
65                  70                  75                  80

Thr Pro Lys Thr Ile Val Asp Val Gly Cys Gly Ile Gly Gly Ser Ser
                85                  90                  95

Arg Tyr Leu Ala Lys Lys Tyr Gly Ala Gln Cys Thr Gly Ile Thr Leu
            100                 105                 110

Ser Pro Val Gln Ala Glu Arg Gly Asn Ala Leu Ala Ala Ala Gln Gly
        115                 120                 125

Leu Ser Asp Gln Val Thr Leu Gln Val Ala Asp Ala Leu Glu Gln Pro
    130                 135                 140

Phe Pro Asp Gly Gln Phe Asp Leu Val Trp Ser Met Glu Ser Gly Glu
145                 150                 155                 160

His Met Pro Asp Lys Arg Lys Phe Val Ser Glu Leu Ala Arg Val Ala
                165                 170                 175

Ala Pro Gly Gly Thr Ile Ile Ile Val Thr Trp Cys His Arg Asn Leu
            180                 185                 190

Asp Pro Ser Glu Thr Ser Leu Lys Pro Asp Glu Leu Ser Leu Leu Arg
        195                 200                 205

Arg Ile Cys Asp Ala Tyr Tyr Leu Pro Asp Trp Cys Ser Pro Ser Asp
    210                 215                 220

Tyr Val Asn Ile Ala Lys Ser Leu Ser Leu Glu Asp Ile Lys Thr Ala
225                 230                 235                 240

Asp Trp Ser Glu Asn Val Ala Pro Phe Trp Pro Ala Val Ile Lys Ser
                245                 250                 255

Ala Leu Thr Trp Lys Gly Phe Thr Ser Leu Leu Thr Thr Gly Trp Lys
            260                 265                 270
```

```
Thr Ile Arg Gly Ala Met Val Met Pro Leu Met Ile Gln Gly Tyr Lys
        275                 280                 285

Lys Gly Leu Ile Lys Phe Thr Ile Ile Thr Cys Arg Lys Pro Gly Ala
    290                 295                 300

Ala
305

<210> SEQ ID NO 39
<211> LENGTH: 280
<212> TYPE: PRT
<213> ORGANISM: Nostoc punctiforme

<400> SEQUENCE: 39

Met Ser Ala Thr Leu Tyr Gln Gln Ile Gln Gln Phe Tyr Asp Ala Ser
1               5                   10                  15

Ser Gly Leu Trp Glu Gln Ile Trp Gly Glu His Met His His Gly Tyr
            20                  25                  30

Tyr Gly Ala Asp Gly Thr Gln Lys Lys Asp Arg Arg Gln Ala Gln Ile
        35                  40                  45

Asp Leu Ile Glu Glu Leu Leu Asn Trp Ala Gly Val Gln Ala Ala Glu
    50                  55                  60

Asp Ile Leu Asp Val Gly Cys Gly Ile Gly Gly Ser Ser Leu Tyr Leu
65                  70                  75                  80

Ala Gln Lys Phe Asn Ala Lys Ala Thr Gly Ile Thr Leu Ser Pro Val
                85                  90                  95

Gln Ala Ala Arg Ala Thr Glu Arg Ala Leu Glu Ala Asn Leu Ser Leu
            100                 105                 110

Arg Thr Gln Phe Gln Val Ala Asn Ala Gln Ala Met Pro Phe Ala Asp
        115                 120                 125

Asp Ser Phe Asp Leu Val Trp Ser Leu Glu Ser Gly Glu His Met Pro
    130                 135                 140

Asp Lys Thr Lys Phe Leu Gln Glu Cys Tyr Arg Val Leu Lys Pro Gly
145                 150                 155                 160

Gly Lys Leu Ile Met Val Thr Trp Cys His Arg Pro Thr Asp Glu Ser
                165                 170                 175

Pro Leu Thr Ala Asp Glu Glu Lys His Leu Gln Asp Ile Tyr Arg Val
            180                 185                 190

Tyr Cys Leu Pro Tyr Val Ile Ser Leu Pro Glu Tyr Glu Ala Ile Ala
        195                 200                 205

His Gln Leu Pro Leu His Asn Ile Arg Thr Ala Asp Trp Ser Thr Ala
    210                 215                 220

Val Ala Pro Phe Trp Asn Val Val Ile Asp Ser Ala Phe Thr Pro Gln
225                 230                 235                 240

Ala Leu Trp Gly Leu Leu Asn Ala Gly Trp Thr Thr Ile Gln Gly Ala
                245                 250                 255

Leu Ser Leu Gly Leu Met Arg Arg Gly Tyr Glu Arg Gly Leu Ile Arg
            260                 265                 270

Phe Gly Leu Leu Cys Gly Asn Lys
        275                 280

<210> SEQ ID NO 40
<211> LENGTH: 280
<212> TYPE: PRT
<213> ORGANISM: Anabaena sp.

<400> SEQUENCE: 40
```

```
Met Ser Ala Thr Leu Tyr Gln Gln Ile Gln Gln Phe Tyr Asp Ala Ser
1               5                   10                  15

Ser Gly Leu Trp Glu Glu Ile Trp Gly Glu His Met His His Gly Tyr
                20                  25                  30

Tyr Gly Ala Asp Gly Thr Glu Gln Lys Asn Arg Arg Gln Ala Gln Ile
            35                  40                  45

Asp Leu Ile Glu Glu Leu Leu Thr Trp Ala Gly Val Gln Thr Ala Glu
50                  55                  60

Asn Ile Leu Asp Val Gly Cys Gly Ile Gly Gly Ser Ser Leu Tyr Leu
65                  70                  75                  80

Ala Gly Lys Leu Asn Ala Lys Ala Thr Gly Ile Thr Leu Ser Pro Val
                85                  90                  95

Gln Ala Ala Arg Ala Thr Glu Arg Ala Lys Glu Ala Gly Leu Ser Gly
                100                 105                 110

Arg Ser Gln Phe Leu Val Ala Asn Ala Gln Ala Met Pro Phe Asp Asp
            115                 120                 125

Asn Ser Phe Asp Leu Val Trp Ser Leu Glu Ser Gly Glu His Met Pro
130                 135                 140

Asp Lys Thr Lys Phe Leu Gln Glu Cys Tyr Arg Val Leu Lys Pro Gly
145                 150                 155                 160

Gly Lys Leu Ile Met Val Thr Trp Cys His Arg Pro Thr Asp Lys Thr
                165                 170                 175

Pro Leu Thr Ala Asp Glu Lys Lys His Leu Glu Asp Ile Tyr Arg Val
            180                 185                 190

Tyr Cys Leu Pro Tyr Val Ile Ser Leu Pro Glu Tyr Glu Ala Ile Ala
            195                 200                 205

Arg Gln Leu Pro Leu Asn Asn Ile Arg Thr Ala Asp Trp Ser Gln Ser
210                 215                 220

Val Ala Gln Phe Trp Asn Ile Val Ile Asp Ser Ala Phe Thr Pro Gln
225                 230                 235                 240

Ala Ile Phe Gly Leu Leu Arg Ala Gly Trp Thr Thr Ile Gln Gly Ala
                245                 250                 255

Leu Ser Leu Gly Leu Met Arg Arg Gly Tyr Glu Arg Gly Leu Ile Arg
                260                 265                 270

Phe Gly Leu Leu Cys Gly Asp Lys
            275                 280

<210> SEQ ID NO 41
<211> LENGTH: 317
<212> TYPE: PRT
<213> ORGANISM: Synechocystis PCC6803

<400> SEQUENCE: 41

Met Val Tyr His Val Arg Pro Lys His Ala Leu Phe Leu Ala Phe Tyr
1               5                   10                  15

Cys Tyr Phe Ser Leu Leu Thr Met Ala Ser Ala Thr Ile Ala Ser Ala
                20                  25                  30

Asp Leu Tyr Glu Lys Ile Lys Asn Phe Tyr Asp Asp Ser Ser Gly Leu
            35                  40                  45

Trp Glu Asp Val Trp Gly Glu His Met His His Gly Tyr Tyr Gly Pro
50                  55                  60

His Gly Thr Tyr Arg Ile Asp Arg Arg Gln Ala Gln Ile Asp Leu Ile
65                  70                  75                  80

Lys Glu Leu Leu Ala Trp Ala Val Pro Gln Asn Ser Ala Lys Pro Arg
                85                  90                  95
```

```
Lys Ile Leu Asp Leu Gly Cys Gly Ile Gly Gly Ser Ser Leu Tyr Leu
            100                 105                 110

Ala Gln Gln His Gln Ala Glu Val Met Gly Ala Ser Leu Ser Pro Val
        115                 120                 125

Gln Val Glu Arg Ala Gly Glu Arg Ala Arg Ala Leu Gly Leu Gly Ser
    130                 135                 140

Thr Cys Gln Phe Gln Val Ala Asn Ala Leu Asp Leu Pro Phe Ala Ser
145                 150                 155                 160

Asp Ser Phe Asp Trp Val Trp Ser Leu Glu Ser Gly Glu His Met Pro
                165                 170                 175

Asn Lys Ala Gln Phe Leu Gln Glu Ala Trp Arg Val Leu Lys Pro Gly
            180                 185                 190

Gly Arg Leu Ile Leu Ala Thr Trp Cys His Arg Pro Ile Asp Pro Gly
        195                 200                 205

Asn Gly Pro Leu Thr Ala Asp Glu Arg Arg His Leu Gln Ala Ile Tyr
    210                 215                 220

Asp Val Tyr Cys Leu Pro Tyr Val Val Ser Leu Pro Asp Tyr Glu Ala
225                 230                 235                 240

Ile Ala Arg Glu Cys Gly Phe Gly Glu Ile Lys Thr Ala Asp Trp Ser
                245                 250                 255

Val Ala Val Ala Pro Phe Trp Asp Arg Val Ile Glu Ser Ala Phe Asp
            260                 265                 270

Pro Arg Val Leu Trp Ala Leu Gly Gln Ala Gly Pro Lys Ile Ile Asn
        275                 280                 285

Ala Ala Leu Cys Leu Arg Leu Met Lys Trp Gly Tyr Glu Arg Gly Leu
    290                 295                 300

Val Arg Phe Gly Leu Leu Thr Gly Ile Lys Pro Leu Val
305                 310                 315
```

<210> SEQ ID NO 42
<211> LENGTH: 957
<212> TYPE: DNA
<213> ORGANISM: Synechocystis PCC6803

<400> SEQUENCE: 42

```
atgcccgagt atttgcttct gcccgctggc ctaatttccc tctccctggc gatcgccgct    60
ggactgtatc tcctaactgc ccggggctat cagtcatcgg attccgtggc caacgcctac   120
gaccaatgga cagaggacgg catttttggaa tattactggg cgaccatat ccacctcggc   180
cattatggcg atccgccagt ggccaaggat ttcatccaat cgaaaattga ttttgtccat   240
gccatggccc agtggggcgg attagataca cttccccccg cacaacggtt attggatgtg   300
ggttgcggca ttggcggtag cagtcgcatt ctcgccaaag attatggttt taacgttacc   360
ggcatcacca ttagtcccca acaggtgaaa cgggcgacgg aattaactcc tcccgatgtg   420
acggccaagt tgcggtgga cgatgctatg gctttgtctt ttcctgacgg tagtttcgac   480
gtagtttggt cggtggaagc agggccccac atgcctgaca agctgtgtt tgccaaggaa   540
ttactgcggg tcgtgaaacc aggggggcatt ctggtggtgg cggattggaa tcaacgggac   600
gatcgccaag tgcccctcaa cttctgggaa aaaccagtga tgcgacaact gttggatcaa   660
tggtcccacc ctgcctttgc cagcattgaa ggttttgcgg aaaatttgga agccacgggt   720
ttggtggagg gccaggtgac tactgctgat tggactgtac cgaccctccc cgcttggttg   780
gataccattt ggcagggcat tatccggccc cagggctggt acaatacgg cattcgtggg   840
```

| | | |
|---|---|---|
| tttatcaaat ccgtgcggga agtaccgact attttattga tgcgccttgc ctttggggta | 900 | |
| ggactttgtc gcttcggtat gttcaaagca gtgcgaaaaa acgccactca agcttaa | 957 | |

<210> SEQ ID NO 43
<211> LENGTH: 993
<212> TYPE: DNA
<213> ORGANISM: Anabaena sp.

<400> SEQUENCE: 43

| | |
|---|---|
| atgagttggt tgttttctac actggtatttt tcttaacgc tattgacagc agggatcgcg | 60 |
| ttatatctca ttactgctag acgttatcaa tcatctaact ccgtagccaa ttcctacgac | 120 |
| cagtggactg aagacggtat tttagagttt tactggggcg aacatatcca tttaggtcat | 180 |
| tatggttcgc cacctcaaag aaaggatttt ctggtggcta aatctgatttt tgtccatgaa | 240 |
| atggtgcgtt ggggtggttt ggataaacta cccctggta ctaccttgtt agatgttggt | 300 |
| tgtggaattg ggggtagtag tcgcattttg gcacgggatt atggatttgc cgttacaggt | 360 |
| atcaccatca gccccaaca agtccaacgc gctcaagagt taacaccaca ggaactgaat | 420 |
| gcacagtttt tggtggatga tgcaatggcg cttttccttcc cagataatag ttttgatgta | 480 |
| gtttggtcaa ttgaagctgg cccacatatg ccagataaag ccattttgc caagaattg | 540 |
| atgcgggtac taaagcctgg tggaatcatg gttttagccg actggaatca gcgagacgat | 600 |
| cgccaaaaac ccctcaattt tgggagaaa ccagtaatgc agcaactact agatcagtgg | 660 |
| tctcatccag cttttccag catcgaaggc ttttctgagc ttttggcagc gacgggatta | 720 |
| gtagaagggg aggtaatcac cgcagactgg acgaaacaaa cactcccctc ttggcttgat | 780 |
| tctatctggc aaggaatagt tagaccagaa ggattagtgc gttttggtct atctggtttc | 840 |
| attaaatctc tgcgagaagt gcctacccta ctactgatga ggctggcatt cggtacagga | 900 |
| ctctgtagat ttgggatgtt ccgcgcttta cgagctgaca ctgtaagatc atcagcagaa | 960 |
| cagacatctg cgatcaaggt tgctcaaaag taa | 993 |

<210> SEQ ID NO 44
<211> LENGTH: 930
<212> TYPE: DNA
<213> ORGANISM: Synechococcus sp.

<400> SEQUENCE: 44

| | |
|---|---|
| atgttggctg gcctgcttct cctgaccggg gctgccggtg ccacggccct gctgatctgg | 60 |
| ttgcagcgtg atcgccgcta ccactcctca gacagcgtcg ccgcggccta cgacgcctgg | 120 |
| accgatgacc aactgctgga acggctctgg ggagaccatg tccacctggg gcattacgga | 180 |
| aacccgccag gttctgtcga cttccgccag gccaaggagg ctttttgtgca cgagctggtg | 240 |
| cgctggagcg gctcgacca actacctcga ggcagtcggg tgttggatgt gggttgcggc | 300 |
| atcggcggca gtgcccggat cctggccagg gattacggct tggacgtgct cggggtgagc | 360 |
| atcagcccag cccagatccg ccgcgccaca gaactcaccc ccgccggcct cagctgtcgc | 420 |
| tttgaagtga tggacgccct taaccttcaa cttcccgatc ggcaattcga tgcggtgtgg | 480 |
| acggtggagg cggggcccca catgccagac aagcagcgtt tcgctgatga gttgctgcgg | 540 |
| gtactccggc ccggggggctg cttagccgcc gctgattgga accgccgcgc ccccaaggat | 600 |
| ggcgccatga acagcaccga acgctgggtg atgcggcagt tgttgaatca atgggcgcat | 660 |
| ccggaattcg ccagcatctc cggcttccgg gccaacctcg aagccagccc tcaccagcgg | 720 |
| ggcctgatca gtaccggcga ctggactctg gccaccctttc cctcctggtt tgattcgatc | 780 |

```
gccgaaggcc tccgtcgccc ctgggctgtc ctgggccttg gtcccaaagc agtgcttcaa      840
ggcctgcgag agaccccgac gctgctgttg atgcattggg cctttgccac agggttgatg      900
cagttcggcg tctttcgcct cagccgctga                                       930
```

<210> SEQ ID NO 45
<211> LENGTH: 936
<212> TYPE: DNA
<213> ORGANISM: Prochlorococcus marinus

<400> SEQUENCE: 45

```
atgtccattt ttttaatatc ttcacttgtt atattttttaa ctttattatt ttcttctcta     60
atactttgga gaattaatac tagaaaatat atttcttcga gaactgtagc tacagcatat     120
gattcctgga ctcaagataa attactagaa agattatggg gagaacatat acatctaggt    180
ttctatcctc taaataaaaa tattgatttt agagaggcta agttcaatt tgtacatgag     240 ttagtaagtt ggagtggttt agataaatta ccaagaggtt ctaggatttt agatgtcggt     300
tgcggaatag gtggaagttc tagaattctc gccaattatt atggatttaa tgtcactgga    360
ataactatta gtccagctca agtaaaaaga gcaaagaaac ttactcctta tgaatgtaaa    420
tgcaacttca agttatgga tgctttggat ttgaaatttg aagagggaat atttgatggt    480
gtttggagtg ttgaggcagg agcccatatg aataataaaa ctaaatttgc agatcaaatg   540
ttaagaactt taagacctgg aggatattta gcattggctg attggaattc aagagattta   600
caaaagcaac ccccatccat gattgaaaaa ataatcttaa acaattact tgaacagtgg    660 gtacatccta aatttattag tatcaatgaa ttcagtagta ttcttataaa taacaaaaat    720
agttcaggtc aagttatatc ctctaattgg aattctttta caaatccctc ttggtttgat    780
tcaatatttg aaggaatgag aagacctaat tcaattttat cccttggtcc aggagcaatt   840
ataaagtcta tcagagagat acctacaata ctttttaatgg attgggcctt taaaaaaggt   900
ttaatggaat ttggagttta taaatgtaga ggttaa                              936
```

<210> SEQ ID NO 46
<211> LENGTH: 318
<212> TYPE: PRT
<213> ORGANISM: Synechocystis PCC6803

<400> SEQUENCE: 46

```
Met Pro Glu Tyr Leu Leu Pro Ala Gly Leu Ile Ser Leu Ser Leu
1               5                   10                  15

Ala Ile Ala Ala Gly Leu Tyr Leu Leu Thr Ala Arg Gly Tyr Gln Ser
            20                  25                  30

Ser Asp Ser Val Ala Asn Ala Tyr Asp Gln Trp Thr Glu Asp Gly Ile
        35                  40                  45

Leu Glu Tyr Tyr Trp Gly Asp His Ile His Leu Gly His Tyr Gly Asp
    50                  55                  60

Pro Pro Val Ala Lys Asp Phe Ile Gln Ser Lys Ile Asp Phe Val His
65                  70                  75                  80

Ala Met Ala Gln Trp Gly Gly Leu Asp Thr Leu Pro Pro Gly Thr Thr
                85                  90                  95

Val Leu Asp Val Gly Cys Gly Ile Gly Gly Ser Ser Arg Ile Leu Ala
            100                 105                 110

Lys Asp Tyr Gly Phe Asn Val Thr Gly Ile Thr Ile Ser Pro Gln Gln
        115                 120                 125
```

```
Val Lys Arg Ala Thr Glu Leu Thr Pro Pro Asp Val Thr Ala Lys Phe
    130                 135                 140

Ala Val Asp Asp Ala Met Ala Leu Ser Phe Pro Asp Gly Ser Phe Asp
145                 150                 155                 160

Val Val Trp Ser Val Glu Ala Gly Pro His Met Pro Asp Lys Ala Val
                165                 170                 175

Phe Ala Lys Glu Leu Leu Arg Val Val Lys Pro Gly Gly Ile Leu Val
            180                 185                 190

Val Ala Asp Trp Asn Gln Arg Asp Asp Arg Gln Val Pro Leu Asn Phe
        195                 200                 205

Trp Glu Lys Pro Val Met Arg Gln Leu Leu Asp Gln Trp Ser His Pro
    210                 215                 220

Ala Phe Ala Ser Ile Glu Gly Phe Ala Glu Asn Leu Glu Ala Thr Gly
225                 230                 235                 240

Leu Val Glu Gly Gln Val Thr Thr Ala Asp Trp Thr Val Pro Thr Leu
                245                 250                 255

Pro Ala Trp Leu Asp Thr Ile Trp Gln Gly Ile Ile Arg Pro Gln Gly
            260                 265                 270

Trp Leu Gln Tyr Gly Ile Arg Gly Phe Ile Lys Ser Val Arg Glu Val
        275                 280                 285

Pro Thr Ile Leu Leu Met Arg Leu Ala Phe Gly Val Gly Leu Cys Arg
    290                 295                 300

Phe Gly Met Phe Lys Ala Val Arg Lys Asn Ala Thr Gln Ala
305                 310                 315

<210> SEQ ID NO 47
<211> LENGTH: 330
<212> TYPE: PRT
<213> ORGANISM: Anabaena sp.

<400> SEQUENCE: 47

Met Ser Trp Leu Phe Ser Thr Leu Val Phe Leu Thr Leu Leu Thr
1               5                   10                  15

Ala Gly Ile Ala Leu Tyr Leu Ile Thr Ala Arg Arg Tyr Gln Ser Ser
            20                  25                  30

Asn Ser Val Ala Asn Ser Tyr Asp Gln Trp Thr Glu Asp Gly Ile Leu
        35                  40                  45

Glu Phe Tyr Trp Gly Glu His Ile His Leu Gly His Tyr Gly Ser Pro
    50                  55                  60

Pro Gln Arg Lys Asp Phe Leu Val Ala Lys Ser Asp Phe Val His Glu
65                  70                  75                  80

Met Val Arg Trp Gly Gly Leu Asp Lys Leu Pro Pro Gly Thr Thr Leu
                85                  90                  95

Leu Asp Val Gly Cys Gly Ile Gly Gly Ser Ser Arg Ile Leu Ala Arg
            100                 105                 110

Asp Tyr Gly Phe Ala Val Thr Gly Ile Thr Ile Ser Pro Gln Gln Val
        115                 120                 125

Gln Arg Ala Gln Glu Leu Thr Pro Gln Glu Leu Asn Ala Gln Phe Leu
    130                 135                 140

Val Asp Asp Ala Met Ala Leu Ser Phe Pro Asp Asn Ser Phe Asp Val
145                 150                 155                 160

Val Trp Ser Ile Glu Ala Gly Pro His Met Pro Asp Lys Ala Ile Phe
                165                 170                 175

Ala Lys Glu Leu Met Arg Val Leu Lys Pro Gly Gly Ile Met Val Leu
            180                 185                 190
```

```
Ala Asp Trp Asn Gln Arg Asp Asp Arg Gln Lys Pro Leu Asn Phe Trp
            195                 200                 205

Glu Lys Pro Val Met Gln Gln Leu Leu Asp Gln Trp Ser His Pro Ala
    210                 215                 220

Phe Ser Ser Ile Glu Gly Phe Ser Glu Leu Leu Ala Ala Thr Gly Leu
225                 230                 235                 240

Val Glu Gly Glu Val Ile Thr Ala Asp Trp Thr Lys Gln Thr Leu Pro
                245                 250                 255

Ser Trp Leu Asp Ser Ile Trp Gln Gly Ile Val Arg Pro Glu Gly Leu
            260                 265                 270

Val Arg Phe Gly Leu Ser Gly Phe Ile Lys Ser Leu Arg Glu Val Pro
        275                 280                 285

Thr Leu Leu Met Arg Leu Ala Phe Gly Thr Gly Leu Cys Arg Phe
    290                 295                 300

Gly Met Phe Arg Ala Leu Arg Ala Asp Thr Val Arg Ser Ser Ala Glu
305                 310                 315                 320

Gln Thr Ser Ala Ile Lys Val Ala Gln Lys
                325                 330

<210> SEQ ID NO 48
<211> LENGTH: 309
<212> TYPE: PRT
<213> ORGANISM: Synechococcus sp.

<400> SEQUENCE: 48

Met Leu Ala Gly Leu Leu Leu Thr Gly Ala Ala Gly Ala Thr Ala
1               5                   10                  15

Leu Leu Ile Trp Leu Gln Arg Asp Arg Arg Tyr His Ser Ser Asp Ser
            20                  25                  30

Val Ala Ala Ala Tyr Asp Ala Trp Thr Asp Asp Gln Leu Leu Glu Arg
        35                  40                  45

Leu Trp Gly Asp His Val His Leu Gly His Tyr Gly Asn Pro Pro Gly
    50                  55                  60

Ser Val Asp Phe Arg Gln Ala Lys Glu Ala Phe Val His Glu Leu Val
65                  70                  75                  80

Arg Trp Ser Gly Leu Asp Gln Leu Pro Arg Gly Ser Arg Val Leu Asp
                85                  90                  95

Val Gly Cys Gly Ile Gly Gly Ser Ala Arg Ile Leu Ala Arg Asp Tyr
            100                 105                 110

Gly Leu Asp Val Leu Gly Val Ser Ile Ser Pro Ala Gln Ile Arg Arg
        115                 120                 125

Ala Thr Glu Leu Thr Pro Ala Gly Leu Ser Cys Arg Phe Glu Val Met
    130                 135                 140

Asp Ala Leu Asn Leu Gln Leu Pro Asp Arg Gln Phe Asp Ala Val Trp
145                 150                 155                 160

Thr Val Glu Ala Gly Pro His Met Pro Asp Lys Gln Arg Phe Ala Asp
                165                 170                 175

Glu Leu Leu Arg Val Leu Arg Pro Gly Gly Cys Leu Ala Ala Ala Asp
            180                 185                 190

Trp Asn Arg Arg Ala Pro Lys Asp Gly Ala Met Asn Ser Thr Glu Arg
        195                 200                 205

Trp Val Met Arg Gln Leu Leu Asn Gln Trp Ala His Pro Glu Phe Ala
    210                 215                 220

Ser Ile Ser Gly Phe Arg Ala Asn Leu Glu Ala Ser Pro His Gln Arg
```

-continued

```
            225                 230                 235                 240
Gly Leu Ile Ser Thr Gly Asp Trp Thr Leu Ala Thr Leu Pro Ser Trp
                245                 250                 255

Phe Asp Ser Ile Ala Glu Gly Leu Arg Arg Pro Trp Ala Val Leu Gly
                260                 265                 270

Leu Gly Pro Lys Ala Val Leu Gln Gly Leu Arg Glu Thr Pro Thr Leu
            275                 280                 285

Leu Leu Met His Trp Ala Phe Ala Thr Gly Leu Met Gln Phe Gly Val
            290                 295                 300

Phe Arg Leu Ser Arg
305

<210> SEQ ID NO 49
<211> LENGTH: 311
<212> TYPE: PRT
<213> ORGANISM: Prochlorococcus marinus

<400> SEQUENCE: 49

Met Ser Ile Phe Leu Ile Ser Ser Leu Val Ile Phe Leu Thr Leu Leu
1               5                   10                  15

Phe Ser Ser Leu Ile Leu Trp Arg Ile Asn Thr Arg Lys Tyr Ile Ser
                20                  25                  30

Ser Arg Thr Val Ala Thr Ala Tyr Asp Ser Trp Thr Gln Asp Lys Leu
            35                  40                  45

Leu Glu Arg Leu Trp Gly Glu His Ile His Leu Gly Phe Tyr Pro Leu
        50                  55                  60

Asn Lys Asn Ile Asp Phe Arg Glu Ala Lys Val Gln Phe Val His Glu
65                  70                  75                  80

Leu Val Ser Trp Ser Gly Leu Asp Lys Leu Pro Arg Gly Ser Arg Ile
                85                  90                  95

Leu Asp Val Gly Cys Gly Ile Gly Gly Ser Ser Arg Ile Leu Ala Asn
            100                 105                 110

Tyr Tyr Gly Phe Asn Val Thr Gly Ile Thr Ile Ser Pro Ala Gln Val
        115                 120                 125

Lys Arg Ala Lys Glu Leu Thr Pro Tyr Glu Cys Lys Cys Asn Phe Lys
130                 135                 140

Val Met Asp Ala Leu Asp Leu Lys Phe Glu Gly Gly Ile Phe Asp Gly
145                 150                 155                 160

Val Trp Ser Val Glu Ala Gly Ala His Met Asn Asn Lys Thr Lys Phe
                165                 170                 175

Ala Asp Gln Met Leu Arg Thr Leu Arg Pro Gly Gly Tyr Leu Ala Leu
            180                 185                 190

Ala Asp Trp Asn Ser Arg Asp Leu Gln Lys Gln Pro Pro Ser Met Ile
        195                 200                 205

Glu Lys Ile Ile Leu Lys Gln Leu Leu Glu Gln Trp Val His Pro Lys
    210                 215                 220

Phe Ile Ser Ile Asn Glu Phe Ser Ser Ile Leu Ile Asn Asn Lys Asn
225                 230                 235                 240

Ser Ser Gly Gln Val Ile Ser Ser Asn Trp Asn Ser Phe Thr Asn Pro
                245                 250                 255

Ser Trp Phe Asp Ser Ile Phe Glu Gly Met Arg Arg Pro Asn Ser Ile
            260                 265                 270

Leu Ser Leu Gly Pro Gly Ala Ile Ile Lys Ser Ile Arg Glu Ile Pro
        275                 280                 285
```

```
Thr Ile Leu Leu Met Asp Trp Ala Phe Lys Lys Gly Leu Met Glu Phe
    290                 295                 300
Gly Val Tyr Lys Cys Arg Gly
305                 310

<210> SEQ ID NO 50
<211> LENGTH: 6864
<212> TYPE: DNA
<213> ORGANISM: Oryza sativa

<400> SEQUENCE: 50
cgaggccccc gtccagctgc catgtggcgg ggacagcaag cgggaagggg acccaggctg      60
aaccgctatc aatgcgcgcg gcgccccaac tgcccctcgc cgcattaaat gcggtagggg     120
cagacatgag gtgccgcccg actgacgcac atcagtcagg agtgaccggt ctgtgaccgg     180
cctatcgccg gtcacgtctg actggacggg cggccgtgcc ccacgtcgc ctctgtcccc     240 ggcggagtgg aggtaggtat gacccgtccc atcggagcgt gattcggagc tccctccacg     300
agaaggacgt ccaccacaag tcttcaccca tttatgaggg aatgacaggg ctgtcccccg     360
tgtcaggcag gggcgacga tgggtcccgc ttaaggacga gcgtggcttt ggcttccggg     420
cgaaggcacg aattgtgatc tggtcaaggt agggtgggtc cccaccctgt agaagagtag     480
gtagaggcgg tgcatgtggt ttccccttga gctataaaag gaggacctta cccaccgaga     540
aagacgacga ctctcaggaa gcctgagctc taggagaaga gaagcgagaa cgctctccgg     600
agtttaggaa cccttgtaac tctcaacctt aaatcccaca cacagaagta gggtattacg     660
ctccatcgcg gcccgaacct gtataattct cttgcccata cgcgactagc aagacttagg     720
gcggatacgc gatctctaga ggcgagcccct tttccctagc cgaactcaca aaaggggatc     780
tcacgatctc ccgatagaga ggattactcc tcgacaatgt catttaata tatttgaata     840 atataatgag aaaacatata tgctattata tgagagaaaa tataatgatg ctagccgcgc     900
aatctgcacg ggccatcatg ctagttttaa taataagaaa atagtacgag aaggttagta     960
aaaagtactg aatggataaa acttctcgat ttacatagca aatactagtt aaagggatat    1020
aagtgaactt attttaagat aactagcaca atatcaatgc gttgtaatgg atattataaa    1080
agaaaaaagg taaaatttac aagtttttag cacaataaat ccatttggca tataatgcct    1140
acctggtgtt aagatttaat gacacaatac gatcaatgta ttgataggca taaacttcga    1200
gtcaactaaa agagcttatt taaggggtgt caaacctatg aacccatacg tcacgaaggg    1260
ggtagtgctg gcaaattcaa tgcccctacc attgctctct tttaaaatgg tatagactta    1320
tactatcatc atcacattct agtatgatgt tggtttattt tggtgtggtg tcgcgtgttc    1380
tctaaacgca ctgtgtcgtg cttcatccat cttaaaataa tcttatcttt tacctatttc    1440
acacgtacca ataaaaatct ctaatttatt aaatgctaat ctcttcgtct caaagtgaac    1500
agaagaatat actagtaata caattatttc tcttctaatc cgctctcagt agatttaccc    1560
cgtacttaca gccctctaca atcctcccta aacacagagt gctatagcac tgtgcagtgc    1620
agtgcctcat tcgtctcaaa ataatcctat cttttaccta tttcacgtac caataaaaat    1680
atctaattta ttaaatatta atatctccat ctcaaaataa acagaaaaat atactagtaa    1740
tacaattact acttatgttc caatccgctc tcagtcgact taccccgcac ttggcagtct    1800
ggcctctacc atccttgcgc cgtcgcgcgc tcgtgccggg gcttggctgc gagcgaataa    1860
aaagaaaaga aaacgtcaag gcctcagacg ccagagcgct acaaaatggc ccacgccgcc    1920
gcggccacgg gcgcactggc accgctgcat ccactgctcc gctgcacgag ccgtcatctc    1980
```

-continued

```
tgcgcctcgg cttcccctcg cgccggcctc tgcctccacc accaccgccg ccgccgccgc    2040
agcagccgga ggacgaaact cgccgtgcgc gcgatggcac cgacgttgtc ctcgtcgtcg    2100
acggcggcgg cagctccccc ggggctgaag gagggcatcg cggggctcta cgacgagtcg    2160
tccggcgtgt gggagagcat ctggggcgag cacatgcacc acggcttcta cgacgccggc    2220
gaggccgcct ccatgtccga ccaccgccgc gcccagatcc gcatgatcga ggaatccctc    2280
gccttcgccg ccgtccccgg tacgtattgc ccgccccact ccgccccccc ggaatctacg    2340
cttgcctggc tgcgcggctg agcccatcca gctttctgt ttggctgcaa gccgctggcc    2400
atagagaatc ccggccattt ttctgctgct taacagttgt ttctgcctac ctaacccctg    2460
ctcgcctcac ggctccagca cgtacggcaa aatcatgaga tattcagggg gttttctttt    2520 tcttttctt tttggagacg ataaactcac catcttgatt ggtgtgggtt taattttgta    2580
cagtaccact attttgttcc attcattcat tcacttggta ctcgtactac gaaaggtgtg    2640
gacctgtgac agttttggca cgcactattc ccaacagggg ttttgcagtc ctatctcaca    2700
cggtagaccg tttgagcatt tagggcccctt taaatcata gaataaaaa aacaaaggaa     2760 taagaaaagc acaggattct aacaggaata caattgtaaa acagaggatt gcaaaacaca    2820
ggaaaaatac aggaatgacc gtttgattgg accacgagaa aatgtagga atcatatgag     2880 agagatagac tcaggaaatg ttccaagagg ttagacttct tgctaacttt cctccaaaat    2940
gtgcatagga ttacccattc cataggaatt ttaaaggatt gtatatgatt caatcctttg    3000
tttcaaagac cttcatatga tttttttttc cataggattg aaatcctcta aaatttctac    3060 attttccta caaatcaaag gggcccttaa gttcgttagc ttttctgttt gaaacatgtt    3120
ttgcacggat tatttagttg attaacacga taaatcaata tttaagaaa taaactttac     3180 acataattta gagtaagtaa tctaacaatg cagtagaagt ttttttttt ttgagaaatc     3240 gtatttaat aagagtggag caaaaacctt tggcaaaaat ttggagaaaa gaagctcaaa     3300
aaacaaaatc cgtggcgaac cggcgattgt ggtattagta ctgcaaagaa tacgaaaaag    3360
accaaaattg ttgcctgaat tcagccgtag tttacccttg gagtacgtac atggttcaat    3420
taatttgctc tagctgataa ttgtgcttga tgcctgcaga tgatgcggag aagaaaccca    3480
aaagtgtagt tgatgttggc tgtggcattg gtggtagctc aagatacttg gcgaacaaat    3540
acggagcgca atgctacggc atcacgttga gtccggtgca ggctgaaaga ggaaatgccc    3600
tcgcggcaga gcaagggtta tcagacaagg tgcgtattac tactgtttat tctgttctaa    3660
aaaaaattct actgtttatt cgtatcggga tttaatctcg ctgtagctag tcatagttac    3720
atttgacaat atcagagggt ttaagctctg attactcact gctggtgtga cgacaatctg    3780
tttaagcagg tctcctttca agttggtgat gcattggagc agccttttcc tgatgggcag    3840
tttgatcttg tctggtccat ggagagtggc gagcacatgc cagacaaacg gcaggtaaga    3900
tactcctctt ttttatcctt acagaaaaaa agaaaatggg aaaatgtaat ccctccgttt    3960
caggttataa gactttctag cattgccacg ttcatataga tgttaatgaa tctaggcaca    4020
catatatgtt tagattcatt aacatatata tgaatatggg taatactaga aagttttata    4080
atatgaaacg gaagaaatat cttggatcgg agaacgtttc aaatctagcc atcaggttac    4140
ggtggcatgg gttaccatgc atcggttgga atcttggttg agcaatcgca tctgtcgatt    4200
ttaatttgcc gggttgcgaa aatgtagaaa aacgagagga tattaatgaa acaattctgc    4260
tatttattaa aatcagatgt caatcaactc atcttgagag gagtctgtat tggatgttac    4320
```

```
tgaatagttt ttggatcttt tcactctctt tttttagcta agagttctta cctgagtctt   4380
ttacagtttg taagcgagct ggcacgcgtc gcagctcctg gggcgagaat aatcattgtg   4440
acctggtgcc ataggaacct cgagccatcc gaagagtccc tgaaacctga tgagctgaat   4500
ctcctgaaaa ggatatgcga tgcatattat ctcccagact ggtgctctcc ttctgattat   4560
gtcaaaattg ccgagtcact gtctcttgag gtaaaaaaac ttttcatgct ctgaactcgt   4620
aagtgaattt aagttacaac ttgatatggt ttgcacatca acttgcgtac catgccgatt   4680
tgcattctcg caagagattc ttgcatgtgt gtgacatgtg aaatgtgcca ggatataagg   4740
acagctgatt ggtcagagaa cgtcgcccca ttctggcctg cggttataaa atcagcattg   4800
acatggaaag gtttaacttc tctgctaaga agtggtatga tcttgccatc ttcctttcct   4860
ccacttatga ttatcggcaa acagatgttg acaaaactg aactaatttg tgttggcttc   4920
gtcttaattt gaagggtgga agacgataag aggtgcaatg gtgatgcctc tgatgatcga   4980
aggatacaag aaagggctca tcaaattcac catcatcacc tgtcgcaagc ccgaaacaac   5040
gcagtagtac cctagtagtg aaattacgct cctgctatct tctccatcac gaataatgca   5100
aattctgacg agttagcacc tactgatggc gatttgttga tttggggaac agccagtgca   5160
ctgttaccac gtcattgatt ttgtactcgt cagacttaaa aaaaaaatat ccatgaatgt   5220
gcactccaaa tacgtcaaga aattcttaga tcttcagacc aactcgtcag ctagaggtgg   5280
ctaaaaagct catttagctc cctcggtgca agattgcttt gattgaccta gttttcttct   5340
taaaactaaa actattttac tttggatgga agttagtttc actctgtctg ggctcggctc   5400
attagctcgt taagaaaaac agtttcaaat gataaaataa cataataaat caatttcgaa   5460
gaaaaatgga gtagataaaa agcacagccg ggctcaaccg agggcttatt tagattgaag   5520
gattttcatg ggaattttgg aggactcaaa tccttgataa aatttctaca agcccctttg   5580
gaacataaca ggatcgctat aaatcctatg cctcccaatt tcataggaaa ataaacatga   5640
gctcaaactc atgtttttat ttcccttga gaaatctaat gcactctctc cctatctctc   5700 tcccctttgag aagtctaatg cactcgctcc ctatctctat agtttctctc ctttgaaatt   5760
tctgtgttta cttgctacta atcatccaaa ggcaactact ctatagtatt catgtatttt   5820
aaatttctgt aggattttat agagcgtggc atcttatttc tatgtttttt ttatcactgt   5880 gttttttaaaa ttttgcgctc caaaggcgca ctagcagtgc agcagcgtca ctatgtcagc   5940
tcgacgccga accgccatcc ttctccgatg gcgcggcgcg ctcaccacgc caccgcgcc   6000 gcacggtgaa ccaaagctgg cacggcacgg gcaggcacca gcacagtcgg gcaaccgacg   6060
gtctgccgcg cgccgcgtgg tgctccggtc acggagacgt cggcaatcgg cgtccatcga   6120
tgttgccgtc tcactctcgt cgtccttcag gatgacccac ttgcccgctc cataattcac   6180
aaaaatagcc aagcaaaaga acggctccat ctggtacgaa aatgacaggg ccctggttaa   6240
gaaatcaacg acgttgcgaa gaaagcttgg tctctgacga gagaatggca ggaaacgata   6300
aggtagtcag gtagagctag aactgtcagt ttcacacagg atcattcact ttctctccag   6360
cagctcaaca aaggctcgcc aaatcacatc aacaagaatg cttattgtat aatcatccct   6420
cgtgttcacc aataaatctg ctgcggctta ttggtattgt atgactaaga acagggttcg   6480
tggctatagc tgacatccgt aaatttgtaa tccatcttgg aattaacaaa aagtagcac   6540 acaatttgag cccaatctct gcttaatttg tcggcaggac gtccaacttt tatcagttct   6600
tcacggtggt tacatgccta agaagcatct ggatcacttc aggggagaca tttgcagcct   6660
gctccttcag ttgcgcaatt ttcgtgtcag tttcttgctc aagccgtttt acgtttgcac   6720
```

```
cagaatcacc gctactctgg aaagaaacag gaaggttagc ggcaatagct cttctaattc    6780
cacgaactat acaagattga aagatgcata cctccgcaac cttcctctgg aactcagctt    6840
ccatctgagc tgatgaacta ctgt                                           6864
```

<210> SEQ ID NO 51
<211> LENGTH: 32
<212> TYPE: DNA
<213> ORGANISM: Artificial Sequence
<220> FEATURE:
<223> OTHER INFORMATION: Synthetic Primer

<400> SEQUENCE: 51

```
gcggccgcac tttcttgttc cgccaacctc tc                                  32
```

<210> SEQ ID NO 52
<211> LENGTH: 30
<212> TYPE: DNA
<213> ORGANISM: Artificial Sequence
<220> FEATURE:
<223> OTHER INFORMATION: Synthetic Primer

<400> SEQUENCE: 52

```
cctgcaggcg ctgaaaagca cttaaaagac                                     30
```

<210> SEQ ID NO 53
<211> LENGTH: 64
<212> TYPE: DNA
<213> ORGANISM: Artificial Sequence
<220> FEATURE:
<223> OTHER INFORMATION: Synthetic Primer

<400> SEQUENCE: 53

```
ggggacaagt ttgtacaaaa aagcaggctg cggccgcaca atgaaagcga cactcgcacc    60
accc                                                                 64
```

<210> SEQ ID NO 54
<211> LENGTH: 59
<212> TYPE: DNA
<213> ORGANISM: Artificial Sequence
<220> FEATURE:
<223> OTHER INFORMATION: Synthetic Primer

<400> SEQUENCE: 54

```
ggggaccact ttgtacaaga aagctgggtc ctgcaggtta tagaggcttc tggcaagtg     59
```

<210> SEQ ID NO 55
<211> LENGTH: 63
<212> TYPE: DNA
<213> ORGANISM: Artificial Sequence
<220> FEATURE:
<223> OTHER INFORMATION: Synthetic Primer

<400> SEQUENCE: 55

```
ggggacaagt ttgtacaaaa aagcaggctg cggccgcaca atgccgataa catctatttc    60
cgc                                                                  63
```

<210> SEQ ID NO 56
<211> LENGTH: 59
<212> TYPE: DNA
<213> ORGANISM: Artificial Sequence
<220> FEATURE:
<223> OTHER INFORMATION: Synthetic Primer

```
<400> SEQUENCE: 56 gggggaccact tgtacaaga aagctgggtc ctgcaggcta ttcgggctta cggcatgtg      59

<210> SEQ ID NO 57
<211> LENGTH: 62
<212> TYPE: DNA
<213> ORGANISM: Artificial Sequence
<220> FEATURE:
<223> OTHER INFORMATION: Synthetic Primer

<400> SEQUENCE: 57
ggggacaagt tgtacaaaa aagcaggctg cggccgcaca atggctgccg cgttacaatt      60
ac                                                                    62

<210> SEQ ID NO 58
<211> LENGTH: 57
<212> TYPE: DNA
<213> ORGANISM: Artificial Sequence
<220> FEATURE:
<223> OTHER INFORMATION: Synthetic Primer

<400> SEQUENCE: 58
ggggaccact tgtacaaga aagctgggtc ctgcaggcta ctcagctggc ttccggc         57

<210> SEQ ID NO 59
<211> LENGTH: 73
<212> TYPE: DNA
<213> ORGANISM: Artificial Sequence
<220> FEATURE:
<223> OTHER INFORMATION: Synthetic Primer

<400> SEQUENCE: 59
ggggacaagt tgtacaaaa aagcaggctt agaaggagat agaaccatgg tggctgtgac      60
ggctgctgct acc                                                        73

<210> SEQ ID NO 60
<211> LENGTH: 59
<212> TYPE: DNA
<213> ORGANISM: Artificial Sequence
<220> FEATURE:
<223> OTHER INFORMATION: Synthetic Primer

<400> SEQUENCE: 60
ggggaccact tgtacaaga aagctgggtc ctgcaggtta gagaggcttc tggcaagtg       59

<210> SEQ ID NO 61
<211> LENGTH: 72
<212> TYPE: DNA
<213> ORGANISM: Artificial Sequence
<220> FEATURE:
<223> OTHER INFORMATION: Synthetic Primer

<400> SEQUENCE: 61
ggggacaagt tgtacaaaa aagcaggctt agaaggagat agaaccatgg ctactgccga      60
caagactcag ag                                                         72

<210> SEQ ID NO 62
<211> LENGTH: 59
<212> TYPE: DNA
<213> ORGANISM: Artificial Sequence
<220> FEATURE:
<223> OTHER INFORMATION: Synthetic Primer

<400> SEQUENCE: 62
```

```
ggggaccact tgtacaaga aagctgggtc ctgcaggcta ttcgggctta cggcatgtg        59
```

<210> SEQ ID NO 63
<211> LENGTH: 73
<212> TYPE: DNA
<213> ORGANISM: Artificial Sequence
<220> FEATURE:
<223> OTHER INFORMATION: Synthetic Primer

<400> SEQUENCE: 63

```
ggggacaagt tgtacaaaa aagcaggctt agaaggagat agaaccatgg tgaaggcggc        60
ggcgtcgtct ttg                                                         73
```

<210> SEQ ID NO 64
<211> LENGTH: 57
<212> TYPE: DNA
<213> ORGANISM: Artificial Sequence
<220> FEATURE:
<223> OTHER INFORMATION: Synthetic Primer

<400> SEQUENCE: 64

```
ggggaccact tgtacaaga aagctgggtc ctgcaggcta ctcagctggc ttccggc           57
```

<210> SEQ ID NO 65
<211> LENGTH: 73
<212> TYPE: DNA
<213> ORGANISM: Artificial Sequence
<220> FEATURE:
<223> OTHER INFORMATION: Synthetic Primer

<400> SEQUENCE: 65

```
ggggacaagt tgtacaaaa aagcaggctt agaaggagat agaaccatgg cccttagcgt        60
ggtcgcggcc gag                                                         73
```

<210> SEQ ID NO 66
<211> LENGTH: 54
<212> TYPE: DNA
<213> ORGANISM: Artificial Sequence
<220> FEATURE:
<223> OTHER INFORMATION: Synthetic Primer

<400> SEQUENCE: 66

```
ggggaccact tgtacaaga agctgggtct tattcaggct ttttgcatgt gatg              54
```

<210> SEQ ID NO 67
<211> LENGTH: 74
<212> TYPE: DNA
<213> ORGANISM: Artificial Sequence
<220> FEATURE:
<223> OTHER INFORMATION: Synthetic Primer

<400> SEQUENCE: 67

```
ggggacaagt tgtacaaaa aagcaggctt agaaggagat agaaccatga gtgcaacact        60
ttaccagcaa attc                                                        74
```

<210> SEQ ID NO 68
<211> LENGTH: 56
<212> TYPE: DNA
<213> ORGANISM: Artificial Sequence
<220> FEATURE:
<223> OTHER INFORMATION: Synthetic Primer

<400> SEQUENCE: 68

```
ggggaccact tgtacaaga aagctgggtc ctactactta ttgccgcaca gtaagc      56
```

<210> SEQ ID NO 69
<211> LENGTH: 76
<212> TYPE: DNA
<213> ORGANISM: Artificial Sequence
<220> FEATURE:
<223> OTHER INFORMATION: Synthetic Primer

<400> SEQUENCE: 69

```
ggggacaagt tgtacaaaa aagcaggctt agaaggagat agaaccatga gtgcaacact   60
ttaccaacaa attcag                                                  76
```

<210> SEQ ID NO 70
<211> LENGTH: 56
<212> TYPE: DNA
<213> ORGANISM: Artificial Sequence
<220> FEATURE:
<223> OTHER INFORMATION: Synthetic Primer

<400> SEQUENCE: 70

```
ggggaccact tgtacaaga aagctgggtc ctatcactta tccccacaaa gcaacc       56
```

<210> SEQ ID NO 71
<211> LENGTH: 71
<212> TYPE: DNA
<213> ORGANISM: Artificial Sequence
<220> FEATURE:
<223> OTHER INFORMATION: Synthetic Primer

<400> SEQUENCE: 71

```
ggggacaagt tgtacaaaa aagcaggctt agaaggagat agaaccatga gttggttgtt   60
ttctacactg g                                                       71
```

<210> SEQ ID NO 72
<211> LENGTH: 56
<212> TYPE: DNA
<213> ORGANISM: Artificial Sequence
<220> FEATURE:
<223> OTHER INFORMATION: Synthetic Primer

<400> SEQUENCE: 72

```
ggggaccact tgtacaaga aagctgggtc ctattacttt tgagcaacct tgatcg       56
```

<210> SEQ ID NO 73
<211> LENGTH: 71
<212> TYPE: DNA
<213> ORGANISM: Artificial Sequence
<220> FEATURE:
<223> OTHER INFORMATION: Synthetic Primer

<400> SEQUENCE: 73

```
ggggacaagt tgtacaaaa aagcaggctt agaaggagat agaaccatgg cctcgtcgac   60
ggctcaggcc c                                                       71
```

<210> SEQ ID NO 74
<211> LENGTH: 62
<212> TYPE: DNA
<213> ORGANISM: Artificial Sequence
<220> FEATURE:
<223> OTHER INFORMATION: Synthetic Primer

<400> SEQUENCE: 74

```
ggggaccact tgtacaaga aagctgggtc ctgcaggcta cgcggctcca ggcttgcgac   60
``` ag                                                              62

<210> SEQ ID NO 75
<211> LENGTH: 31
<212> TYPE: DNA
<213> ORGANISM: Artificial Sequence
<220> FEATURE:
<223> OTHER INFORMATION: Synthetic Primer

<400> SEQUENCE: 75
catgccatgg gaatgaaagc aactctagca g                              31

<210> SEQ ID NO 76
<211> LENGTH: 33
<212> TYPE: DNA
<213> ORGANISM: Artificial Sequence
<220> FEATURE:
<223> OTHER INFORMATION: Synthetic Primer

<400> SEQUENCE: 76
gtcagaattc ttattagagt ggcttctggc aag                            33

<210> SEQ ID NO 77
<211> LENGTH: 37
<212> TYPE: DNA
<213> ORGANISM: Artificial Sequence
<220> FEATURE:
<223> OTHER INFORMATION: Synthetic Primer

<400> SEQUENCE: 77
gcggccgcac aatgaaagca actctagcag caccctc                        37

<210> SEQ ID NO 78
<211> LENGTH: 33
<212> TYPE: DNA
<213> ORGANISM: Artificial Sequence
<220> FEATURE:
<223> OTHER INFORMATION: Synthetic Primer

<400> SEQUENCE: 78
cctgcaggtt agagtggctt ctggcaagtg atg                            33

<210> SEQ ID NO 79
<211> LENGTH: 24
<212> TYPE: DNA
<213> ORGANISM: Artificial Sequence
<220> FEATURE:
<223> OTHER INFORMATION: Synthetic Primer

<400> SEQUENCE: 79
ccacgtgagc tccttcctct tccc                                      24

<210> SEQ ID NO 80
<211> LENGTH: 33
<212> TYPE: DNA
<213> ORGANISM: Artificial Sequence
<220> FEATURE:
<223> OTHER INFORMATION: Synthetic Primer

<400> SEQUENCE: 80
gtgccatggc agatctgatg atggattgat gga                            33

<210> SEQ ID NO 81
<211> LENGTH: 51
<212> TYPE: DNA

<213> ORGANISM: Artificial Sequence
<220> FEATURE:
<223> OTHER INFORMATION: Synthetic Primer

<400> SEQUENCE: 81
gagtgatggt taatgcatga atgcatgatc agatctgcca tggtccgtcc t          51

<210> SEQ ID NO 82
<211> LENGTH: 51
<212> TYPE: DNA
<213> ORGANISM: Artificial Sequence
<220> FEATURE:
<223> OTHER INFORMATION: Synthetic Primer

<400> SEQUENCE: 82
gagtgatggt taatccatca atccatcatc agatctgcca tggtccgtcc t          51

<210> SEQ ID NO 83
<211> LENGTH: 71
<212> TYPE: DNA
<213> ORGANISM: Artificial Sequence
<220> FEATURE:
<223> OTHER INFORMATION: Synthetic Primer

<400> SEQUENCE: 83
ggggacaagt ttgtacaaaa aagcaggctt agaaggagat agaaccatga gttggttgtt   60
ttctacactg g                                                       71

<210> SEQ ID NO 84
<211> LENGTH: 56
<212> TYPE: DNA
<213> ORGANISM: Artificial Sequence
<220> FEATURE:
<223> OTHER INFORMATION: Synthetic Primer

<400> SEQUENCE: 84
ggggaccact ttgtacaaga aagctgggtc ctattacttt tgagcaacct tgatcg       56

<210> SEQ ID NO 85
<211> LENGTH: 1363
<212> TYPE: DNA
<213> ORGANISM: Zea mays

<400> SEQUENCE: 85
aacagtgccg cggtgcgcgc acacacagcc accaccccc cgtcccctcg cctcggcctc    60
ttttaaatat cgcgcatccc ggcgccgcaa atggctcacg cggcgctgct ccattgctcc   120
cagtcctcca ggagcctcgc agcctgccgc cgcggcagcc actaccgcgc cccttcgcac   180
gtcccgcgcc actcccgccg tctccgacgc gccgtcgtca gcctgcgtcc gatggcctcg   240
tcgacggctc aggcccccgc gacggcgccg ccgggtctga aggagggcat cgcggggctg   300
tacgacgagt cgtcggggct gtgggagaac atctggggcg accacatgca ccacggcttc   360
tacgactcga gcgaggccgc ctccatggcc gatcaccgcc gcgcccagat ccgcatgatc   420
gaggaggcgc tcgccttcgc cggtgtccca gcctcagatg atccagagaa gacaccaaaa   480
acaatagtcg atgtcggatg tggcattggt ggtagctcaa ggtacttggc gaagaaatac   540
ggagcgcagt gcactgggat cacgttgagc cctgttcaag ccgagagagg aaatgctctc   600
gctgcagcgc aggggttgtc ggatcaggtt actctgcaag ttgctgatgc tctggagcaa   660
ccgtttcctg acgggcagtt cgatctggtg tggtccatgg agagtggcga gcacatgccg   720
gacaagagaa agtttgttag tgagctagca cgcgtggcgg ctcctggagg gcaataatc   780

```
                                         -continued atcgtgacat ggtgccatag gaacctggat ccatccgaaa cctcgctaaa gcccgatgaa     840
ctgagcctcc tgaggaggat atgcgacgcg tactacctcc cggactggtg ctcaccttca     900
gactatgtga acattgccaa gtcactgtct ctcgaggata tcaagacagc tgactggtcg     960
gagaacgtgg ccccgttttg gcccgccgtg ataaaatcag cgctaacatg gaagggcttc    1020
acctctctgc tgacgaccgg atggaagacg atcagaggcg cgatggtgat gccgctaatg    1080
atccagggct acaagaaggg gctcatcaaa ttcaccatca tcacctgtcg caagcctgga    1140
gccgcgtagg aggaggccaa ggagcacaag ttactagcac aggcacagga gtgccaagtg    1200
caataatgta gatccgtggc cccatcgccg tctactcatc tatactgcac caaaatcaac    1260
attctcctag gacatgttaa ataattttct gccactcgtc gagatatttc aaattcactg    1320
ttccacaaaa aaaaaaaagg cgccgccgac tagtgagctg tcg                      1363
```